United States Patent
Ory et al.

(10) Patent No.: US 10,983,112 B2
(45) Date of Patent: Apr. 20, 2021

(54) BILE ACID BIOMARKERS FOR NIEMANN-PICK DISEASES, METHODS AND USES THEREFOR

(71) Applicants: Daniel Ory, Saint Louis, MO (US); Xuntian Jiang, Saint Louis, MO (US)

(72) Inventors: Daniel Ory, Saint Louis, MO (US); Xuntian Jiang, Saint Louis, MO (US)

(73) Assignee: Washington University, St. Louis, MO (US)

(*) Notice: Subject to any disclaimer, the term of this patent is extended or adjusted under 35 U.S.C. 154(b) by 76 days.

(21) Appl. No.: 15/581,389

(22) Filed: Apr. 28, 2017

(65) Prior Publication Data
US 2017/0285015 A1 Oct. 5, 2017

Related U.S. Application Data

(63) Continuation of application No. PCT/US2015/057840, filed on Oct. 28, 2015.
(Continued)

(51) Int. Cl.
*G01N 33/53* (2006.01)
*G01N 33/68* (2006.01)
(Continued)

(52) U.S. Cl.
CPC ....... *G01N 33/5308* (2013.01); *A61K 31/575* (2013.01); *G01N 33/6848* (2013.01);
(Continued)

(58) Field of Classification Search
CPC ........... G01N 2800/04; G01N 33/6848; G01N 33/5308; G01N 2800/28; G01N 2800/38;
(Continued)

(56) References Cited

U.S. PATENT DOCUMENTS

| 8,497,122 B2 | 7/2013 | Ory et al. |
| 2009/0286272 A1* | 11/2009 | Ory ................... G01N 33/6893 435/29 |

FOREIGN PATENT DOCUMENTS

| WO | 2013072060 A2 | 5/2013 |
| WO | 2013090857 A1 | 6/2013 |

OTHER PUBLICATIONS

Tint et al. (J. Inher. Metab. Dis. 1998, 21: 853-863) (Year: 1998).*
(Continued)

*Primary Examiner* — Rebecca M Fritchman

(57) ABSTRACT

Methods for identification and quantification of bile acids are disclosed. Bile acids in plasma, serum and/or blood such as a dried blood spot are used to identify subjects with a Niemann-Pick disease. The methods include measuring levels of a bile acid, such as $3\beta,5\alpha,6\beta$-trihydroxycholanic acid, N-($3\beta,5\alpha,6\beta$-trihydroxy-cholan-24-oyl)glycine, N-($3\beta,5\alpha,6\beta$-trihydroxy-cholan-24-oyl)taurine, or a combination thereof. Detection of bile acids involve mass spectroscopy and/or a combination of mass spectroscopy and liquid chromatography such as a LC-MS/MS assay. The methods can be used with sphingomyelinase assays to detect, diagnose and differentiate between Niemann-Pick A/B and Niemann-Pick C (NPC) disease.

38 Claims, 56 Drawing Sheets

Related U.S. Application Data

(60) Provisional application No. 62/072,004, filed on Oct. 29, 2014, provisional application No. 62/069,491, filed on Oct. 28, 2014.

(51) Int. Cl.
| | |
|---|---|
| *G01N 33/92* | (2006.01) |
| *A61K 31/575* | (2006.01) |
| *G01N 33/74* | (2006.01) |
| *G01N 30/72* | (2006.01) |
| *C12M 3/00* | (2006.01) |

(52) U.S. Cl.
CPC .......... *G01N 33/743* (2013.01); *G01N 33/92* (2013.01); *C12M 3/00* (2013.01); *G01N 30/7233* (2013.01); *G01N 2800/04* (2013.01); *G01N 2800/085* (2013.01); *G01N 2800/28* (2013.01); *G01N 2800/38* (2013.01)

(58) Field of Classification Search
CPC .......... G01N 2800/085; G01N 33/743; G01N 30/7233; G01N 33/92; A61K 31/575; C12M 3/00
See application file for complete search history.

(56) References Cited

OTHER PUBLICATIONS

Dzeletovic (1995, Analytical Biochemistry, 225:73-80) (Year: 1995).*
J.B. Nietupski et al.(2012) Iminosugar-based inhibitors of glucosylceramide synthase prolong survival but paradoxically increase brain glucosylceramide levels in Niemann-Pick C mice. / Molecular Genetics and Metabolism 105 (2012) 621-628.*
Bjorkhem,I. formation of Bile Acids in Man: Conversion of Cholesterol into 5B 3alpha, 7 alpha, 12 alpha tril in Liver homogenates. (1968). The Journal of Clinical Investigation.47: 1573-1582.*
Alnouti, Y., et al., Quantitative-profiling of bile acids and their conjugates in mouse liver, bile, plasma, and urine using LC-MS/MS. Journal of Chromatography B, 2008, 873, 209-217.
Alvelius, G., et al., Identification of unusual 7-oxygenated bile acid sulfates in a patient with Niemann-Pick disease, type C., J. Lipid Res., 42, 1571-1577, 2001.
Bauer, P., et al., Genetic screening for Niemann-Pick disease type C in adults with neurological and psychiatric symptoms: findings from the ZOOM study., Human Molecular Genetics, 22, 4349-4356, 2013.
Cluzeau, et al., Microarray expression analysis and identification of serum biomarkers for Niemann-Pick disease, type C1., Hum. Mol. Genet., 21, 3632-3646, 2012.
Everson, G.T., et al., HepG2. A human hepatoblastoma cell line exhibiting defects in bile acid synthesis and conjugation., J. Biol. Chem., 261, 2197-2201, 1986.
Fan, M., et al., Identification of Niemann-Pick C1 disease biomarkers through sphingolipid profiling., J. Lipid Res. 54, 2800-2814, 2013.
Jiang, X., et al., A sensitive and specific LC-MS/MS method for rapid diagnosis of Niemann-Pick C1 disease from human plasma., J. Lipid Res. 52, 1435-1445, 2011.
Jiang, X., et al., Alkaline methanolysis of lipid extracts extends shotgun lipidomics analyses to the low-abundance regime of cellular sphingolipids., Anal Biochem, 371, 135-145, 2007.
Jiang, X., et al., Characterization of oxysterols by electrospray ionization tandem mass spectrometry after one-step derivatization with dimethylglycine., Rapid Commun Mass Spectrom., 21, 141-152, 2007.
Jiang, X., Han, X., Characterization and direct quantitation of sphingoid base-1-phosphates from lipid extracts: a shotgun lipidomics approach., J Lipid Res, 47, 1865-1873, 2006.
Liu, B., et al., Cyclodextrin overcomes the transport defect in nearly every organ of NPC1 mice leading to excretion of sequestered cholesterol as bile acid., J. Lipid Res., 51, 933-944, 2010.
Maekawa, M., et al., LC/ESI-MS/MS analysis of urinary 3β-sulfooxy-7β-N-acetylglucosaminyl-5-cholen-24-oic acid and its amides: new biomarkers for the detection of Niemann-Pick type C disease., Steroids, 78, 967-972, 2013.
Porter, F.D., et al., Cholesterol oxidation products are sensitive and specific blood-based biomarkers for Niemann-Pick C1 disease., Sci. Transl. Med., 2, 56ra81, 2010.
Scherer, M., et al., Rapid quantification of bile acids and their conjugates in serum by liquid chromatography-tandem mass spectrometry. Journal of Chromatography B, 877, 3920-3925, 2009.
Tortelli , Brett, et al. Cholesterol homeostatic responses provide biomarkers for monitoring treatment for the neurodegenerative disease Niemann-Pick C1 (NPC2). Human molecular genetics, Human Molecular Genetics, 23, 6022-6033, 2014.
Yang, K., et al., Identification and quantitation of fatty acid double bond positional isomers: a shotgun lipidomics approach using charge-switch derivatization., Anal. Chem., 85, 9742-9750, 2013.
Curia G, Cananzi M, Giordano G, et al. Early identification of type C2 Niemann-Pick disease by urinary bile acid profile determination in a newborn: Potential of tandem mass spectrometry for the differential diagnosis of neonatal cholestasis. Digestive and Liver Disease. 2013;45:e271. doi:10.1016/j.dld.2013.08.158.
Jiang X, Sidhu R, Mydock-Mcgrane L, et al. Development of a bile acid-based newborn screen for Niemann-Pick disease type C. Sci Transl Med. 2016;8(337):337ra63. doi:10.1126/scitranslmed.aaf2326.

* cited by examiner

Bile Acid A

Bile Acid B

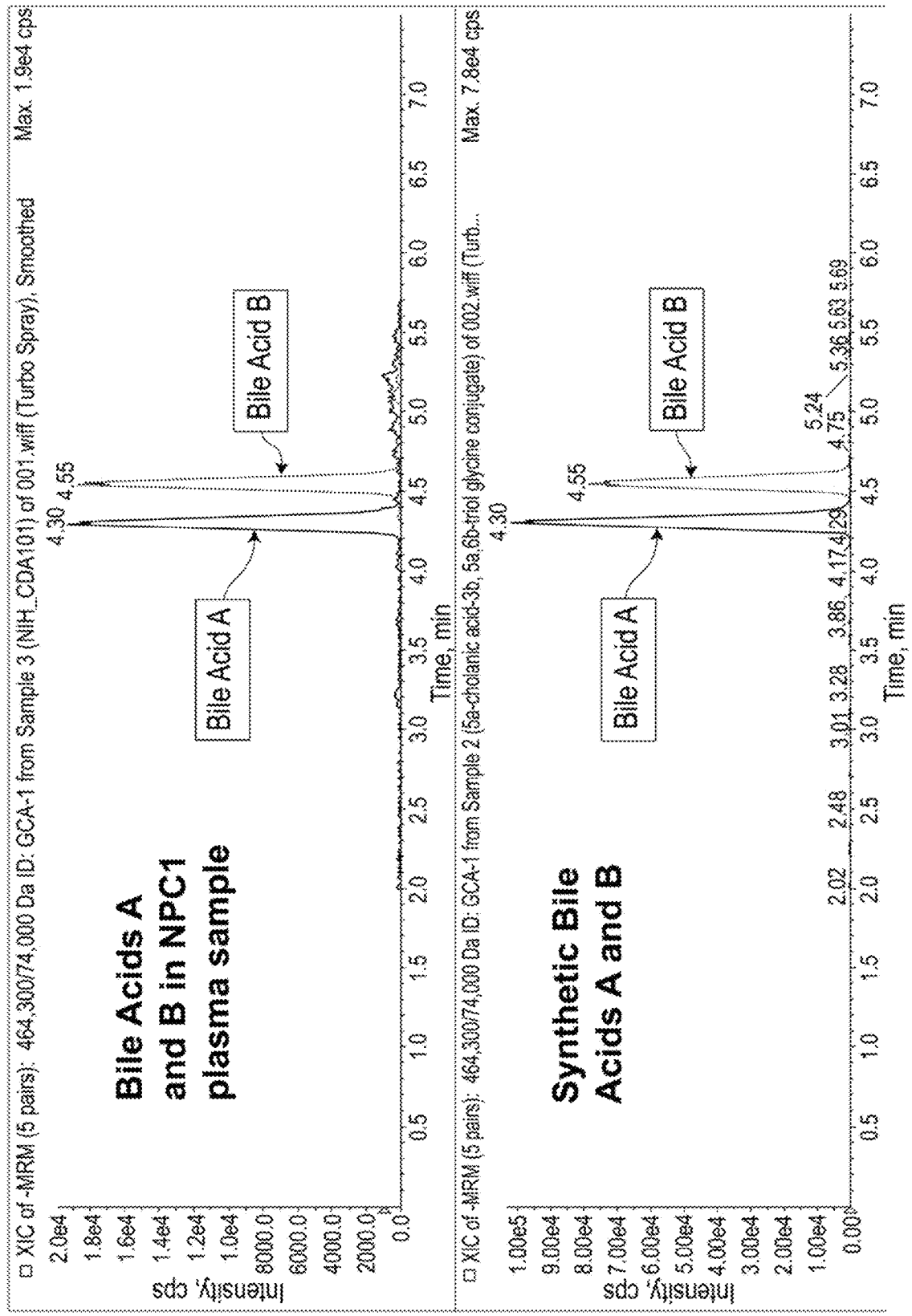

AMPP Derivative of Bile Acid A

AMPP Derivative of Bile Acid B

A: 407.2800, $C_{24}H_{39}O_5$ = 407.2792, 0.8175 mmu

B: 408.2833, $C_{23}{}^{13}H_{39}O_5$ = 408.2826, 0.7777 mmu

C: 409.2867, $C_{23}{}^{13}C_3H_{39}O_5$ =409.2859. 0.7935 mmu

A: 464.3016, C_{26}H_{42}O_6N=464.3007, 0.9278 mmu

B: 465.3048, C_{25}$^{13}$CH_{42}O_6N = 465.3040, 0.8089 mmu

C: 466.3083, C_{24}$^{13}$C_2H_{42}O_6N = 466.3074, 0.9596 mmu

A: 407.2798, $C_{24}H_{39}O_5$ = 407.2792, 0.6091 mmu

B: 408.2861, $C_{24}H_{38}DO_5$ = 408.2855, 0.6065 mmu

C: 409.2923, $C_{24}H_{37}D_2O_5$ = 409.2918, 0.5004 mmu

D: 410.2986, $C_{24}H_{36}D_3O_5$ = 410.2980, 0.5613 mmu

A: 464.3014, $C_{26}H_{42}O_6N$ = 464.3007, 0.7097 mmu

B: 465.3063, $C_{26}H_{41}DO_6N$ = 465.3069, -0.6441 mmu

C: 466.3129, $C_{26}H_{40}D_2O_6N$ = 466.3132, -0.2969 mmu

D: 467.3192, $C_{26}H_{39}D_3O_6N$ = 467.3195, -0.3018 mmu

E: 468.3254, $C_{26}H_{38}D_4O_6N$ = 468.3258, -0.3256 mmu

FIG. 35
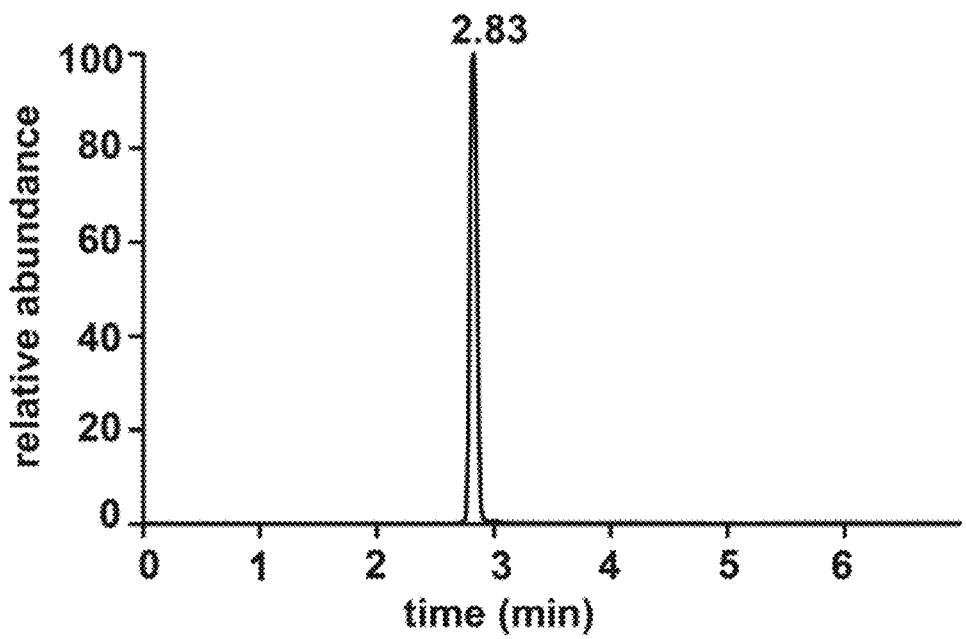
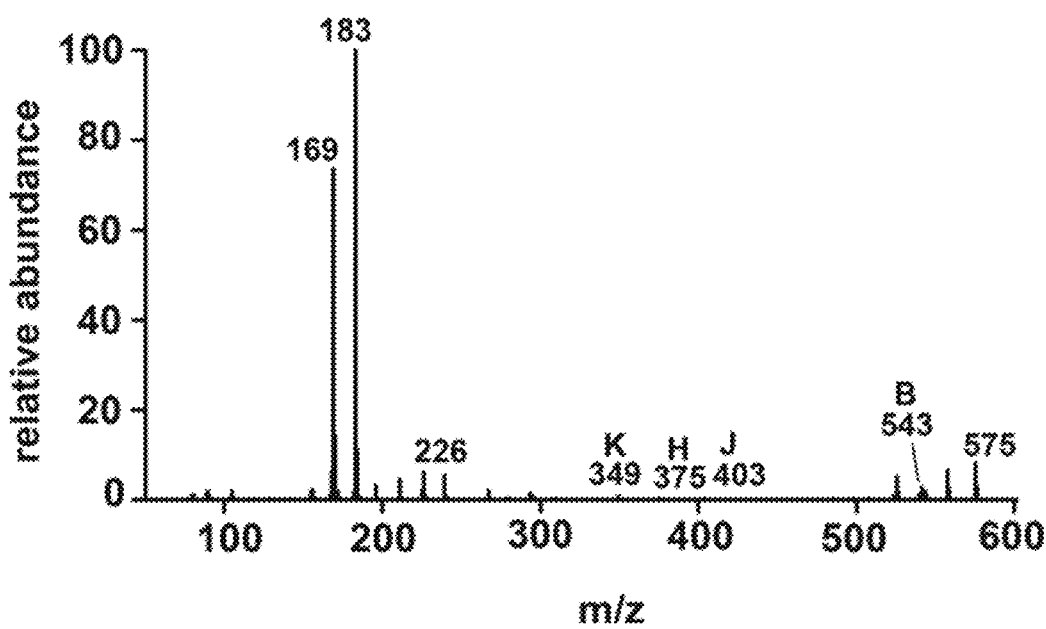

FIG. 37
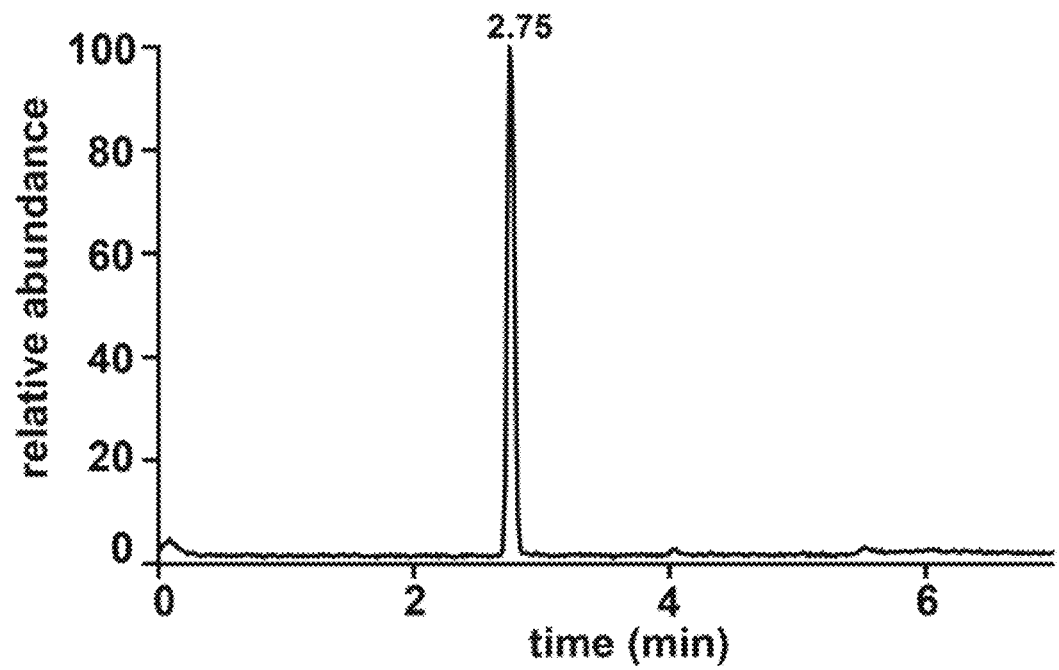
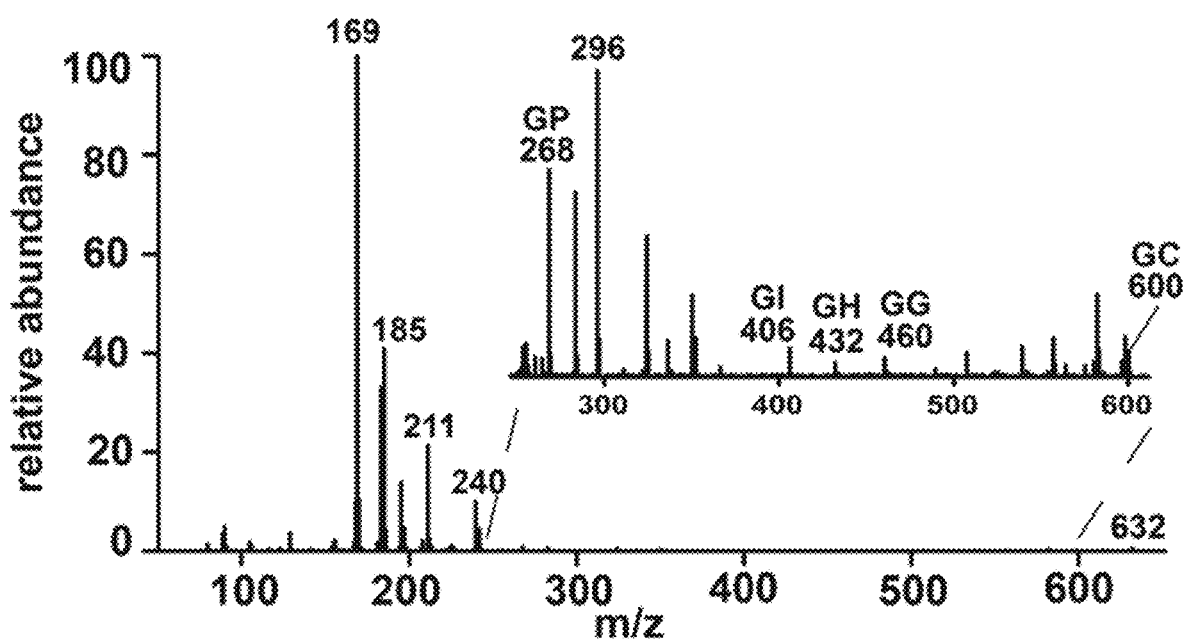

FIG. 40
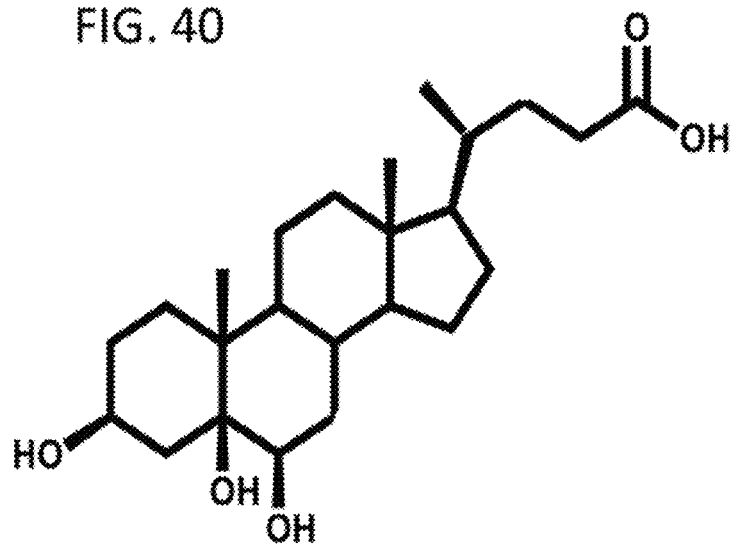
Synthetic Bile Acid A
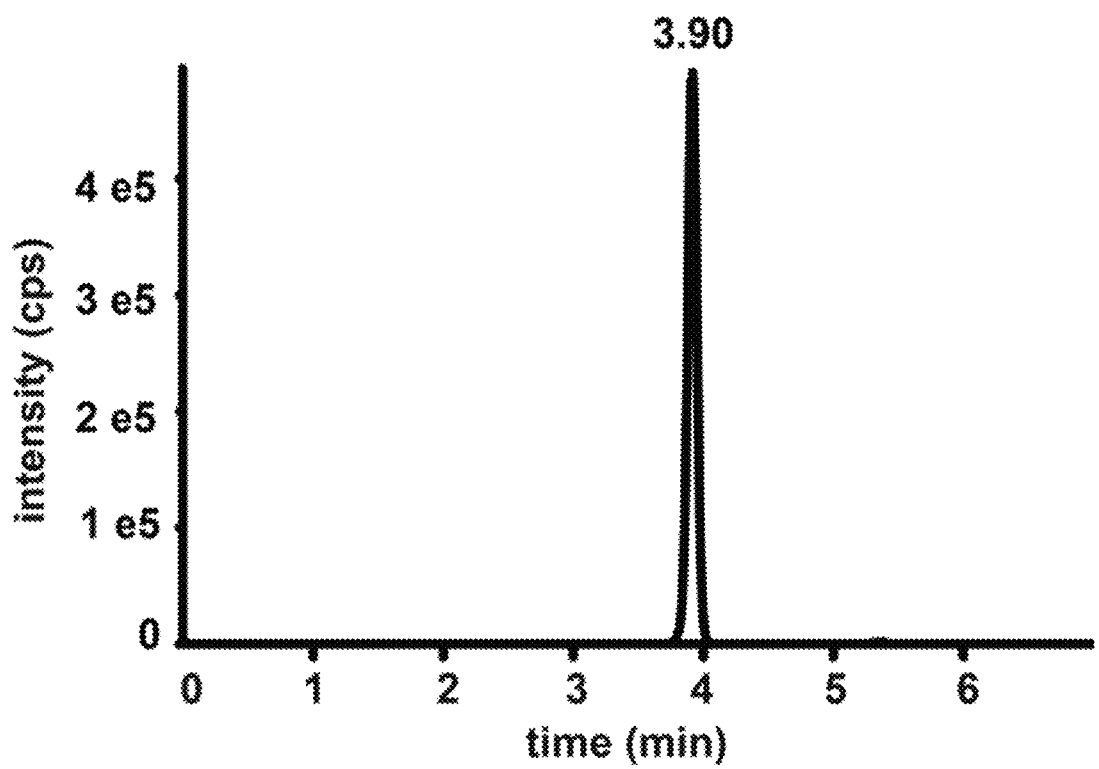

FIG. 41A
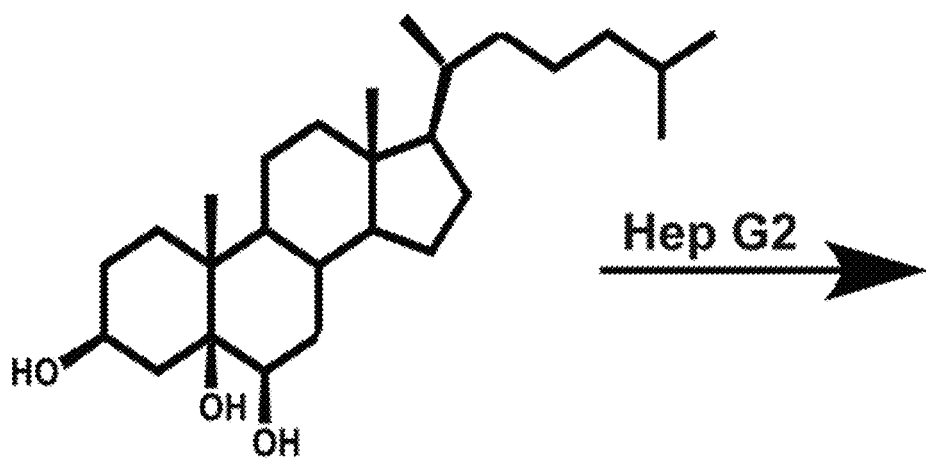
cholestane-
3β,5α,6β-triol
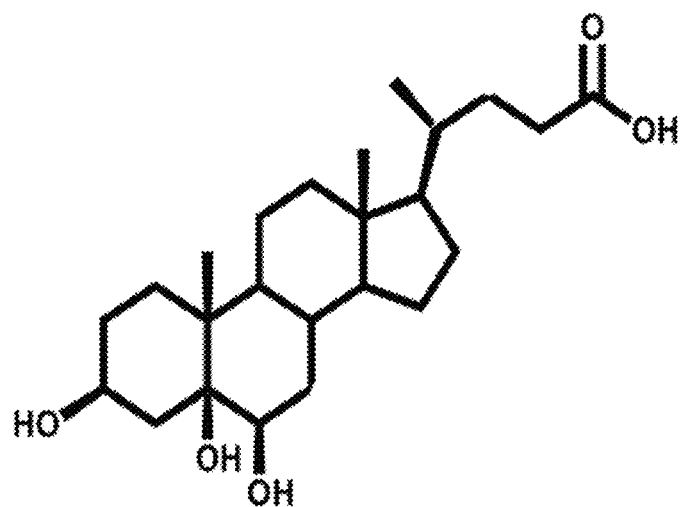
Bile Acid A

FIG. 42A
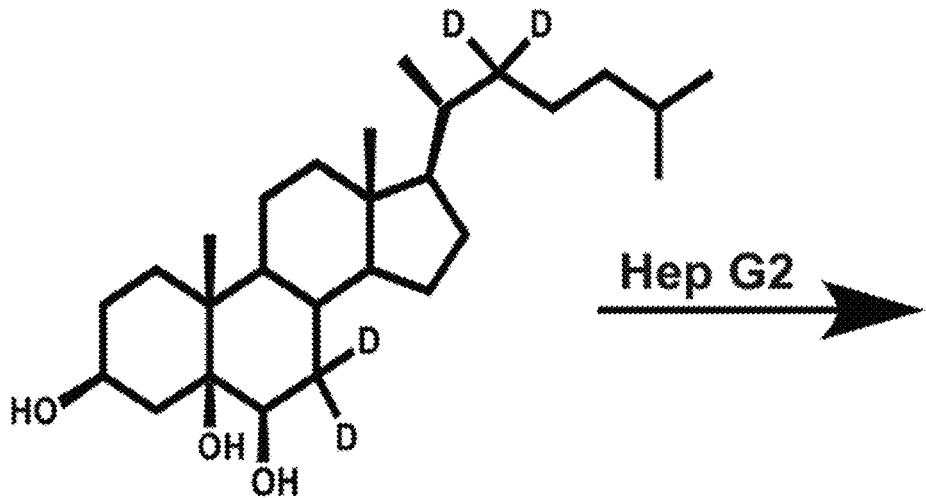
d4-cholestane-
3β,5α,6β-triol
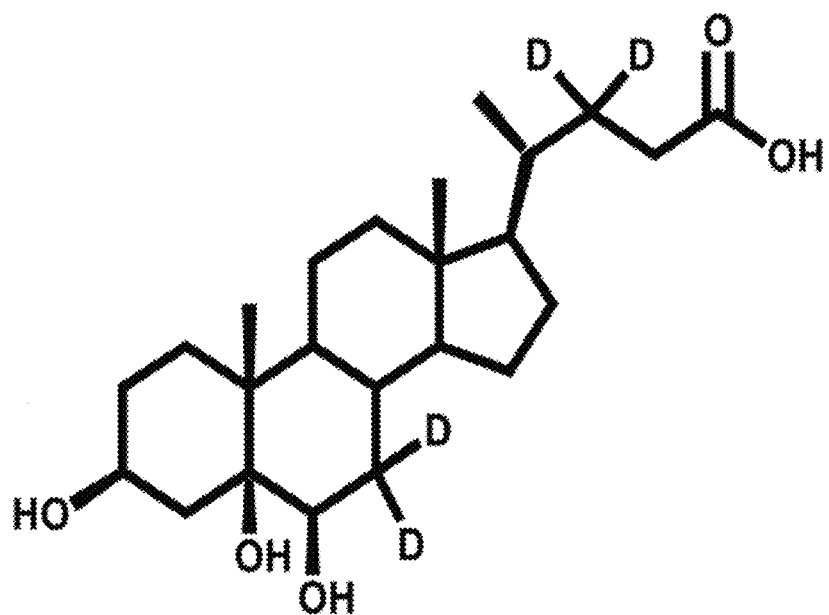
d4-Bile Acid A

BILE ACID BIOMARKERS FOR NIEMANN-PICK DISEASES, METHODS AND USES THEREFOR

RELATED APPLICATIONS

This application claims priority to PCT Application PCT/US15/57840 filed Oct. 28, 2015, which claims priority to U.S. Provisional Patent Application 62/069,491 filed Oct. 28, 2014 and to U.S. Provisional Patent application 62/072,004, filed Oct. 29, 2014, each of which is incorporated by reference each in its entirety.

STATEMENT REGARDING FEDERALLY SPONSORED RESEARCH OR DEVELOPMENT

This invention was made with government support under NS081985 awarded by the National Institutes of Health. The government has certain rights in the invention.

INTRODUCTION

Niemann-Pick diseases, including Niemann-Pick types A, B and C are each genetic diseases affecting lysosomal storage. Niemann-Pick type C (NPC) disease is a fatal neurodegenerative genetic disease that affects about 1 in 120,000 live births (Vanier, M. T. *Orphanet J. Rare Dis.* 5, 16 (2010)). NPC is associated with mutations in the NPC1 gene (95% of patients) (Carstea, E. D., et al. *Science* 277, 228-231 (1997)) and/or the NPC2 gene (also known as HE1; Naureckiene, S., et al., *Science* 290, 2298-2301 (2000)). Mutations in NPC1 or NPC2 protein can result in massive accumulation of cholesterol and other lipids in endolysosomes (Vanier, M. T., et al. *Clin. Genet.* 64, 269-281 (2003); Vanier, M. T., el al, *Biochimica et Biophysica Acta (BBA)— Molecular and Cell Biology of Lipids* 1685, 14-21 (2004); Blom, T. S., et al., *Human Molecular Genetics* 12, 257-272, 2003). Clinically, this accumulation is associated with cognitive impairment and progressive loss of motor function, generally leading to death by late adolescence/early adulthood.

Niemann-Pick diseases type A and B (collectively, NPA/B) involve acid sphingomyelinase deficiency. In NPA/B, sphingomyelin is not correctly metabolized, and improperly accumulates in cells. NPA/B can lead to cell or organ malfunction or death.

Miglustat, (Zervas, M., et al *Curr. Biol.* 11, 1283-1287 (2001)) an iminosugar inhibitor of glucosylceramide synthase, is approved outside the U.S. for slowing NPC disease progression (Patterson, M. C., et al. *Lancet Neurol* 6, 765-772 (2007)). 2-Hydroxypropyl-β-cyclodextrin (cyclodextrin), (Davidson, C. D., et al. *PLoS One* 4, e6951 (2009); Liu, B., et al. *J. Lipid Res.* 49, 663-669 (2008); Liu, B., et al *J. Lipid Res.* 51, 933-944 (2010); Ramirez, C. M., el al. *Pediatr. Res.* 68, 309-315 (2010)) delays neurodegeneration and prolongs survival in NPC1 animal models, and is currently being studied in a Phase 1 trial at the NIH.

A barrier to delivery of effective treatment for NPC disease has been the significant delay in diagnosis (which can be >5 years), due in part to the lack of a simple test for diagnosis (Sevin, M., et al. *Brain* 130, 120-133 (2007); Stampfer, M., et al. *Orphanet J. Rare Dis.* 8, 35 (2013)). The current diagnostic standard, cholesterol staining in fibroblasts, can be a time-consuming and invasive procedure with limited sensitivity. Efforts have been made to identify markers of NPC disease, including oxysterols in plasma, (Porter, F. D., et al. *Sci. Transl. Med.* 2, 56ra81 (2010)) bile acids in urine, (Alvelius, G., et al. *J. Lipid Res.* 42, 1571-1577 (2001); Maekawa, M., et al. *Steroids* 78, 967-972 (2013)) sphingolipids in plasma and cerebrospinal fluid, (Fan, M., et al. *J. Lipid Res.* 54, 2800-2814 (2013)) galectin-3 and cathepsin D in serum. (Cluzeau, C. V., et al. *Hum. Mol. Genet.* 21, 3632-3646 (2012))

Porter, F. D., et al, *Sci. Transl. Med.* 2010 Nov. 3, 2(56), 56ra81 describes oxysterol blood-based biomarkers for Niemann-Pick type C disease, Alvelius, G., et al., *J. Lipid Res.* 2001, 42(10): 1571-1577 describes the detection of bile acids in one subject. Maekawa., M., et al. *Steroids* 2013, 78(10):967-972 describes a method of diagnosing Niemann-Pick type C disease. Fan, M., et al., *J. Lipid Res.* 2013, 54(10):2800-2814 discloses methods of using lipid biomarkers to monitor efficacy of Niemann-Pick type C therapy. WO2013090857 A1 of Porter, F. D., et al discloses measurement of galectin-3 (LGALS3), cathepsin D (CTSD), in combination with at least one additional NPC associated biomarker such as 7-ketocholesterol or 3β,5α,6β-cholestane-triol for NPC diagnosis. WO 2013072060 A2 of Rolfs, A., et al. discusses methods of diagnosing Niemann-Pick type C disease through measurement of free lysosphingomyelin and "compound 509" of unspecified structure.

Plasma oxysterols prompted development of a clinical assay to measure cholestane-3β,5α,6β-triol ("triol") in human plasma. In previous studies, the inventors identified two oxysterols (cholestane-3β,5α,6β-triol (triol) and 7-ketocholesterol) that are elevated 10-fold in the plasma of NPC1 subjects (Porter, F. D., et al. *Sci. Transl Med.* 2, 56ra81 (2010)). The inventors developed a diagnostic assay based on liquid chromatography-tandem mass spectrometry (LC-MS/MS) for quantifying oxysterols in human plasma (Jiang, X., et al. *J. Lipid Res.* 52, 1435-1445 (2011)). However, the triol levels in plasma can be relatively low and may be subject to chromatographic interference. Triol is also poorly ionized without derivatization, which requires additional steps that can introduce artifacts. The reference range for triol in heterozygotes (~0.6% of the general population) partially overlaps with NPC1 subjects, resulting in difficulty in discriminating some heterozygotes from NPC1 subjects (Jiang, X., et al. *J. Lipid Res.* 52, 1435-1445 (2011)). The genetic mutation analysis is used as a second-tier test for confirming a biochemical diagnosis of NPC.

Technological advances in tandem mass spectrometry have expanded the scope of newborn screening. A multiplex tandem mass spectrometry assay was introduced to screen for five lysosomal storage disorders (LSDs) such as Fabry, Gaucher, Krabbe, Niemann-Pick A/B and Pompe diseases (Matern, D., et al. *Developmental Disabilities Research Reviews* 17, 247-253 (2013)). Newborn screening using this MS/MS method is now mandated in at least four U.S. states (Illinois, Missouri, Mississippi and New Mexico) (Marsden, D., et al. *Clin. Chem.* 56, 1071-1079 (2010)).

Diagnostic assays that can identify Niemann-Pick diseases and discriminate between NPA/B and NPC, are needed. No newborn screening method for NPC has been available. However, diagnosis of NPA/B or NPC disease before onset of symptoms could allow early medical intervention and provide the opportunity to slow disease progression. Moreover, development of a newborn screening assay would facilitate, for the first time, routine initiation of treatment in NPC patients before onset of symptoms as a general approach, which may improve quality of life and survival. Thus, there is still a need for a diagnostic test for Niemann-Pick diseases that can identify NPC disease and discriminate between NPA/B and NPC diseases and that can be inexpensive, reliable, and easy to use and/or can be used to screen newborns for NPA/B or NPC disease.

SUMMARY

The inventors describe novel biomarkers for Niemann-Pick diseases, including Niemann-Pick A/B and C diseases, non-invasive methods for screening and diagnosing Niemann-Pick diseases including Niemann-Pick A/B disease, or Niemann-Pick C disease (NPC) in human subjects including newborns, methods for monitoring the progress of Niemann-Pick diseases including NPA/B or NPC, and methods for determining therapeutic efficacy of a treatment of an Niemann-Pick disease including NPA/B or NPC disease. In various embodiments, methods of the present teachings can be used to detect, diagnose and/or monitor a Niemann-Pick disease such as, without limitation, NPA/B, NPC1 and/or NPC2.

The inventors have identified and characterized bile acids in the plasma of NPC1 subjects. These bile acids can serve as non-invasive markers for diagnosis of Niemann-Pick diseases including NPC, such as NPC disease resulting from mutations in NPC1 and/or NPC2. Bile acid markers of the present teachings also have applicability to screening of newborns.

Bile acids of the present teachings that have been identified as human blood biomarkers for Niemann-Pick diseases such as NPC disease, include at least 3β,5α,6β-trihydroxy-cholanic acid

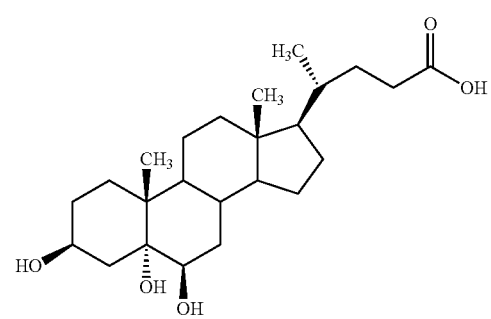 [SMILES: C[C@H](CCC(=O)O)[C@H]1CCC2C3C[C@@H](O)[C@@]4(O)C[C@@H](O)CC[C@]4(C)C3CC[C@@]21C]

(also known as "THCA," "5α-cholanic acid-3β,5α,6β-triol," (4R)-4-{(2R,5S,7R,8R,14R,15R)-5,7,8-Trihydroxy-2,15-dimethyltetracyclo[8.7.0.02,7.011,15]heptadec-14-yl}valeric acid and "Bile Acid A"); N-(3β,5α,6β-trihydroxy-cholan-24-oyl)glycine

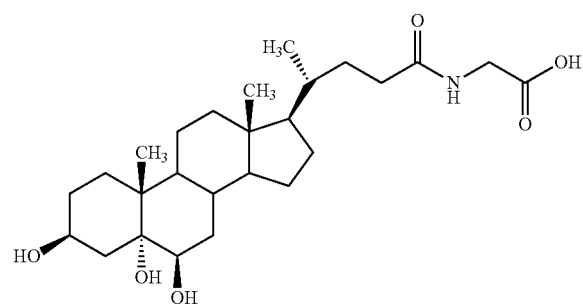 [SMILES: C[C@H](CCC(=O)NCC(=O)O)[C@H]1CCC2C3C[C@@H](O)[C@@]4(O)C[C@@H](O)CC[C@]4(C)C3CC[C@@]21C]

(also known as "THCG," "5α-cholanic acid-3β,5α,6β-triol N-(carboxymethyl)-amide," [(4R)-4-{(2R,5S,7R,8R,14R,15R)-5,7,8-Trihydroxy-2,15-dimethyltetracyclo[8.7.0.02, 7.011,15]heptadec-14-yl}valerylamino]acetic acid and "Bile Acid B"); and N-(3β,5α,6β-trihydroxy-cholan-24-oyl)taurine

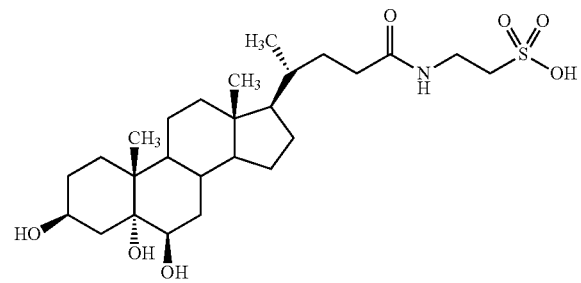 [SMILES: C[C@H](CCC(=O)NCCS(=O)(=O)O)[C@H]1CCC2C3C[C@@H](O)[C@@]4(O)C[C@@H](O)CC[C@]4(C)C3CC[C@@]21C]

(also known as "THCT"). 3β,5α,6β-trihydroxycholanic acid and N-(3β,5α,6β-trihydroxy-cholan-24-oly)glycine showed sensitivity and specificity at least comparable to oxysterol biomarkers in diagnosis and monitoring the process of NPC disease. Bile acids of the present teachings can be statistically significantly elevated in NPC plasma, blood or serum compared to a control group. In some embodiments, the sensitivity and specificity in newborn screening of NPC using N-(3β,5α,6β-trihydroxy-cholan-24-oyl)glycine can be significantly greater than that of oxysterols. In some configurations, bile acid B can be elevated >100-fold in NPC1 plasma, serum and dried blood spots and can be even more specific than oxysterols for discrimination of NPC subjects from controls. In various embodiments, bile acid B can be detected without derivatization and can be more readily extracted from dried blood spots on newborn screening cards.

Some embodiments of the present teachings include liquid chromatography-tandem mass spectrometry (LC-MS/MS) methods for identification and quantification of bile acids such as 3β,5α,6β-trihydroxycholanic acid, N-(3β,5α,6β-trihydroxy-cholan-24-oyl)glycine, and/or N-(3β,5α,6β-trihydroxy-cholan-24-oyl)taurine in samples of human plasma, serum and dried blood spots. Detection of statistically significant elevated levels of 3β,5α,6β-trihydroxycholanic acid and/or N-(3β,5α,6β-trihydroxy-cholan-24-oyl)glycine in plasma, serum and/or blood such as a dried blood spot can be used to differentiate subjects with NPC from controls.

In various embodiments, detection of levels of bile acids in plasma, serum or blood can compare favorably to that of oxysterol in discrimination power for diagnosis of NPC disease. While oxysterol levels in a portion of NPC dried blood spots overlapped with that of control samples, at least the bile acid N-(3β,5α,6β-trihydroxy-cholan-24-oyl)glycine concentration in dried blood spots in NPC subjects can be statistically greater than that of control subjects and can completely distinguish NPC subjects from control subjects. In some embodiments, detection and measurement of levels of bile acids of the present teachings can be used for screening of newborns for NPC.

In various embodiments, NPA/B or NPC diagnosis by LC-MS/MS detection and quantification of a bile acid of the present teachings can have advantages over current methods of NPA/B or NPC diagnosis including, without limitation, comparative ease of detection and simplification of a diagnostic assay. In some configurations, LC-MS/MS detection of a bile acid can be more sensitive than that of oxysterols, and a bile acid assay of the present teachings can be easier to implement in clinical laboratories than the oxysterol assay, which requires derivatization. While the triol marker is increased 10-fold in NPC plasma compared to controls, bile acid B can be elevated approximately 100-fold or greater compared to controls in NPC1 plasma and dried blood spots. Furthermore, detection of bile acids such as bile acid B does not require a derivatization step, and has the greatest discriminative power of any biomarkers identified thus far for NPC disease. In various embodiments, there can be no interferences in a blank dried blood spot card regarding a bile acid such as bile acid B.

In some embodiments, bile acid assays of the present teachings can include a screening method for Niemann-Pick diseases such as NPA/B or NPC disease for newborns and a screening method for an inborn error of sterol metabolism. In various configurations, the disclosed assays can provide early diagnosis of Niemann-Pick diseases such as NPA/B or NPC disease and allow for medical intervention in pre-symptomatic patients.

In some embodiments, coupling of measurement of a bile acid biomarker with a cut-off value can discriminate NPC cases, including NPC1 cases and NPC2 cases, from controls.

In some embodiments, a bile acid assay of the present teachings can be used to identify carriers.

In some embodiments, a bile acid assay of the present teachings can include a diagnostic test and newborn screen for Niemann-Pick diseases such as NPA/B or NPC disease.

In some embodiments, assays of the present teachings include a liquid chromatography-mass spectrometry (LC-MS/MS) method for determination of a bile acid biomarker in plasma for diagnosis of Niemann-Pick diseases such as NPA/B or NPC disease. In some embodiments, assays of the present teachings include a liquid chromatography-mass spectrometry (LC-MS/MS) method for determination of a bile acid biomarker of the present teachings in dried blood spots. In some configurations, newborn screening for Niemann-Pick diseases such as NPA/B or NPC disease can be facilitated by use of dried blood spots.

In some embodiments, assays of the present teachings can allow early diagnosis of Niemann-Pick diseases such as NPA/B or NPC disease, and intervention before onset of clinical disease.

In some embodiments, assays of the present teachings can include a newborn screen capable of integration into a newborn screening program, such as, for example, a state or regional newborn screening program.

In some embodiments, a newborn screen for a Niemann-Pick disease such as NPA/B or NPC disease can comprise a chromatography-mass spectroscopy analysis of bile acids. In various configurations, a subject can be a mammal such as a human, including without limitation a newborn human.

In some embodiments, the present teachings include a diagnostic test for a Niemann-Pick disease such as NPC disease and a newborn screening method based on measurement of 3β,5α,6β-trihydroxycholanic acid, N-(3β,5α,6β-trihydroxy-cholan-24-oyl)glycine, N-(3β,5α,6β-trihydroxy-cholan-24-oyl)taurine, or a combination thereof.

The present teachings include, in various embodiments, methods of detecting, diagnosing, or monitoring a Niemann-Pick disease such as Niemann-Pick NPA/B or NPC disease in a subject. In various configurations, these methods can comprise (a) obtaining or providing a sample from the subject; (b) subjecting the sample to a liquid chromatography-mass spectroscopy analysis to determine the concentration in the sample of at least one bile acid selected from the group consisting of 3β,5α,6β-trihydroxycholanic acid, N-(3β,5α,6β-trihydroxy-cholan-24-oyl)glycine, N-(3β,5α, 6β-trihydroxy-cholan-24-oyl)taurine, and a combination thereof; (c) comparing the amount of the at least one bile acid present in the sample to a reference value of the at least one bile acid obtained from a control population consisting of individuals not afflicted with a Niemann-Pick disease; and (d) diagnosing the subject as afflicted with a Niemann-Pick disease such as NPA/B or NPC disease if the amount of the at least one bile acid from the subject is statistically significantly greater than that of the reference value. In some configurations, the subject can be identified as afflicted with NPA/B or NPC disease if the concentration of the at least one bile acid in the sample is greater than the reference value. In some configurations, the Neimann-Pick disease can be selected from the group consisting of Neimann-Pick A and Niemann-Pick B. In some configurations, the Niemann-Pick disease can be Neimann-Pick C.

In various embodiments, the present teachings include methods for determining whether a subject is afflicted with a Niemann-Pick disease such as Niemann-Pick C disease or NPA/B disease. In various configurations, these methods can comprise: (a) obtaining a plasma sample, a serum sample or a blood sample such as a dried blood spot sample from the subject; (b) subjecting the sample to an extraction procedure such as solid phase extraction; (c) injecting an extracted sample into a mass spectrometer to determine the concentration in the sample of at least one bile acid selected from the group consisting of THCA, THCG and THCT; (d) comparing the concentration of the at least one bile acid present in the sample to a reference value of the at least one bile acid obtained from a control population consisting of individuals not afflicted with a Niemann-Pick disease; and (e) diagnosing the subject as afflicted with a Niemann-Pick disease if the concentration of the at least one bile acid from the subject is statistically significantly greater than the reference value. In some configurations, determining the concentration of the at least one bile acid can comprise: (a) adding a known amount of a bile acid internal standard to the body fluid sample; (b) extracting the at least one bile acid from the body fluid sample; and (c) quantifying the extracted at least one bile acid using a non-chromatography procedure such as mass spectroscopy. In some configurations, a control population can comprise individuals not afflicted with a Niemann-Pick disease who are matched with the subject in either one or both of age and sex. In some configurations, the reference value can be an average concentration of the at least one bile acid of a non-Niemann-Pick afflicted control group. In some configurations, a subject can be identified as afflicted with a Niemann-Pick disease when the concentration of the at least one bile acid in the sample is statistically significantly greater than the reference value, which can be at least 2-fold greater than the reference value, and wherein the reference value can be an average concentration of the at least one bile acid in the same sample type from a control population not afflicted with a Niemann-Pick disease and matched with the subject in at least one of sex or age. In some configurations, the subject can be a neonatal subject and the control population can be a neonatal control population.

In various embodiments, the present teachings include methods for determining whether a subject is afflicted with a Niemann-Pick disease such as Niemann-Pick C disease or NPA/B disease. In various configurations, these methods can comprise: (a) providing a sample from a subject; (b) subjecting the sample to a mass spectroscopy analysis to determine the concentration in the sample of at least one bile acid; (c) comparing the amount of the at least one bile acid present in the sample to a reference value of the at least one bile acid obtained from a control population consisting of individuals not afflicted with a Niemann-Pick disease; and (d) diagnosing the subject as afflicted with a Niemann-Pick disease if the amount of the at least one bile acid from the subject is statistically significantly greater than that of the reference value.

The present teachings include, in various embodiments, methods of distinguishing between Niemann-Pick type A or type B (collectively, "NPA/B") from Niemann-Pick type C disease in a subject. In various configurations, these methods can comprise determining the concentration in the sample of at least one bile acid selected from the group consisting of 3β,5α,6β-trihydroxycholanic acid, N-(3β,5α,6β-trihydroxycholan-24-oyl)glycine, N-(3β,5α,6β-trihydroxy-cholan-24-oyl)taurine, and a combination thereof in a sample as described above, and measuring sphingomyelinase activity in the sample. If sphingomyelinase activity in the sample is normal, then elevated bile acids can indicate NPC disease. If sphingomyelinase activity in the sample is low or absent, then elevated bile acids can indicate NPA/B disease.

In various configurations, these methods can comprise determining the concentration in the sample of at least one bile acid selected from the group consisting of 3β,5α,6β-trihydroxycholanic acid, N-(3β,5α,6β-trihydroxy-cholan-24-oyl)glycine, N-(3β,5α,6β-trihydroxy-cholan-24-oyl)taurine, and a combination thereof. In various configurations, these methods can comprise determining the concentration in the sample of at least one bile acid selected from the group consisting of 3β,5α,6β-trihydroxycholanic acid, N-(3β,5α,6β-trihydroxy-cholan-24-oyl)glycine, and N-(3β,5α,6β-trihydroxy-cholan-24-oyl)taurine. In various configurations, these methods can comprise determining the concentration in the sample of 5α-cholanic acid-3β,5α,6β-triol N-(carboxymethyl)-amide.

In some configurations, a sample can be "spiked" with bile acid A or bile acid B for a standard curve. In some configurations, a sample can be "spiked" with an isotope-labeled standard, such as, without limitation, isotope-labeled bile acid A or isotope-labeled bile acid B. In various aspects, an isotope can be, without limitation, $^{2}H$, $^{13}C$, and/or $^{15}N$. In various aspects, $^{2}H_{7}$-THCA, $^{2}H_{4}$, $^{13}C_{2}$, $^{15}N$-THCG and $^{2}H_{4}$, $^{13}C_{2}$, $^{15}N$-THCT can be used as surrogate standards for THCA, THCG and THCT, respectively. For example, without limitation, $^{2}H_{4}$, $^{13}C_{2}$, $^{15}N$-bile acid B can be used as surrogate standard for a standard curve or as an internal standard.

In some configurations, quantity of bile acid A in a dried blood spot sample from an NPC subject can be statistically significantly greater than that of non-NPC controls, such as, for example, at least 2-fold greater or at least 2.1 fold greater than the average of non-NPC control samples. In some configurations, quantity of bile acid A in a plasma sample of an NPC subject can be statistically significantly greater than that of non-NPC controls, such as, for example, at least 2-fold greater, at least 3-fold greater, or at least 3.7 fold greater than the average of control samples. In some configurations, quantity of bile acid B in a dried blood spot from an NPC subject can be statistically significantly greater than that of non-NPC controls, such as, for example at least 2-fold greater, at least 3-fold greater, at least 4-fold greater, at least 5-fold greater, at least 6-fold greater, at least 7-fold greater, or at least 7.2 fold greater than the average of control samples. In some configurations, quantity of bile acid B in plasma of an NPC subject can be statistically significantly greater than that of non-NPC controls, such as, for example at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 11-fold greater, at least 12-fold greater, at least 13-fold greater, at least 14-fold greater, at least 15-fold greater, at least 16-fold greater, at least 17-fold greater, at least 18-fold greater, at least 19-fold greater, at least 20-fold greater, at least 21-fold greater, at least 22-fold greater, or at least 22.6 fold greater than the average of non-NPC control samples. In some configurations, the reference value can be an average bile acid concentration in the same sample type from a control population without a Niemann-Pick disease and matched with the subject in at least one of sex or age. In various embodiments, a sample can be a body fluid sample such as a plasma sample, a serum sample, a blood sample, a dried blood spot sample, a sputum sample, a urine sample and/or an amniotic fluid sample. In some configurations, a sample can be a body fluid sample selected from the group consisting of a plasma sample, a serum sample and a blood sample such as a dried blood spot sample. In some configurations, a subject can be human subject such as a neonatal subject and the control population can be a neonatal control population.

In some embodiments, the present teachings include a two-tiered method of screening blood samples. In some configurations, the first tier can comprise an LC/MS analysis with a run time of about 1, about 1.5, about 1.7, about 2, about 2.5, about 3 minutes or less than 3 minutes. In some configurations, a sample comprising a bile acid above a reference value can be subjected to a second LC/MS with a longer running time of about 5, 5, about 6, 6, about 7, 7, about 8, 8, about 9, 9, about 10, or 10 minutes. In some configurations, the cut-off can be about 10 ng/ml, 10 ng/ml, about 10.5 ng/ml, 10.5 ng/ml, about 11 ng/ml, 11 ng/ml, about 11.5 ng/ml, 11.5 ng/ml, about 12 ng ml, 12 ng/ml, about 12.5 ng/ml, 12.5 ng/ml, about 13 ng/ml, 13 ng/ml, about 13.5 ng/ml, 13.5 ng/ml, about 14 ng/ml, 14 ng/ml, about 14.5 ng/ml, 14.5 ng/ml, about 15 ng/ml, or 15 ng/ml. In some configurations, Niemann-Pick disease can be diagnosed if the second-tier concentration of the at least one bile acid is above the reference value.

In some embodiments, the present teachings include methods for determining whether a subject is afflicted with a Niemann-Pick disease such as Niemann-Pick C disease or NPA/B disease. In various configurations, these methods can comprise: (a) obtaining a plasma sample, a serum sample or a blood sample such as a dried blood spot sample from the subject; (b) subjecting the sample to a chromatography-mass spectroscopy analysis to determine the concentration in the sample of at least one bile acid selected from the group consisting of THCA, THCG and THCT; (c) comparing the concentration of the at least one bile acid present in the sample to a reference value of the at least one bile acid obtained from a control population consisting of individuals not afflicted with a Niemann-Pick disease; and (d) diagnosing the subject as afflicted with a Niemann-Pick disease if the concentration of the at least one bile acid from the subject is statistically significantly greater than the reference value. In some configurations, determining the concentration of the at least one bile acid can comprise: (a) adding a known amount of a bile acid internal standard to the body fluid sample; (b) extracting the at least one bile acid from the body fluid sample; and (c) quantifying the extracted at least one bile acid using a chromatography procedure. In some configurations, a control population can comprise individuals not afflicted with a Niemann-Pick disease who are matched with the subject in either one or both of age and sex. In some configurations, the reference value can be an average concentration of the at least one bile acid of a non-Niemann-Pick afflicted control group. In some configurations, a subject can be identified as afflicted with a Niemann-Pick disease when the concentration of the at least one bile acid in the sample is statistically significantly greater than the reference value, which can be at least 2-fold greater than the reference value, and wherein the reference value can be an average concentration of the at least one bile acid in the same sample type from a control population not afflicted with a Niemann-Pick disease and matched with the subject in at least one of sex or age. In some configurations, the subject can be a neonatal subject and the control population can be a neonatal control population.

In some configurations, determining the concentration of the at least one bile acid can comprise: (a) providing a neonatal screening card spotted with a body fluid sample such as a blood, plasma or serum sample from the neonatal subject; (b) extracting the at least one bile acid in the presence of internal standard from the neonatal screening card; and (c) determining the concentrations of the extracted at least one bile acid using a chromatography procedure. In various configurations, the reference value can be an average of the at least one bile acid concentration of a non-Niemann-Pick disease afflicted control group. In some configurations, a neonatal subject can be identified as afflicted with a Niemann-Pick disease when the concentration of the at least one bile acid in the subject body fluid sample is about 2-fold higher, or more than 2-fold higher, than the average of the at least one bile acid concentration found in the same body fluid sample from sex-matched controls of non-NPC afflicted neonates.

In some embodiments, the present teachings include methods for determining the status of Niemann-Pick C disease in a subject with a Niemann-Pick disease such as Niemann-Pick A/B disease or Niemann-Pick C disease. In various configurations, these methods can comprise: (a) obtaining at least one body fluid sample from the subject; (b) quantifying at least one bile acid selected from the group consisting of 3β,5α,6β-trihydroxycholanic acid, N-(3β,5α, 6β-trihydroxy-cholan-24-oyl)glycine, N-(3β,5α,6β-trihydroxy-cholan-24-oyl)taurine and a combination thereof, in the body fluid sample to determine a quantification value; (c) determining the magnitude of the difference between the quantification value and a reference value of the same at least one bile acid obtained from the subject at an earlier time, thereby identifying the status of Niemann-Pick A/B disease or Niemann-Pick C disease in the subject. In some configurations, the quantification value can comprise the concentration of 3β,5α,6β-trihydroxycholanic acid, N-(3β, 5α,6β-trihydroxy-cholan-24-oyl)glycine and N-(3β,5α,6β-trihydroxy-cholan-24-oyl)taurine or a combination thereof. In these configurations, if the quantification value is statistically significantly greater than or equal to the reference value, then the subject is not deemed to exhibit remission of the Niemann-Pick A/B disease or Niemann-Pick C disease.

In some embodiments, the present teachings include methods for determining the status of Niemann-Pick C disease in a subject with a Niemann-Pick disease such as Niemann-Pick A/B disease or Niemann-Pick C disease. In various configurations, these methods can comprise: (a) obtaining at least one body fluid sample from the subject; (b) determining a quantification value of at least one bile acid selected from the group consisting of 3β,5α,6β-trihydroxycholanic acid, N-(3β,5α,6β-trihydroxy-cholan-24-oyl)glycine and N-(3β,5α,6β-trihydroxy-cholan-24-oyl)taurine by subjecting the at least one body fluid sample to a mass spectroscopy analysis; (c) determining the magnitude of the difference between the quantification value and a reference value of the at least one bile acid obtained from the subject at an earlier time, wherein if the quantification value is statistically significantly greater than or equal to the reference value, then the subject is not deemed to exhibit remission of the Niemann-Pick disease.

In some embodiments, the present teachings include methods for determining the status of a Niemann-Pick disease such as Niemann-Pick A/B disease or Niemann-Pick C disease in a subject with a Niemann-Pick disease. In various configurations, these methods can comprise: (a) obtaining at least one body fluid sample from the subject; (b) quantifying at least one bile acid selected from the group consisting of 3β,5α,6β-trihydroxycholanic acid, N-(3β,5α, 6β-trihydroxy-cholan-24-oyl)glycine and N-(3β,5α,6β-trihydroxy-cholan-24-oyl)taurine, in the body fluid sample to determine a quantification value; (c) determining the magnitude of the difference between the quantification value and a reference value of the same at least one bile acid obtained from a control population consisting of individuals not afflicted with a Niemann-Pick disease, thereby identifying the status of a Niemann-Pick disease in the subject. In some configurations, the quantification value can comprise the concentration of 3β,5α,6β-trihydroxycholanic acid, N-(3β, 5α,6β-trihydroxy-cholan-24-oyl)glycine and N-(3β,5α,6β-trihydroxy-cholan-24-oyl)taurine or a combination thereof. In these configurations, if the quantification value is statistically significantly greater than the reference value, then the subject is not deemed to exhibit remission of the Niemann-Pick A/B disease or Niemann-Pick C disease.

In various configurations of these embodiments, quantifying the at least one bile acid of a sample can comprise: (a) adding a known amount of a bile acid internal standard to the body fluid sample; (b) extracting the at least one bile acid from the body fluid sample; and (c) quantifying the extracted at least one bile acid using a LC-MS/MS procedure. In some configurations, quantifying the at least one bile acid can comprise determining peak area for the bile acid internal standard; determining peak area for the at least one bile acid of the sample; and comparing the peak area obtained for the known amount of bile acid internal standard with the peak area obtained for the at least one bile acid of the sample. In some configurations, quantifying the at least one bile acid can comprise determining peak area for the bile acid at different concentrations and bile acid internal standard; and calculating the peak area ratio of bile acid to its internal standard. In some configurations, quantifying the at least one bile acid can further comprise plotting peak area ratio vs. concentration of bile acid to establish a standard curve, and calculating the bile acid concentration in the sample from the standard curve. In various configurations, the body fluid can be selected from the group consisting of plasma, serum, blood, sputum and amniotic fluid. In various configurations, the body fluid can be selected from the group consisting of plasma, serum and blood. In some configurations, the body fluid can be plasma, and in some configurations, the body fluid can be cord blood.

In some embodiments, the present teachings can comprise an in vitro method of detecting, diagnosing, or monitoring a Niemann-Pick disease in a subject, the method comprising, on a body fluid sample obtained from the subject: (a) subjecting the sample to a liquid chromatography-mass spectroscopy analysis to determine the concentration in the sample of at least one bile acid; (b) comparing the amount of the at least one bile acid present in the sample to a reference value of the at least one bile acid obtained from a control population consisting of individuals not afflicted with a Niemann-Pick disease; and (c) diagnosing the subject as afflicted with a Niemann-Pick disease if the amount of the at least one bile acid from the subject is statistically significantly greater than the reference value. In some configurations, an in vitro method in accordance with the present teachings, the bile acid can be 3β,5α,6β-trihydroxycholanic acid, N-(3β,5α,6β-trihydroxy-cholan-24-oyl)glycine, N-(3β,5α,6β-trihydroxy-cholan-24-oyl)taurine, 5α-cholanic acid-3β,5α,6β-triol, 5α-cholanic acid-3β,5α,6β-triol N-(carboxymethyl)-amide, or a combination thereof. In some configurations, the bile acid can be 5α-cholanic acid-3β,5α,6β-triol N-(carboxymethyl)-amide.

In some configurations, in an in vitro method of the present teachings, the sample can be a blood spot. In some configurations, in an in vitro method in accordance with the present teachings, the sample can be provided on a screening card. In some configurations, in an in vitro method of the present teachings the body fluid sample can be a plasma sample, a serum sample, a blood sample, a sputum sample, a urine sample, an amniotic fluid sample, cord blood, or a combination thereof. In some configurations, an in vitro method of the present teachings can further comprise adding a known amount of a bile acid internal standard to the body fluid sample. In some configurations, in an in vitro method of the present teachings, a Niemann-Pick disease can be diagnosed if the at least one bile acid concentration is at least 2 fold greater than the reference value. In some configurations, in an in vitro method of the present teachings, the reference value can be an average concentration of the at least one bile acid of a non-Niemann-Pick afflicted control group. In some configurations, in an in vitro method of the present teachings, the Niemann-Pick disease can be Niemann-Pick A or Niemann-Pick B. In some configurations, in an in vitro method of the present teachings, the Niemann-Pick disease can be Niemann-Pick C.

In some embodiments, the present teachings can comprise an in vitro method of detecting, diagnosing, or monitoring a Niemann-Pick disease in a subject, the method comprising, on a body fluid sample obtained from the subject: (a) subjecting the sample to a liquid chromatography-mass spectroscopy analysis to determine the concentration in the sample of at least one bile acid; (b) comparing the amount of the at least one bile acid present in the sample to a reference value of the at least one bile acid obtained from a control population consisting of individuals not afflicted with a Niemann-Pick disease; and (c) diagnosing the subject as afflicted with a Niemann-Pick disease if the amount of the at least one bile acid from the subject is statistically significantly greater than the reference value. Various embodiments of the present teachings include the following aspects:

1. A method of detecting a Niemann-Pick disease in a subject comprising:
   (a) providing a sample from a subject;
   (b) subjecting the sample to a liquid chromatography-mass spectroscopy analysis to determine the concentration in the sample of at least one bile acid;
   (c) comparing the amount of the at least one bile acid present in the sample to a reference value of the at least one bile acid obtained from a control population consisting of individuals not afflicted with a Niemann-Pick disease; and
   (d) diagnosing the subject as afflicted with a Niemann-Pick disease if the amount of the at least one bile acid from the subject is statistically significantly greater than that of the reference value.

2. A method in accordance with aspect 1, wherein the Niemann-Pick disease is selected from the group consisting of Niemann-Pick A disease and Niemann-Pick B disease.

3. A method in accordance with aspect 1, wherein the Niemann-Pick disease is Niemann-Pick C disease.

4. A method in accordance with aspect 1, wherein the at least one bile acid is selected from the group consisting of 3β,5α,6β-trihydroxycholanic acid, N-(3β,5α,6β-trihydroxy-cholan-24-oyl)glycine, N-(3β,5α,6β-trihydroxy-cholan-24-oyl)taurine, 5α-cholanic acid-3β,5α,6β-triol, 5α-cholanic acid-3β,5α,6β-triol N-(carboxymethyl)-amide, and a combination thereof.

5. A method in accordance with aspect 1, wherein the at least one bile acid is 5α-cholanic acid-3β,5α,6β-triol N-(carboxymethyl)-amide.

6. A method in accordance with aspect 1, wherein the subject is a human.

7. A method in accordance with aspect 1, wherein the subject is a newborn.

8. A method in accordance with aspect 1, wherein the sample is a blood spot.

9. A method in accordance with aspect 1, wherein the sample is provided on a screening card.

10. A method in accordance with aspect 1, wherein the sample is a body fluid sample.

11. A method in accordance with aspect 10, wherein the body fluid sample is selected from the group consisting of a plasma sample, a serum sample, a blood sample, a sputum sample, a urine sample, an amniotic fluid sample, cord blood, and a combination thereof.

12. A method in accordance with aspect 10, further comprising adding a known amount of a bile acid internal standard to the body fluid sample.

13. A method in accordance with aspect 1, wherein a Niemann-Pick disease is diagnosed if the at least one bile acid concentration is at least 2 fold greater than the reference value.

14. A method in accordance with aspect 1, wherein the reference value is an average concentration of the at least one bile acid of a non-Niemann-Pick afflicted control group.

15. A method in accordance with aspect 14, wherein the control group is matched with the subject in sex.

16. A method in accordance with aspect 14, wherein the control group is matched with the subject in age.

17. A method for determining the status of a Niemann-Pick disease in a subject with a Niemann-Pick disease comprising:
   (a) obtaining at least one body fluid sample from the subject;
   (b) determining a quantification value of at least one bile acid selected from the group consisting of 3β,5α,6β-trihydroxycholanic acid, N-(3β,5α,6β-trihydroxy-cholan-24-oyl)glycine and N-(3β,5α,6β-trihydroxy-cholan-24-oyl)taurine by subjecting the at least one body fluid sample to a liquid chromatography-mass spectroscopy analysis; and
   (c) determining the magnitude of the difference between the quantification value and a reference value of the at least one bile acid obtained from the subject at an earlier time, wherein if the quantification value is statistically significantly greater than or equal to the reference value, then the subject is not deemed to exhibit remission of the Niemann-Pick disease.

18. A method for determining the status of a Niemann-Pick disease in a subject in accordance with aspect 17, wherein the reference value is an average bile acid concentration in the same sample type from a control population without a Niemann-Pick disease and matched with the subject in at least one of sex or age.

19. An in vitro method of detecting, diagnosing, or monitoring a Niemann-Pick disease in a subject, the method comprising, on a body fluid sample obtained from the subject:
 (a) subjecting the sample to a liquid chromatography-mass spectroscopy analysis to determine the concentration in the sample of at least one bile acid;
 (b) comparing the amount of the at least one bile acid present in the sample to a reference value of the at least one bile acid obtained from a control population consisting of individuals not afflicted with a Niemann-Pick disease; and
 (c) diagnosing the subject as afflicted with a Niemann-Pick disease if the amount of the at least one bile acid from the subject is statistically significantly greater than the reference value.

20. An in vitro method in accordance with aspect 19, wherein the bile acid is 3β,5α,6β-trihydroxycholanic acid, N-(3β,5α,6β-trihydroxy-cholan-24-oyl)glycine, N-(3β,5α,6β-trihydroxy-cholan-24-oyl)taurine, 5α-cholanic acid-3β,5α,6β-triol, 5α-cholanic acid-3β,5α,6β-triol N-(carboxymethyl)-amide, or a combination thereof.

21. An in vitro method in accordance with aspect 19, wherein the bile acid is 5α-cholanic acid-3β,5α,6β-triol N-(carboxymethyl)-amide.

22. An in vitro method in accordance with aspect 19, wherein the sample is a blood spot.

23. An in vitro method in accordance with aspect 19, wherein the sample is provided on a screening card.

24. An in vitro method in accordance with aspect 19, wherein the body fluid sample is a plasma sample, a serum sample, a blood sample, a sputum sample, a urine sample, an amniotic fluid sample, cord blood, or a combination thereof.

25. An in vitro method in accordance with aspect 19, further comprising adding a known amount of a bile acid internal standard to the body fluid sample.

26. An in vitro method in accordance with aspect 19, wherein Niemann-Pick disease is diagnosed if the at least one bile acid concentration is at least 2 fold greater than the reference value.

27. An in vitro method in accordance with aspect 19, wherein the reference value is an average concentration of the at least one bile acid of a non-Niemann-Pick afflicted control group.

28. An in vitro method in accordance with aspect 19, wherein the Neimann-Pick disease is Niemann-Pick A or Niemann-Pick B.

29. An in vitro method in accordance with aspect 19, wherein the Neimann-Pick disease is Niemann-Pick C.

30. A method of detecting a Niemann-Pick disease in a subject comprising:
 (a) providing a sample from a subject;
 (b) subjecting the sample to a mass spectroscopy analysis to determine the concentration in the sample of at least one bile acid;
 (c) comparing the amount of the at least one bile acid present in the sample to a reference value of the at least one bile acid obtained from a control population consisting of individuals not afflicted with a Niemann-Pick disease; and
 (d) diagnosing the subject as afflicted with a Niemann-Pick disease if the amount of the at least one bile acid from the subject is statistically significantly greater than that of the reference value.

31. A method in accordance with aspect 30, wherein the Neimann-Pick disease is selected from the group consisting of Niemann-Pick A disease and Niemann-Pick B disease.

32. A method in accordance with aspect 30, wherein the Neimann-Pick disease is Niemann-Pick C disease.

33. A method in accordance with aspect 30, wherein the at least one bile acid is selected from the group consisting of 3β,5α,6β-trihydroxycholanic acid, N-(3β,5α,6β-trihydroxy-cholan-24-oyl)glycine, N-(3β,5α,6β-trihydroxy-cholan-24-oyl)taurine, 5α-cholanic acid-3β,5α,6β-triol, 5α-cholanic acid-3β,5α,6β-triol N-(carboxymethyl)-amide, and a combination thereof.

34. A method in accordance with aspect 30, wherein the at least one bile acid is 5α-cholanic acid-3β,5α,6β-triol N-(carboxymethyl)-amide.

35. A method in accordance with aspect 30, wherein the subject is a human.

36. A method in accordance with aspect 30, wherein the subject is a newborn.

37. A method in accordance with aspect 30, wherein the sample is a blood spot.

38. A method in accordance with aspect 30, wherein the sample is provided on a screening card.

39. A method in accordance with aspect 30, wherein the sample is a body fluid sample.

40. A method in accordance with aspect 39, wherein the body fluid sample is selected from the group consisting of a plasma sample, a serum sample, a blood sample, a sputum sample, a urine sample, an amniotic fluid sample, chord blood, and a combination thereof.

41. A method in accordance with aspect 39, further comprising adding a known amount of a bile acid internal standard to the body fluid sample.

42. A method in accordance with aspect 1, wherein a Niemann-Pick disease is diagnosed if the at least one bile acid concentration is at least 2 fold greater than the reference value.

43. A method in accordance with aspect 1, wherein the reference value is an average concentration of the at least one bile acid of a non-Niemann-Pick afflicted control group.

44. A method in accordance with aspect 43, wherein the control group is matched with the subject in sex.

45. A method in accordance with aspect 43, wherein the control group is matched with the subject in age.

46. A method for determining the status of a Niemann-Pick disease in a subject with a Niemann-Pick disease comprising:
 (a) obtaining at least one body fluid sample from the subject;
 (b) determining a quantification value of at least one bile acid selected from the group consisting of 3β,5α,6β-trihydroxycholanic acid, N-(3β,5α,6β-trihydroxy-cholan-24-oyl)glycine and N-(3β,5α,6β-trihydroxy-cholan-24-oyl)taurine by subjecting the at least one body fluid sample to a mass spectroscopy analysis; and
 (c) determining the magnitude of the difference between the quantification value and a reference value of the at least one bile acid obtained from the subject at an earlier time, wherein if the quantification value is statistically significantly greater than or equal to the reference value, then the subject is not deemed to exhibit remission of the Niemann-Pick disease.

47. A method for determining the status of a Niemann-Pick disease in a subject in accordance with aspect 46, wherein the reference value is an average bile acid concentration in the same sample type from a control population without a Niemann-Pick disease and matched with the subject in at least one of sex or age.

48. An in vitro method of detecting, diagnosing, or monitoring a Niemann-Pick disease in a subject, the method comprising, on a body fluid sample obtained from the subject:

(a) subjecting the sample to a mass spectroscopy analysis to determine the concentration in the sample of at least one bile acid;

(b) comparing the amount of the at least one bile acid present in the sample to a reference value of the at least one bile acid obtained from a control population consisting of individuals not afflicted with a Niemann-Pick disease; and (c) diagnosing the subject as afflicted with a Niemann-Pick disease if the amount of the at least one bile acid from the subject is statistically significantly greater than the reference value.

BRIEF DESCRIPTION OF THE DRAWINGS

FIG. 11A illustrates bile acid A in plasma. FIG. 11B illustrates bile acid A in a dried blood spot. FIG. 11C illustrates bile acid B in plasma. FIG. 11D illustrates bile acid B in a dried blood spot. Bile acid A and B were measured in control (n=11) and NPC1 (n=12) subjects. p<0.0001 for bile acids A and B in NPC1 vs. control plasma and dried blood spot.

FIG. 12A-F illustrate identification of bile acids A and B. FIG. 12A-B illustrates extracted ion chromatograms of bile acids A and B in NPC1 and synthetic samples. FIG. 12C-D illustrates extracted ion chromatograms and product ion spectra of AMPP (N-(4-aminomethylphenyl)pyridinium) derivatives of bile acid A in NPC1 and synthetic samples. FIG. 12E-F illustrates extracted ion chromatograms and product ion spectra of AMPP derivatives of bile acid B in NPC1 and synthetic samples.

FIG. 35 illustrates chromatograms (detected by HCD MS/MS) and HCD mass spectra of AMPP derivatives of bile acid A in solution of synthetic compound.

FIG. 37 illustrates chromatograms (detected by HCD MS/MS) and HCD mass spectra of AMPP derivative of bile acid B (detected by MS2) in in solution of synthetic compound.

FIG. 40 illustrates biosynthesis of Synthetic bile acid A detected by MRM transition.

FIG. 41A-B illustrates bile acid A generated from cholestane-3β,5α,6β-triol in HepG2 cells and detected by MRM transition.

FIG. 42A-B illustrates d4-bile acid A generated from d4-cholestane-3β,5α,6β-triol in HepG2 cells and detected by MRM transition.

DETAILED DESCRIPTION

Figure 1:
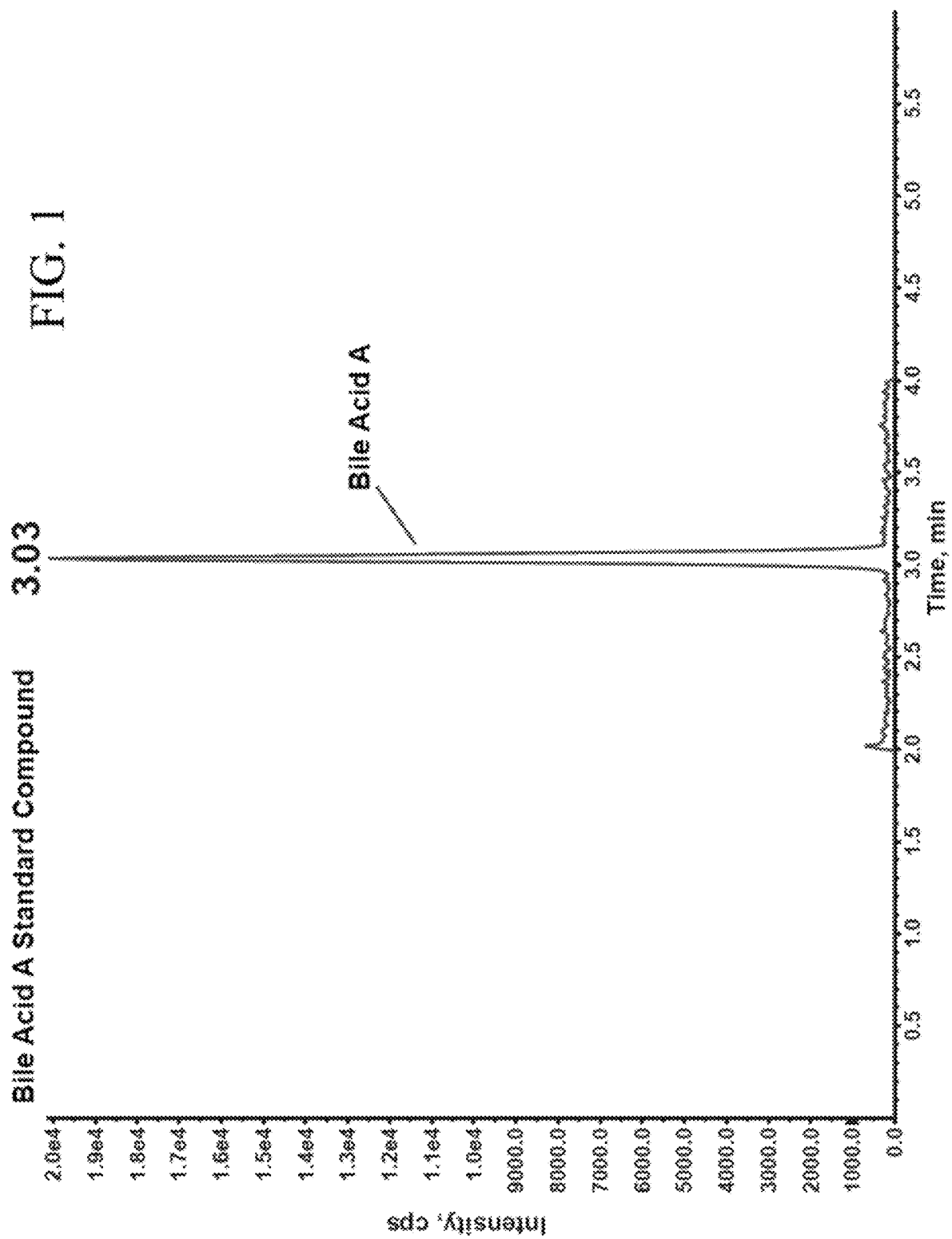
FIG. 1 illustrates an LC-MS/MS analysis of bile acid A standard compound.
Figure 2:
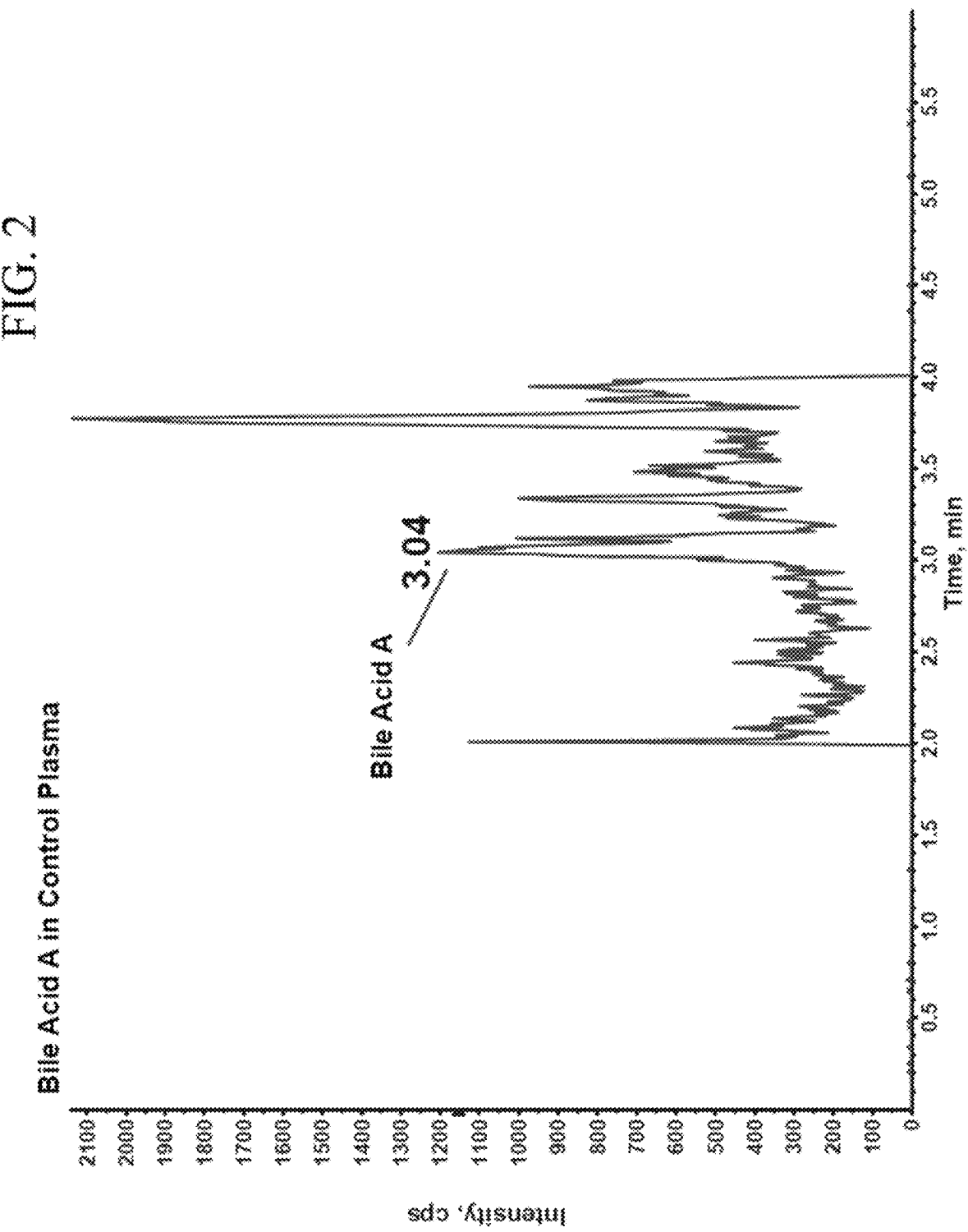
FIG. 2 illustrates an LC-MS/MS analysis of bile acid A in control plasma.
Figure 3:
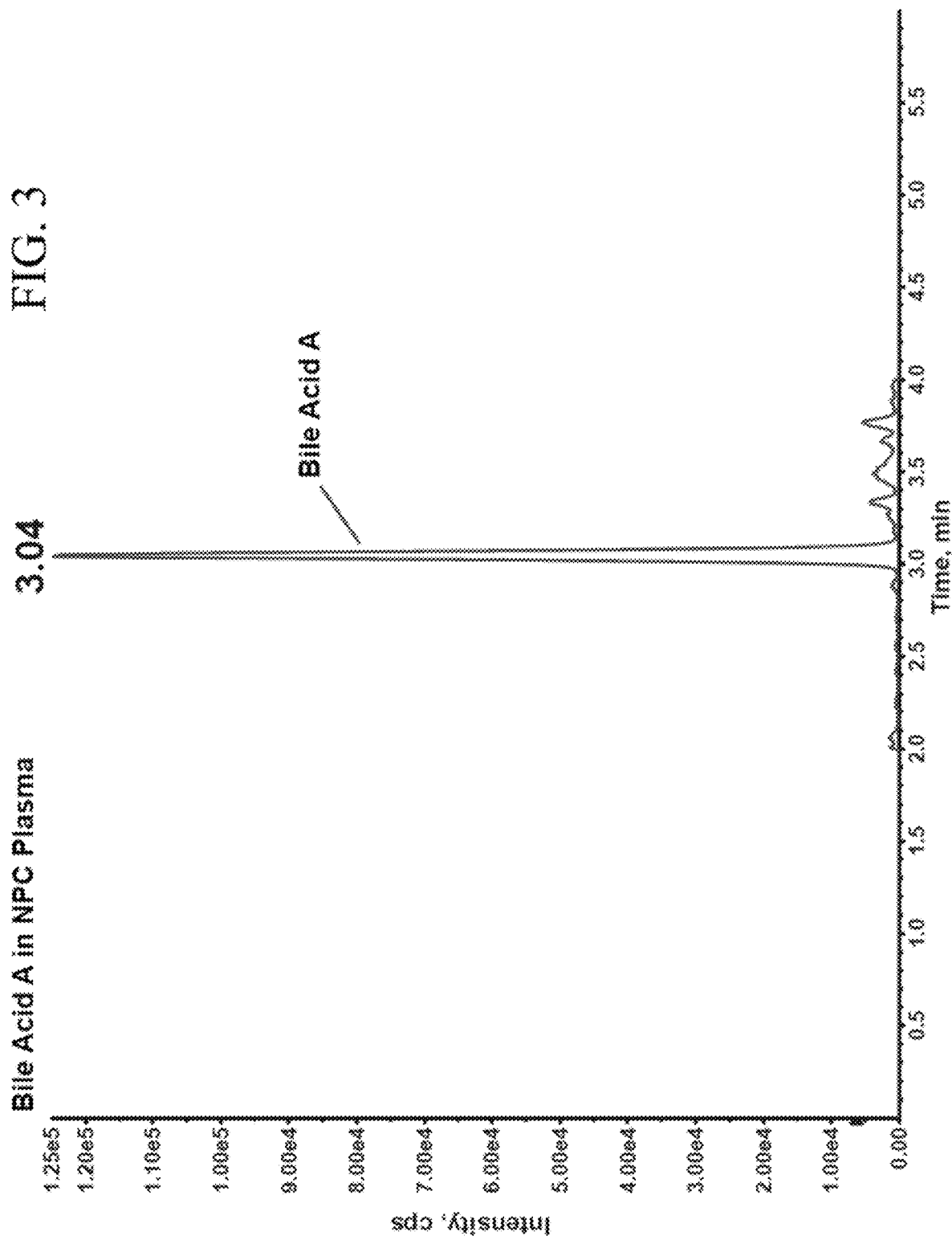
FIG. 3 illustrates an LC-MS/MS analysis of bile acid A in NPC Plasma.
Figure 4:
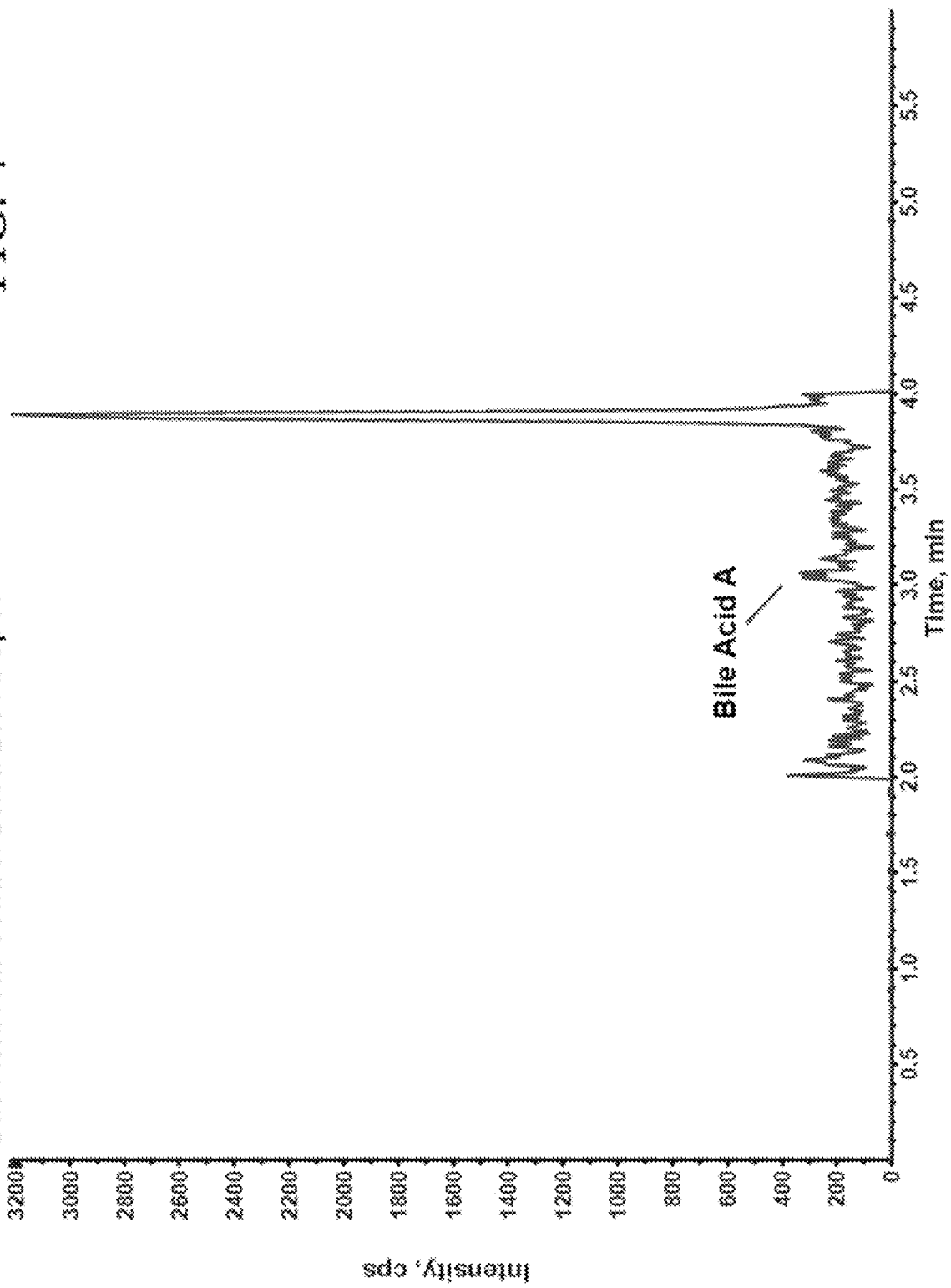
FIG. 4 illustrates an LC-MS/MS analysis of bile acid A in control dried blood spot.
Figure 5:
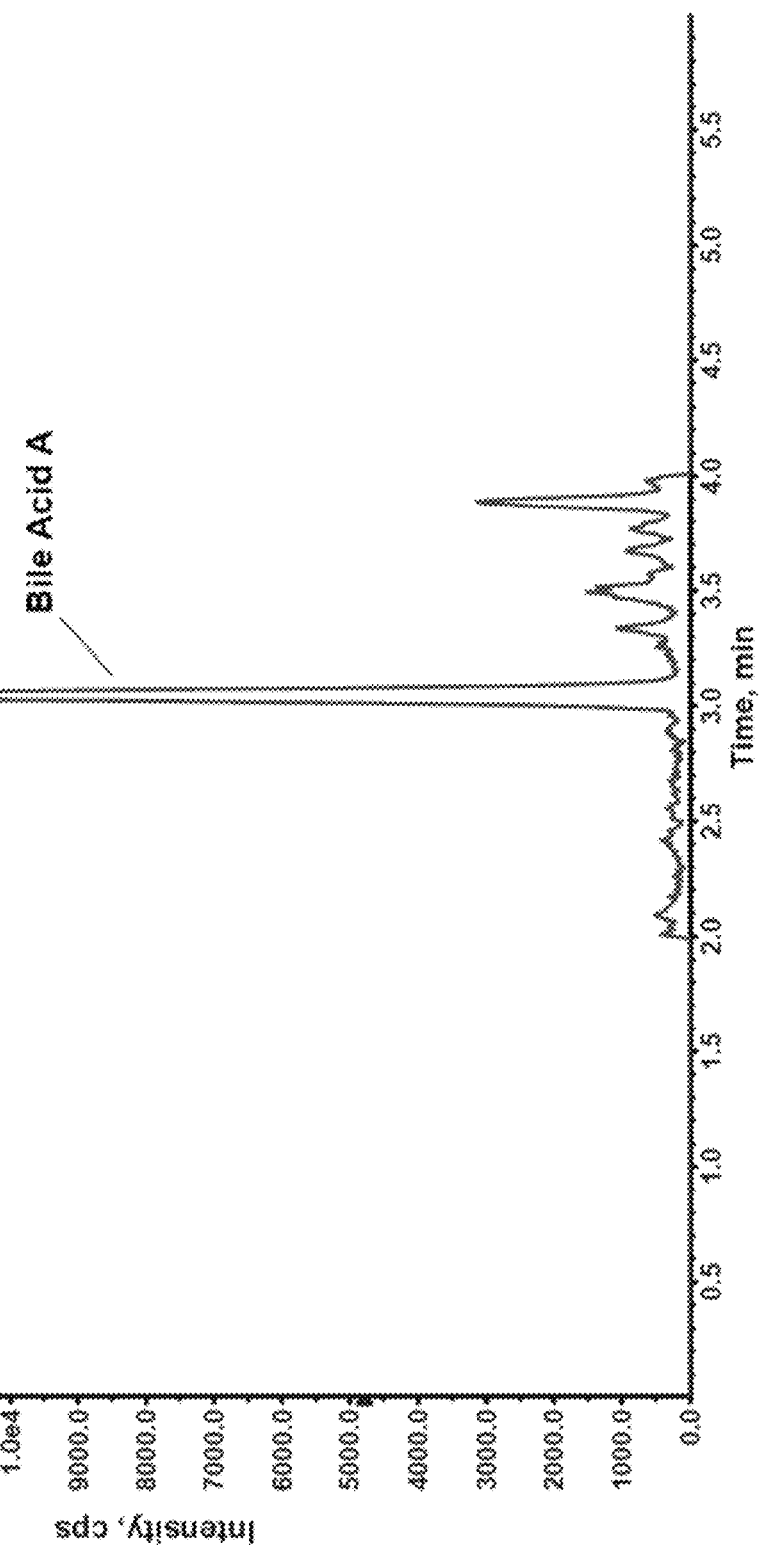
FIG. 5 illustrates an LC-MS/MS analysis of bile acid A in NPC dried blood spot.
Figure 6:
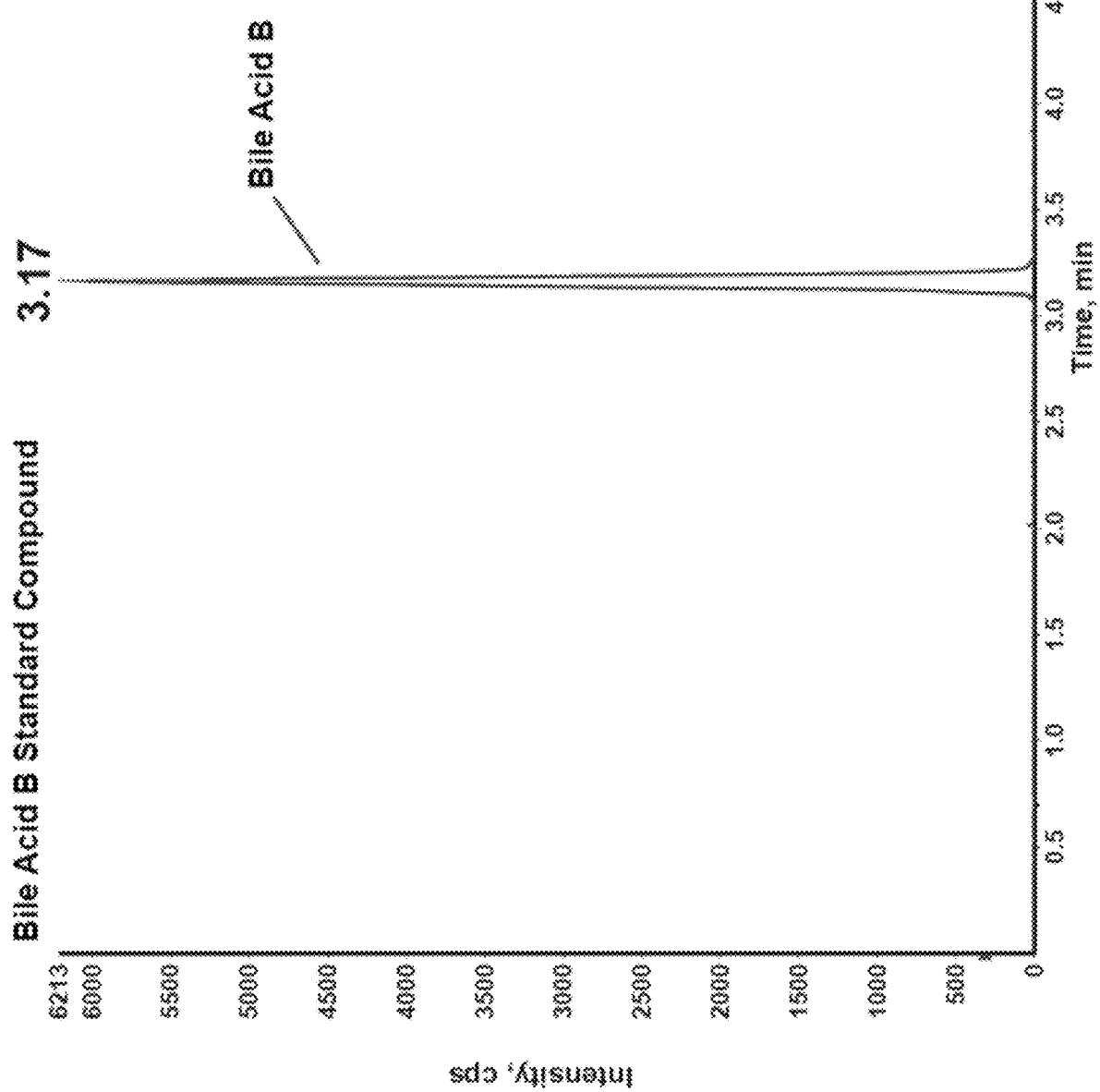
FIG. 6 illustrates an LC-MS/MS analysis of bile acid B standard compound.
Figure 7:
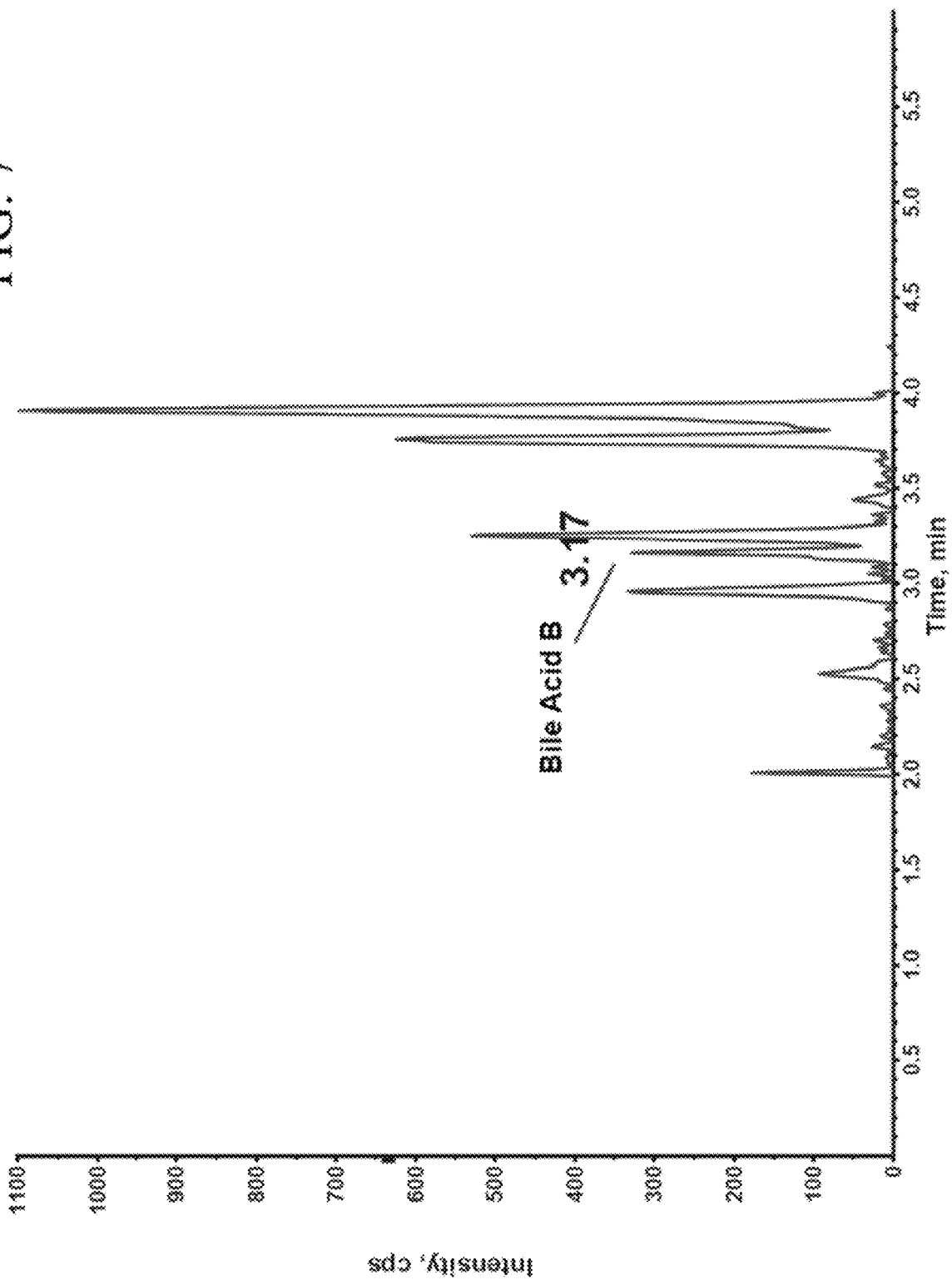
FIG. 7 illustrates an LC-MS/MS analysis of bile acid B in control plasma.
Figure 8:
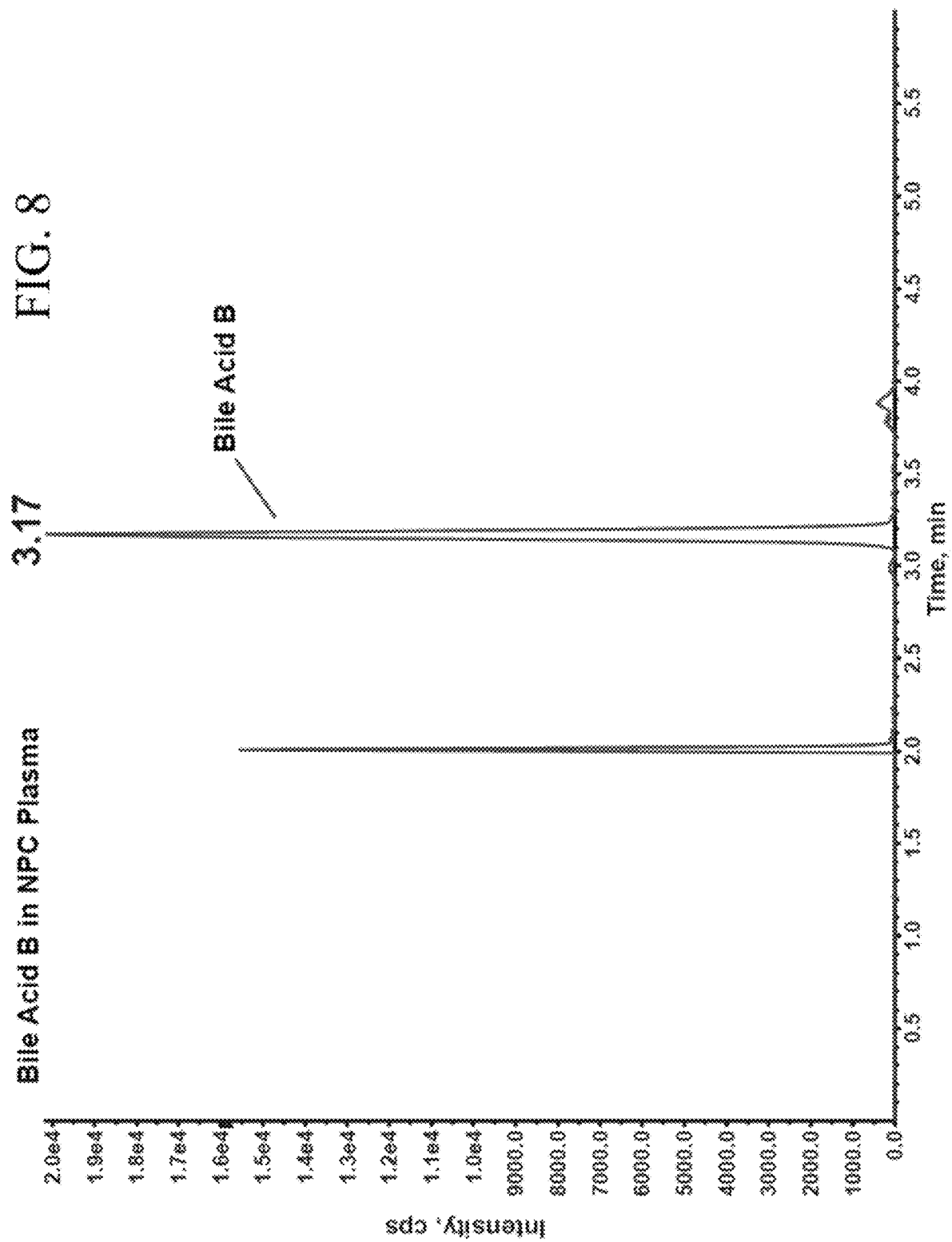
FIG. 8 illustrates an LC-MS/MS analysis of bile acid B in NPC plasma.
Figure 9:
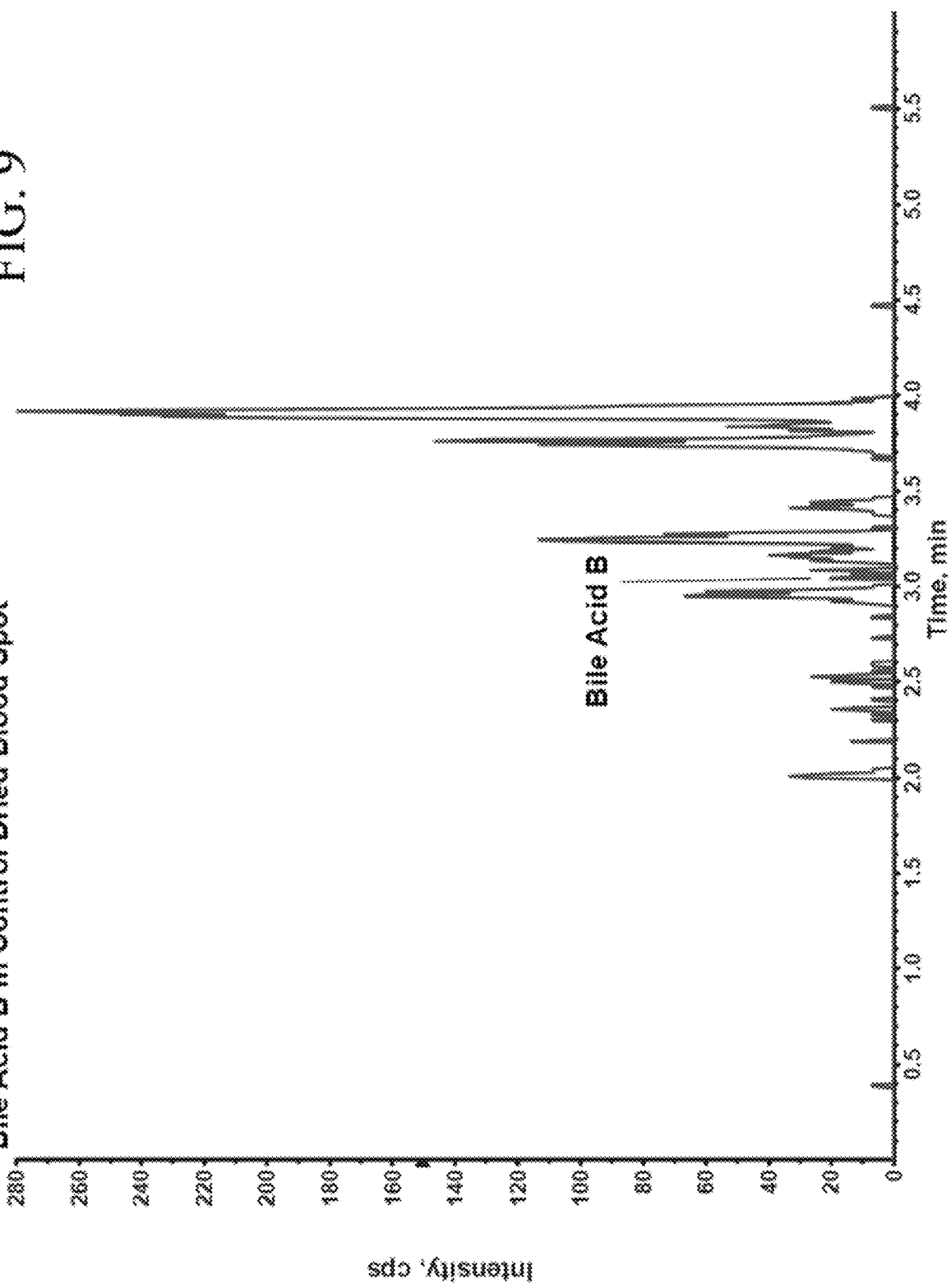
FIG. 9 illustrates an LC-MS/MS analysis of bile acid B in control dried blood spot.
Figure 10:
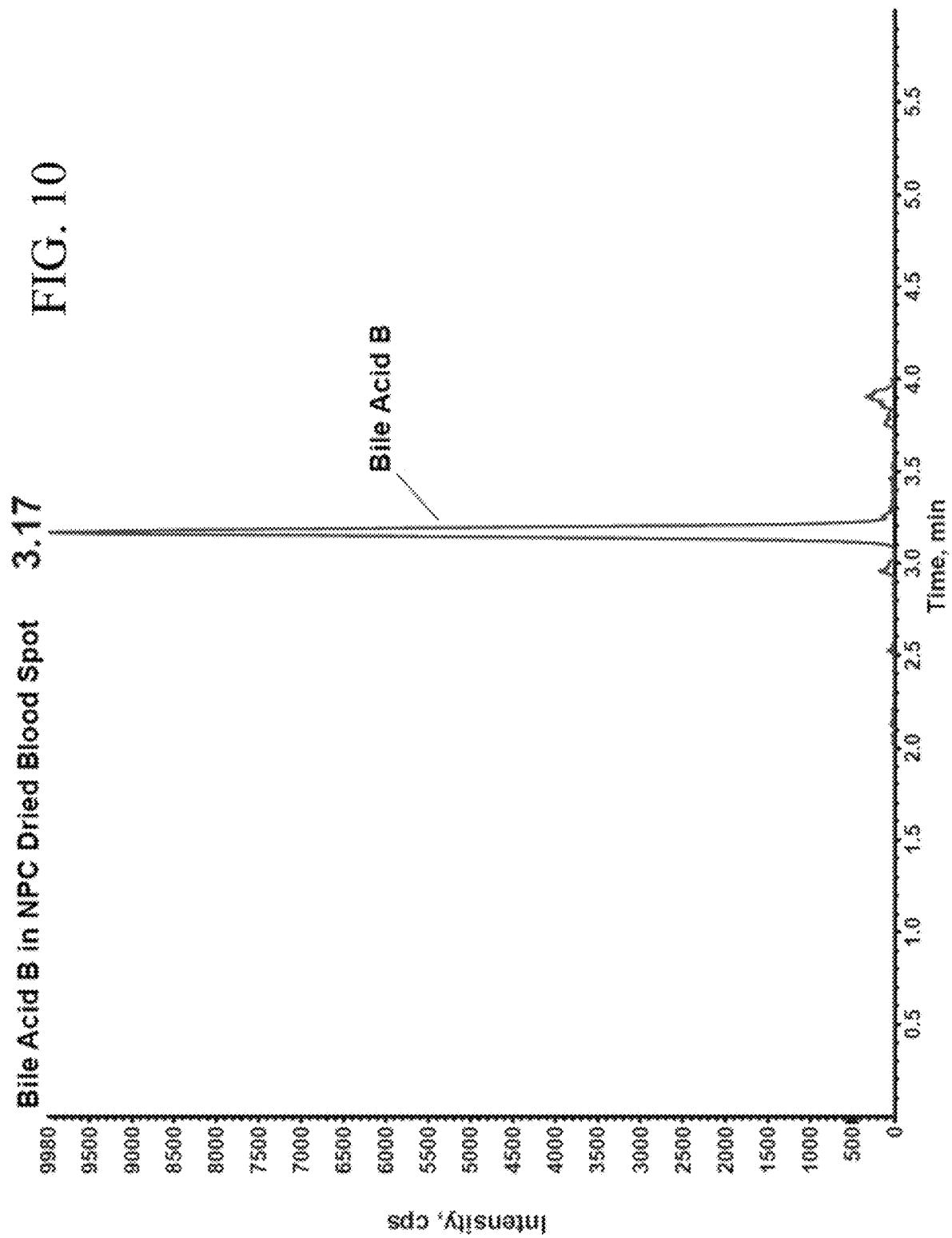
FIG. 10 illustrates an LC-MS/MS analysis of bile acid B in NPC dried blood spot.
Figure 11A:
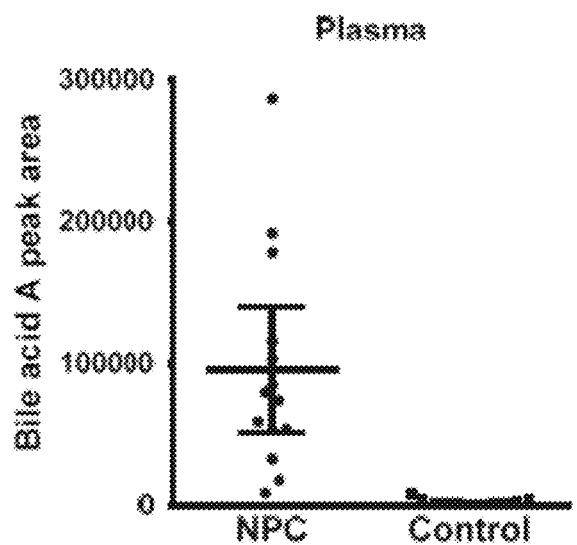
FIG. 11A-D illustrate bile acids in plasma and dried blood spots in samples obtained from NPC subjects and controls.
Figure 11B:
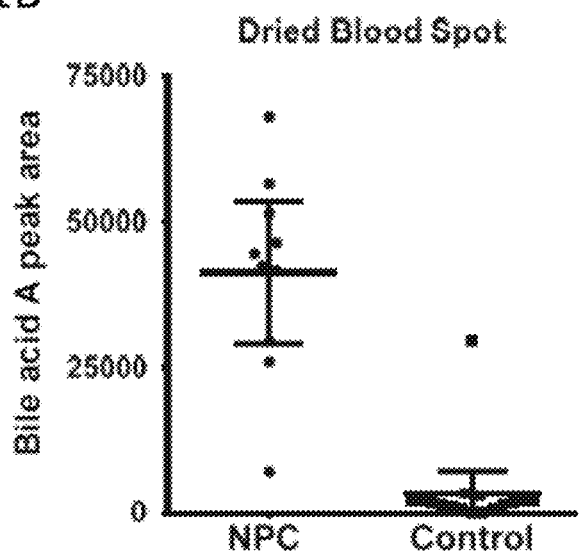
Figure 11C:
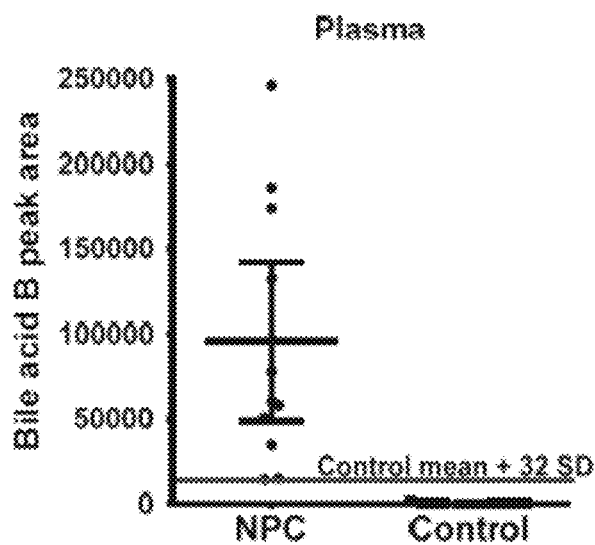
Figure 11D:
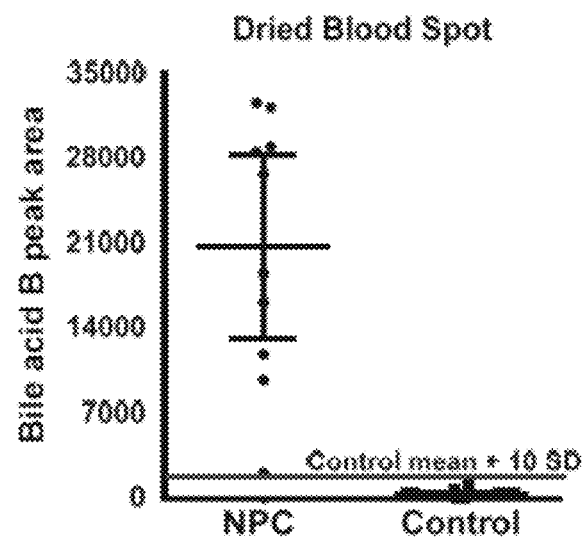
Figure 12A:
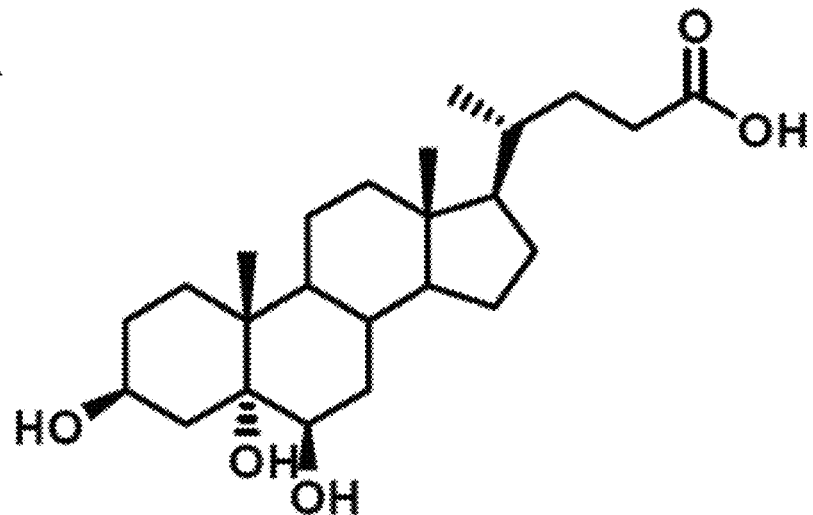
Figure 12C:
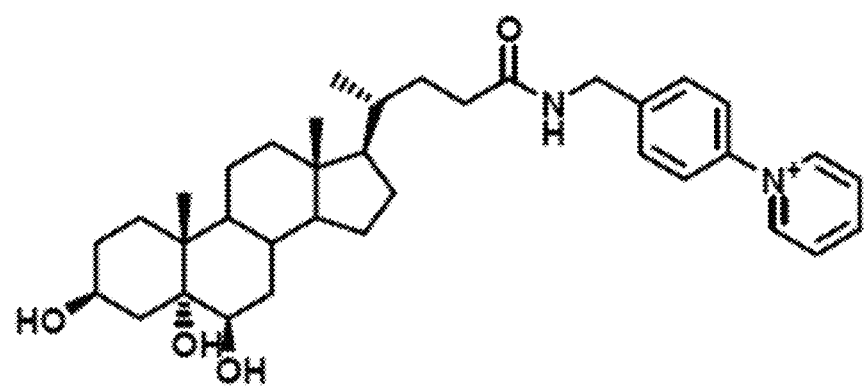
Figure 12D:
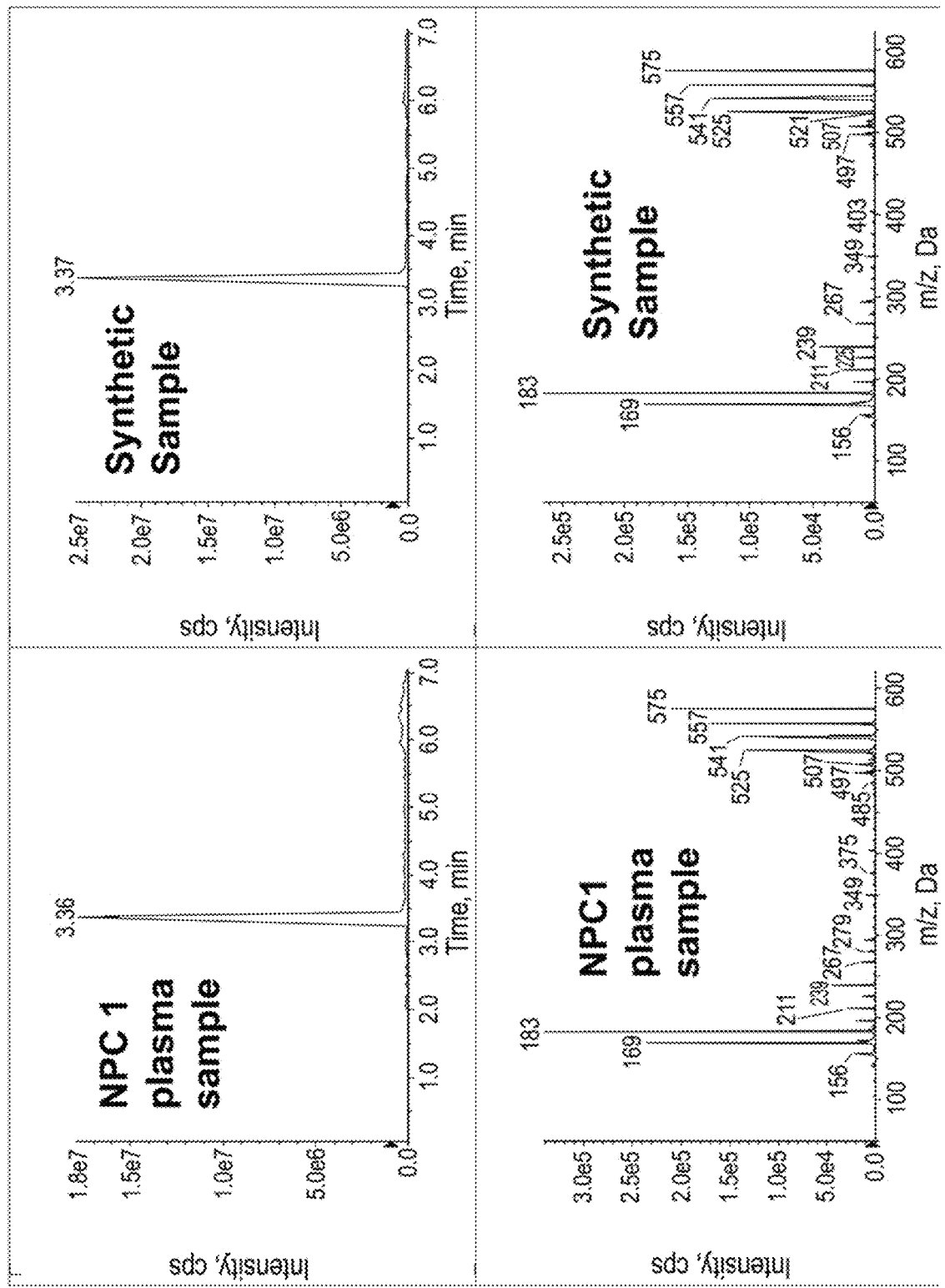
Figure 12E:
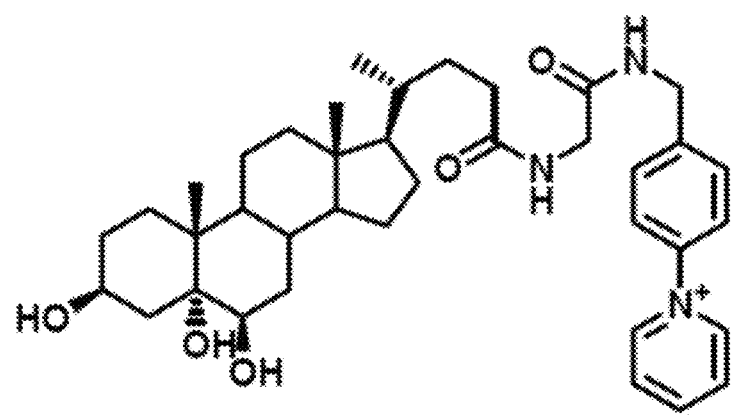
Figure 12F:
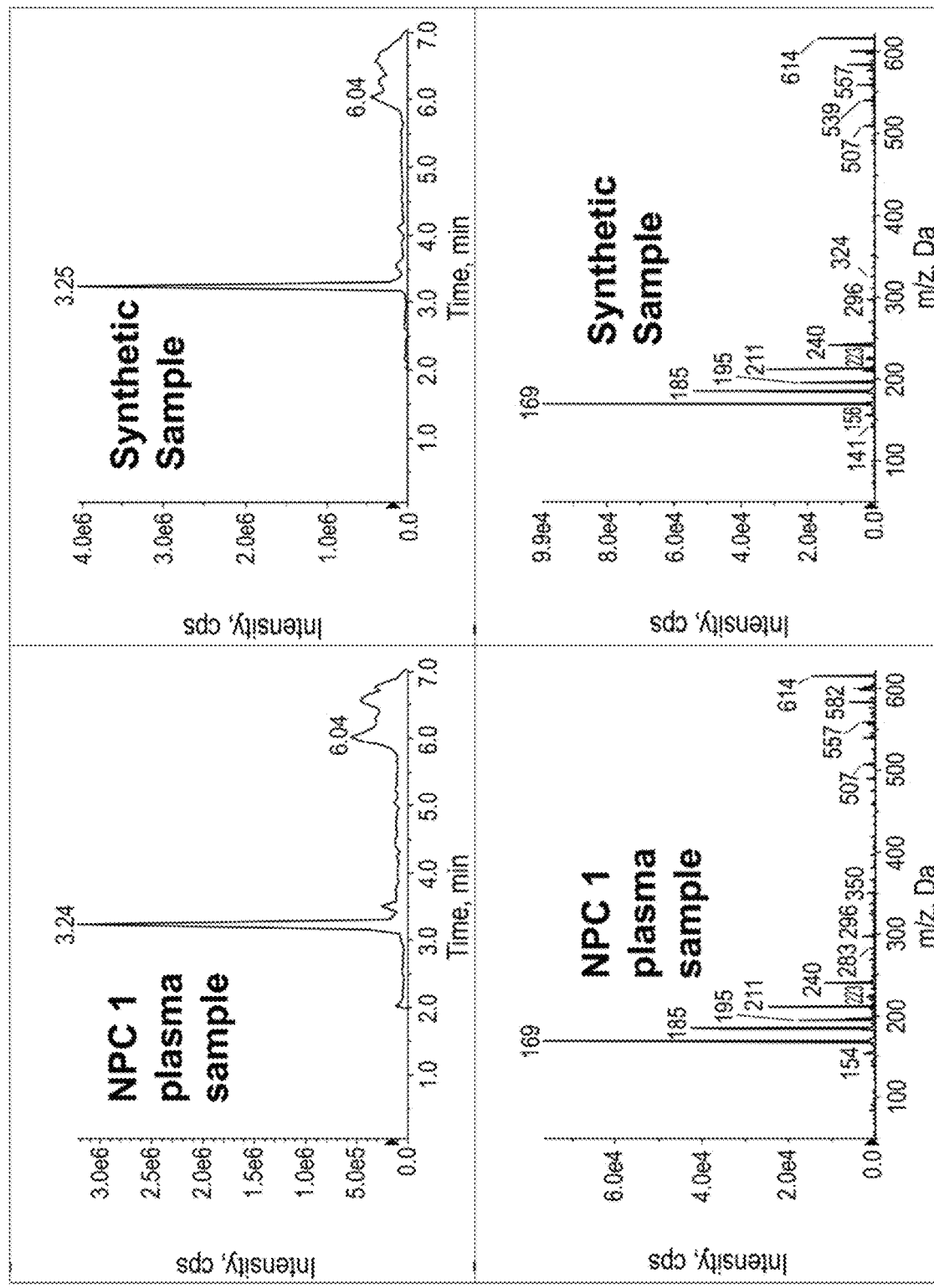

The present inventors disclose quantitative bile acid tests for diagnosis of NPC disease. In various configurations, the tests can provide opportunities for, without limitation, early disease detection, monitoring of disease progression, and evaluation of efficacy of therapeutics for Niemann-Pick A/B disease or Niemann-Pick C disease in clinical trials.

Methods of NPA/B or NPC detection based on bile acid measurements can facilitate early detection of a Niemann-Pick disease, for example in screening of newborns, and can allow for medical intervention in pre-symptomatic Niemann-Pick disease subjects. The inventors developed a LC-MS/MS methodology for quantification of bile acids such as bile acid B in dried blood spots on newborn screening cards for implementation in clinical laboratories as a testing method for patients. The short LC-MS/MS run (~2 minutes) can be used to achieve throughput of >400 samples/day. A screening method can be established that is suitable for implementation in a newborn screening laboratory.

Methods and compositions described herein utilize laboratory techniques well known to skilled artisans, and can be found in laboratory manuals such as Li, W., et al., Handbook of LC-MS Bioanalysis: Best Practices, Experimental Protocols, and Regulations. John Wiley & Sons, Hoboken, N.J., 2013; Fischbach, F., and Dunning, M. B., A Manual of Laboratory and Diagnostic Tests, Lippincott Williams & Wilkins •Philadelphia, Pa., 2004; Sambrook, J., et al., Molecular Cloning: A Laboratory Manual, 3rd ed. Cold Spring Harbor Laboratory Press, Cold Spring Harbor, N.Y., 2001; Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. As used in the present description and any appended claims, the singular forms "a", "an" and "the" are intended to include the plural forms as well, unless the context indicates otherwise.

Abbreviations
AMPP N-(4-aminomethylphenyl) pyridinium
DQC Dilution quality control
ESI Electrospray ionization
FDA Food and Drug Administration
HPLC High-performance liquid chromatography
HQC high quality control
LC-MS/MS liquid chromatography-tandem mass spectrometry
LLOQ Lower limit of quantification
LQC Low quality control
LSD lysosomal storage disorder
MQC Medium quality control
MS Mass spectrometry
MS/MS Tandem mass spectrometry
NIH National Institutes of Health
NPA Niemann-Pick type A
NPB Niemann-Pick type B
NPA/B Niemann-Pick type A or B
NPC Niemann-Pick type C
NPC1 Niemann-Pick type C1
QC Quality control
ROC Receiver-operator characteristic
THCA 3β,5α,6β-trihydroxycholanic acid
THCG N-(3β,5α,6β-trihydroxy-cholan-24-oyl)glycine
THCT N-(3β,5α,6β-trihydroxy-cholan-24-oyl)taurine
ULOQ Upper limit of quantification Methods Chemicals and Reagents Deoxycholic acid (DCA, 1) chenodeoxycholic acid (CDCA, 2), cholic acid (CA, 3), α-muricholic acid (4), β-muricholic acid (5), glycodeoxycholic acid (GDCA, 8), glycochenodeoxycholic acid (GCDCA, 9), and glycocholic acid (GCA, 10), were obtained from Steraloids, Inc. (Newport, R.I.). The bile acid A, 5-cholanic acid-3α,4β,7α-triol, and AMPP were synthesized according to literature procedures. N-(3-Dimethylaminopropyl)-N-ethylcarbodiimide hydrochloride (EDC), 4-(dimethylamino)pyridine (DMAP), diethylamine, acetic acid, N,N-dimethylformamide, acetyl chloride, potassium bis(trimethylsilyl)amide (KHMDS) solution, $LiCuC_4$ solution, isopentylmagnesium bromide solution, m-chloroperbenzoic acid, dichloromethane, ammonium chloride ($NH_4Cl$), $RUCl_3—H_2O$, sodium sulfate ($Na_2SO_4$), N-hydroxysuccinimide, sodium carbonate ($Na_2CO_3$), p-toluenesulfonic acid monohydrate, N,N-diisopropylethylamine, acetic anhydride, glycine methyl ester, sodium bicarbonate ($NaHCO_3$), sodium hydroxide (NaOH), hydrochloride solution (HCl), silica gel, dioxane, tetrahydrofuran (THF), ethyl acetate, chloroform, diethyl ether, hexane, Dulbecco's modified Eagle's medium, fetal calf serum, and penicillin G and streptomycin sulfate were obtained from Sigma-Aldrich (St. Louis, Mo.). Glycine-[$^{13}C_2$, $^{15}N$], D4-methanol ($CD_3OD$), D-chloroform ($CDCl_3$), were obtained from Cambridge Isotope (Tewksbury, Mass.). All HPLC solvents (methanol, and acetonitrile) were HPLC grade and were purchased from EMD Chemicals (Gibbstown, N.J.). Milli-Q ultrapure water was prepared in-house with a Milli-Q Integral Water Purification System (Billerica, Mass.).

Sample Preparation for Plasma and Dried Blood Spot

In some experiments, plasma samples (50 μL) were aliquoted into 2 mL polypropylene tubes (VWR, West Chester, Pa.). To each tube methanol (150 μL) was added. The sample was vortexed for 3 min, centrifuged for 10 min at 3000 g, and supernatant transferred to a clean glass insert in a 1.5 mL HPLC vial for an LC-MS/MS assay.

A 3 mm disc was punched from each dried blood spot using a Harris Micro-Punch (Thermo Fisher Scientific, Waltham, Mass.). Each punch was transferred to a 2 mL polypropylene tube (VWR, West Chester, Pa.). An aliquot of 50 μl of water was added to each punch and the mixture was vortexed for 10 min. To each tube methanol (150 μL) was added. Each sample was vortexed for 3 min and centrifuged for 10 min at 3000 g. Each supernatant was transferred to a glass insert in a 1.5 mL HPLC vial for an LC-MS/MS assay.

Sample Preparation for Plasma and Dried Blood Spot

In some experiments, plasma samples (50 μL) were aliquoted into 2 mL polypropylene tubes (VWR, West Chester, Pa.). To each tube internal standard working solution (50 μL) and methanol (150 μL) was added. The sample was vortexed for 3 min, centrifuged for 10 min at 3000 g, and supernatant transferred to a clean glass insert in a 1.5 mL HPLC vial for an LC-MS/MS assay.

A 3 mm disc was punched from each dried blood spot using a Harris Micro-Punch (Thermo Fisher Scientific, Waltham, Mass.). Each punch was transferred to a 2 mL polypropylene tube (VWR, West Chester, Pa.), An aliquot of 50 µl of internal standard in water was added to each punch and the mixture was vortexed for 10 min. To each tube methanol (150 µL) was added. Each sample was vortexed for 3 min and centrifuged for 10 min at 3000 g. Each supernatant was transferred to a glass insert in 1.5 mL HPLC vial for an LC-MS/MS assay.

In some experiments, NPC1 plasma and dried blood spot samples were obtained from NIH, Rush University Medical Center Universitätsklinikum Münster, and University of Heidelberg. Normal plasmas and dried blood spots were obtained from anonymized residual samples at St. Louis Children's Hospital, and New York State Newborn Screening Program. The NPB dried blood spot samples were provided by Genzyme. All plasma samples were collected in ethylenediamine tetraacetic acid dipotassium salt (EDTA-K2) containing tubes. The analysis of de-identified human samples was approved by the Human Studies Committee at Washington University.

Plasma samples (50 µL) were aliquoted into 2 mL polypropylene tubes (VWR, West Chester, Pa.). To each tube methanol (150 µL) was added. The sample was vortexed for 3 min, centrifuged for 10 min at 3000 g, and supernatant transferred to clean glass insert in 1.5 mL HPLC vial for LC-MS/MS assay.

A 3 mm disc was punched from each dried blood spot using a Harris Micro-Punch (Thermo Fisher Scientific, Waltham, Mass.). Each punch was transferred to a clean 2 mL polypropylene tube (VWR, West Chester, Pa.). An aliquot of 50 µl of water was added to each punch and the mixture was vortexed for 10 min. To each tube methanol (150 µL) was added. The sample was vortexed for 3 min, centrifuged for 10 min at 3000 g, and supernatant transferred to clean glass insert in 1.5 mL HPLC vial for LC-MS/MS assay.

Analysis of Clinical Dried Blood Spot Samples

All the clinical samples were first submitted to first-tier assay. Samples consisting of calibration standards in duplicate, a blank, a blank with internal standard, QC samples (LQC, MQC and HQC), and unknown clinical samples were analyzed. The clinical samples with bile acid B above the LLOQ in the first tier assay together with calibration standards, blank, blank with internal standard, QC samples in the same batch were re-assayed with second-tier assay. The LC-MS/MS acceptance criteria were as indicated in FDA recommendations (U.S. Department of Health and Human Services Guidance for Industry: Bioanalytical Method Validations. (2001)).

Statistical Analysis

The GraphPad Prism version 6.0 (GraphPad Software) was used to perform unpaired Student's ttest, receiver-operator curve (ROC) analysis, Pearson correlations. Microsoft Excel was used for calculations of percent coefficient of variance (% CV) and percent relative error (% RE). Unpaired Student's t-test was applied to calculate differences between NPC1 and normal (control or control and NPC1 carrier) groups. All presented P values are two-sided and P<0.05 was considered to be statistically significant. Bile acid A and B correlation was analyzed using Pearson correlations, as data show normal distribution.

EXAMPLES

The present teachings include descriptions provided in the examples that are not intended to limit the scope of any aspect or claim. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example illustrates LC-MS/MS-based profiling of bile acids in plasma and dried blood spots.

The inventors identified bile acid A and bile acid B elevated 4.1- and 144-fold in the NPC1 plasmas, respectively, and 12- and 101-fold in the NPC dried blood spots, respectively of NPC1 subjects compared to controls (FIG. 13A-13D). Only 50 µL of plasma and 3 mm disk of dried blood spot were used in analysis. The structures of bile acid A and B were confirmed by comparison with synthesized authentic compounds by LC-MS/MS (FIG. 12A-12F).

Figure 13A:
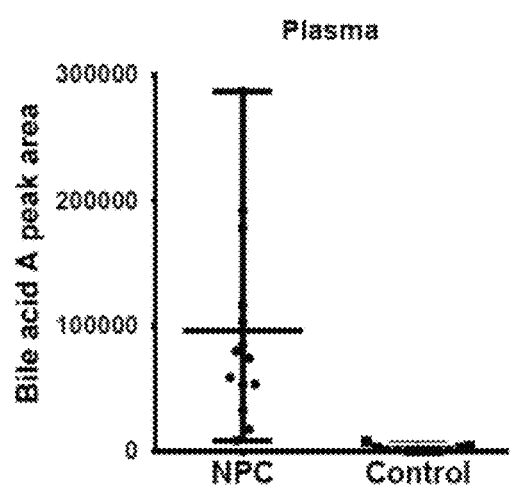
FIG. 13A-D illustrate measurement of bile acid A in plasma (FIG. 13A) and dried blood spots (FIG. 13B) and bile acid B in plasma (FIG. 13C) and dried blood spots (FIG. 13D) in samples from NPC subjects and controls. Bile acid A and B were measured in control (n=1) and NPC1 (n=12) subjects. p<0.0001 for bile acids A and B in NPC1 vs. control plasma and dried blood spot.
Figure 13B:
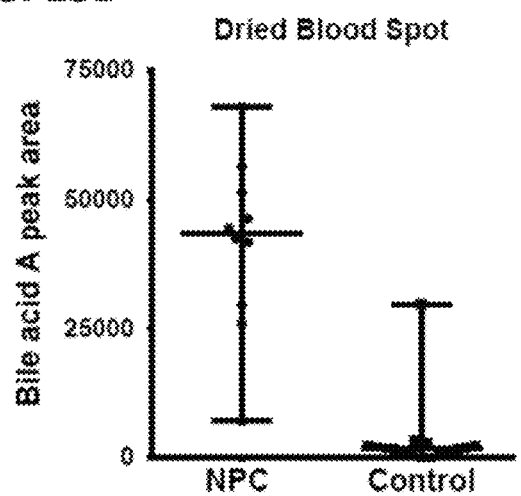
Figure 13C:
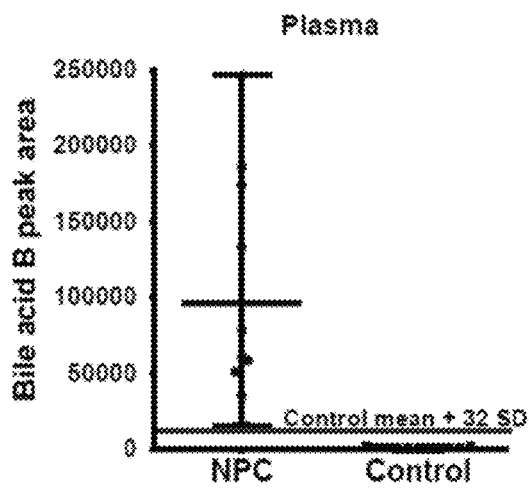
Figure 13D:
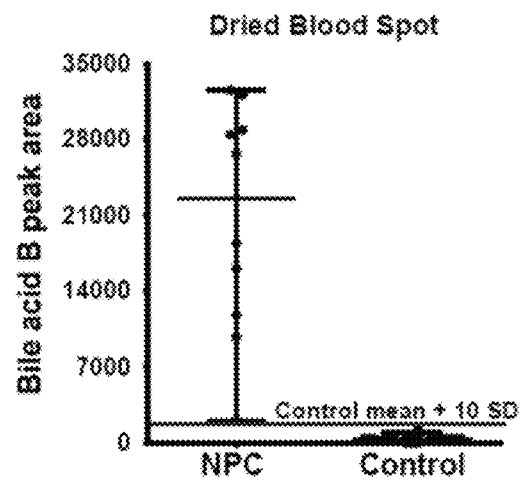

The plasma bile acid B values in NPC (peak area mean 95831, peak area range 14951-246534) and control (peak area mean 661, peak area range 174-1654) groups do not overlap (p<0.0001) (FIG. 13C). Similarly, bile acid B in dried blood spots allows discrimination of the NPC1 (peak area mean 20704, peak area range 2040-32575) and control (peak area mean 203, peak area range 2-1009) groups (p<0.0001) (FIG. 13D). The lowest bile acid B value in the NPC1 plasma is above the mean+32 SD of control group. The lowest bile acid B in the NPC1 dried blood spots is above the mean+10 SD of control group. Thus, in this population, bile acid B showed 100% sensitivity and 100% specificity in both plasma and dried blood spots.

The inventors performed LC-MS/MS-based profiling of bile acids in plasma and dried blood spots. Two unknown peaks were significantly elevated in NPC1 samples; however, little structural information was obtained from direct analysis of high-resolution product ion mass spectra of these unknown bile acids. The structural elucidation of the novel bile acids was facilitated by derivatization with N-(4-aminomethylphenyl) pyridinium (AMPP) to give pre-charged cationic amides, which generated informative product ions in higher energy collision dissociation. The structures of unknown bile acids were assigned as 5α-cholanic acid-3β, 5α,6β-triol (bile acid A) and its glycine conjugate (bile acid B) based on the tandem mass spectra of their AMPP derivatives. The final confirmation of assigned structures was achieved by synthesis of authentic compounds and comparison of the retention times and mass spectra using LC-MS/MS (FIG. 12A-12D).

Example 2

This example illustrates LC-MS/MS analysis of bile acid A and bile acid B in plasma and dried blood spot samples.

In these experiments, the NPC1 and control samples were randomized so that each group was evenly distributed in the run order. In this way, bias and noise/variance in the results caused by the instrument fluctuation are reduced, enabling subsequent unbiased statistical analysis of the data. LC-MS/MS analysis was conducted on a Shimadzu (Columbia, Md.) Prominence UFLC system coupled with an Applied Biosystems/MDS Sciex (Ontario, Canada) 4000QTRAP mass spectrometer using multiple reaction monitoring (MRM). Separation of bile acids A and B was carried out at 50° C. using a Waters (Milford, Mass.) XBridge C18 analytical column (4.6×100 mm, 3.5 μm) connected to a PHENOMENEX® (Torrance, Calif.) SECURITYGUARD™ C18 guard column (4×3 mm) at a flow rate of 1 mL/min. The mobile phase consisted of 0.03% diethylamine in water (solvent A), and acetonitrile-methanol (1:10) (solvent B). The step gradient was as follows: 0-3 min, 40% to 55% solvent B; 3-3.1 min, 55% to 100% solvent B; 3.1-4 min, 100% solvent B; 4-4.1 min, 100% to 40% solvent B; 4.1-6 min, 40% solvent B. The HPLC eluate was directed into the mass spectrometer for data acquisition within the 2-min time window (2-4 min) in which bile acid A and bile acid B were eluted; elsewhere, eluate was sent to waste to minimize source contamination. The injection volume was 5 μL and the total run-time was 6 min. The ESI source temperature was 550° C.; the ESI needle was −4500 V; the declustering potential was −120 V; the entrance potential was −10 V; and the collision cell exit potential was −10 V. The collision and curtain gas were set at medium and 20, respectively. The desolvation gas and nebulizing gas were set at 60 and 30 L/min, respectively. The collision energies were −35 and −72 eV for bile acids A and B, respectively. For MRM, the dwell time was set at 50 ms for each of the signal from transitions of m/z 407 to 407 (bile acid A) and m/z 464 to 74 (bile acid B). Data were acquired and analyzed by Analyst software (version 1.5.1). Analysis is presented at least in FIG. 1-11.

Example 3

This example illustrates development of an LC-MS/MS method for determination of the 3β,5α,6β-trihydroxycholanic acid (also known as "THCA," "5α-cholanic acid-3β,5α,6β-triol," and "Bile Acid A") bile acid biomarker in plasma for diagnosis of NPC disease.

The LC-MS/MS method for quantification of bile acid A in plasma is developed and validated according to Food and Drug Administration (FDA) guidance (U.S. Department of Health and Human Services Guidance for Industry: Bioanalytical Method Validations. (2001)). The reference ranges for controls, heterozygotes, NPC subjects and cut-off value for diagnosis are established.

Preparation of standard curve and quality control sample is performed. The standard curve is prepared in bile acid A-free human umbilical cord plasma. When bile acid A-free human umbilical cord plasma is not available, 5% bovine serum albumin (BSA) in water or plasma from other species is evaluated as surrogate matrix for calibration standards. The standard curve prepared in bile acid A-free human umbilical cord plasma or surrogate matrix is used to quantity bile acid A in human plasma. Three levels of plasma quality control (QC) samples including low, medium and high quality control (LQC, MQC and HQC) samples are prepared to evaluate the accuracy, precision, and stability. The lower limit of quantification (LLOQ) is prepared by spiking bile acid A to analyte-free human blood or to surrogate matrix to evaluate the sensitivity. A dilution quality control (DQC) sample of which bile acid is higher than the upper limit of quantification (ULOQ) is also prepared to evaluate dilution integrity.

For sample preparation and LC-MS/MS analysis, bile acid A is extracted from plasma with protein precipitation after spiking isotope-labeled internal standard. The extracted sample is directly injected to LC-MS/MS system comprised of a Prominence UFLC system and a 4000QTRAP mass spectrometer. A reversed phase HPLC column is used for the separation of bile acid A and internal standard from matrix and interferences.

For evaluation of linearity, sensitivity, accuracy, precision and stability, the linearity of the standard curve is assessed over calibration range for three days. The slopes of standard curves prepared in surrogate and authentic matrixes are used to evaluate parallelism. The precision and accuracy of the assay is evaluated at LLOQ, LQC, MQC and HQC concentration levels over the three-day period. The dilution QC is used to assess the dilution integrity by dilution with surrogate matrix prior to extraction. For each QC concentration, analysis is performed in six replicates on each day for three days. The stabilities of long-term storage (−80° C.) and freeze/thaw, stability on the bench-top, and stability in the auto-sampler is determined at the LQC and HQC concentration levels (n=3).

Reference ranges and cut-off values are established. The validated LC-MS/MS method is used to analyze bile acid A in plasma from NPC (~100 subjects), controls (~100 subjects), obligate heterozygotes (parents of NPC subjects) or known sibling carriers (~40 subjects) to establish the reference ranges. The cut-off value can be determined from receiver operator characteristic (ROC) curves. (Jiang, X., el al., *J. Lipid Res.* 52, 1435-1445 (2011)) Direct comparison of the ROC curves between bile acid A and triol markers is performed in the same sample sets.

After developing an extraction method with high recovery and LC-MS/MS condition that can separate interferences and eliminate matrix effect, method performance meets the requirements in FDA guidance (U.S. Department of Health and Human Services Guidance for Industry: Bioanalytical Method Validations. (2001)) regarding sensitivity, selectivity, accuracy, precision, and stability. Accurate reference ranges for bile acid A in NPC, controls, heterozygotes, and cut-off value from ROC curves are obtained. Bile acid A ROC performance can be more robust than that of the triol assay, and a bile acid A assay is easier for clinical laboratories to adopt.

To further evaluate diagnostic specificity of bile acid A, the inventors collect and analyze additional control samples from patients with enlarged livers or spleens, with other lysosomal storage disorders, and with primary bile acid disorders.

Example 4

This example illustrates development of an LC-MS/MS method for determination of bile acid 3β,5α,6β-trihydroxycholanic acid (also known as "THCA," "5α-cholanic acid-3β,5α,6β-triol," and "Bile Acid A") biomarker in dried blood spots for newborn screening of NPC disease.

The LC/MS/MS methodology with short LC-MS/MS run (ca. 2 minutes) for quantification of bile acid A in dried blood spots is developed and validated according to FDA guidance. (U.S. Department of Health and Human Services Guidance for Industry: Bioanalytical Method Validations. (2001)) Reference ranges for bile acid A in control, heterozygote, and NPC dried blood spot samples are established. The cut-off value for identification of neonatal NPC patients is determined.

The standard curve samples are prepared by spiking bile acid A into human umbilical cord blood that is free of bile acid A. In the case that human blood free of bile acid A is not available, the standard curve samples are prepared by spiking a stable isotope-labeled bile acid A (surrogate standard) into human blood with 55% hematocrit, and the standard curve samples using bile acid A is also prepared to evaluate parallelism of standard curves prepared with surrogate and authentic analytes. Three levels of QC samples including LQC, MQC and HQC samples are prepared by spiking bile acid A to human blood to evaluate the accuracy, precision, and stability. The lower limit of quantification (LLOQ) is prepared by spiking bile acid A to analyte-free human blood or by spiking surrogate standard to human blood to evaluate the sensitivity. The standard curve and QC samples are spotted on blank newborn screening cards and dried in the air for three hours.

For sample preparation and LC-MS/MS analysis, bile acid A is extracted from a dried blood spot with methanol containing internal standard. The extracted sample is directly injected to LC-MS/MS system comprised of a Prominence UFLC system and a 4000QTRAP mass spectrometer. A short LC-MS/MS method (~2 minutes) is used to separate bile acid A from interferences in dried blood spots.

The linearity, accuracy, stability, and precision are evaluated for the assay. The linearity of the standard curve is assessed over calibration range for three days. The slopes of standard curves prepared with surrogate and authentic analytes are used to evaluate parallelism. The precision and accuracy of the assay is evaluated at LLOQ, LQC, MQC and HQC concentration levels over the three days. For each QC concentration, analysis is performed in six replicates on each day. The stability of long-term storage (−20° C. and room temperature) and stability in the auto-sampler is determined at the LQC and HQC concentration levels (n=3).

To establish reference ranges and cut-off values, the LC-MS/MS method is used to analyze bile acid A in dried blood spots from controls (~1000 subjects), NPC subjects (~50 subjects), and heterozygotes (~50 subjects). The reference ranges for controls, NPC subjects, and heterozygotes are generated. The cut-off value is set at control mean plus 6 standard deviations or $99.5^{th}$ percentile of the controls as the upper cut-off limit and the lowest 0.5 percentile of the NPC range as the lower cut-off limit. Cut-offs are selected to maximize area of under the curve of the ROC curves and the positive predictive value of the screen.

The method performance meets the requirements in FDA guidance (U.S. Department of Health and Human Services Guidance for Industry: Bioanalytical Method Validations. (2001)) with respect to sensitivity, selectivity, accuracy, precision, and stability for most dried blood spots. The reference ranges for bile acid A in NPC, control, and heterozygote dried blood spots are obtained. NPC subjects can be differentiated with high sensitivity and specificity from controls and heterozygotes. Since the sample preparation for bile acid A is compatible with other screening platforms (e.g., amino acids and acylcarnitines), the NPC screening is multiplexed for simultaneous multi-disease screening using a single dried blood spot punch.

To reduce false positive results, a second-tier LC-MS/MS method (longer LC run time) that can separate interferences to bile acid A is developed. Using the first-tier method >400 samples a day can be analyzed, and small number of suspicious samples with bile acid A values above the cut-off value can be submitted to a second-tier assay. The second-tier assay can adjudicate the false positives from the first-tier assay. To clinically validate cut-off value for the dried blood spot assay, a larger number of dried blood spots (100,000 or more) are collected and analyzed. The overall performance metrics (Rinaldo, P., et al. *Ment. Retard. Dev. Disabil. Res. Rev.* 12, 255-261 (2006)) including detection rate, positive predictive value, and false positive rate can be evaluated.

Example 5

This example illustrates development of an LC-MS/MS method for determination of bile acid N-(3β,5α,6β-trihydroxy-cholan-24-oyl)glycine (also known as "THCG," "5α-cholanic acid-3β,5α,6β-triol N-(carboxymethyl)-amide," and "Bile Acid B") biomarker in plasma for diagnosis of NPC disease The LC-MS/MS method for quantification of bile acid B in plasma is developed and validated according to Food and Drug Administration (FDA) guidance. (U.S. Department of Health and Human Services Guidance for Industry: Bioanalytical Method Validations. (2001)) Reference ranges for controls, heterozygotes, NPC subjects and cut-off value for diagnosis are established.

Preparation of standard curve and quality control sample is performed. The standard curve is prepared in bile acid B-free human umbilical cord plasma. When bile acid B-free human umbilical cord plasma is not available, 5% bovine serum albumin (BSA) in water or plasma from other species is evaluated as surrogate matrix for calibration standards. The standard curve prepared in bile acid B-free human umbilical cord plasma or surrogate matrix is used to quantify bile acid B in human plasma. Three levels of plasma QC samples including LQC, MQC and HQC samples are prepared to evaluate the accuracy, precision, and stability. The LLOQ is prepared in surrogate matrix to evaluate the sensitivity. A DQC sample of which bile acid is higher than the ULOQ is also prepared to evaluate dilution integrity.

For sample preparation and LC-MS/MS analysis, bile acid B is extracted from plasma with protein precipitation after spiking isotope-labeled internal standard. The extracted sample is directly injected to LC-MS/MS system comprised of a Prominence UFLC system and a 4000QTRAP mass spectrometer. A reversed phase HPLC column is used for the separation of bile acid B and internal standard from matrix and interferences.

For evaluation of linearity, sensitivity, accuracy, precision and stability, the linearity of the standard curve is assessed over calibration range for three days. The slopes of standard curves prepared in surrogate and authentic matrixes are used to evaluate parallelism. The precision and accuracy of the assay is evaluated at LLOQ, LQC, MQC and HQC concentration levels over the three-day period. The dilution QC is used to assess the dilution integrity by dilution with surrogate matrix prior to extraction. For each QC concentration, analysis is performed in six replicates on each day for three days. The stabilities of long-term storage (−80° C.) and freeze/thaw, stability on the bench-top, and stability in the auto-sampler is determined at the LQC and HQC concentration levels (n=3).

Reference ranges and cut-off values are established. The validated LC-MS/MS method is used to analyze bile acid B in plasma from NPC (~100 subjects), controls (~100 subjects), obligate heterozygotes (parents of NPC subjects) or known sibling carriers (~40 subjects) to establish the reference ranges. The cut-off value can be determined from ROC curves. (Jiang, X., et al., *J. Lipid Res.* 52, 1435-1445 (2011)) Direct comparison of the ROC curves between bile acid B and triol markers is performed in the same sample sets.

After developing an extraction method with high recovery and LC-MS/MS condition that can separate interferences and eliminate matrix effect, method performance meets the requirements in FDA guidance (U.S. Department of Health and Human Services Guidance for Industry: Bioanalytical Method Validations. (2001)) regarding sensitivity, selectivity, accuracy, precision, selectivity, and stability. Accurate reference ranges for bile acid B in NPC, controls, heterozygotes, and cut-off value from ROC curves are obtained. The bile acid B ROC performance can be more robust than that of the triol assay, and a bile acid assay is easier for clinical laboratories to adopt.

To further evaluate diagnostic specificity of bile acid B, the inventors collect and analyze additional control samples from patients with enlarged livers or spleens or both, with jaundice due to either or both elevations of unconjugated and conjugated bilirubin, with other lysosomal storage disorders, and with primary bile acid disorders.

Example 6

This example illustrates development of an LC-MS/MS method for determination of bile acid N-(3β,5α,6β-trihydroxy-cholan-24-oyl)glycine (also known as "THCG," "5α-cholanic acid-3β,5α,6β-triol N-(carboxymethyl)-amide," and "Bile Acid B") biomarker in dried blood spots for newborn screening of NPC disease:

The LC/MS/MS methodology with short LC-MS/MS run (ca. 2 minutes) for quantification of bile acid B in dried blood spots is developed and validated according to FDA guidance. (U.S. Department of Health and Human Services Guidance for Industry: Bioanalytical Method Validations. (2001)) Reference ranges for bile acid B in control, heterozygote, and NPC dried blood spot samples are established. The cut-off value for identification of neonatal NPC patients is determined.

The standard curve samples are prepared by spiking bile acid B into human umbilical cord blood that is free of bile acid B. In the case that human blood free of bile acid B is not available, the standard curve samples are prepared by spiking a stable isotope-labeled bile acid B (a surrogate standard) into human blood with 55% hematocrit, and the standard curve samples using bile acid B is also prepared to evaluate parallelism of standard curves prepared with surrogate and authentic analytes. Three levels of QC samples including LQC, MQC and HQC samples are prepared by spiking bile acid B to human blood to evaluate the accuracy, precision, and stability. The LLOQ is prepared by spiking bile acid B to analyte-free human blood or by spiking surrogate standard to human blood to evaluate the sensitivity. The standard curve and QC samples are spotted on blank newborn screening cards and dried in the air for three hours.

For sample preparation and LC-MS/MS analysis, bile acid B is extracted from dried blood spot with methanol containing internal standard. The extracted sample is directly injected to LC-MS/MS system comprised of a Prominence UFLC system and a 4000QTRAP mass spectrometer. A short LC-MS/MS method (~2 minutes) is used to separate bile acid B from interferences in dried blood spots.

The linearity, accuracy, stability, and precision are evaluated for the assay. The linearity of the standard curve is assessed over calibration range for three days. The slopes of standard curves prepared with surrogate and authentic analytes are used to evaluate parallelism. The precision and accuracy of the assay is evaluated at LLOQ, LQC, MQC and HQC concentration levels over the three days. For each QC concentration, analysis is performed in six replicates on each day. The stability of long-term storage (−20° C. and room temperature) and stability in the auto-sampler is determined at the LQC and HQC concentration levels (n=3).

To establish reference ranges and cut-off values, the LC-MS/MS method is used to analyze bile acid B in dried blood spots from controls (~1000 subjects), NPC subjects (~50 subjects), and heterozygotes (~50 subjects). The reference ranges for controls, NPC subjects, and heterozygotes are generated. The cut-off value is set at control mean plus 6 standard deviations or $99.5^{th}$ percentile of the controls as the upper cut-off limit and the lowest 0.5 percentile of the NPC range as the lower cut-off limit Cut-offs are selected to maximize area of under the curve of the ROC curves and the positive predictive value of the screen.

The method performance meets the requirements in FDA guidance (U.S. Department of Health and Human Services Guidance for Industry: Bioanalytical Method Validations. (2001)) with respect to sensitivity, selectivity, accuracy, precision, selectivity, and stability for most dried blood spots. The reference ranges for bile acid B in NPC, control, and heterozygote dried blood spots are obtained. NPC subjects can be differentiated with high sensitivity and specificity from controls and heterozygotes. Since the sample preparation for bile acid B is compatible with other screening platforms (e.g., amino acids and acylcarnitines), the NPC screening is multiplexed for simultaneous multi-disease screening using a single dried blood spot punch.

To eliminate false positive results, a second-tier LC-MS/MS method (longer LC run time) that can separate all the interferences to bile acid B is developed. Using the first-tier method >400 samples a day can be analyzed, and small number of suspicious samples with bile acid B values above the cut-off value are submitted to second-tier assay. The highly selective second-tier assay adjudicates the false positives from the first-tier assay. To clinically validate cut-off value for the dried blood spot assay, a larger number of dried blood spots (100,000 or more) are collected and analyzed in a prospective study. The overall performance metrics (Rinaldo, P., et al., Ment. Retard. Dev. Disabil Res. Rev. 12, 255-261 (2006)) including detection rate, positive predictive value, and false positive rate are evaluated.

Example 7

This example illustrates development of an LC-MS/MS method for determination of bile acid N-(3β,5α,6β-trihydroxy-cholan-24-oyl)taurine (also known as "THCT") biomarker in plasma for diagnosis of NPC disease The LC-MS/MS method for quantification of bile acid THCT in plasma is developed and validated according to Food and Drug Administration (FDA) guidance. (U.S. Department of Health and Human Services Guidance for Industry: Bioanalytical Method Validations. (2001)) The reference ranges for controls, heterozygotes, NPC subjects and cut-off value for diagnosis are established.

Preparation of standard curve and quality control sample is performed. The standard curve is prepared in bile acid THCT-free human umbilical cord plasma. When bile acid THCT-free human umbilical cord plasma is not available, 5% bovine serum albumin (BSA) in water or plasma from other species is evaluated as surrogate matrix for calibration standards. The standard curve prepared in bile acid A-free human umbilical cord plasma or surrogate matrix is used to quantify bile acid THCT in human plasma. Three levels of plasma QC samples including LQC, MQC and HQC samples are prepared to evaluate the accuracy, precision, and stability. The LLOQ is prepared by spiking bile acid THCT to analyte-free human plasma or to surrogate matrix to evaluate the sensitivity. A DQC sample of which bile acid is higher than the ULOQ is also prepared to evaluate dilution integrity.

For sample preparation and LC-MS/MS analysis, bile acid THCT is extracted from plasma with protein precipitation after spiking isotope-labeled internal standard. The extracted sample is directly injected to LC-MS/MS system comprised of a Prominence UFLC system and a 4000QTRAP mass spectrometer. A reversed phase HPLC column is used for the separation of bile acid B and internal standard from matrix and interferences.

For evaluation of linearity, sensitivity, accuracy, precision and stability, the linearity of the standard curve is assessed over the calibration range for three days. The slopes of standard curves prepared in surrogate and authentic matrixes are used to evaluate parallelism. The precision and accuracy of the assay is evaluated at LLOQ, LQC, MQC and HQC concentration levels over the three-day period. The dilution QC is used to assess the dilution integrity by dilution with surrogate matrix prior to extraction. For each QC concentration, analysis is performed in six replicates on each day for three days. The stabilities of long-term storage (−80° C.) and freeze/thaw, stability on the bench-top, and stability in the auto-sampler is determined at the LQC and HQC concentration levels (n=3).

Reference ranges and cut-off values are established. The validated LC-MS/MS method is used to analyze bile acid THCT in plasma from NPC (~100 subjects), controls (~100 subjects), obligate heterozygotes (parents of NPC subjects) or known sibling carriers (~40 subjects) to establish the reference ranges. The cut-off value can be determined from ROC curves. (Jiang, X., et al. *J Lipid Res* 52, 1435-1445 (2011)) Direct comparison of the ROC curves between bile acid THCT and triol markers is performed in the same sample sets.

After developing an extraction method with high recovery and LC-MS/MS condition that can separate interferences and eliminate matrix effect, method performance meets the requirements in FDA guidance (U.S. Department of Health and Human Services Guidance for Industry: Bioanalytical Method Validations. (2001)) regarding sensitivity, selectivity, accuracy, precision, selectivity, and stability. Accurate reference ranges for bile acid THCT in NPC, controls, heterozygotes, and cut-off value from ROC curves are obtained. The bile acid THCT ROC performance can be more robust than that of the triol assay, and a bile acid assay is easier for clinical laboratories to adopt.

To further evaluate diagnostic specificity of bile acid THCT, the inventors collect and analyze additional control samples from patients with enlarged livers or spleens, with jaundice due to either or both elevations of unconjugated and conjugated bilirubin, with other lysosomal storage disorders, and with primary bile acid disorders.

Example 8

This example illustrates development of an LC-MS/MS method for determination of a bile acid N-(3β,5α,6β-trihydroxy-cholan-24-oyl)taurine (also known as "THCT") biomarker in dried blood spots for newborn screening of NPC disease:

The LC/MS/MS methodology with short LC-MS/MS run (ca. 2 minutes) for quantification of bile acid THCT in dried blood spots is developed and validated according to FDA guidance. (U.S. Department of Health and Human Services Guidance for Industry: Bioanalytical Method Validations. (2001)) Reference ranges for bile acid THCT in control, heterozygote, and NPC dried blood spot samples are established. The cut-off value for identification of neonatal NPC patients is determined.

The standard curve samples are prepared by spiking bile acid THCT into human umbilical cord blood that is free of bile acid THCT. In the case that human blood free of bile acid THCT is not available, the standard curve samples are prepared by spiking a stable isotope-labeled bile acid THCT (surrogate standard) into human blood with 55% hematocrit, and the standard curve samples using bile acid THCT is also prepared to evaluate parallelism of standard curves prepared with surrogate and authentic analytes. Three levels of QC samples including LQC, MQC and HQC samples are prepared by spiking bile acid THCT to human blood to evaluate the accuracy, precision, and stability. The LLOQ is prepared by spiking bile acid THCT to analyte-free human blood or by spiking surrogate standard to human blood to evaluate the sensitivity. The standard curve and QC samples are spotted on blank newborn screening cards and dried in the air for three hours.

For sample preparation and LC-MS/MS analysis, bile acid THCT is extracted from dried blood spot with methanol containing internal standard. The extracted sample is directly injected to LC-MS/MS system comprised of a Prominence UFLC system and a 4000QTRAP mass spectrometer. A short LC-MS/MS method (~2 minutes) is used to separate bile acid THCT from interferences in dried blood spots.

The linearity, accuracy, stability, and precision are evaluated for the assay. The linearity of the standard curve is assessed over calibration range for three days. The slopes of standard curves prepared with surrogate and authentic analytes are used to evaluate parallelism. The precision and accuracy of the assay is evaluated at LLOQ, LQC, MQC and HQC concentration levels over the three days. For each QC concentration, analysis is performed in six replicates on each day. The stability of long-term storage (−20° C. and room temperature) and stability in the auto-sampler is determined at the LQC and HQC concentration levels (n=3).

To establish reference ranges and cut-off values, the LC-MS/MS method is used to analyze bile acid THCT in dried blood spots from controls (~1000 subjects), NPC subjects (~50 subjects), and heterozygotes (~50 subjects). The reference ranges for controls, NPC subjects, and heterozygotes are generated. The cut-off value is set at control mean plus 6 standard deviations or 99.5$^{th}$ percentile of the controls as the upper cut-off limit and the lowest 0.5 percentile of the NPC range as the lower cut-off limit. Cut-offs are selected to maximize area of under the curve of the ROC curves and the positive predictive value of the screen.

The method performance meets the requirements in FDA guidance (U.S. Department of Health and Human Services Guidance for Industry: Bioanalytical Method Validations. (2001)) with respect to sensitivity, selectivity, accuracy, precision, selectivity and stability for most dried blood spots. The reference ranges for bile acid THCT in NPC, control, and heterozygote dried blood spots are obtained. NPC subjects can be differentiated with high sensitivity and specificity from controls and heterozygotes. Since the sample preparation for a bile acid THCT is compatible with other screening platforms (e.g., amino acids and acylcarnitines), the NPC screening is multiplexed for simultaneous multi-disease screening using a single dried blood spot punch.

To reduce or eliminate false positive results, a second-tier LC-MS/MS method (longer LC run time) that can separate all the interferences to bile acid THCT is developed. Using the first-tier method >400 samples a day can be analyzed, and small number of suspicious samples with bile acid THCT values above the cut-off value are submitted to second-tier assay. The highly selective second-tier assay adjudicates the false positives from the first-tier assay. To clinically validate cut-off value for the dried blood spot assay, a larger number of dried blood spots (100,000 or more) are collected and analyzed in a prospective study. The overall performance metrics (Rinaldo, P., et al., *Ment Retard Dev Disabil Res Rev* 12, 255-261 (2006)) including detection rate, positive predictive value, and false positive rate are evaluated.

Example 9

This example illustrates diagnosis of Niemann-Pick type C disease in a subject exhibiting at least one symptom of Niemann-Pick type C disease.

In this example, a patient exhibits at least one symptom that is possibly attributable to Niemann-Pick type C disease. A phlebotomist obtains a blood sample from the patient. A physician orders a bile acid assay of the present teachings to determine the level of bile acid $3\beta,5\alpha,6\beta$-trihydroxycholanic acid. The bile acid assay results indicate that the $3\beta,5\alpha,6\beta$-trihydroxycholanic acid level is at a statistically significant elevated level compared to a control or above a cut-off value. The patient is diagnosed with Niemann-Pick type C disease. The physician orders genetic mutation analysis for the patient as a second-tier test for confirming the biochemical diagnosis of Niemann-Pick type C disease.

Example 10

This example illustrates diagnosis of Niemann-Pick type C disease in a subject exhibiting at least one symptom of Niemann-Pick type G disease.

In this example, a patient exhibits at least one symptom that is possibly attributable to Niemann-Pick type C disease. A phlebotomist obtains a blood sample from the patient. A physician orders a bile acid assay of the present teachings to determine the level of bile acid N-($3\beta,5\alpha,6\beta$-trihydroxy-cholan-24-oyl)glycine. The bile acid assay results indicate that the N-($3\beta,5\alpha,6\beta$-trihydroxy-cholan-24-oyl)glycine level is at a statistically significant elevated level compared to a control or above a cut-off value. The patient is diagnosed with Niemann-Pick type C disease. The physician orders genetic mutation analysis for the patient as a second-tier test for confirming the biochemical diagnosis of Niemann-Pick type C disease.

Example 11

This example illustrates diagnosis of Niemann-Pick type C disease in a subject exhibiting at least one symptom of Niemann-Pick type C disease.

In this example, a patient exhibits at least one symptom that is possibly attributable to Niemann-Pick type C disease. A phlebotomist obtains a blood sample from the patient. A physician orders a bile acid assay of the present teachings to determine the level of bile acid N-($3\beta,5\alpha,6\beta$-trihydroxy-cholan-24-oyl)taurine. The bile acid assay results indicate that the N-($3\beta,5\alpha,6\beta$-trihydroxy-cholan-24-oyl)taurine level is not at a statistically significant elevated level compared to a control or below a cut-of value. The patient is not diagnosed with Niemann-Pick type C disease.

Example 12

This example illustrates diagnosis of Niemann-Pick type C disease in a subject suspected of having Niemann-Pick type C disease.

In this example, a patient is suspected of having Niemann-Pick type C disease. A phlebotomist obtains a blood sample from the patient. A physician orders a bile acid assay of the present teachings to determine the level of bile acid N-($3\beta,5\alpha,6\beta$-trihydroxy-cholan-24-oyl)glycine. The bile acid assay results indicate that the N-($3\beta,5\alpha,6\beta$-trihydroxy-cholan-24-oyl)glycine level is at a statistically significant elevated level compared to a control or above a cut-off value. The patient is diagnosed with Niemann-Pick type C disease. The physician orders genetic mutation analysis for the patient as a second-tier test for confirming the biochemical diagnosis of Niemann-Pick type C disease.

Example 13

This example illustrates diagnosis of Niemann-Pick type C disease in a newborn human.

In this example, a phlebotomist obtains a blood sample for a newborn screening card from a newborn human. A physician orders a newborn screening assay that includes a bile acid test for Niemann-Pick type C disease. The bile acid assay results indicate that N-($3\beta,5\alpha,6\beta$-trihydroxy-cholan-24-oyl)glycine is at a statistically significant elevated level compared to that of a control population or above a cut-off value. The newborn is diagnosed with Niemann-Pick type C disease. The physician orders genetic mutation analysis for the patient as a second-tier test for confirming the biochemical diagnosis of Niemann-Pick type C disease.

Example 14

This example illustrates use of bile acids as part of a general metabolic screen. In this example, a phlebotomist obtains a blood sample from a human subject in the setting of an abnormal bilirubin level detected in a routine clinical laboratory test. A physician orders a bile acid test for Niemann-Pick type C disease in view of the abnormal bilirubin. The bile acid assay results indicate that the concentration of N-($3\beta,5\alpha,6\beta$-trihydroxy-cholan-24-oyl)glycine is at a statistically significant elevated level compared to a control or is above a cut-off value. The subject is diagnosed with Niemann-Pick type C disease. The physician orders genetic mutation analysis for the patient as a second-tier test for confirming the biochemical diagnosis of Niemann-Pick type C disease as a mutation in NPC1 or NPC2.

Example 15

This example illustrates use of bile acids as part of a general metabolic screen. In this example, a phlebotomist obtains a blood sample from a human subject in the setting of an abnormally enlarged liver or spleen or both. A physician orders a bile acid test for Niemann-Pick type C disease in view of the abnormal physical finding. The bile acid assay results indicate that N-($3\beta,5\alpha,6\beta$-trihydroxy-cholan-24-oyl)glycine is at a statistically significant elevated level compared to that of a control or above a cut-off value. The subject is diagnosed with Niemann-Pick type C disease. The physician orders genetic mutation analysis for the patient as a second-tier test for confirming the biochemical diagnosis of Niemann-Pick type C disease as a mutation in NPC1 or NPC2.

Example 16

This example illustrates use of bile acid measurement in the identification and diagnosis of NPC in a subject with neurological and psychiatric symptoms.

Genetic testing for NPG involving NPC1 and NPC2 exonic gene sequencing has revealed an underdiagnosed pool of NPC patients among adults who share common neurological and psychiatric symptoms (Bauer, P., et al., *Human Molecular Genetics* 22, 4349-4356 (2013)). In this example, a phlebotomist obtains a blood sample from a human subject in the setting of neurological and psychiatric symptoms. A physician orders a bile acid test for Niemann-Pick type C disease in view of the abnormal findings. The bile acid assay results indicate that the N-(3β,5α,6β-trihydroxy-cholan-24-oyl)glycine level is at a statistically significant elevated level compared to a control or above a cut-off value. The subject is diagnosed with Niemann-Pick type C disease. The physician orders genetic mutation analysis for the patient as a second-tier test for confirming the biochemical diagnosis of Niemann-Pick type C disease as a mutation in NPC1 or NPC2.

Example 17

This example illustrates use of bile acids for screening of children with cognitive impairment for NPC.

In this example, a physician orders a bile acid test for Niemann-Pick type C disease in view of cognitive impairment findings in a child. A phlebotomist obtains a blood sample from the child. A bile acid assay in accordance with the present teachings is performed. The results indicate that N-(3β,5α,6β-trihydroxy-cholan-24-oyl)glycine is at a level that is statistically significantly elevated compared to controls or above a cut-off value. The child is diagnosed with Niemann-Pick type C disease. The physician orders a genetic mutation analysis for the patient as a second-tier test for confirming the biochemical diagnosis of Niemann-Pick type C disease as a mutation in NPC1 or NPC2.

Example 18

This example illustrates use of bile acids for evaluating therapeutic efficacy of treatments for NPC disease.

In this example, a phlebotomist obtains a first blood sample from a subject with Niemann-Pick type C disease prior to commencement of an experimental treatment. The treatment is administered, and a second blood sample is obtained after the treatment Bile acid content of each sample is determined. The bile acid assay results indicate that N-(3β,5α,6β-trihydroxy-cholan-24-oyl)glycine of the second assay is at a level that is statistically significantly lower level compared to the first assay, indicating that the therapy is effective for treatment of NPC in the subject.

Example 19

This example illustrates the use of bile acids and secondary tests to differentiate between types of Niemann-Pick diseases.

In this example, a physician suspects Niemann-Pick disease due to an enlarged liver or spleen or both and orders a bile acid test. A phlebotomist obtains a blood sample from the patient and the bile acid content of each sample is determined. The bile acid results indicate that N-(3β,5α,6β-trihydroxy-cholan-24-oyl)taurine is elevated relative to a control population or above a cut-off value. The physician orders a sphingomyelinase activity test. The activity of sphingomyelinase is significantly lower than that in a control population and Niemann-Pick disease type A/B is diagnosed.

Example 20

This example illustrates the use of bile acid tests to differentially diagnose Niemann-Pick diseases in newborn humans.

In this example, a phlebotomist takes a blood sample from a newborn human and creates a blood spot card. The level of bile acid in the blood spot is determined using the present teachings and the level of N-(3β,5α,6β-trihydroxy-cholan-24-oyl)glycine is found to be elevated relative to a control population or above a cut-off value. A sphingomyelinase activity test is performed. The activity of sphingomyelinase does not significantly differ from that of a control population. Niemann-Pick disease type C is diagnosed.

Example 21

This example illustrates the use of bile acid tests to differentially diagnose Niemann-Pick diseases in an individual exhibiting neurological and psychiatric symptoms.

In this example, a phlebotomist collects a blood sample from a subject exhibiting neurological and psychiatric symptoms. The bile acid level is analyzed according to the present teachings, and the level of 3β,5α,6β-trihydroxycholanic acid is found to be elevated relative to that of a control population or above a cut-off value. A physician orders a sphingomyelinase activity test. The measured activity is less than 1% of the activity of a control population. Niemann-Pick disease type A/B is diagnosed.

Example 22

This example illustrates the use of bile acid tests and sphingomyelinase activity assays to differentially diagnose Niemann-Pick diseases in a child with cognitive impairment.

In this example, a phlebotomist collects a blood sample from a child subject exhibiting cognitive impairment. The bile acid level of the sample is analyzed using the present teachings and the level of THCG N-(3β,5α,6β-trihydroxy-cholan-24-oyl)glycine is found to be elevated relative to that of a control population or above a cut-off value. A sphingomyelinase activity test is performed and the activity is found to be less than 1% of the activity of a control population. Niemann-Pick disease type A/B is diagnosed.

Example 23

This example illustrates the profiling of bile acids in NPC1 and control plasma samples.

Figure 14:
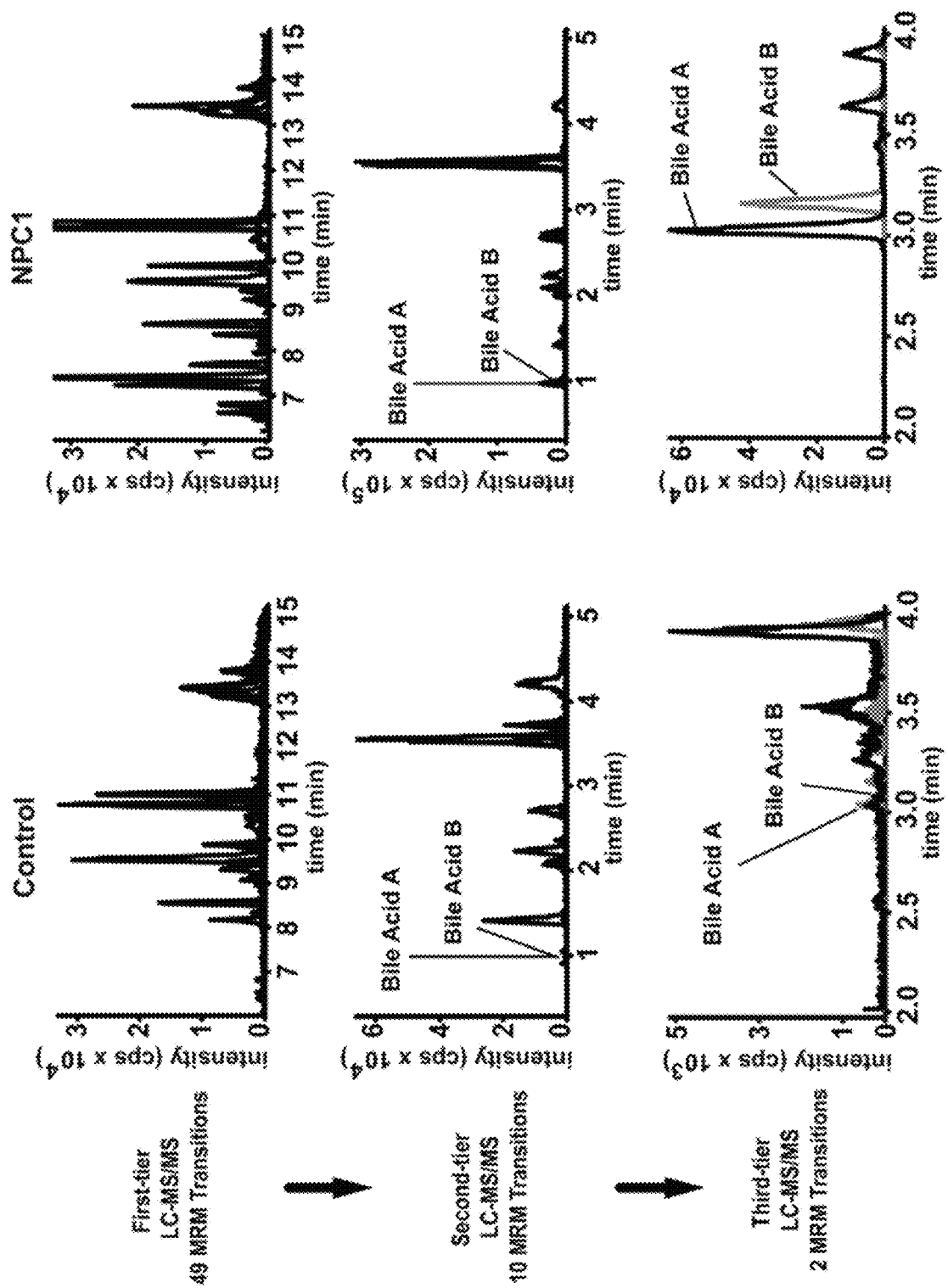
FIG. 14 illustrates a Three-tier targeted metabolomics strategy for identification of bile acid biomarkers.

For biomarker discovery, the inventors profiled bile acids in NPC1 and control plasmas using a three-tier targeted metabolomics strategy based on LC-MS/MS operated in multiple reaction monitoring (MRM) mode (FIG. 14). First-tier screen includes 49 multiple reaction monitoring (MRM) transition (17 min run time). Second tier includes 10 MRM transitions (7.5 min run time) to characterize peaks with signal-to-noise ratio greater than five. Third tier (6 min run time) quantifies unknown bile acid peaks (A and B) that are elevated in NPC1 compared to control.

For the first tier assay, the NPC1 and control samples were randomized so that each group was evenly distributed in the run order. In this way bias and noise/variance in the results caused by the instrument fluctuation are reduced, enabling subsequent unbiased statistical analysis of the data. LC-MS/MS analysis was conducted on a Shimadzu (Columbia, Md.) Prominence UFLC system coupled with an Applied Biosystems/MDS Sciex (Ontario, Canada) 4000QTRAP mass spectrometer using multiple reaction monitoring (MRM). Separation of bile acids was carried out at 50° C. using a Waters (Milford, Mass.) XBridge C18 analytical column (4.6×50 mm, 2.5 μm) connected to a PHENOMENEX® (Torrance, Calif.) SECURITYGUARD™ C18 guard column (4×3 mm) at a flow rate of 1 mL/min. The mobile phase consisted of 10 mM ammonium acetate and 0.1% ammonium hydroxide in water (solvent A), and acetonitrile-methanol (1:4) (solvent B). The step gradient was as follows: 0-0.1 min, 10%; 0.1-10 min, 10 to 75% solvent B; 10-12 min, 75% solvent B; 12-12.1 min, 75 to 100% solvent B; 12.1-15 min, 100%; 15-15.1 min, 100 to 10% solvent B; 15.1-17 min, 10% solvent B. The effluent was directed into the mass spectrometer for data acquisition within the 13-min time window (2-15 min); elsewhere, effluent was sent to waste to minimize source contamination. The injection volume was 5 μL and the total run-time was 17 min. The ESI source temperature was 500° C.; the ESI needle was −4500 V; the entrance potential was −10 V; and the collision cell exit potential was −10 V. The collision and curtain gas were set at medium and 20, respectively. Both desolvation gas and nebulizing gas were set at 35 L/min. The MRM transitions, declustering potentials, and the collision energies are listed in Table 1. The dwell time was set at 20 ms for each of MRM transition. Data were acquired and analyzed by Analyst software (version 1.5.2). In a separate LC run, fractions containing the bile acids of interest were collected for further structure analysis. The first-tier assay included 49 MRM transitions with 17 minute (min) run time to broadly detect possible bile acids.

The same LC-MS/MS system and column as that in the first-tier bile acid biomarker screening were used for the second-tier screening. The chromatography was carried out at 50° C. The mobile phase consisted of 0.1% ammonium hydroxide in water (solvent A), and acetonitrilemethanol (1:4) (solvent B). The step gradient was as follows: 0-5 min, 45 to 75% solvent B; 5-5.1 min, 75 to 100% solvent B; 5.1-6 min, 100% solvent B; 6-6.1 min, 100 to 45% solvent B; 6.1-7.5 min, 45% solvent B. The effluent was directed into the mass spectrometer for data acquisition from 0.9 to −6 min; elsewhere, effluent was sent to waste to minimize source contamination. The injection volume was 5 μL and the total run-time was 7.5 min. The ESI source temperature was 500° C.; the ESI needle was −4500 V; the entrance potential was −10 V; and the collision cell exit potential was −10 V. The collision and curtain gas were set at medium and 20, respectively. Both desolvation gas and nebulizing gas were set at 35 L/min. The MRM transitions, declustering potentials, and the collision energies are listed in Table 2. The dwell time was set at 20 ms for each of MRM transition. Data were acquired and analyzed by Analyst software (version 1.5.2). For the second-tier, 10 MRM transitions and 7.5 min run time were used to detect only those bile acids with signal-to-noise ratio greater than five.

Figure 15:
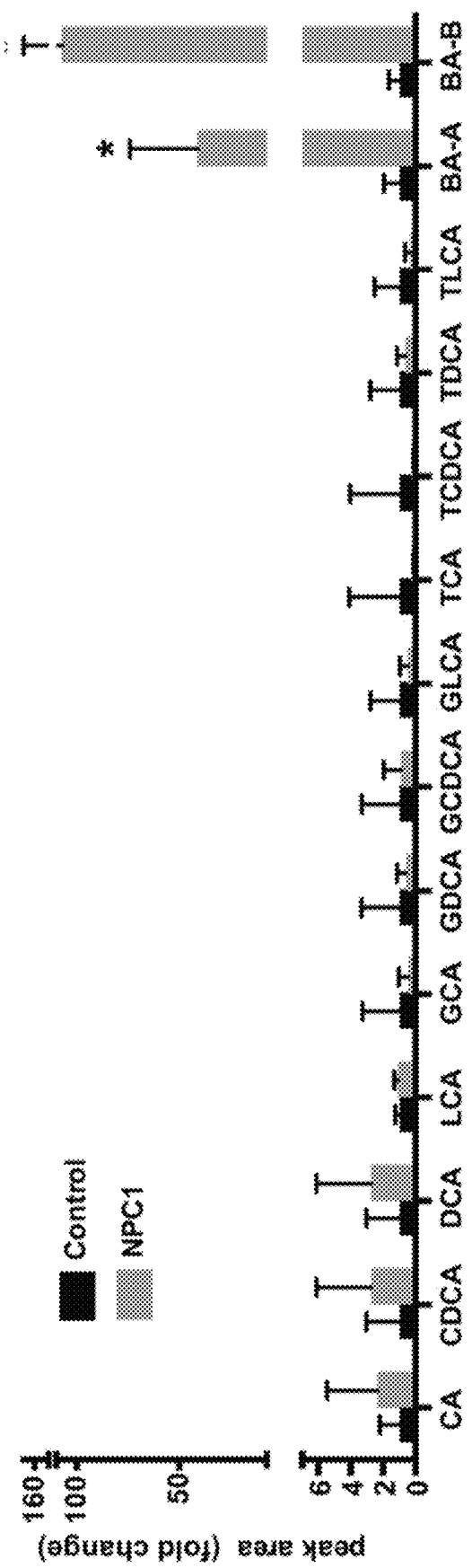
FIG. 15 illustrates a comparison of bile acid concentration in NPC1 versus control samples obtained from second-tier profiling.
Figure 16:
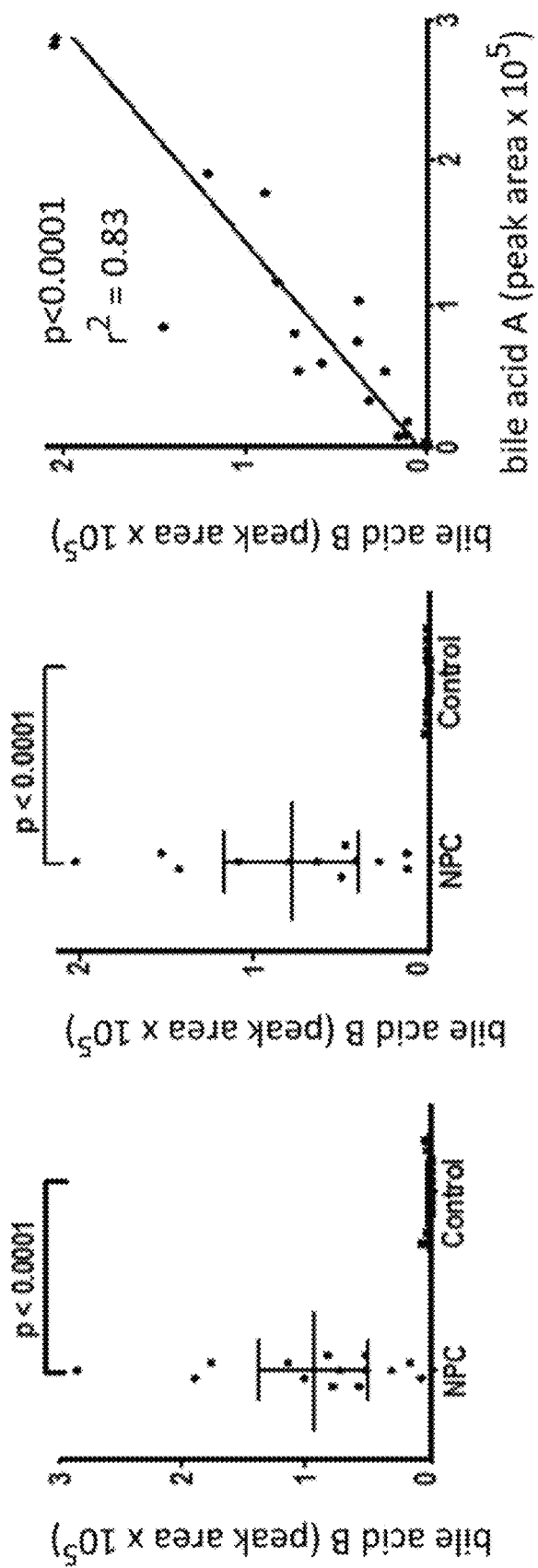
FIG. 16 illustrates bile acids A and B concentration in NPC1 and control plasma samples.

The same LC-MS/MS system as that in the first- and second-tier bile acid biomarker screening was used for the third-tier screening. Separation of bile acids A and B was carried out at 50° C. using a Waters (Milford, Mass.) XBridge C18 analytical column (4.6×100 mm, 3.5 μm) connected to a PHENOMENEX® (Torrance, Calif.) SECURITYGUARD™ C18 guard column (4×3 mm) at a flow rate of 1 mL/min. The mobile phase consisted of 2.9 mM diethylamine in water (solvent A), and acetonitrile-methanol (1:9) (solvent B). The step gradient was as follows: 0-3 min, 40% to 55% solvent B; 3-3.1 min, 55% to 100% solvent B; 3.1-4 min, 100% solvent B; 4-4.1 min, 100% to 40% solvent B; 4.1-6 min, 40% solvent B. The effluent was directed into the mass spectrometer for data acquisition within the 2-min time window (2-4 min) in which bile acids A and B were eluted; elsewhere; effluent was sent to waste to minimize source contamination. The total runtime was 6 min. The injection volume was 2 μL for plasma samples and 20 μL for dried blood spot samples. The ESI source temperature was 500° C.; the ESI needle was −4500 V; the declustering potential was −120 V; the entrance potential was −10 V; and the collision cell exit potential was −10 V. The collision and curtain gas were set at medium and 20, respectively. Both desolvation gas and nebulizing gas were set at 35 L/min and the collision energies were −35 and −75 eV for bile acids A and B, respectively. For MRM, the dwell time was set at 50 ms for each of the signal from transitions of m/z 407 to 407 (bile acid A) and m/z 464 to 74 (bile acid B). Data were acquired and analyzed by Analyst software (version 1.5.2). In a separated LC run, fractions containing the bile acids of interest were collected from plasma samples for further structure analysis. Only two MRM transitions and six min run time were used in the third-tier assay to confirm the two candidate bile acid species (referred to as bile acid A and B) identified by second-tier assay. FIG. 15 depicts a comparison of bile acid concentration in NPC1 versus control samples obtained from second-tier profiling. Data are presented as mean fold-change+SD normalized to control. *P<0.0005 for A and B in NPC1 versus controls. CA, cholic acid; CDCA, chenodeoxycholic acid; DCA, deoxycholic acid; LCA, lithocholic acid; GCA, glycocholic acid; GDCA, glycodeoxycholic acid; GCDCA, glycochenodeoxycholic acid; GLCA, glycolithocholic acid; TCA, taurocholic acid; TDCA, taurodeoxycholic acid; TCDCA, taurochenodeoxycholic acid; TLCA, taurolithocholic acid; BAA, bile acid A; BA-B, bile acid B. In contrast to other bile acids monitored, these two unknown species were markedly elevated in the NPC1 but not control plasma samples (FIG. 15). The unknown bile acids were detected in same MRM transitions as cholic acid and glycocholic acid, respectively, but their retention times differed, suggesting that they might be isomers of these bile acids. FIG. 16 depicts bile acids A and B concentration in NPC1 (n=12) and control (n=11) plasma samples. Data are presented as mean±95% CI peak area. P<0.0001 for bile acids A and B in NPC1 versus controls. Bile acids A and B were increased 41-fold and 144-fold, respectively, in NPC1 plasma, and were able to completely discriminate between NPC1 and control plasma samples (FIG. 16). The high correlation between their plasma concentrations suggested that they are related, possibly within the same metabolic pathway.

Example 24

This example illustrates elucidation of the structure of the novel bile acids.

Figure 17:
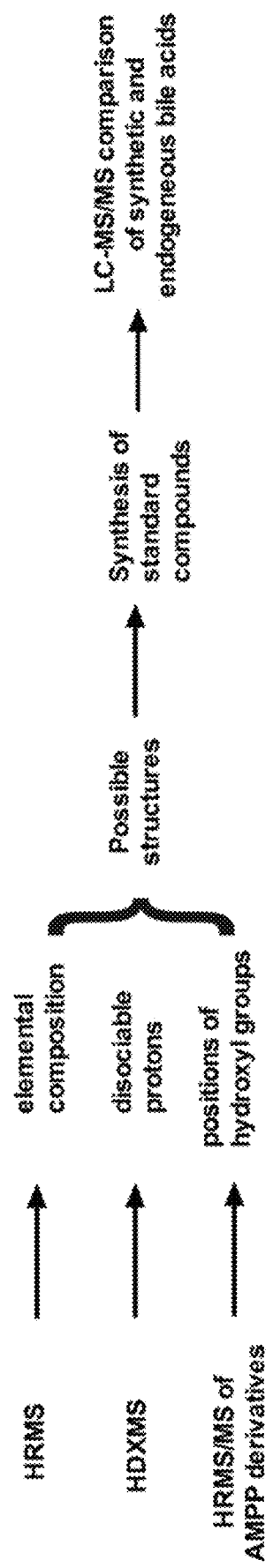
FIG. 17 illustrates identification and confirmation of structure of unknown bile acids.

The present inventors' strategy for identification of bile acid structures is outlined in FIG. 17 (HRMS, high-resolution mass spectrometry; HDXMS, hydrogen/deuterium exchange mass spectrometry; HRMS/MS, high-resolution tandem mass spectrometry; AMPP, N-(4-aminomethylphenyl) pyridinium.). High resolution mass spectrometry and H/D exchange experiments of underivatized bile acids A and B were performed to elucidate the structure further. The bile acids A and B isolated from third tier screening were dissolved in methanol and directly infused to a LTQ Orbitrap Velos ETD™ mass spectrometer (Thermo Fisher Scientific, San Jose, Calif.) via Harvard syringe pump at 5 µL/min. The full FT-MS scan (m/z 250-800) and HCD MS/MS scans were performed with precursor isolation width of 1 m/z. Full scan and HCD MS/MS mass spectra were recorded at a resolution of 100,000 at m/z 400. Automatic gain control (AGC) was used to accumulate sufficient ions. For survey scans, AGC target was $1\times10^6$ (maximum injection time 1 s). For HCD, AGC target was $1\times10^5$ (maximum inject time 100 and 25 ms, respectively). HCD was performed at normalized collision energy of 95%. Helium was used as the buffer and collision gas at a pressure of $1\times10^{-3}$ mbar (0.75 mTorr). Data acquisition was controlled by Xcalibur 2.1 software package. Spray voltage was set to −4 kV and temperature of the heated transfer capillary was 300° C. The vaporizer temperature was off. Sheath and auxiliary nitrogen gas were applied at a flow rate of 0 and 0 arbitrary units (AU), respectively.

Figure 18:
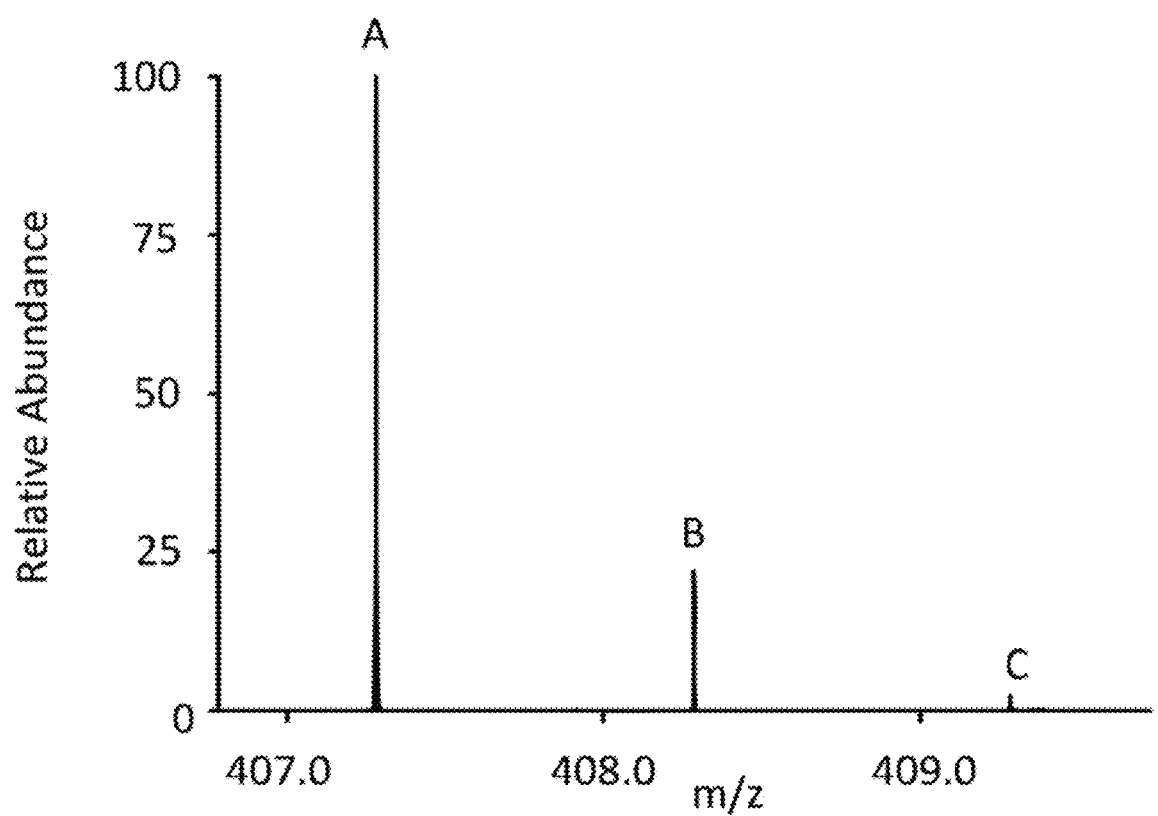
FIG. 18 illustrates high resolution mass spectra of bile acid A.
Figure 19:
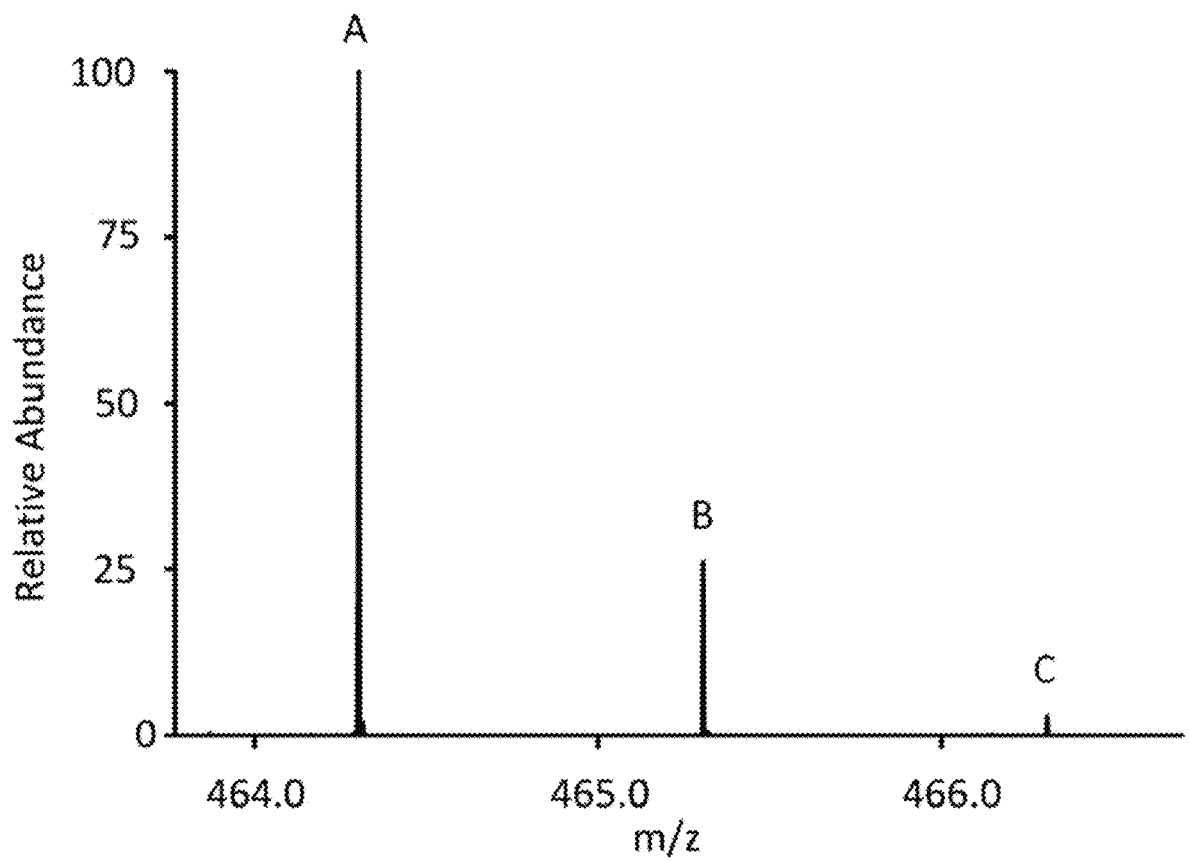
FIG. 19 illustrates high resolution mass spectra of bile acid B.

The exchange of the labile hydrogen atoms in bile acids A and B by deuterium atoms was carried out by preparing solutions of the analytes in deuterated methanol. The final samples were immediately infused directly into the ESI LTQ Orbitrap Velos ETD™ mass spectrometer. High resolution mass spectrometric analysis of bile acids A and B on LTQ-Orbitrap mass spectrometer in the negative mode showed accurate m/z value of 407.2800 and 464.3016, respectively, for [M-H]-corresponding to formulas $C_{24}H_{39}O_5$ (calculated mass, 407.2803) and $C_{26}H_{42}NO_6$ (calculated mass, 464.3018) with mass errors less than 1 mDa, respectively (FIG. 18-19, respectively).

Figure 20:
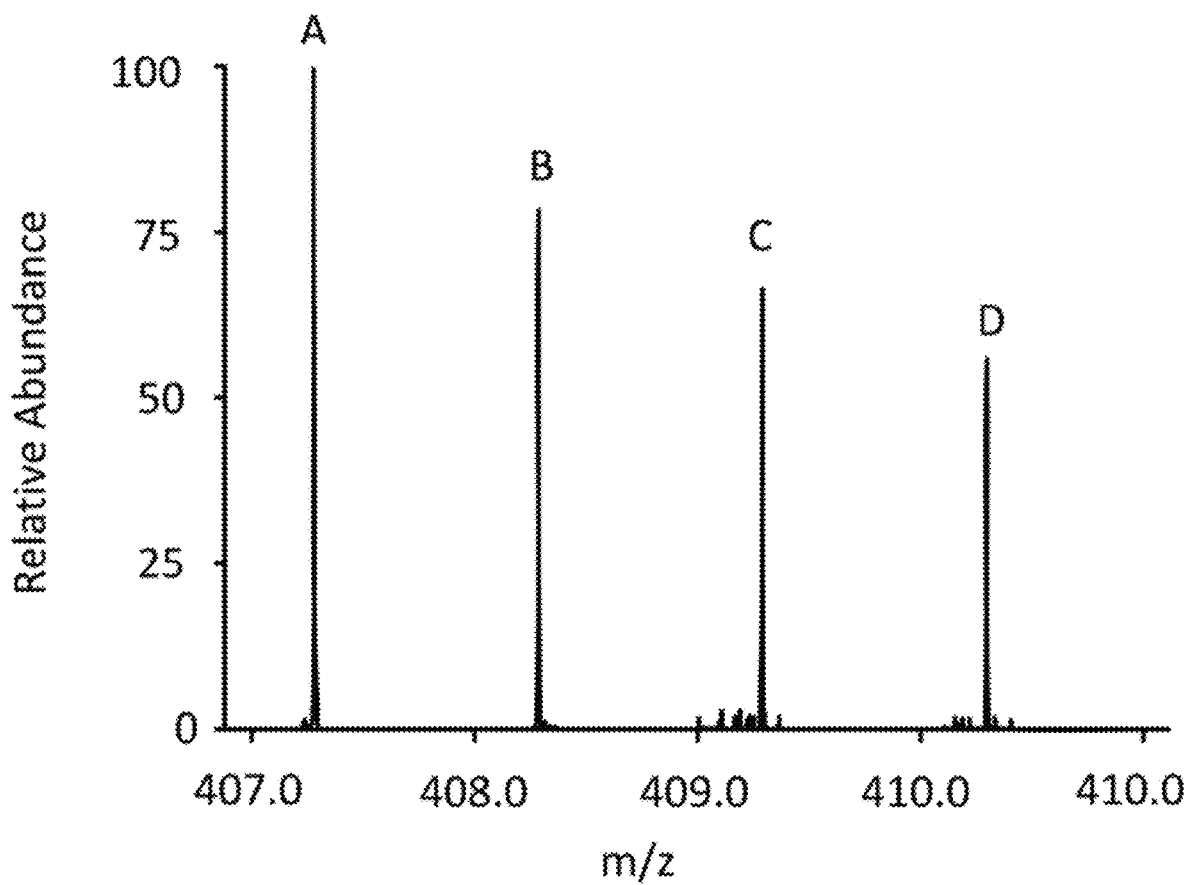
FIG. 20 illustrates H/D exchange mass spectra of bile acid A.
Figure 21:
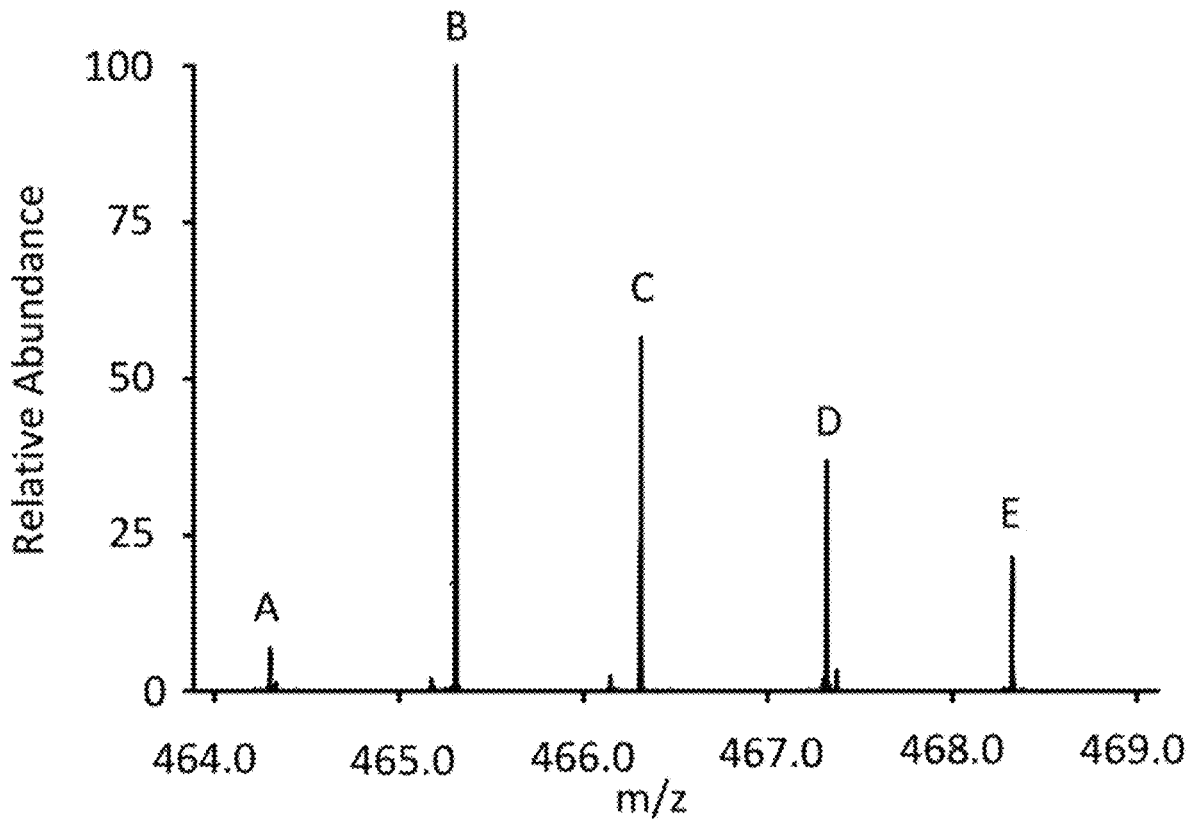
FIG. 21 illustrates H/D exchange mass spectra of bile acid B.
Figure 22:
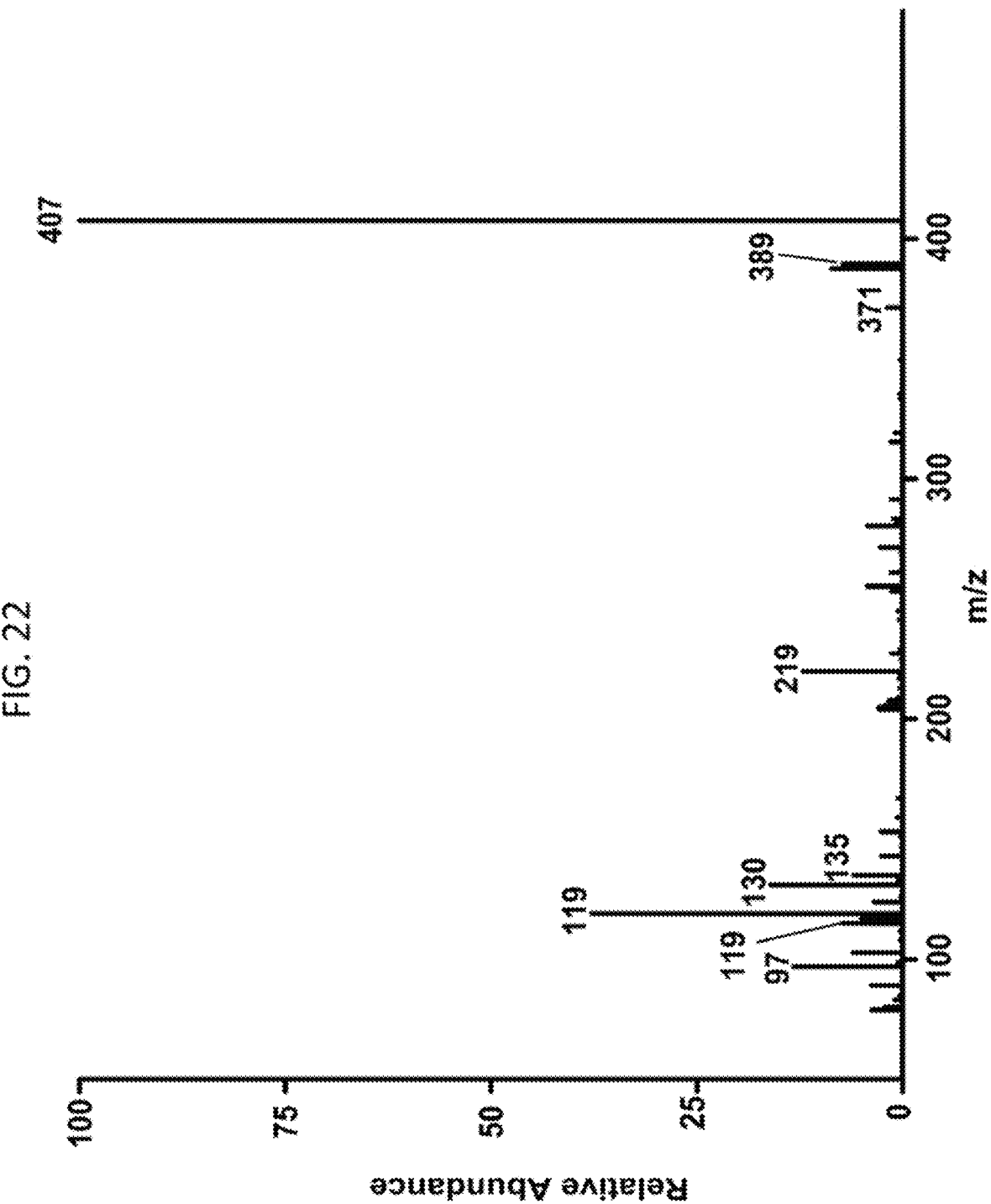
FIG. 22 illustrates HCD mass spectra of bile acid A.
Figure 23:
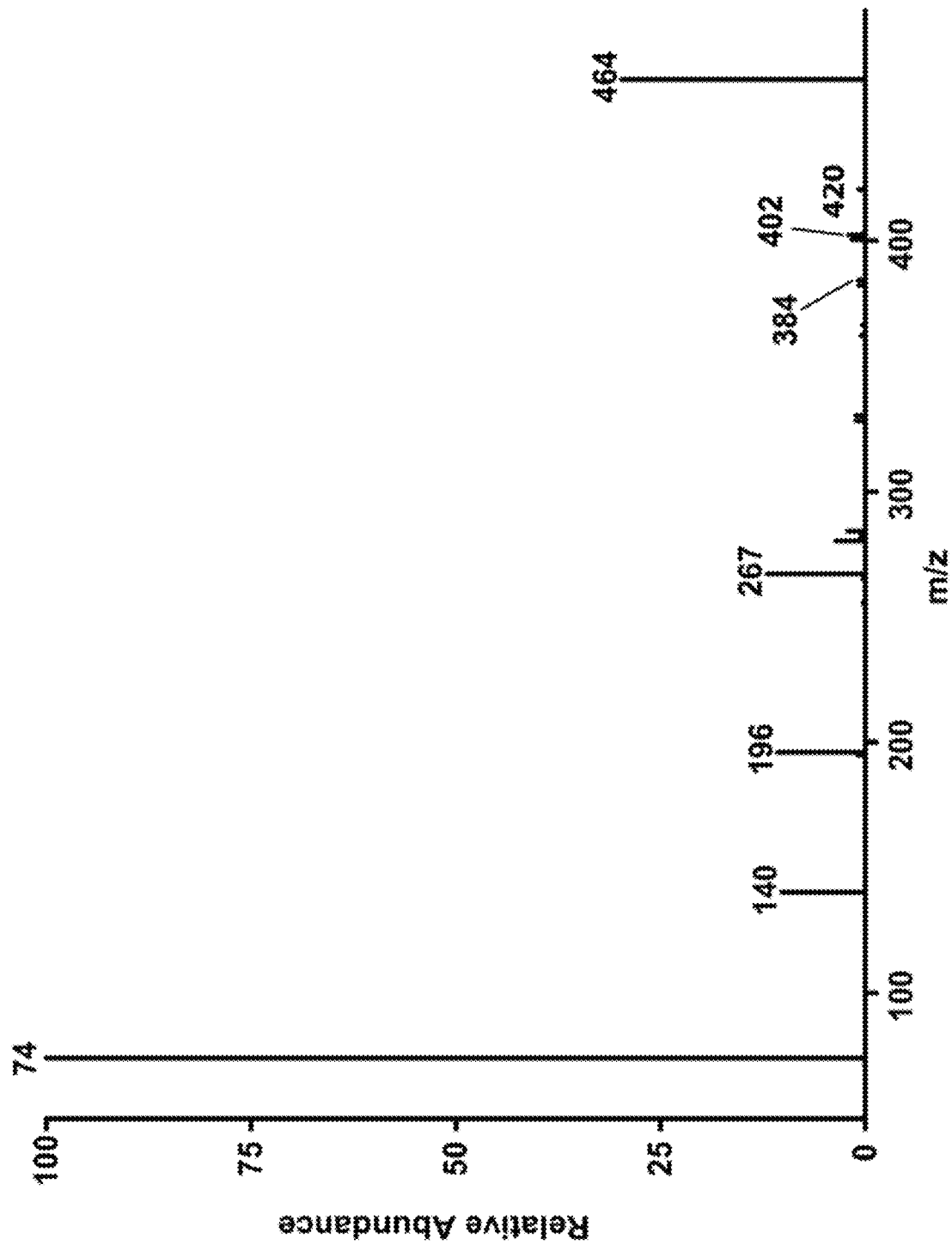
FIG. 23 illustrates HCD mass spectra of bile acid B.
Figure 24:
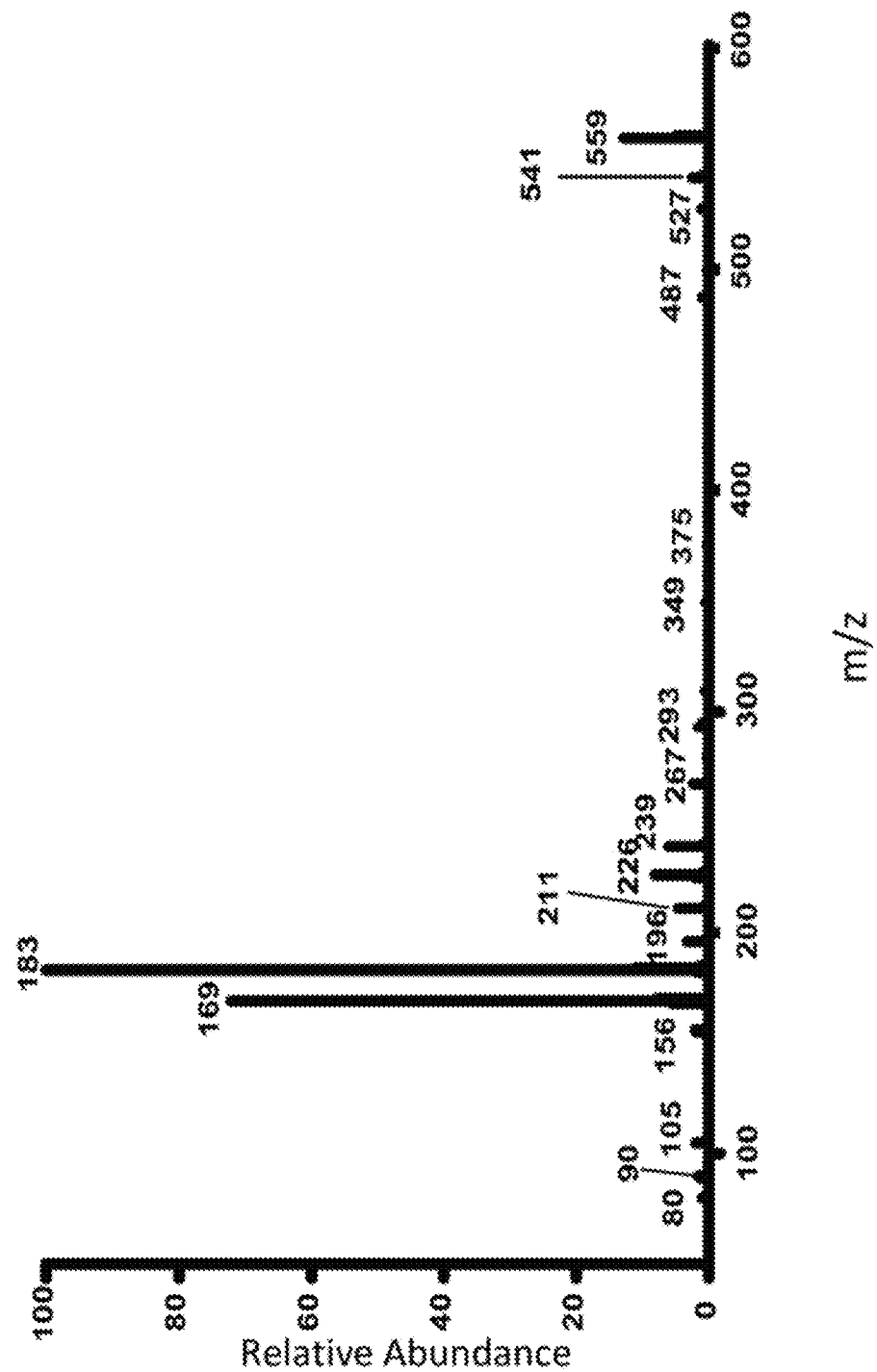
FIG. 24 illustrates HCD mass spectra of AMPP-derivatized analogue 1.
Figure 25:
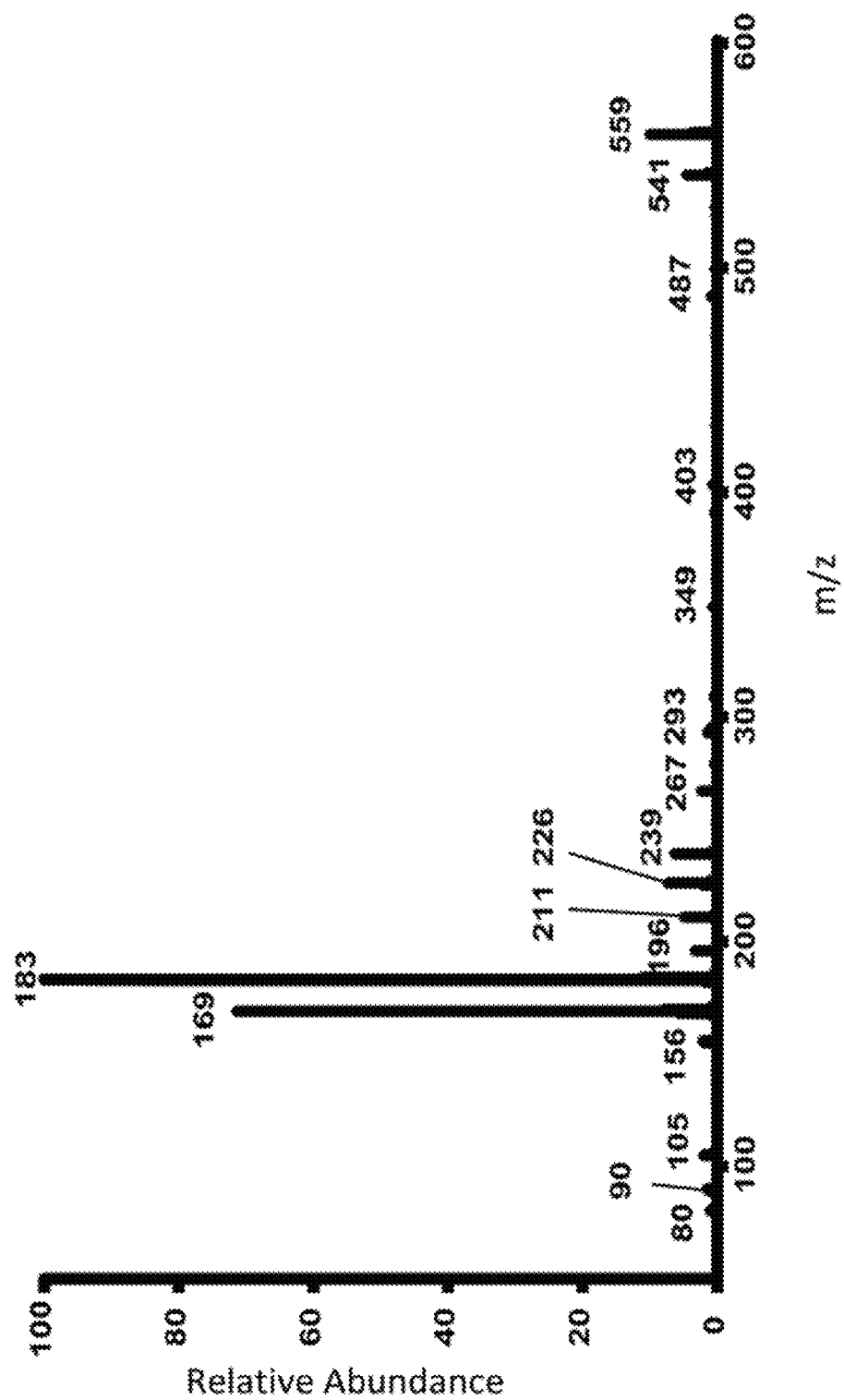
FIG. 25 illustrates HCD mass spectra of AMPP-derivatized analogue 2.
Figure 26:
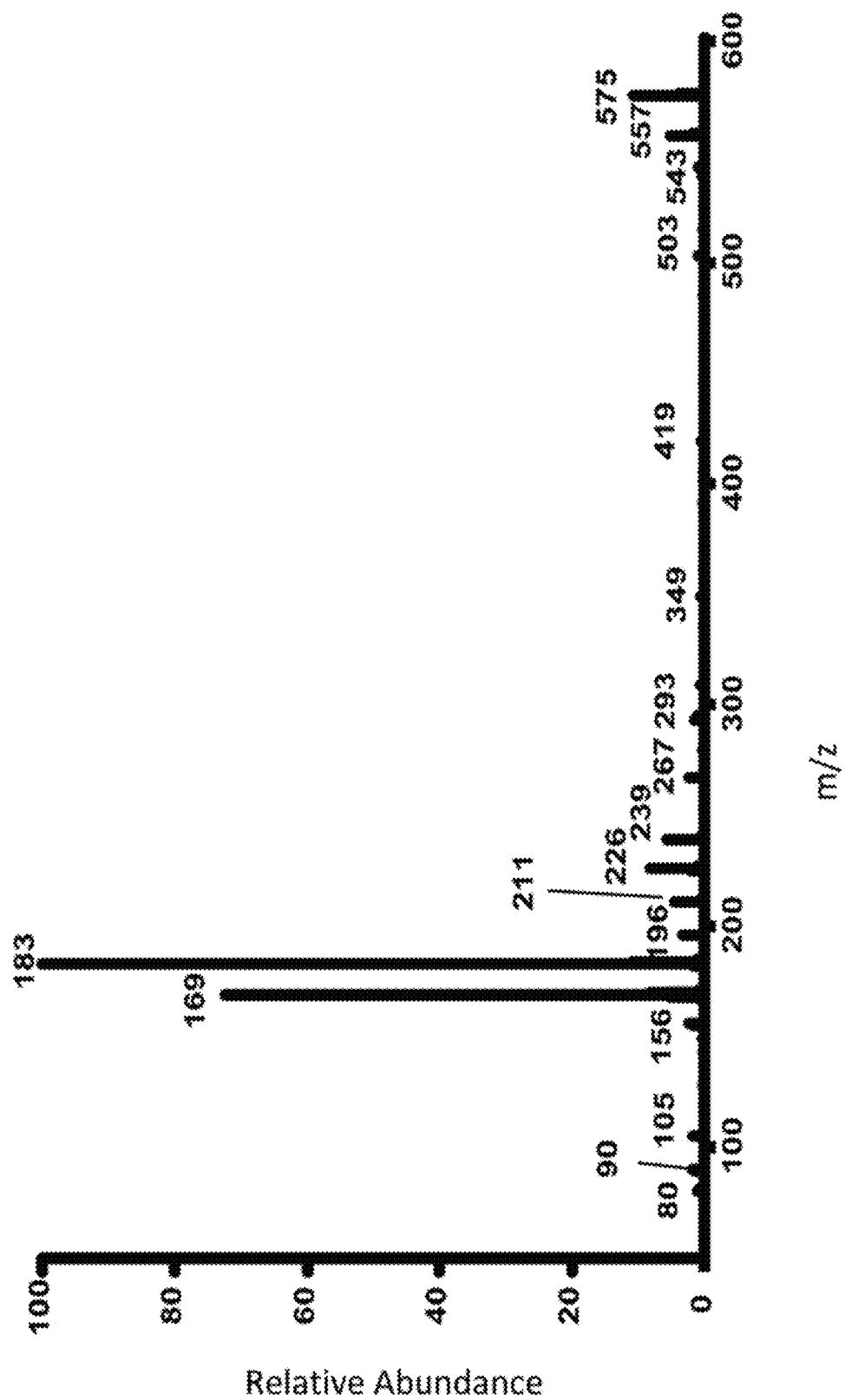
FIG. 26 illustrates HCD mass spectra of AMPP-derivatized analogue 3.
Figure 27:
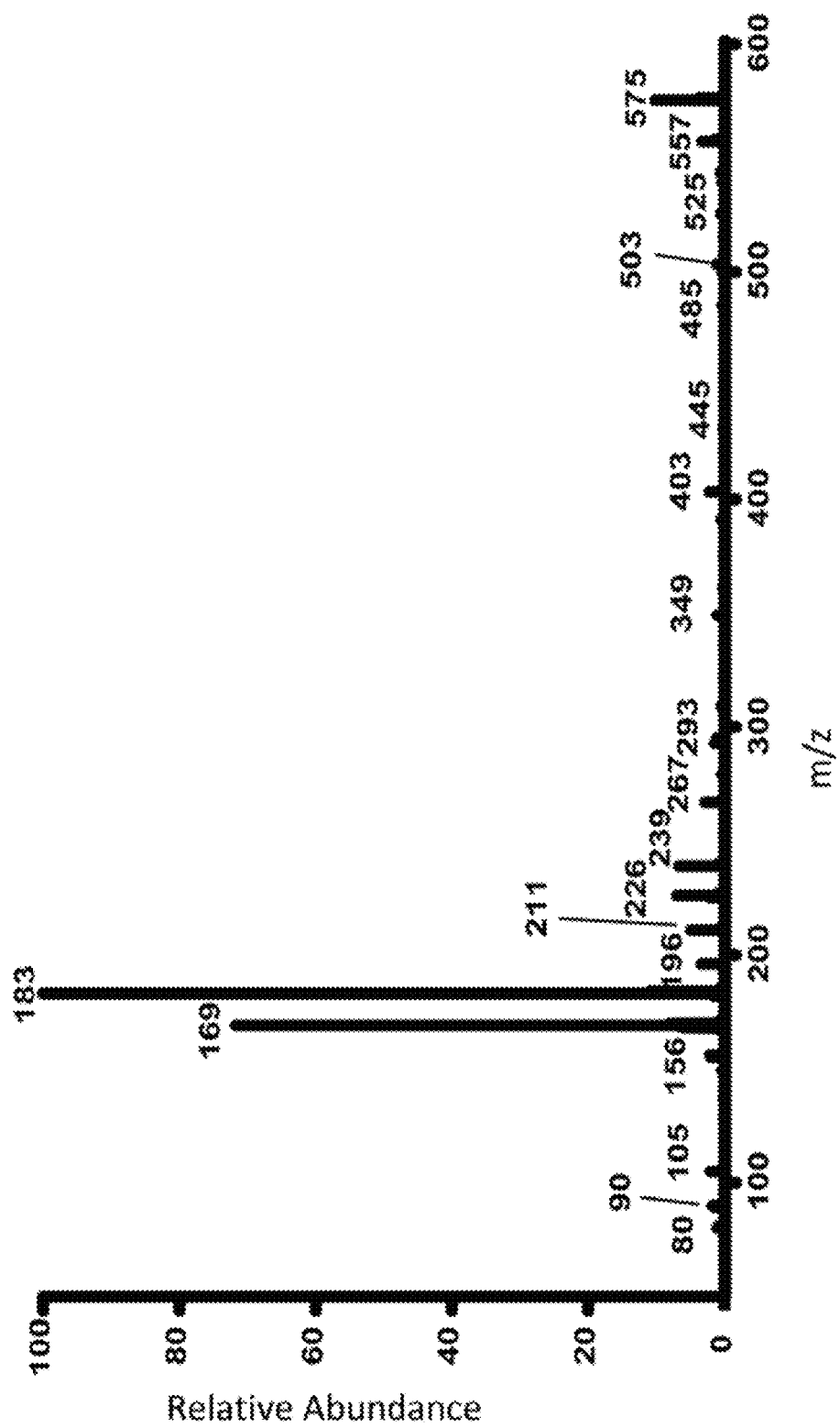
FIG. 27 illustrates HCD mass spectra of AMPP-derivatized analogue 4.
Figure 28:
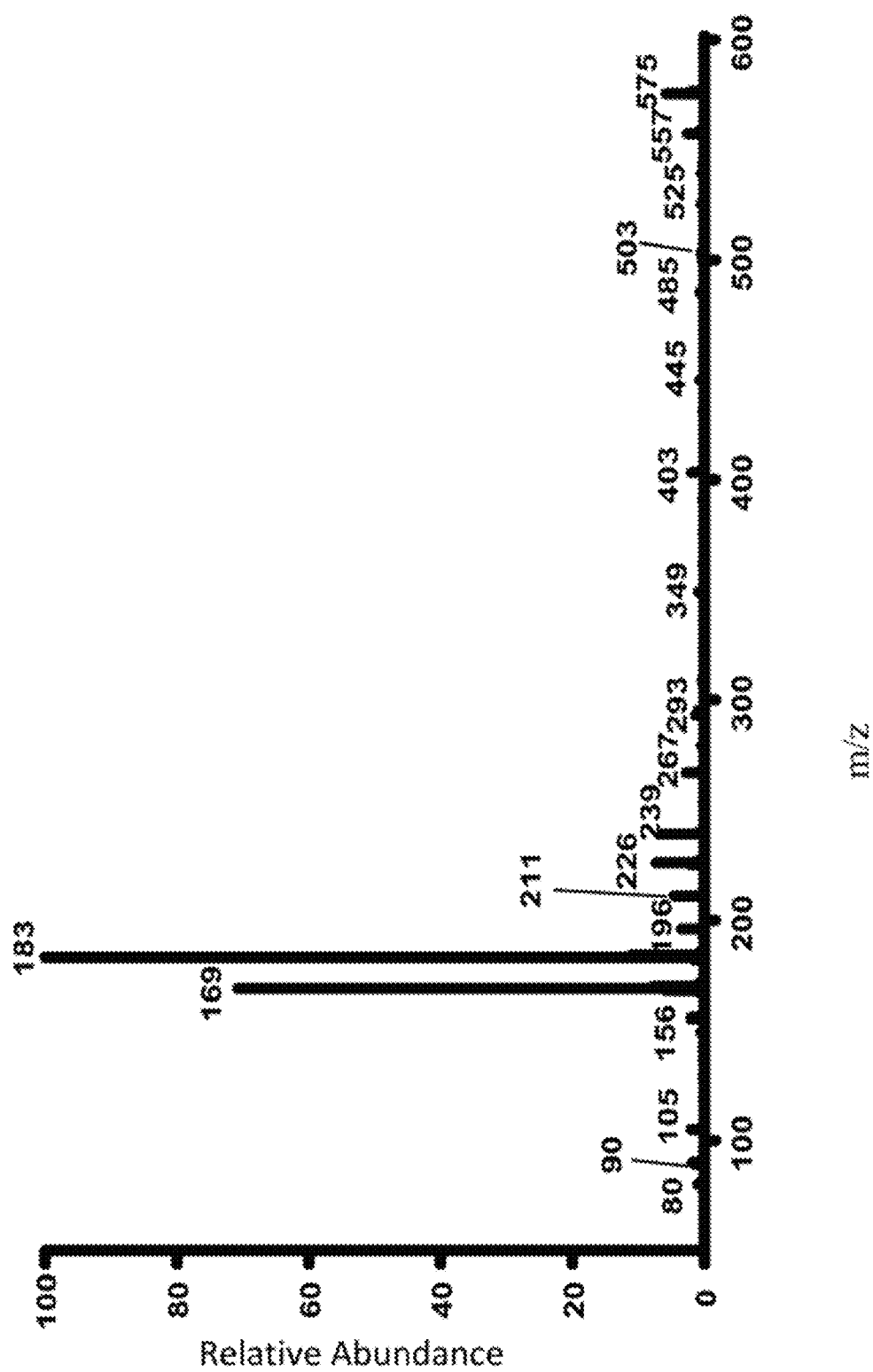
FIG. 28 illustrates HCD mass spectra of AMPP-derivatized analogue 5.
Figure 29:
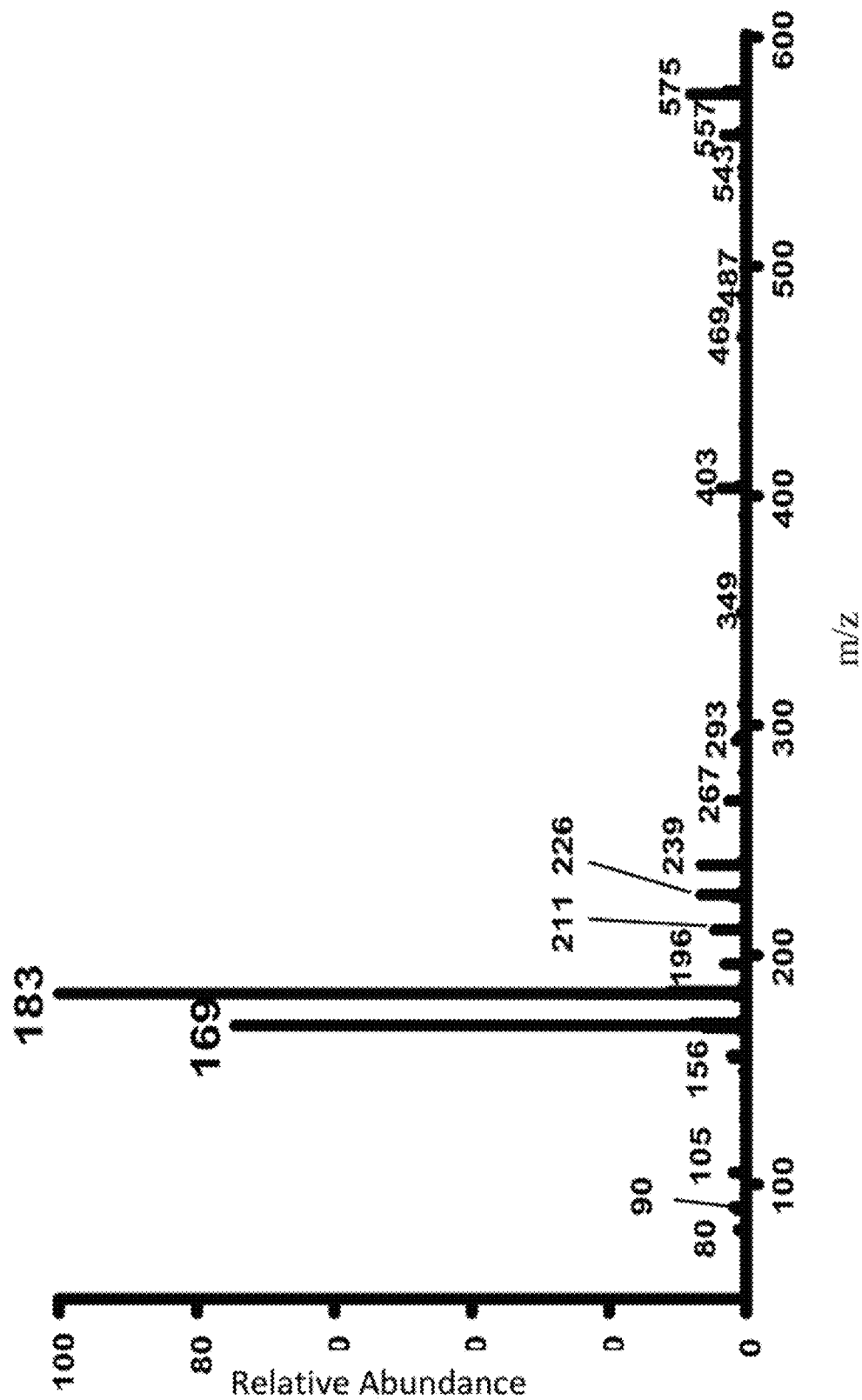
FIG. 29 illustrates HCD mass spectra of AMPP-derivatized analogue 6.
Figure 30:
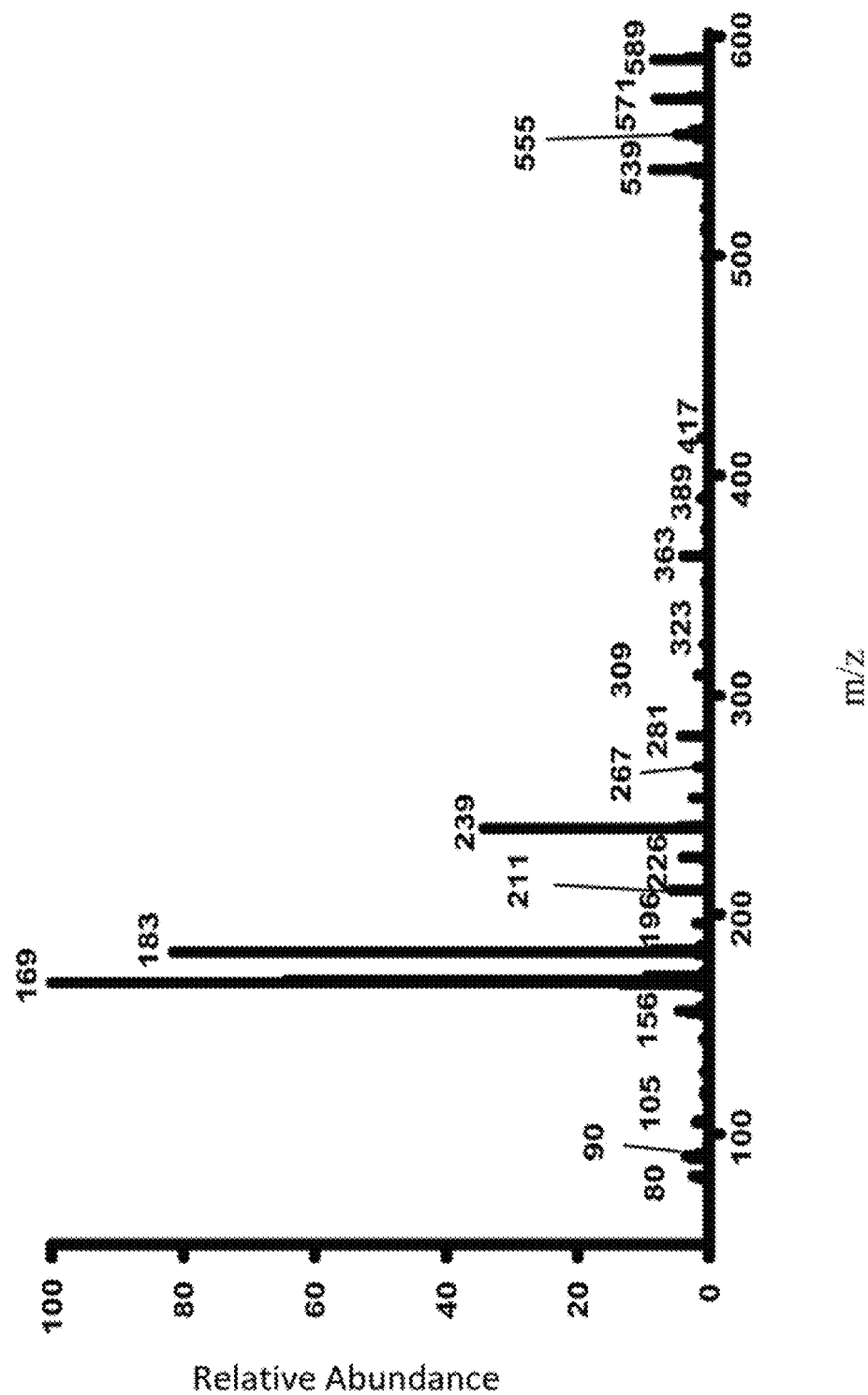
FIG. 30 illustrates HCD mass spectra of AMPP-derivatized analogue 7
Figure 31:
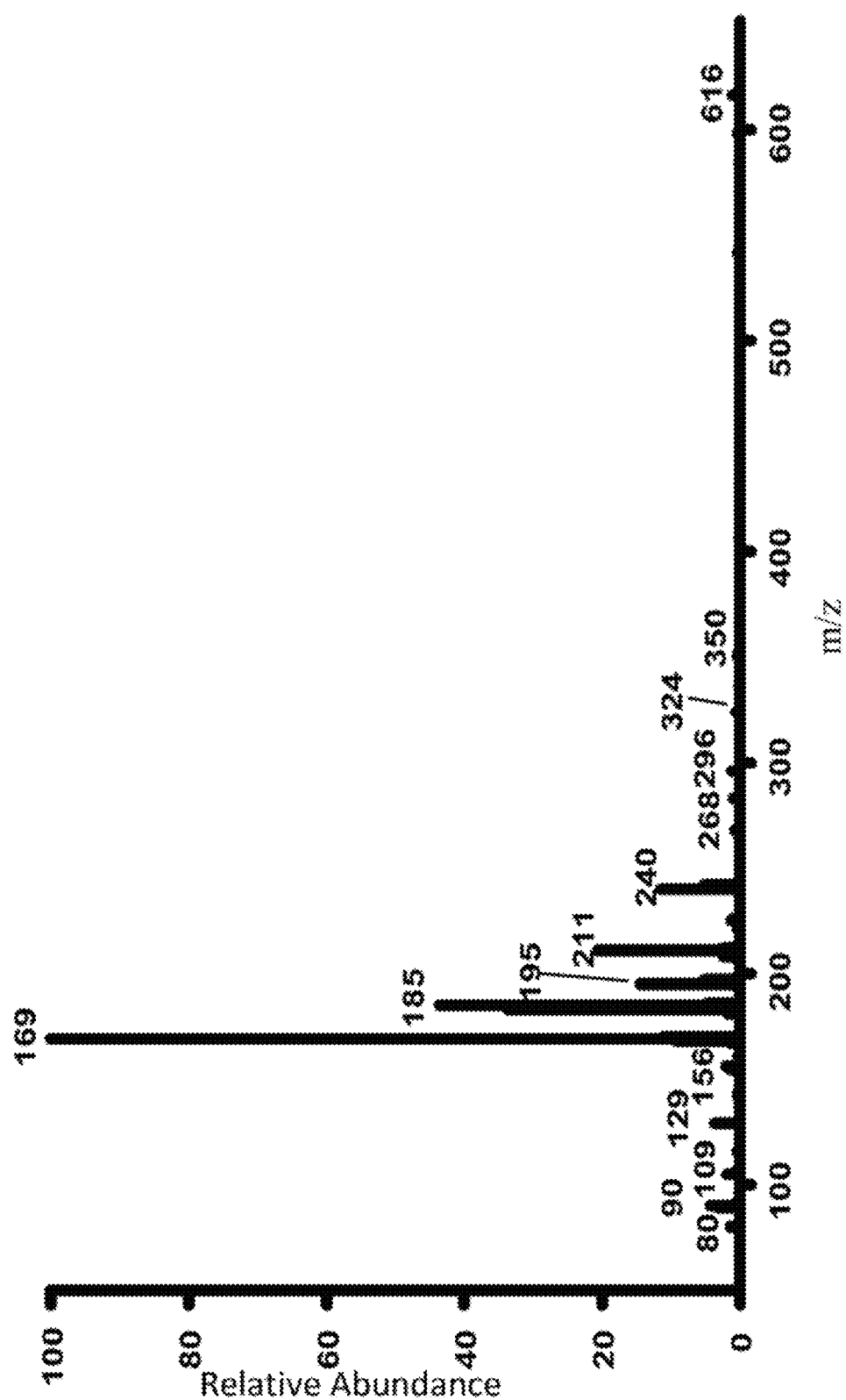
FIG. 31 illustrates HCD mass spectra of AMPP-derivatized analogue 8
Figure 32:
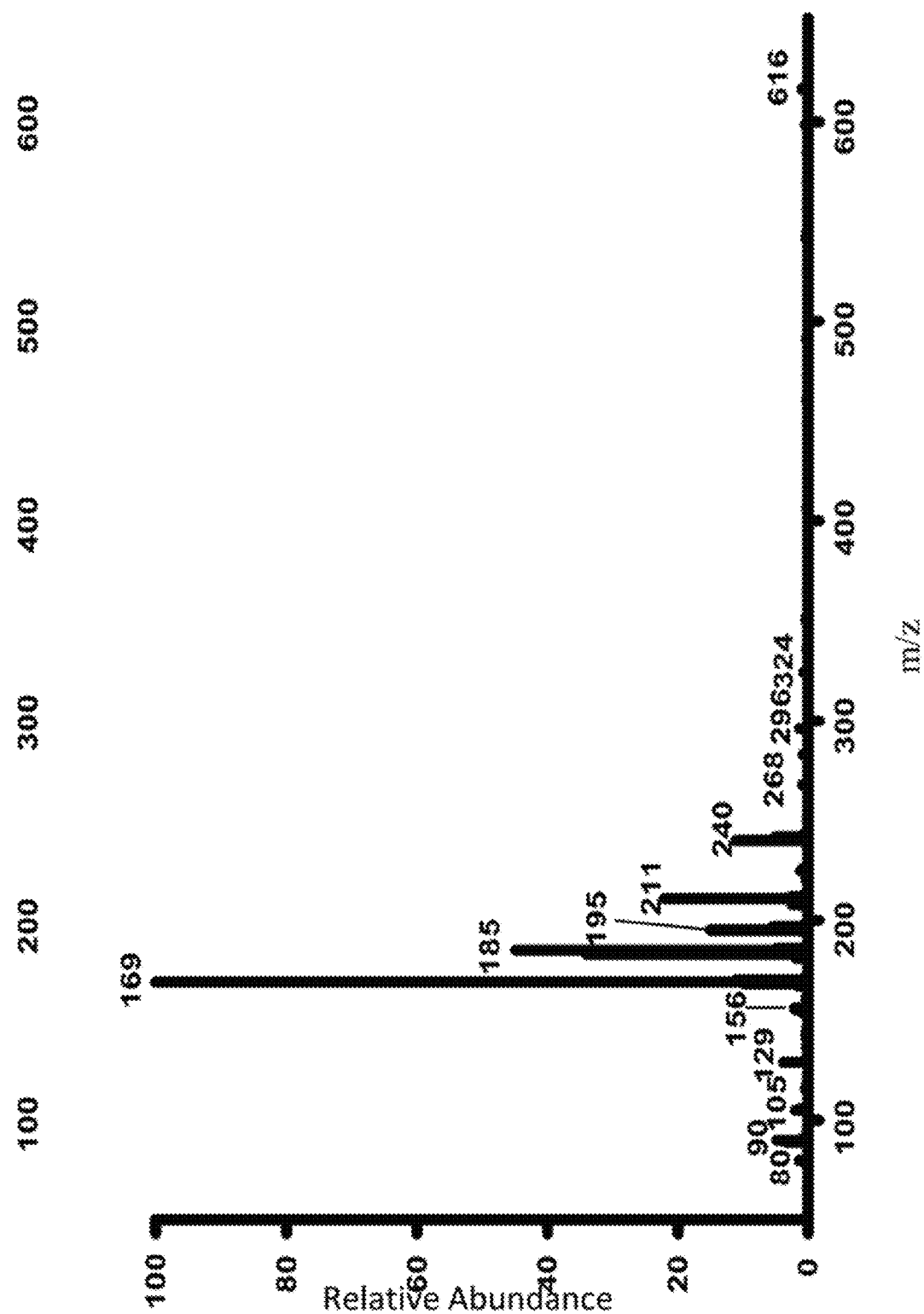
FIG. 32 illustrates HCD mass spectra of AMPP-derivatized analogue 9.
Figure 33:
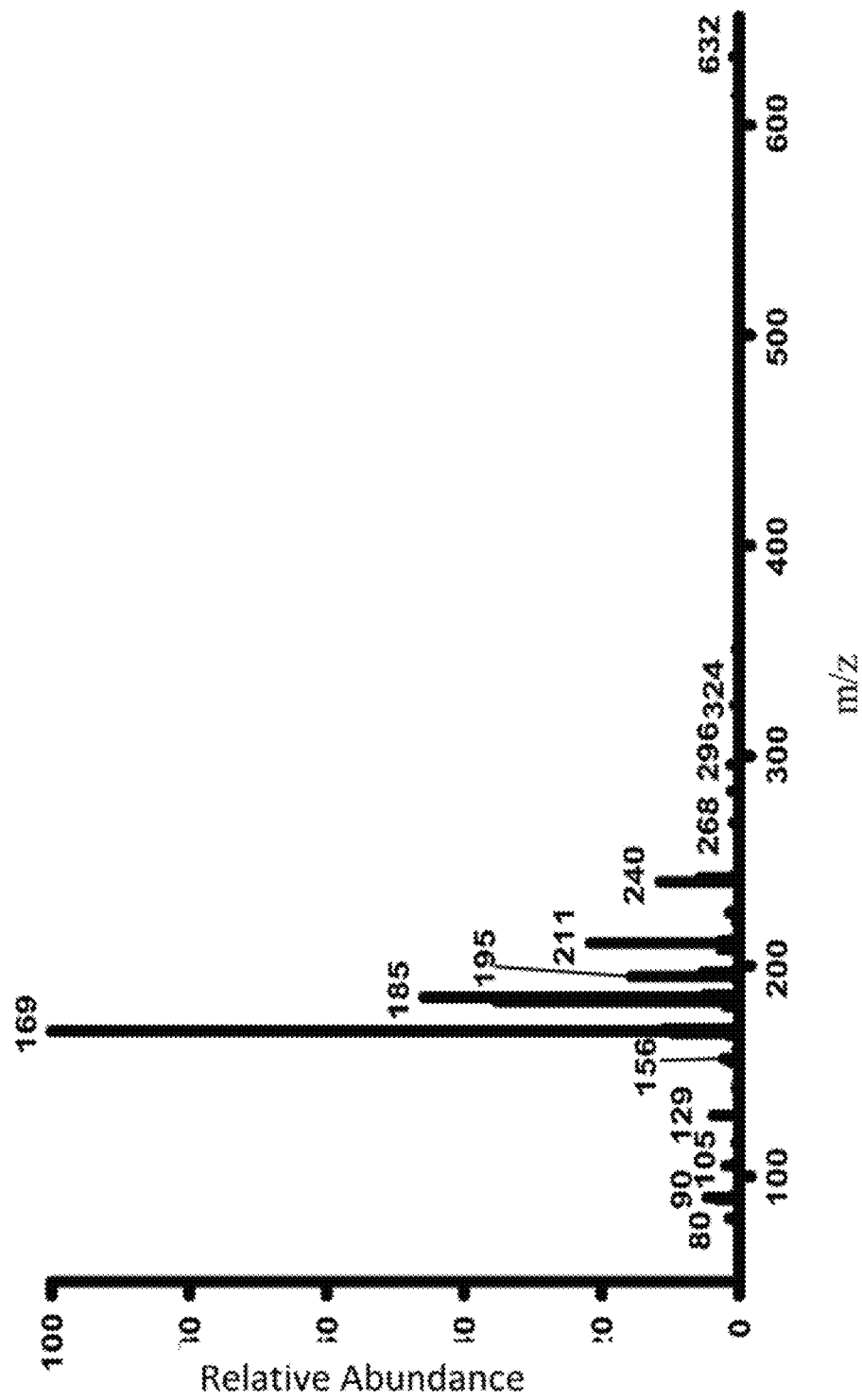
FIG. 33 illustrates HCD mass spectra of AMPP-derivatized analogue 10.

The H/D exchange experiment indicated that there are four (3 OH, COOH) and five exchangeable hydrogens (3 OH, NH, COOH) in bile acids A and B (FIGS. 20 and 21), respectively. The higher energy collisional dissociation (HCD) spectrum of bile B contains an abundant ion at m/z 74.0256, corresponding to deprotonated glycine ($C_2H_4O_2N$; calculated mass: 74.0248), confirming that bile acid B is a glycine conjugate. However, the assignment of structures for bile acids A and B was impeded by lack of interpretable fragments from steroid skeletons in HCD spectra (FIG. 22-23). Therefore, isolated bile acids A and B were converted into their N-(4-aminomethylphenyl) pyridinium (AMPP) amides. To the dried bile acid in 1.2 mL glass insert of µL Plate (VWR, West Chester, Pa.), 10 µL of 5 mg/mL AMPP suspension in acetonitrile, 10 µL of 1M EDC/1 M DMAP in chloroform, and 10 µL of N,N-dimethylformamide were added to derivatize the samples. Mixtures were capped, vortexed, and heated for 1 hour at 50° C. The mixture was dried with nitrogen stream at 50° C., and reconstituted with 200 µL of methanol-water (1:1).

LC-HRMS analysis of bile acid AMPP derivatives was then performed. The separation was performed on a Shimadzu 10A HPLC system (Shimadzu Scientific Instruments, Columbia, Md.) coupled with the LTQ Orbitrap Velos ETD™ mass spectrometer, operating with ESI source in positive mode. A MAC-MOD ACE 3 C18 (2×50 mm, 3 µm) (Chadds Ford, Pa.) connected to a Phenomenex (Torrance, Calif.) SecurityGuard C18 guard column (4×3 mm) was used for the chromatographic separation and it was maintained at room temperature. The mobile phase consisted of 0.1% formic acid in water (solvent A), and 0.1% formic acid in acetonitrile-methanol (1:4) (solvent B). The step gradient was as follows: 0-2.5 min, 20% to 100% solvent B; 2.5-6 min, 100% solvent B; 6-6.1 min, 100% to 20% solvent B; 6.1-7 min, 20% solvent B. The effluent was directed into the mass spectrometer for data acquisition within the 4-min time window (2-6 min) in which bile acids A and B were eluted; elsewhere, effluent was sent to waste to minimize source contamination. The mass spectrometer performed a full FT-MS scan (m/z 250-800) and HCD MS/MS scans precursor isolation width was 1 m/z. Full scan and HCD MS/MS mass spectra were recorded at a resolution of 100,000 at m/z 400. Automatic gain control (AGC) was used to accumulate sufficient ions. For survey scans, AGC target was $1\times10^6$ (maximum injection time 1 s). For HCD, AGC target was $1\times10^5$ (maximum inject time 100 and 25 ms, respectively). HCD was performed at normalized collision energy of 80%. Data acquisition was controlled by Xcalibur 2.1 software package. Spray voltage was set to 4.5 kV. The vaporizer temperature and temperature of the heated transfer capillary were 380 and 250° C., respectively. Sheath and auxiliary nitrogen gas were applied at a flow rate of 60 and 20 arbitrary units (AU), respectively. The data from these experiments produced informative charge-remote fragmentation for structure identification in HCD and identified the key fragments that can differentiate the positions of hydroxylation (Tables 3 and 4).

To aid interpretation of the product ion spectra of derivatized bile acids A and B, the inventors studied the fragmentation patterns of the AMPP derivatives of a series of bile acids and analogs (Tables 5-6, analogs 1-10; Tables 1-3, 7-9; Schemes 1-10).

For the preparation of [7,7,22,22-d4]-3β-(tert-Butyldimethylsilanyloxy)cholest-5-ene, a solution of $LiCuCl_4$ (0.1 M solution in THF, 3.62 mL, 0.362 mmol) and [7,7,22,22-d4]-3β-(tert-butyldimethylsilyl)oxy-20-methylpregna-5-en-22-iodide (2.03 g, 3.62 mmol), dissolved in THF (15 mL) was cooled to −15° C. The isopentylmagnesium bromide solution (2 M in diethyl ether, 3.62 mL, 7.24 mmol) is added slowly. After further stirring at −15° C. for 0.5 h, the reaction mixture was carefully quenched with saturated $NH_4Cl$ (10 mL). The reaction mixture was extracted with dichloromethane (3×30 ml). The combined organic layers were washed with saturated brine, dried over $Na_2SO_4$ and evaporated under reduced pressure. The crude product is purified on a silica gel column using 0-10% diethyl ether in hexane to give [7,7,21,21-d4]-3β-(tert-butyldimethylsilanyloxy) cholest-5-ene in 88% yield (1.62 g, 3.21 mmol) $^1H$ NMR (400 MHz, $CDC_3$): δ 5.29 (d, 1H, J=2.1 Hz), 3.46 (dddd, 1H, J=4.9, 4.9, 11.2 and 11.2 Hz), 2.19-2.27 (m, 1H), 2.14-2.18 (m, 1H), 1.99-2.02 (m, 1H), 1.63-1.86 (m, 3H), 1.11-1.62 (m, 17H), 0.97 (s, 3H), 0.86-0.96 (m, 19H), 0.68 (s, 3H), 0.06 (s, 6H). $^{13}C$ NMR (100 MHz, $CDCl_3$): δ 146.2, 125.6, 77.2, 61.3, 60.7, 54.7, 47.4, 46.8, 44.4, 44.0, 41.9, 41.1, 40.1, 36.6, 36.3, 32.8, 32.5, 30.5, 28.8, 28.2, 27.4, 27.1, 25.6, 24.0, 23.2, 22.8, 16.4, 0.03.

Preparation of [7,7,22,22-d4)-cholestane-3β,5α,6β-triol was carried out as follows: to a solution of [7,7,22,22-d4]-3β-(tert-butyldimethylsilanyloxy)cholest-5-ene (1.62 g, 3.21 mmol) in dichloromethane (100 ml) was added, by small portions, an excess of mchloroperbenzoic acid (70.1%, 0.95 g, 3.85 mmol) at room temperature. The reaction mixture was stirred overnight at room temperature, washed with aqueous $Na_2CO_3$, water and brine. After drying over $Na_2SO_4$, the evaporation of the solvent under reduced pressure afforded crude [7,7,22,22-d4]-3β-(tert-butyldimethylsilanyloxy)cholestane-5,6-epoxide (two diastereoisomers, α and β-epoxides).

A mixture of above crude product, p-toluenesulfonic acid monohydrate (87 mg, 0.321 mmol) in dioxane-water (9:1 v/v; 20 mL) was stirred and heated under reflux for 1.5 h, and evaporated under reduced pressure to dryness. The crude product was purified on a silica gel column using 0-10% methanol in dichloromethane to give impure [7,7,22,22-d4]-cholestane-3b,5a,6b-triol. Recrystallization from chloroform gave pure [7,7,22,22-d4]-cholestane-3b,5a,6b-triol in 60% yield (46 mg). $^1$H NMR (400 MHz, CD3OD): δ 3.46 (dddd, 1H, J=4.9, 4.9, 11.2 and 11.2 Hz), 3.44 (s, 1H), 1.96-2.12 (m, 2H), 1.66-1.95 (m, 3H), 1.24-1.65 (m, 12H), 1.05-1.23 (m, 10H), 0.93 (d, 3H, J=6.3 Hz), 0.88 (d, 6H, J=6.3 Hz), 0.71 (s, 3H). $^{13}$C NMR (100 MHz, CD3OD): δ 76.9, 76.5, 68.4, 57.8, 57.5, 46.6, 44.0, 41.6, 41.5, 40.8, 39.4, 37.1, 33.6, 31.8, 31.5, 29.5, 29.3, 25.3, 24.9, 23.3, 23.1, 22.4, 19.3, 17.4, 12.7.

For the preparation of 3β-hydroxy-21,26,27-trinor cholesta-5,20(22)-dien-25-oic acid methyl ester, (4-Carboxybutyl)triphenylphosphonium bromide (5.12 g, 11.54 mmol) was dissolved into anhydrous THF (30 ml) under a nitrogen atmosphere, and the reaction mixture was cooled to 0° C. KHMDS in toluene (0.5 M, 57.72 mL, 28.86 mmol) was added dropwise, and the reaction was stirred at 0° C. for 5 minutes. The reaction was then cooled to −40° C., and (3β,17β)-3-methoxymethoxyandrost-5-ene-17-carboxaldehyde (1.0 g, 2.89 mmol) dissolved in anhydrous THF (30 mL) was added dropwise, and the reaction was stirred at −40° C. for 15 min, and then allowed to slowly warm to room temperature (rt) over 1 h. The reaction was then quenched with saturated aqueous NH$_4$Cl solution and extracted with ethyl acetate (3×25 mL). The organic phases were then combined, dried over Na$_2$SO$_4$ and concentrated in vacuum. The crude 3β-Methoxymethoxy-21,26,27-trinor cholesta-5,20(22)-dien-25-oic acid was obtained by passing the extract through a column of silica gel (methanol-dichloromethane, gradient elution) and used directly in the next step.

The crude 3β-Methoxymethoxy-21,26,27-trinor cholesta-5,20(22)-dien-25-oic acid was dissolved in methanol (50 mL), and acetyl chloride (2.6 mL) was added dropwise over 1 h. The reaction was then stirred for 16 h at rt. Upon completion, the reaction was cooled to 0° C. and neutralized with saturated aqueous NaHCO$_3$, water (50 mL) was added, and the reaction mixture was extracted with dichloromethane (5×30 mL). The organic phases were then combined, dried over Na$_2$SO$_4$ and concentrated in vacuo. Column chromatography on silica gel (ethyl acetate-hexane, gradient elution) yielded 3β-hydroxy-21,26,27-trinor cholesta-5,20(22)-dien-25-oic acid methyl ester as a white solid (1.09 g, 2.45 mmol; 85% over 2 steps). $^1$H NMR (400 MHz, CDCl$_3$): δ 5.22-5.42 (m, 3H), 3.68 (s, 3H), 3.46 (dddd, 1H, J=4.9, 4.9, 11.2 and 11.2 Hz), 2.19-2.37 (m, 5H), 1.03-2.18 (m, 21H), 1.02 (s, 3H), 0.86-0.96 (m, 1H), 0.68 (s, 3H). $^{13}$C NMR (100 MHz, CDCl$_3$): δ 174.4, 141.0, 132.4, 129.5, 121.8, 71.9, 56.2, 51.6, 50.5, 48.7, 44.4, 42.4, 37.9, 37.4, 36.8, 33.7, 32.2, 32.1, 31.8, 29.1, 27.1, 25.4, 25.3, 20.9, 19.6, 12.8.

For the preparation of 3β,5α,6β-hydroxy-21,26,27-trinor cholesta-5-en-25-oic acid methyl ester, 3β-Hydroxy-21,26,27-trinor cholesta-5,20(22)-dien-25-oic acid methyl ester (133 mg, 0.33 mmol) was dissolved in a 3:1 mixture of THF-water (1 mL) at 0° C. under a nitrogen atmosphere. RUCl$_3$—H$_2$O (22 mg, 0.083 mmol) was added, followed by the portionwise addition of NaBH$_4$ (25 mg, 0.66 mmol). The reaction was allowed to slowly warm to room temperature and was stirred 16 h. The reaction was filtered through a small pad of silica, eluting with dichloromethane. The product was then further diluted with dichloromethane (5 mL), and washed with saturated aqueous NaHCO$_3$ (1 mL) then water (1 mL). The organic phases were combined, dried over Na$_2$SO$_4$ and concentrated in vacuo. The crude 3β-hydroxy-21,26,27-trinor cholesta-5-en-25-oic acid methyl ester (containing a slight amount of Δ5,6 reduced) was then used directly in the next step.

Crude product from the last step (53 mg, 0.124 mmol) was dissolved into formic acid (0.5 mL) by stirring at 75° C. for 5 min. After the reaction mixture was cooled, 30% H$_2$O$_2$ (0.05 mL) was added dropwise. Dichloromethane (0.4 mL) was immediately added, and the reaction mixture was stirred at room temperature for 1 h. The dichloromethane was evaporated on a rotary evaporator, and dioxane (0.5 mL) water (0.75 mL) were added to the residue. The reaction mixture was then refluxed for 16 h. The reaction mixture was evaporated to dryness on a rotary evaporator, and re-dissolved in methanol (2 mL). To the mixture was added NaOH (13 mg, 0.32 mmol) and the reaction mixture was stirred 2 h at room temperature. The reaction mixture was neutralized with formic acid and the reaction was evaporated to dryness to give the crude 3β,5α,6β-hydroxy-21,26,27-trinor cholesta-5-en-25-oic acid as a white residue.

The crude 3β,5α,6β-hydroxy-21,26,27-trinor cholesta-5-en-25-oic acid was suspended in methanol (5 mL), and acetyl chloride (0.25 mL) was added dropwise. The reaction mixture was allowed to stir for 1 h. The reaction was cooled to 0° C., and neutralized with saturated aqueous NaHCO$_3$. The reaction mixture was diluted with water (5 mL) and was extracted with dichloromethane (5×5 mL). The organic phases were combined, dried over Na$_2$SO$_4$, and concentrated in vacuo. The residue was purified by column chromatography on silica gel (methanol-dichloromethane, gradient elution), to yield 3β,5α,6β-hydroxy-21,26,27-trinor cholesta-5-en-25-oic acid methyl ester as a white solid (34.0 mg, 60% yield over 3 steps). $^1$H NMR (400 MHz, CD3OD): δ 4.08 (dddd, 1H, J=4.9, 4.9, 11.2 and 11.2 Hz), 3.62 (s, 3H), 3.42 (dd, 1H, J=4.9 and 11.2 Hz), 2.32 (d, 2H, J=6.4 Hz), 2.10-2.19 (m, 1H), 1.03-2.18 (m, 22H), 1.02 (s, 3H), 0.86-0.96 (m, 3H), 0.68 (s, 3H). $^{13}$C NMR (100 MHz, CDCl$_3$): δ 176.4, 77.1, 76.9, 56.2, 52.6, 52.5, 47.7, 43.8, 41.8, 39.8, 35.5, 35.1, 33.7, 31.9, 31.8, 30.8, 30.7, 29.4, 26.2, 25.6, 22.2, 17.7, 13.5, For preparation of 3β,5α,6β-hydroxy-21,26,27-trinor cholesta-5-en-25-oic acid (7), 3β,5α,6β-Hydroxy-21,26,27-trinor cholesta-5-en-25-oic acid methyl ester (34.0 mg, 0.078 mmol) was dissolved in a 4:1 mixture of dioxane-water (1.25 mL) and NaOH (6 mg, 150 mmol) was added. The reaction was stirred overnight at 40° C. and quenched with 1N HCl, and the solvents were evaporated. The remaining solids were washed with water (1 mL×3). The remaining solid was recrystallized in a 1:1 mixture of warm methanol-dichloromethane to yield 3β,5α,6β-hydroxy-21,26,27-trinor cholesta-5-en-25-oic acid as colorless crystals in 90% yield (29.6 mg). $^1$H NMR (400 MHz, CD3OD): δ 3.81 (dddd, 1H, J=4.9, 4.9, 11.2 and 11.2 Hz), 3.63 (dd, 1H, J=4.9 and 11.2 Hz), 2.15 (d, 2H, J=6.4 Hz), 1.03-2.18 (m, 23H), 1.02 (s, 3H), 0.86-0.96 (m, 3H), 0.51 (s, 3H). $^{13}$C NMR (100 MHz, CDCl$_3$): δ 174.4, 73.1, 72.9, 61.9, 55.2, 50.6, 45.7, 42.1, 41.9, 38.9, 34.7, 33.8, 31.8, 30.7, 28.1, 24.4, 20.2, 16.3, 12.6.

For the preparation of bile acid A N-hydroxysuccinimide ester, bile acid A (0.62 g, 1.52 mmol) was dissolved into a mixture of dioxane (15 mL) and dichloromethane (15 mL) and 1-Ethyl-3-(3-dimethylaminopropyl)carbodiimide (1.41 g, 9.10 mmol) was added. N-hydroxysuccinimide (1.05 g, 9.10 mmol) was then added and the reaction was stirred 16 h at 35° C. Upon reaction completion, the reaction mixture was loaded directly onto a silica gel column, and purified using methanol-dichloromethane, gradient elution, to yield the bile acid A N-hydroxysuccinimide ester in 66% yield (0.50 mg, 0.99 mmol). $^1$H NMR (400 MHz, CDCl$_3$:CD$_3$OD; 5:1) δ 2.77 (m, 4H, succinate), 1.06 (s, 3H), 0.87 (d, 3H, J=6.4 Hz), 0.70 (s, 3H); $^{13}$C NMR (100 MHz, CDCl$_3$: CD$_3$OD, 2:1) δ 172.9 169.9, 169.4, 75.8, 75.4, 67.3, 55.9, 55.7, 45.4, 42.8, 39.9, 38.1, 35.2, 34.0, 32.3, 30.6, 30.3, 30.3, 28.1, 27.9, 25.6 (×2), 25.5, 24.1, 21.1, 18.1, 16.6.

For the preparation of N-(3β,5α,6β)-3,6-Diacetoxy-5-hydroxy-cholan-24-oyl)glycine methyl ester, bile acid A N-hydroxysuccinimide ester (2.08 g, 4.1 mmol) was dissolved in anhydrous THF (200 mL). N,N-disopropylethylamine (2.9 mL, 16.45 mmol) was added, followed by glycine methyl ester (0.77 g, 6.2 mmol) and the reaction was stirred 16 h at room temperature, and the reaction mixture was then concentrated in vacuo, to give the 2.5 g of crude N-(3β,5α,6β-trihydroxy-cholan-24-oyl)glycine methyl ester.

N-(3β,5α,6β-trihydroxy-cholan-24-oyl)glycine methyl ester was acetylated as part of the purification process. Accordingly, a portion of the impure N-(3β,5α,6β-trihydroxy-cholan-24-oyl)glycine methyl ester (2.5 g, 5.2 mmol) was dissolved in pyridine (40 mL) and 4-dimethylaminopyridine (327 mg, 2.6 mmol) was added, followed by acetic anhydride (4.0 mL, 41.8 mmol). After 16 h at room temperature, the pyridine was evaporated under vacuum, and the reaction was re-dissolved in dichloromethane (75 mL) and washed with water (30 mL), 1N HCl (30 mL), water (30 mL), saturated aqueous NaHCO$_3$ solution (30 mL), water (30 mL). The organic layer was concentrated in vacuo, and the residue was purified by column chromatography on silica gel (methanol-dichloromethane, gradient elution), to yield N-(3β,5α,6β)-3,6-diacetoxy-5-hydroxy-cholan-24-oyl)glycine methyl ester in 73% yield (1.7 g, 3.0 mmol). $^1$H NMR (400 MHz, CDCl$_3$) δ 6.53 (t, 1H, J=5.6 Hz), 5.05 (m, 1H), 4.64 (br s, 1H), 3.92 (t, 2H, J=5.4 Hz), 3.65 (s, 3H, OCH$_3$), 2.98 (s, 1H), 1.98 (s, 3H), 1.92 (s, 3H), 1.05 (s, 3H), 0.83 (d, 3H, J=6.4 Hz), 0.59 (s, 3H); $^{13}$C NMR (100 MHz, CDCl$_3$) δ 174.1, 170.8, 170.7, 170.3, 76.2, 74.4, 70.9, 56.0, 55.7, 52.2, 44.7, 42.7, 41.1, 39.9, 38.3, 36.5, 35.5, 33.1, 31.8, 31.6, 31.3, 30.7, 28.1, 26.6, 24.0, 21.5, 21.4, 21.0, 18.3, 16.3, 12.2.

For preparation of bile acid B, N-(3β,5α,6β)-3,6-Diacetoxy-5-hydroxy-cholan-24-oyl)glycine methyl ester (1.03 g, 1.83 mmol) was dissolved into a mixture of methanol (50 mL) and water (50 mL), crushed NaOH (4.0 g, 100 mmol) was added, and the reaction was stirred at 40° C. for 16 h. Upon completion, the solvents were evaporated under vacuum, and the reaction contents were heated in hot methanol, and the remaining insoluble solids were filtered. This step was repeated 2 more times on the remaining solids to ensure the majority of the steroid was dissolved. The filtrates were combined and concentrated to give bile acid B as a white solid in quantitative yield (0.85 g, 1.83 mmol). m.p. 259-261° C. (methanol); IR: 3274, 2918, 2863, 1713, 1651, 1594, 1403, 1036 cm−1; $^1$HNMR (400 MHz, CD$_3$OD) δ 4.01 (m, 1H), 3.76 (s, 2H), 3.45 (s, 1H), 2.36-2.25 (m, 1H), 2.10-2.19 (m, 2H), 1.90-2.10 (m, 2H), 1.21-1.90 (m, 16H), 1.05-1.21 (m, 7H), 0.97 (d, 3H, J=5.2 Hz), 0.72 (s, 3H); $^{13}$C NMR (100 MHz, CD$_3$OD) δ 176.5, 175.9, 76.8, 76.5, 68.3, 57.4, 57.4, 46.5, 44.0, 44.0, 41.5 (×2), 39.3, 36.9, 35.3, 34.0, 33.5, 33.1, 31.7, 31.6, 29.2, 25.2, 22.3, 18.9, 17.3, 12.6.

For the preparation of N-(3β,5α,6β)-3,6-diacetoxy-5-hydroxy-cholan-24-oyl)glycine-[$^{13}$C$_2$, $^{15}$N] methyl ester, bile acid A N-hydroxysuccinimide ester (1.5 g, 2.97 mmol) was dissolved in anhydrous THF (150 mL) and glycine methyl ester (2.1 mL, 11.87 mmol) was added. Glycine-[$^{13}$C$_2$, $^{15}$N] (0.57 g, 4.45 mmol) was dissolved into water (15 mL) and added to the reaction flask. The reaction was stirred vigorously for 10 min (or until reaction becomes a clear homogenous mixture). The reaction was then stirred an additional 16 h at rt. Solvents were then evaporated under vacuum, and the reaction contents were re-dissolved in hot THF and the insoluble solids were filtered off, and the filtrate was concentrated to give crude bile acid B-[$^{13}$C$_2$, $^{15}$N]. The impure bile acid B-[$^{13}$C$_2$, $^{15}$N] (200 mg, 0.43 mmol) was then re-dissolved into methanol (50 mL) and cooled to 0° C. Acetyl chloride (2.5 mL) was added dropwise. After 10 min at 0° C., the reaction was brought to rt and stirred 16 h. Upon completion, the reaction was cooled to 0° C. and was carefully neutralized with saturated aqueous NaHCO$_3$ solution followed by adding water (50 mL). The reaction mixture was extracted with dichloromethane (4×50 mL) and concentrated in vacuo. The crude glycine-[$^{13}$C$_2$, $^{15}$N] methyl ester was re-dissolved in pyridine (10 mL) and 4-dimethylaminopyridine (26 mg, 0.21 mmol) was added, followed by acetic anhydride (0.34 mL, 3.42 mmol). After 16 h at rt, the pyridine was evaporated under vacuum, and the reaction was redissolved in dichloromethane (30 mL) and washed with water (10 mL), 1N HCl (10 mL), water (10 mL), saturated aqueous NaHCO$_3$ solution (10 mL), water (10 mL). The organic layer was concentrated in vacuo, and the residue was purified by column chromatography on silica gel (methanol-dichloromethane, gradient elution), to yield N-(3β,5α,6β)-3,6-diacetoxy-5-hydroxycholan-24-oyl)glycine-[$^{13}$C$_2$, $^{15}$N] methyl ester in 64% yield (157 mg, 0.28 mmol). $^1$H NMR (400 MHz, CDCl3) δ 6.07 (d, 1H, J=9.4 Hz), 5.14 (m, 1H), 4.70 (s, 1H), 4.21 (br s, 1H), 3.86 (br s, 1H), 3.75 (d, 3H, J=3.6 Hz, OCH3), 2.06 (s, 3H), 2.01 (s, 3H), 1.14 (s, 3H), 0.92 (d, 3H, J=6.4 Hz), 0.68 (s, 3H); $^{13}$C NMR (100 MHz, CDCl$_3$) δ 174.1, 173.9, 171.2 (13C), 170.6 (13C), 76.3, 74.8, 71.0, 56.1, 55.8, 52.5, 44.9, 42.9, 41.7 (13C), 41.5 (13C), 41.0 (13C), 40.9 (13C), 40.0, 38.5, 36.8, 35.6, 33.4, 33.3, 31.9, 31.7, 31.4, 30.8, 28.3, 26.8, 24.2, 21.6, 21.6, 21.1, 18.5, 16.4, 12.3.

For the preparation of bile acid B-[$^{13}$C$_2$, $^{15}$N], N-(3β,5α,6β)-3,6-Diacetoxy-5-hydroxy-cholan-24-oyl)glycine-[13C$_2$, $^{15}$N] methyl ester (157 mg, 0.28 mmol) was dissolved into a mixture of methanol (5 mL) and water (5 mL), crushed NaOH (0.5 g, 12.5 mmol) was added, and the reaction was stirred at 40° C. for 16 h. Upon completion, the solvents were evaporated under vacuum, and the reaction contents were heated in hot methanol, and the remaining insoluble solids were filtered. This step was repeated 2 more times on the remaining solids to ensure the majority of the steroid was dissolved. The filtrates were combined and concentrated to give bile acid B as a white solid in 70% yield (91 mg, 0.19 mmol). m.p. 275-277° C.; IR: 3391, 2936, 2867, 1629, 1551, 1376, 1042 cm−1; $^1$H NMR (400 MHz, CD$_3$OD) δ 4.01 (m, 1H), 3.91 (d, 1H, J=5.6 Hz), 3.56 (d, 1H, J=5.2 Hz), 3.45 (br s, 1H), 2.36-2.25 (m, 1H), 2.10-2.19 (m, 2H), 1.90-2.10 (m, 2H), 1.21-1.90 (m, 16H), 1.05-1.21 (m, 7H), 0.97 (d, 3H, J=6.4 Hz), 0.72 (s, 3H); $^{13}$C NMR (100 MHz, CD$_3$OD) δ 177.0 ($^{13}$C), 176.7, 176.4 (13C), 176.3, 76.8, 76.5, 68.3, 57.4, 57.4, 46.5, 44.9 ($^{13}$C), 44.8 ($^{13}$C), 44.3 ($^{13}$C), 44.2 ($^{13}$C), 44.0 ($^{13}$C), 41.5, 41.4, 39.3, 37.0, 35.3, 33.5, 33.1, 31.7, 31.6, 29.2, 25.2, 22.3, 18.9, 17.3, 12.6.

Shown in FIG. 24-33 are the product ion spectra of bile acid AMPP derivatives studied. The diagnostically significant fragment ions are presented in Tables 3, 7-9. In addition to the two major fragment ions present at m/z 169 (fragment T) and m/z 183 (fragment S) arising from AMPP tag, tandem mass spectra of AMPP-derivatized bile acids demonstrated less abundant but informative fragment ions result from cleavages of ring systems and side chains of bile acids. The structures of fragments S and T have been proposed by Gross et al. (Yang, K., et al., Anal. Chem., 85, 9742-9750).

Fragmentation of AMPP derivatives of unconjugated bile acids (analogues 1-7). The HGD spectra of all unconjugated bile acid AMPP derivatives showed ions formed by neutral loss of 18 Da (fragment A, —$H_2O$), 32 Da (fragment B, —$CH_3OH$), while only some AMPP derivatives produce product ions from loss of 34 Da (fragment D, —$CH_3OH$—$H_2$), 36 Da (fragment E, -$2H_2O$), 50 Da (fragment C, —$H_2O$—$CH_3OH$), 52 Da (fragment F, —$CH_3OH$—$H_2O$—$H_2$), 68 Da (fragment G, -$2H_2O$—$CH_3OH$) (Scheme 1). The fragment B generated by the loss of $CH_3OH$ is presented in all bile acids (1-7) examined, requesting fragmentation on a common structural moiety. The neutral loss of 19-methyl and 3-hydroxyl groups accompanied by cleavage of the bond between C-4 and C-5 is postulated, giving rise to fragment B (Scheme 1, route a). The presence of a double bond between C5 and C10 in fragment B probably encourages C8-C9 bond fragmentation by a retro Diels Alder reaction (Scheme 1, route b), and subsequent hydrogen rearrangement leads to fragment H via cleavage of the bond between C-13 and C-17 and neutral loss of A and B ring moieties. The 7-hydroxyl group in CDCA (2), CA (3), α-muricholic acid (4), β-muricholic acid (5), 5β-cholanic acid-3β,4β,7α-triol (6) was not lost during the formation of fragment H, thus, fragment H can be used to assign 7-hydroxyl group.

The fragmentations at ring junctions provide the most important information about the nature and location of substituents on the steroid ring (Scheme 2). A retro-cycloaddition mechanism accounts for these cleavages to yield Fragments I (Scheme 2, route a), J (Scheme 2, route b) and K (Scheme 2, route c). The bile acid isomers, which differed in the position of hydroxylation, could be differentiated from their product ion spectra. The DCA (1), CDCA (2), CA (3), α-muricholic acid (4), β-muricholic acid (5), 5β-cholanic acid-3β,4β,7α-triol (6) have no hydroxyl group presented on D ring and side chain, and a common Fragment K at m/z 349 was observed. The fragment J at m/z 419 was observed for DCA (1) and CA (3) due to the presence of a hydroxyl group on C ring, and at m/z 403 for α/β-muricholic acid (4/5) and 5β-cholanic acid-3β,4β,7α-triol 6 due to the absence of hydroxyl group on C ring. The CA (3) and α/β-muricholic acid (4/5) gave fragment I at m/z 503 due to the presence of 2 hydroxyl groups on B and C rings, while the CDCA (2) and 5β-cholanic acid-3β,4β,7α-triol (6) gave fragment I at m/z 487 due to only 1 hydroxyl group on B and C rings. Introduction of a hydroxyl group at C-5 position inhibited the cleavage at A/B ring junction of 21,26,27-trinorcholestan-25-oic acid-3β,5α,6β-triol (7). The lack of fragment I is characteristic of 5-hydroxylation.

For the AMPP derivatives of natural occurring bile acids 1-6, the D-ring fragmentation probably involved hydrogen rearrangement and cycloelimination to give fragment L at m/z 309, which produced fragment M at m/z 293 by lose a methane involving H-transfer via six20 membered ring transition state (Scheme 3). The cleavage of D-ring of AMPP derivative of 21,26,27-trinorcholestan-25-oic acid-3β,5α,6β-triol (7) gave fragment L* at m/z 323 and a fragment M at m/z 309 that was formed via cycloelimination (Scheme 3).

The bile acids 1-6 are naturally occurring bile acids that have a common 5 carbons branched side chain at position 17 of steroid core. Series of charge-remote fragment ion at m/z 267 (fragment N), 239 (fragment O), 211 (fragment P), and 226 (fragment Q), were observed and were consistent with side-chain bond cleavages. The side chain fragments N (Scheme 4, route a), O (Scheme 4, route b), P (Scheme 4, route c) and S (Scheme 5, route b) can be formed via 1,4-hydrogen elimination. The fragments Q (Scheme 5, route a) and T (Scheme 5, route c) are formed by hemolytic cleavage. The subsequent cyclization of fragment Q and elimination of hydrogen radical and methyleneamine gave fragment R (Scheme 5). The 21,26,27-trinorcholestan-25-oic acid-3β,5α,6β-triol (7) has a 6 carbons straight side chain at position 17 of steroid core, which underwent similar side chain fragmentation. The fragments N and O from trinorcholestan-25-oic acid-3β,5α,6β-triol (7) are shifted up in mass by 14 Da to m/z 281, 253, respectively (Table 3).

Fragmentation of AMPP derivatives of glycine conjugated bile acids (8-10). Similar to unconjugated bile acids AMPP derivatives of (1-7), glycine conjugated bile acid AMPP derivatives (8-10) generated many charge remote fragment ions in the HCD (Table 9). The ions arising from neutral of loss of 18 Da (fragment GA, —$H_2O$) and 32 Da (fragment GC, —$CH_3OH$, Scheme 6, route a) were again observed in (8-10), while the ion corresponding to loss of 36 Da (fragment GB, —2H2O) was only observed in 8 (Scheme 6). The retro Diels Alder reaction in fragment GC cleaves C8-C9 bond (Scheme 6, route b), and subsequent hydrogen rearrangement and cleavage of the bond between C-13 and C-17 leads to fragment GH. Again the 7-hydroxyl group in GCDCA (9) and GCA (10) was intact in fragment GH, which can be used to assign 7-hydroxyl group. The cleavages at A/B, B/C, C/D ring junctions via retrocycloaddition mechanism yielded fragments GF (Scheme 7, route a), GG (Scheme 7, route b), and GI (Scheme 7, route c), respectively. The hydrogen rearrangement (Scheme 8, route a) and cycloelimination (Scheme 8, route b) of D-ring in AMPP derivatives (8-10) gives rise to fragment GK at m/z 366 and GJ at m/z 352, respectively. The later loses methane to produce fragment GL at m/z 350, and eliminates an ethane after 1,3-H shift to afford fragment GM at m/z 336. The neutral loss of methane and ethane is postulated to proceed via six-membered ring transition state (Scheme 8).

The cleavage of side chain of glycine conjugated bile acid AMPP derivatives gives rise to not only fragment ions that are similar to those observed for unconjugated counterparts but also those unique for acyl glycine moiety. Fragments GV (Scheme 9, route g) and GW (Scheme 9, route h) at m/z 183 and 169 are same as fragment S and T, respectively, and they are probably formed in the same way. The formation of fragments GN (m/z 324, Scheme 9, route a), GO (m/z 296, Scheme 9, route b), and GP (m/z 268, Scheme 9, route c) is postulated through 1,4-hydrogen elimination in comparable ways as suggested for generation of fragments N, O and P. The 1,4-hydrogen elimination on side chain also leads to fragment GQ at m/z 211 (Scheme 9, route d) and GR at m/z 240 (Scheme 9, route e). The elimination of an isocyanic acid from fragment GR give rise to fragment GS, and its formation may involve a rearrangement to 1,4-Dihydro-3 (2H)-isoquinolone followed by retro Diels Alder reaction and cyclization. Expulsion of hydrogen from fragment GS yields fragment GT. A major ion (fragment GU) at m/z 185 probably results from β-elimination (Scheme 9, route f).

The glycine moiety can be eliminated as aziridinone to give fragment GX, which is corresponding unconjugated bile acid AMPP derivative. Further loss of one and two waters from fragment GX yields fragments GY and GZ, respectively (Scheme 10). However, the further ring and side chain fragmentation of fragment GX was not observed because of its low abundance. The elimination of aziridinone may involve rearrangement of amides and subsequent nucleophilic attack of released amino on the glycine amide (Scheme 10, route a). Loss of CO probably from glycine moiety in fragment GA produces fragment GAA that loses a pyridine by charge driven fragmentation to afford fragment GAB (Scheme 10, route b).

Figure 34A:
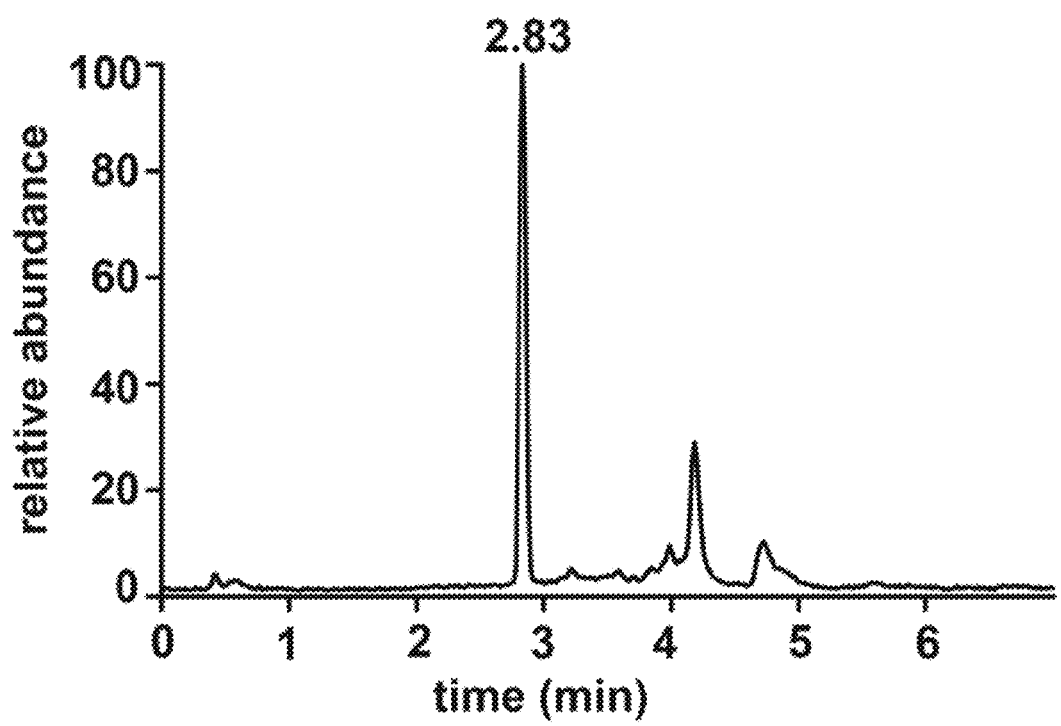
FIG. 34A-B illustrates chromatograms (detected by HCD MS/MS) and HCD mass spectra of AMPP derivatives of bile acid A in NPC1 plasma.
Figure 34B:
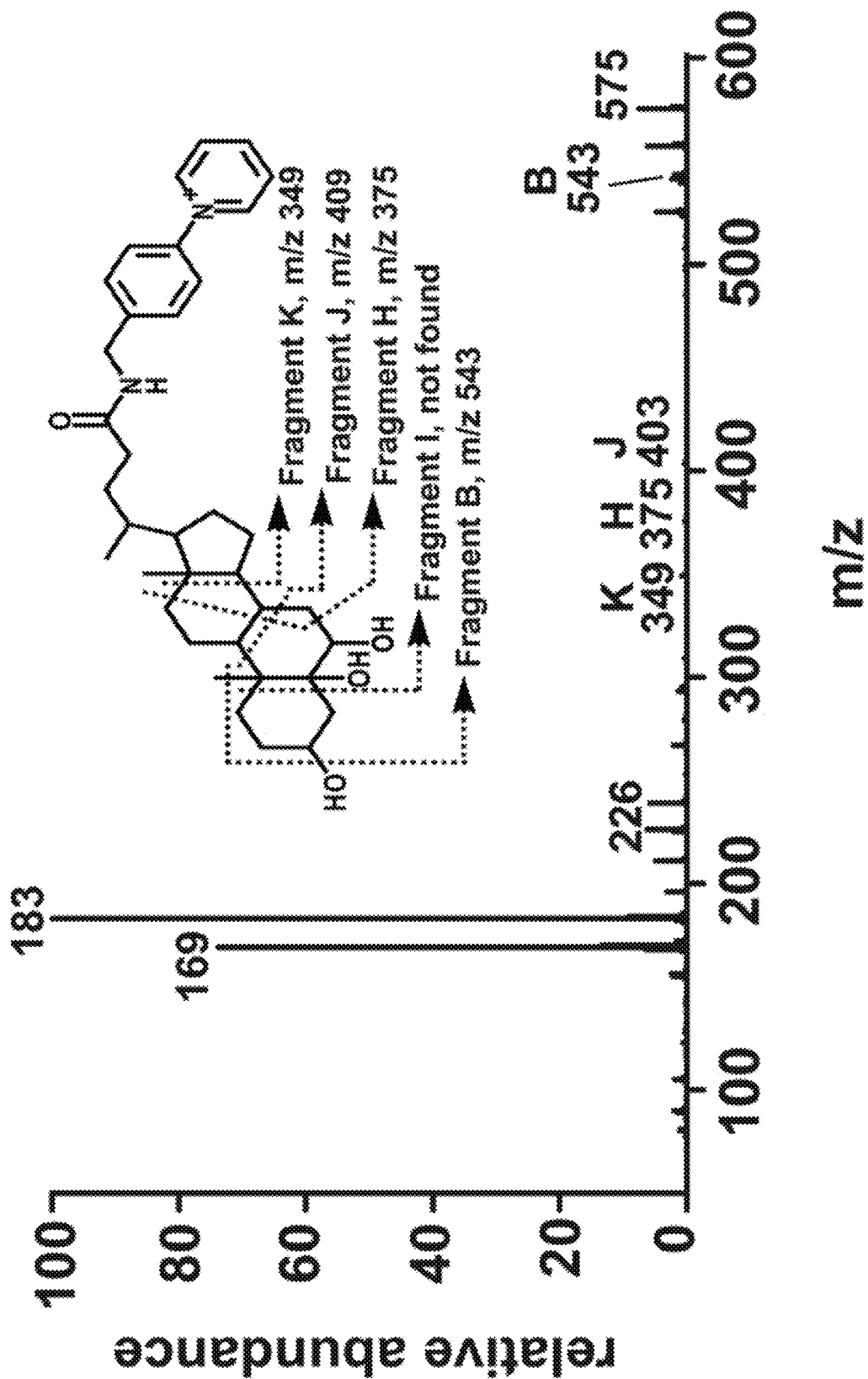

Fragmentation of AMPP derivatives of bile acid A and B. The HCD spectrum of bile acid A AMPP derivative is dominated with fragment T at m/z 169 and fragment S at m/z 183 arising from AMPP tag (FIG. 34A-B). The fragment B at m/z 543 resulting from neutral loss of a methanol suggests there is 3-hydroxyl group on A ring. The fragment K at m/z 349 indicates there is no hydroxyl group on D ring and side chain, which is also confirmed by fragments L (m/z 309) and M (m/z 293) from cleavage of D ring, as well as fragments N (m/z 267), O (m/z 239), P (m/z 211), Q (m/z 226), R (m/z 196) from cleavage of side chain. The fragment J at m/z 403 indicates there is no hydroxyl group on C ring. The fragment H at m/z 375 suggests that no hydroxyl group is located at C-7 position of B ring. The lack of fragment I suggests there is 5-hydroxyl group. The ions corresponding to neutral loss of 18 Da (fragment A, —$H_2O$), 32 Da (fragment B, —$CH_3OH$), while only some AMPP derivatives produce product ions from loss of 34 Da (fragment D, —$CH_3OH$—$H_2$), 36 Da (Fragment E, -2$H_2O$), 50 Da (Fragment C, —$H_2O$—$CH_3OH$), 52 Da (Fragment F, —$CH_3OH$—$H_2O$—$H_2$), 68 Da (fragment G, -2$H_2O$—$CH_3OH$) were also observed (Table 3). The bile acid A is temporarily assigned as 5α-cholanic acid-3β,5α,6β-triol.

The HCD spectrum of bile acid B AMPP derivative is dominated with fragment GW at m/z 169, fragment GU at m/z 185, and fragment GV at m/z 183 arising from AMPP tag (FIG. 35). The elimination of aziridinone to yield fragment X at m/z 575 indicates the presence of glycine conjugate. Other fragments that are characteristics of glycine conjugate include fragments GP (m/z 268), GQ (m/z 211), GR (m/z 240), GS (m/z 197), GT (m/z 195), GY (m/z 586), and GZ (m/z 507). The fragment GC at m/z 600 resulting from neutral loss of a methanol suggests there is 3-hydroxyl group on A ring. The fragment GI at m/z 406 indicates there is no hydroxyl group on D ring and side chain. The D ring cleavage fragments at m/z 352 (fragment GJ), m/z 366 (fragment GK), m/z 350 (fragment GL) and m/z 336 (fragment GM), and side chain cleavage at m/z 324 (fragment GN) and m/z 296 (fragment GO) also confirm that no hydroxyl group presents on D ring and side chain. The fragments GG at m/z 460 and GH at m/z 432 indicate there is no hydroxyl group on C ring. The lack of fragment GF suggests there is 5-hydroxyl group. The ions corresponding to neutral loss of 18 Da (fragment GA, —$H_2O$), 36 Da (fragment GB, -2$H_2O$), 34 Da (fragment GD, —$CH_3OH$—$H_2$), and 50 Da (fragment GE, —$H_2O$—$CH_3OH$) were also observed (Table 4). The structure of bile acid A is temporarily assigned as 5α-cholanic acid-3β,5α,6β-triol N-(carboxymethyl)-amide.

Figure 36A:
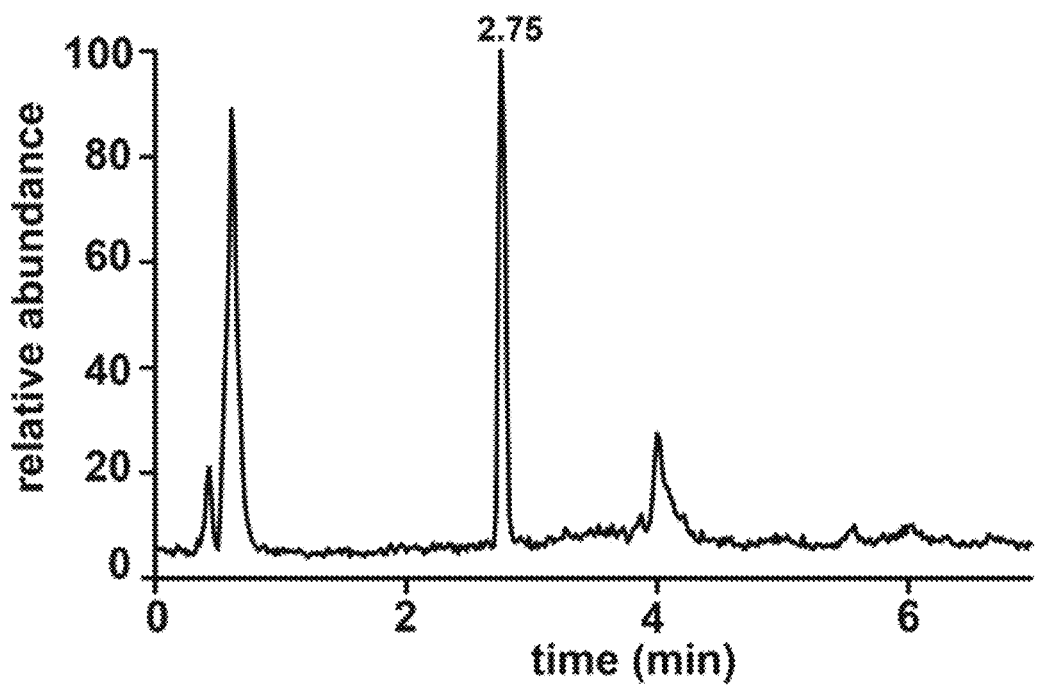
FIG. 36A-B illustrates chromatograms (detected by HGD MS/MS) and HCD mass spectra of AMPP derivative of bile acid B (detected by MS2) in NPC1 plasma.
Figure 36B:
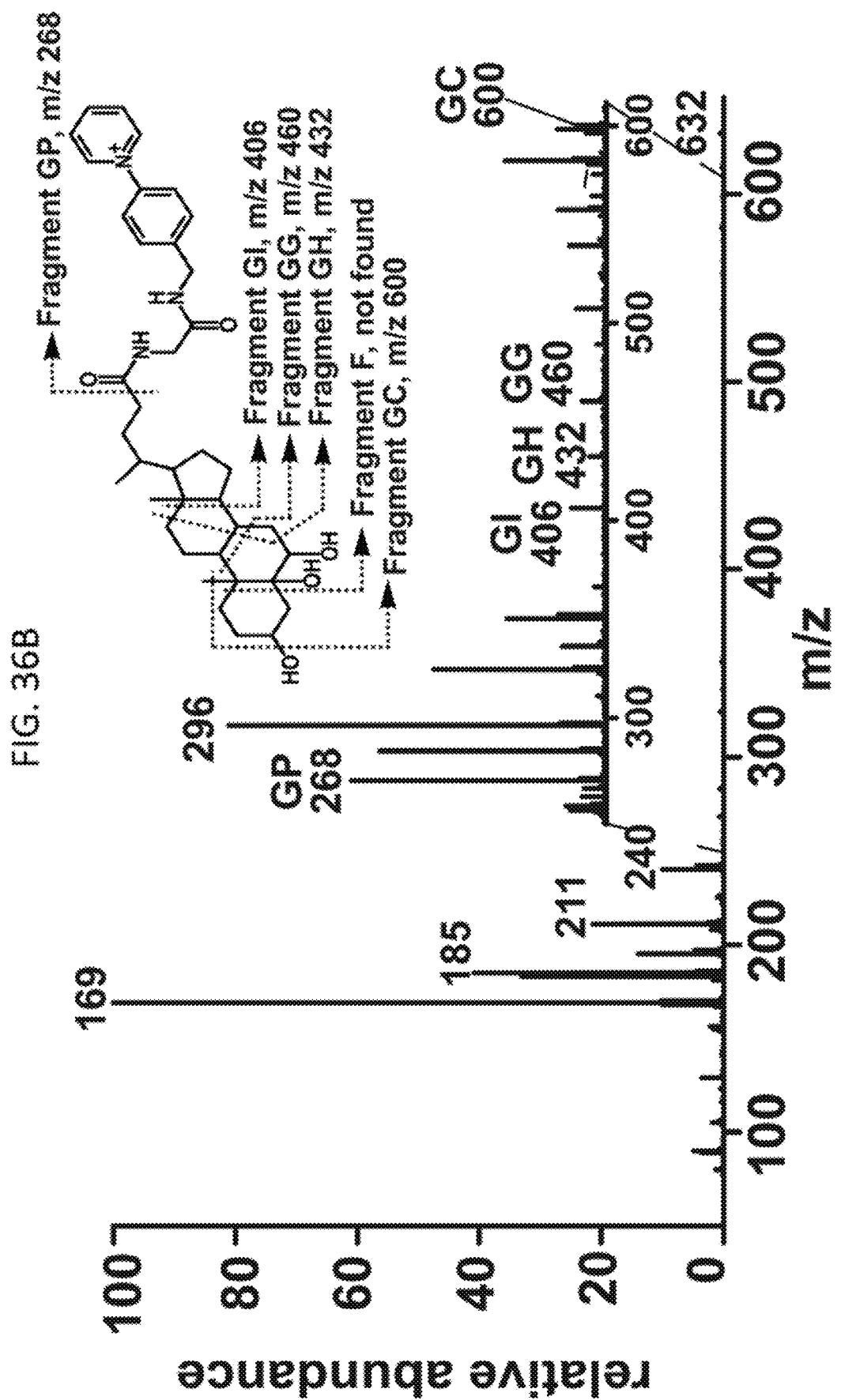
Figure 38:
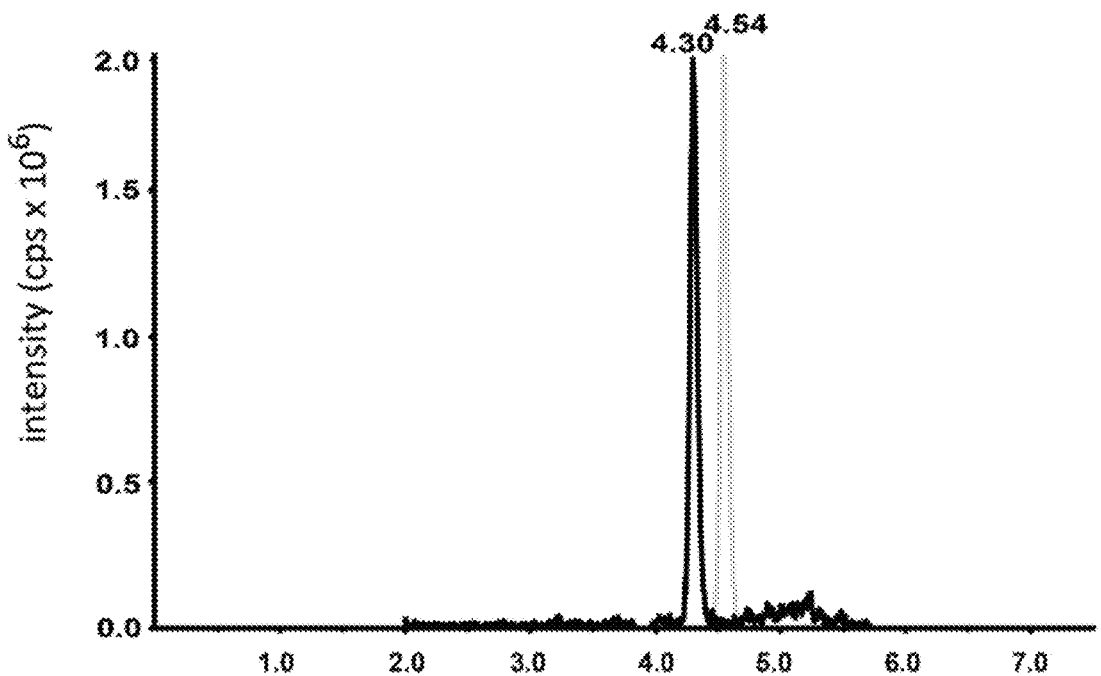
FIG. 38 illustrates chromatograms of bile acid A and bile acid B in NPC1 plasma.

The fragmentation patterns of the above AMPP derivatives of bile acids and analogues allowed the inventors to identify the key fragments that can differentiate the positions of hydroxylation (FIG. 34-37; the key fragments of AMPP derivative of bile acid A and B are depicted in FIGS. 34B and 36B.) Based on these fragmentation patterns, the hydroxyl groups were assigned to bile acid A and B, respectively.

Figure 39:
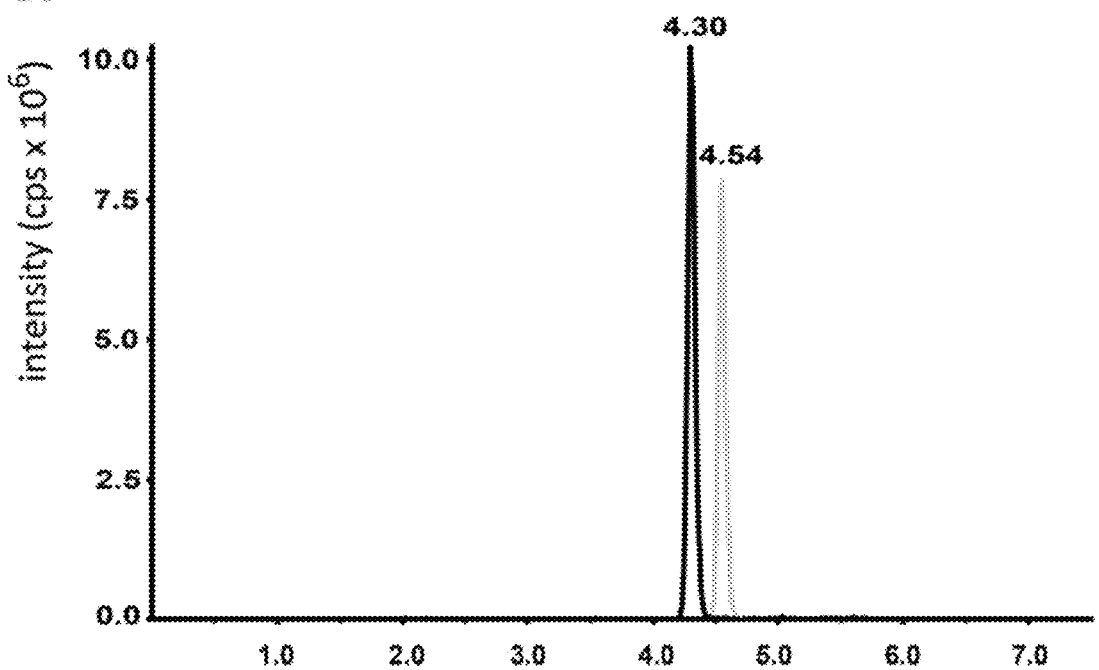
FIG. 39 illustrates chromatograms of bile acid A and bile acid B in solution of synthetic compounds.

The structures of bile acid A and B were preliminarily proposed as 5α-cholanic acid-3β,5α,6β-triol and 5α-cholanic acid-3β,5α,6β-triol N-(carboxymethyl)-amide, respectively. These structures were then confirmed with absolute certainty by the synthesis of the reference compounds and comparative LCMS/MS analysis of endogenous and synthesized compounds (FIG. 34-39). Bile acid A was detected by MRM transition m/z 411→411 retention time: 4.30 min. Bile acid B was detected by MRM transition m/z 464→74; retention time: 4.54 min in NPC1 plasma (FIG. 38) and solution of synthetic compounds (FIG. 39).

Example 25

This example illustrates the biosynthesis of novel bile acids from cholestane-3β,5α,6β-triol in Hep G2 cells.

Although bile acid A has been reported as a major metabolite of cholestane-3β,5α,6β-triol in rat (Kikuchi, S., et al., J. Pharmacol. Exp. Ther., 159, 399-408, 1968), the biosynthesis of bile acids A and B in humans has not previously been described. To explore the biosynthetic route of the bile acids, the human hepatoblastoma-derived cell line Hep G2 was incubated with cholestane-3β,5α,6β-triol and 7,7,22,22,22-d4-cholestane-3β,5α,6β-triol. Hep G2 cells ($1 \times 10^6$ cells/well) were seeded in a 6-well plate in triplicate and maintained in Dulbecco's modified Eagle's medium supplemented with 15% fetal calf serum and 100 U of penicillin G/mL and 100 ng streptomycin sulfate at 37° C. in a humidified atmosphere with 5% $CO_2$. Hep G2 cells were treated when they were 80% confluent. For the treatment, 100× stock solutions were made in DMSO for triol and d4-triol. DMSO concentration never exceeded 1% in the culture medium. Cells were exposed to the test compounds (2.5 ng/mL cholestane-3β,5α,6β-triol or 7,7,22,22,22-d4-cholestane-3β,5α,6β-triol) or solvent control (1% DMSO) for 24 h. The conditioned medium (50 µL) was removed and transferred to a new 2 mL polypropylene tube, to which was added methanol (200 µl). The plates were centrifuged at 9391 g for 10 minutes at room temperature. The supernatant was transferred to a glass HPLC insert and analyzed immediately after preparation by the LC-MS/MS.

Figure 41B:
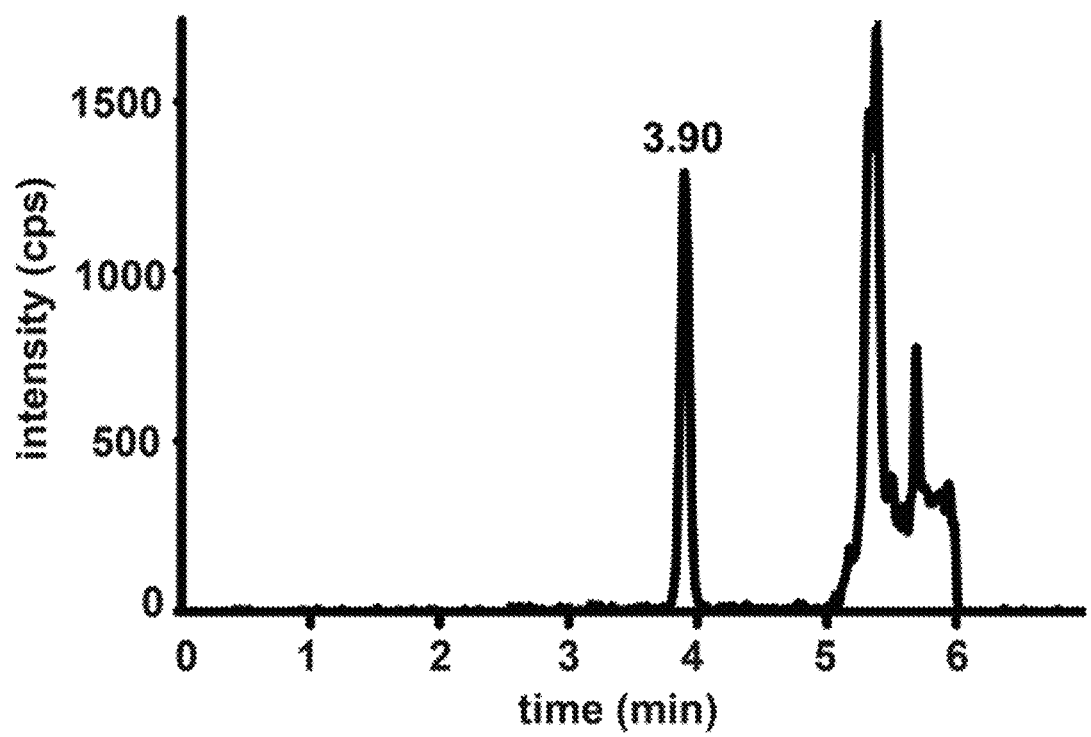
Figure 42B:
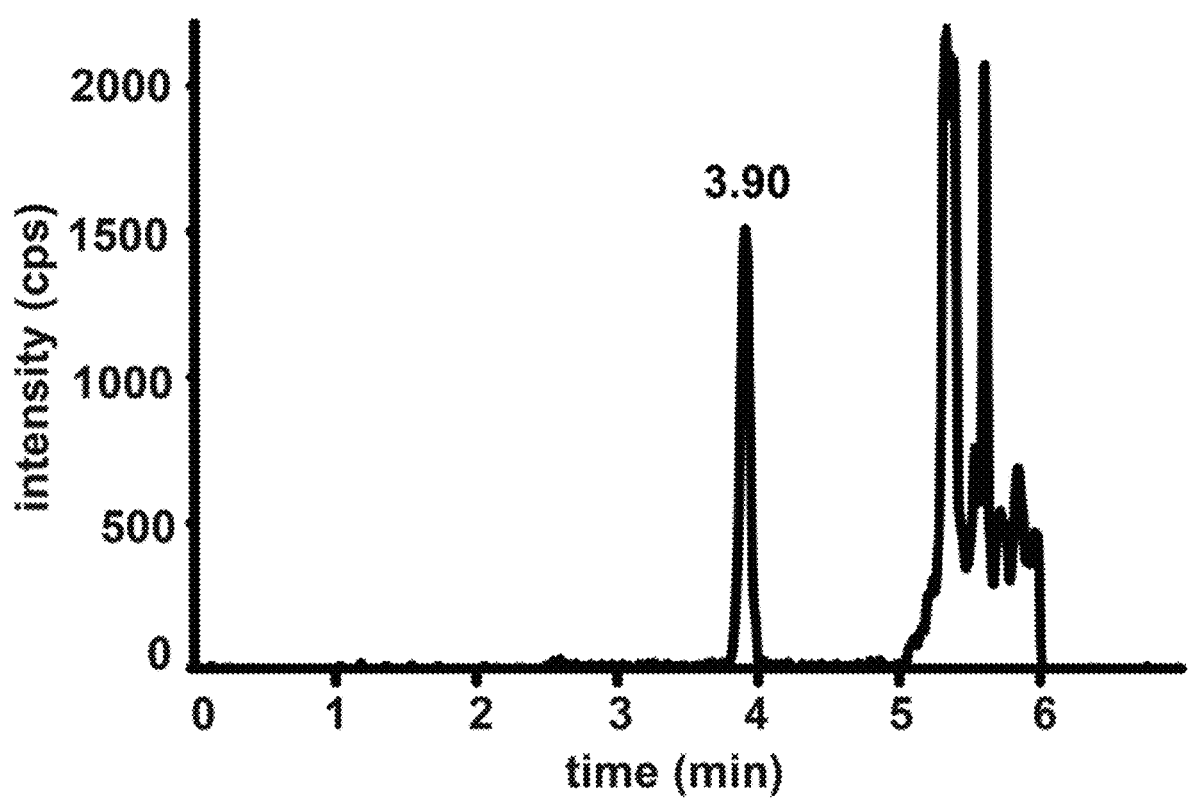

LC-MS/MS analysis was conducted on a Shimadzu (Columbia, Md.) Prominence UFLC system coupled with an Applied Biosystems/MDS Sciex (Ontario, Canada) 4000QTRAP mass spectrometer using multiple reaction monitoring (MRM). The ESI source temperature was 550° C.; the ESI needle was -4500 V; the declustering potential was -120 V for bile acid A and d4-bile acid A and -140 V for bile acid B and d4-bile acid B, respectively; the collision energy were -35 eV for bile acid A and d4-bile acid A and -72 eV for bile acid B and d4-bile acid B, respectively; the entrance potential was -10 V for bile acid A, d4-bile acid A, bile acid B and d4-bile acid B; and the collision cell exit potential was -11 V for bile acid A, d4-bile acid A, bile acid B and d4-bile acid B. The collision and curtain gas were set at medium and 20, respectively. The desolvation gas and nebulizing gas were set at 60 and 35 L/min, respectively. For MRM, the dwell time was set at 50 ms for the transitions of m/z 407 to 407 (bile acid A), m/z 411 to 411 (d4-bile acid A), m/z 464 to 74 (bile acid B) and m/z 468 to 74 (d4-bile acid B). Data were acquired and analyzed by Analyst software (version 1.5.2). The liquid chromatography was carried out at ambient temperature using an ACE Excel 3 Super C18 column (4.6×100 mm, 3 µm) (MAC-MOD Analytical, Chadds Ford, Pa.) connected to a PHENOMENEX® (Torrance, Calif.) SECURITYGUARD™ C18guard column (4×3 mm). The solvent gradient using 2.9 mM diethylamine and 20 mM hexafluoro-2-propanol in water (phase A) and acetonitrile/methanol (1:4) (phase B) at a flow rate of 1 ml/min was as follows: 0-3.5 min 50-60% B, 3.5-3.6 min 60-100% D, 3.6-5.0 min 100% B, 5.0-5.1 min 100-50% B, and 5.1-7.0 min 50% B. The effluent was directed to waste during 0-2.5 and 5-7 min, and to mass spectrometer during 2.5-6 min. The injection volume was 2 µL. FIG. 40 depicts synthetic bile acid A detected by MRM transition m/z 407→407. FIG. 41 depicts bile acid A generated from cholestane-3β,5α,6β-triol in HepG2 cells and detected by MRM transition m/z 407→407. FIG. 42 depicts d4-bile acid A generated from d4-cholestane-3β,5α,6β-triol in HepG2 cells and detected by MRM transition m/z 411→411. Taken together, these data demonstrate that bile acid A and 7,7,22,22,22-d4-bile acid A were produced, thus confirming that bile acid A was a product of cholestane-3β,5α,6β-triol metabolism. No bile acid B was found, consistent with the known defects in synthesis of conjugated bile acids in Hep G cells (Everson, G. T., et al., J. Biol. Chem., 261, 2197-2201, 1986), presumably due to deficiency of bile acid CoA:amino acid N-acyltransferase (BAAT).

Example 26

This example illustrates selection of bile acid biomarker for newborn screening of NPC1 disease. To explore the ability of bile acids A and B to serve as biomarkers for newborn screening of NPC1 disease, the inventors measured these metabolites in 10 NPC and 16 control dried blood spots.

Figure 43:
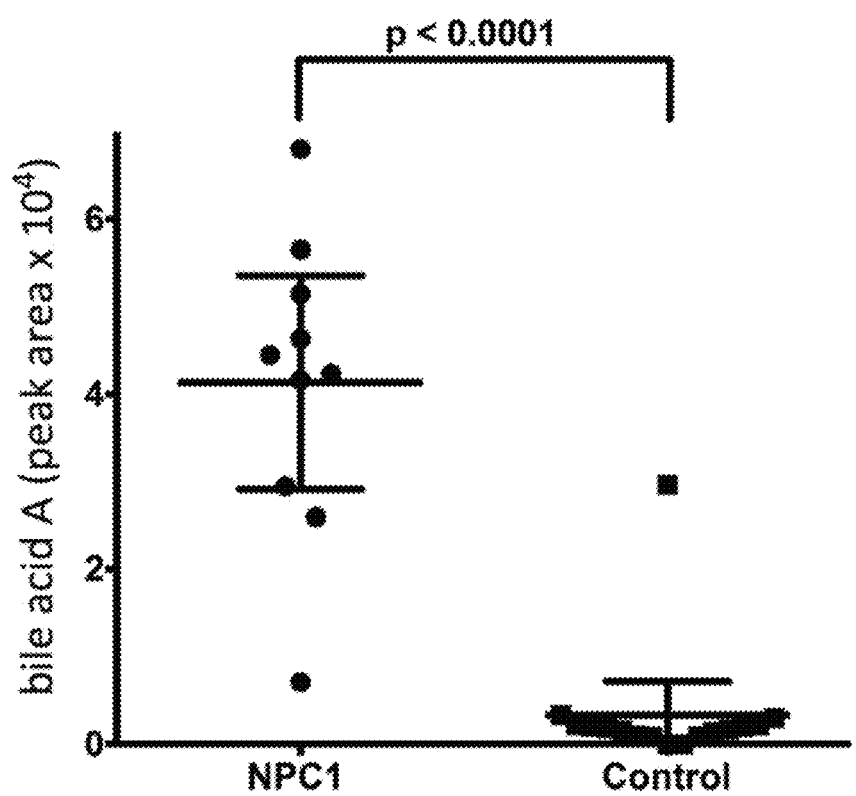
FIG. 43 illustrates detection of bile acid A in NPC1 and control dried blood spot samples.
Figure 44:
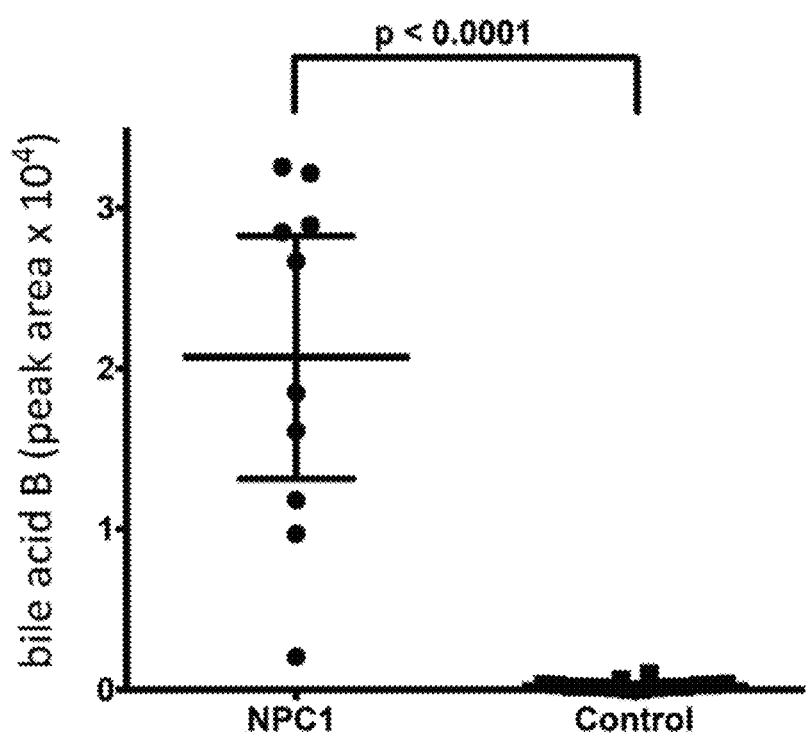
FIG. 44 illustrates detection of bile acid B in NPC1 and control dried blood spot samples.

Bile acids A and B were elevated 12- and 101-fold, respectively, in NPC1 subjects compared to control group. FIG. 43 depicts Bile acid A in NPC1 (n=10) and control (n=16) dried blood spot samples. Data are presented as mean±95% CI peak area. P<0.0001 for NPC1 versus controls. FIG. 44 depicts Bile acid B in NPC1 (n=10) and control (n=16) dried blood spots sample. Data are presented as mean±95% CI peak area. P<0.0001 for NPC1 versus controls. Whereas bile acid A could separate all but one control subject from NPC subjects (FIG. 43), bile acid B could unambiguously discriminate NPC1 subjects from control subjects (FIG. 44).

Example 27

The example illustrates the development and validation of two-tiered LC-MS/MS method for bile acid B in dried blood spots. The object of these experiments was to develop a short LC-MS/MS method (~2 min) that would allow sufficient throughput to meet a general requirement for a newborn screening assay.

Stock solution preparation. All the stock solutions (1 mg/mL) and working solutions (10 ng/mL) of bile acid B and bile acid B-[$^{13}C_2$, $^{15}N$] were prepared in acetonitrile-water (1:1). A working solution containing 25 µg/mL of bile acid B was prepared by the dilution of the stock solution with methanol. The internal standard working solution (12 ng/mL of bile acid B-[$^{13}C_2$, $^{15}N$]) was prepared in 1% SDS and 50 mM trisodium citrate in water, pH 12.

Selection of matrix for calibration and quality control samples. Ideally, the matrix for calibration and quality control (QC) dried blood spot samples is bile acid B free blood to which accurately known concentration of the bile acid B can be spiked. Many normal newborn dried blood spots were found with negligible levels of bile acid B, suggesting that blood from normal neonate is an ideal matrix for calibration and QC dried blood spot samples. The inventors screened umbilical cord bloods from normal neonates and found that bile acid B in most of them was negligible. In addition, they found that the red blood cells from adult donors contained no bile acid B. As freshly drawn umbilical cord blood may not always be available, they prepared blood with hematocrit of 55% by mixing plasma from umbilical cord blood and fresh red blood cells from an adult donor. This artificial blood was used as matrix for calibration and QC dried blood spot samples. When calibration and QC samples in blood were prepared in polypropylene containers, part of bile acid B was lost due to non-specific binding to the container surface. The absorption loss was not found in regular glass containers, therefore the calibration and QC samples were prepared in glass containers before spiking to newborn screening cards.

Sample preparation. A two-step extraction was used in dried blood spot sample preparation. First, the internal standard ($^{15}N$, $^{13}C_2$-bile acid B) in aqueous solution was added to the dried blood spot disk to dissolve the dried blood into the aqueous phase, followed by the addition of acetonitrile to precipitate proteins that were eluted from the dried blood spot cards. The internal standard working solution contains 1% sodium dodecyl sulfate (SDS) and 50 mM trisodium citrate at pH 12. The SDS was used to prevent nonspecific binding of the bile acid B and internal standard to the plastic surface, and citrate under basic condition can release bile acid B from ionic interaction with iron of hemoglobin and improve the extraction recovery. The extraction was performed in 96 well plates, and application of a 96 channels pipette to add internal standard and transfer extracts allows preparation of several hundreds of samples a day.

Standard curve and quality control samples. Freshly collected adult blood unit was washed with three portions of saline to remove anticoagulants and the buffy coat. After centrifugation and removal of the last saline wash, the combined red cells were reconstituted to a hematocrit of 55%±0.5% with pooled human cord plasma (Blood Bank at Barnes-Jewish Hospital) that had been verified with undetectable bile acid B. The calibration standards (5, 10, 20, 50, 100, 200, 250, 500 ng/mL), lower limit of quantification (LLOQ, 5 ng/mL), lower limit (LLQC, 10 ng/mL), low (LQC, 30 ng/mL), middle (MQC, 150 ng/mL), high (HQC, 300 ng/mL) quality control samples were prepared by serial dilution after bile acid B working solution was spiked into reconstituted blood. All blood samples were spotted onto WHATMAN 903® newborn screening cards in 50 µL aliquots, then dried for at least 3 hours at room temperature and stored at −20° C. in airtight bags with desiccant to minimize moisture levels. To evaluate the effect of spotting volume, LQC and HQC were also spotted in 75 and 100 µL aliquots onto WHATMAN 903® newborn screening cards. To evaluate the effect of hematocrit, LQC and HQC were prepared in blood at five hematocrit levels (40%, 50%, 55%, 60%, and 70%), and spotted onto WHATMAN 903® newborn screening cards in 50 µL aliquots.

A major challenge for development of a high throughput LC-MS/MS method is separation of interferences from bile acid B within short LC run time. A long LC run time (7 min) was initially developed, which separated all the interferences from bile acid B. Two interference peaks eluted closely to bile acid B (retention time at 4.05 min, FIG. 45).

LC-MS/MS analysis was conducted on a Shimadzu (Columbia, Md.) Prominence UFLC system coupled with an Applied Biosystems/MDS Sciex (Ontario, Canada) 4000QTRAP mass spectrometer using multiple reaction monitoring (MRM). The ESI source temperature was 550° C.; the ESI needle was −4500 V; the declustering potential was −140 V; the collision energy were −72 eV; the entrance potential was −10 V; and the collision cell exit potential was −11 V. The collision and curtain gas were set at medium and 20, respectively. The desolation gas and nebulizing gas were set at 60 and 35 L/min, respectively. For MRM, the dwell time was set at 200 and 50 ms for the transition of m/z 464 to 74 (bile acid B) and m/z 467 to 77 (internal standard), respectively. Data were acquired and analyzed by Analyst software (version 1.5.2).

Figure 45:
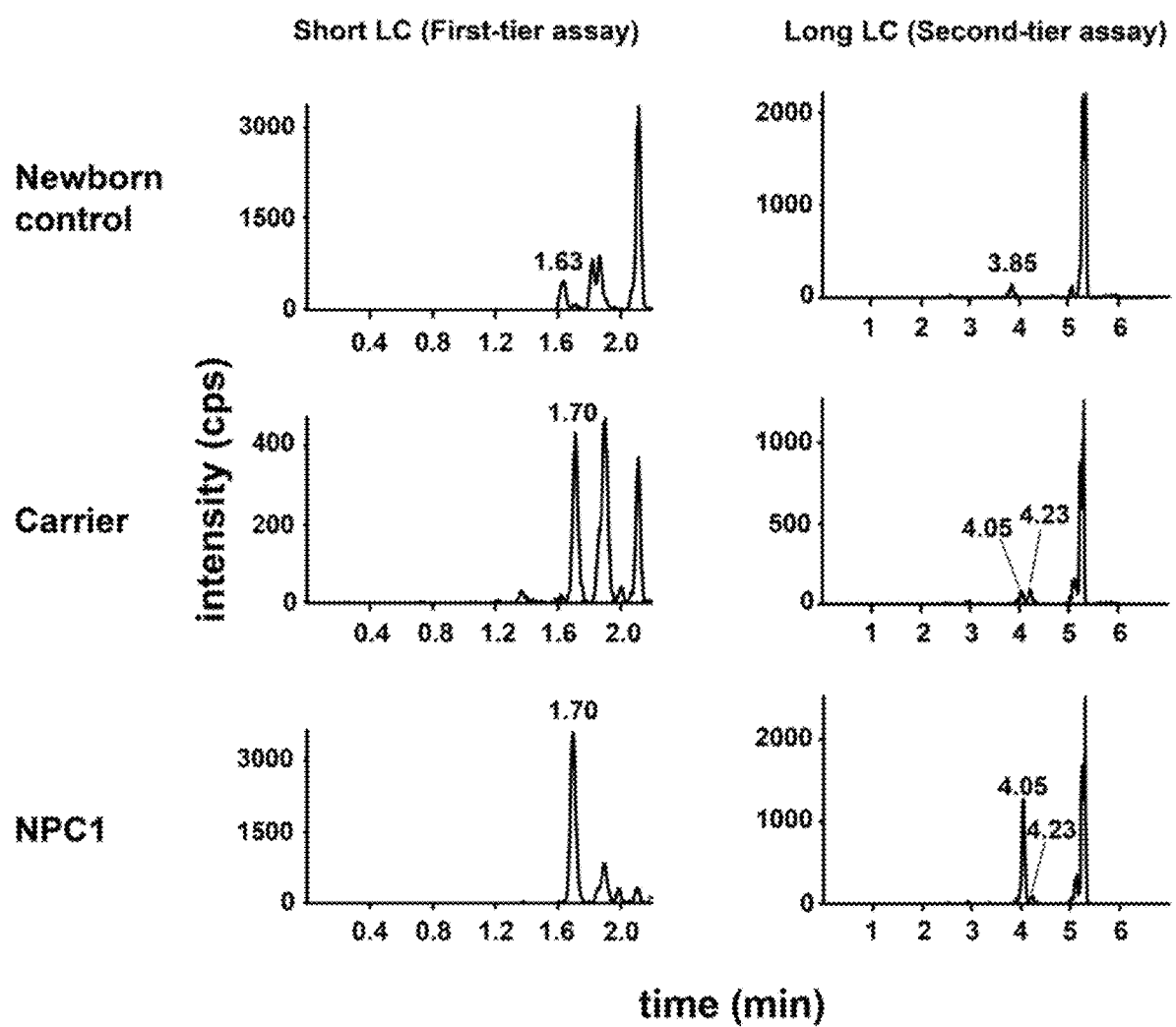
FIG. 45 illustrates chromatograms of bile acid B in dried blood spots from a newborn control, adult NPC1 carrier, and NPC1 patient, as resolved with short LC (first-tier assay) and long LC conditions (second-tier assay).

FIG. 45 depicts chromatograms of bile acid B in dried blood spots from a newborn control, adult NPC1 carrier, and NPC1 patient, as resolved with short LC (first-tier assay) and long LC conditions (second-tier assay). The bile acid B was eluted at 1.7 and 4.05 min under short and long LC conditions, respectively. There are two interferences eluted close to bile acid B. An interference peak presents in most newborn dried blood spots was baseline resolved from bile acid B under both short (1.63 min) and long LC (3.85 min) conditions. The dried blood spots from NPC1 subjects and carriers showed an interference peak that was co-eluted with bile acid at 1.7 min under short LC condition, but baseline separated from bile acid B under long LC condition at 4.23 min. Most newborn dried blood spots only showed an interference peak that eluted at 3.85 min, while dried blood spots from NPC1 subjects and carriers showed an interference peak that eluted at 4.23 min.

Figure 46:
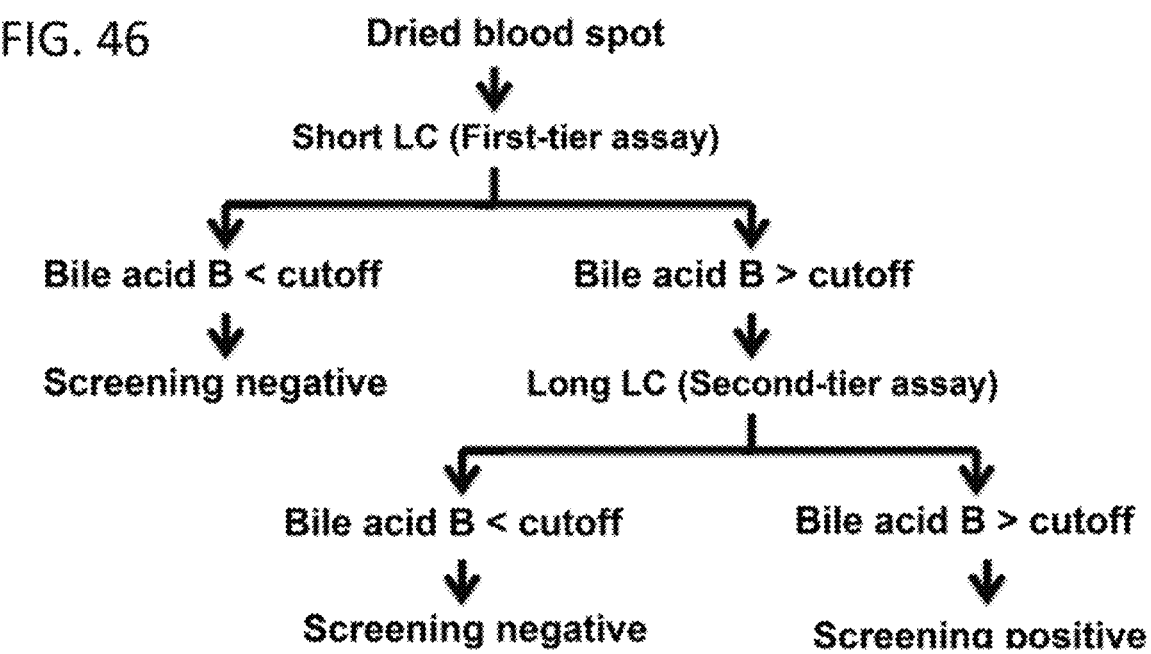
FIG. 46 illustrates an algorithm for two-tier newborn screening of NPC1 disease.

The inventors therefore developed a first tier assay with a short LC condition. In this first-tier assay, the chromatography was performed using an ACE Excel 3 Super C18 column (4.6×50 mm, 3 μm) (MAC-MOD Analytical, Chadds Ford, Pa.) connected to a PHENOMENEX® (Torrance, Calif.) SECURITYGUARD™ C18 guard column (4×3 mm) at ambient temperature. The compartment of the autosampler was set at 4° C. The mobile phase A (2.9 mM diethylamine and 20 mM hexafluoro-2-propanol in water) and mobile phase B (methanol) were operated with a gradient elution as follows: 0-1.3 min 50-80% B, 1.3-1.4 min 80-100% B, 1.4-1.6 min 100% B, 1.6-1.7 min 100-50% B, and 1.7-2.2 min 50% B at a flow rate of 1 ml/min. The effluent was directed to waste during 0-1.2 min, and to mass spectrometer during 1.2-2.2 min. The injection volume was 20 μL. In this assay with a sample analysis time of 2.2 min, bile acid B (retention time at 1.7 min) was baseline resolved from the major interference peak (retention time at 1.63 min) in normal newborn dried blood spots (FIG. 45). However, under the short LC condition the bile acid B could not be separated from the interference peak in NPC1 and carrier dried blood spots. Therefore, a two-tier assay strategy was adopted, in which a short (2.2 minutes) and long (7 minutes) LC conditions were used as first and second tier assays, respectively. The liquid chromatography in second-tier assay was carried out at ambient temperature using an ACE® EXCEL™ 3 Super C18 column (4.6×100 mm, 3 μm) (MAC-MOD Analytical, Chadds Ford, Pa.) connected to a PHENOMENEX® (Torrance, Calif.) SECURITYGUARD™ C18 guard column (4×3 mm). The solvent gradient using 2.9 mM diethylamine and 20 mM hexafluoro-2-propanol in water (phase A) and acetonitrile/methanol (1:4) (phase B) at a flow rate of 1 ml/min was as follows: 0-3.5 min 50-60% B, 3.5-3.6 min 60-100% D, 3.6-5.0 min 100% B, 5.0-5.1 min 100-50% B, and 5.1-7.0 min 50% B. The effluent was directed to waste during 0-2.5 and 5-7 min, and to mass spectrometer during 2.5-5 min. The injection volume was 20 μL. FIG. 46 depicts an algorithm for two-tier newborn screening of NPC1 disease. Method development including selection of matrix for calibration and quality control samples and sample preparation is described supra.

To assess the performance of the method for the quantification of bile acid B, a series of validation experiments was performed to address all FDA recommendations for bioanalytical method validation, as well as testing several additional variables of the dried blood spot technique (U.S. Department of Health and Human Services, Guidance for Industry: Bioanalytical Method Validations, 2001; Spooner, N., et al., Anal. Chem. 81, 1557-1563, 2009).

Linearity, precision and accuracy. Calibration curves were constructed with Analyst software (version 1.5.2) by plotting the corresponding peak area ratios of analyte/internal standard versus the corresponding analyte concentrations using weighted (1/x2) least squares regression analysis. The linearity response of bile acid B was assessed over their respective calibration range from three batches of analytical runs. The precision and accuracy of the assay were determined at LLOQ, LLQC, LQC, MQC and HQC concentration levels over the three batch runs. For each QC concentration, analysis was performed in six replicates on each batch. Precision and accuracy are denoted by percent coefficient of variance (% CV) and percent relative error (% RE), respectively. The accuracy and precision were required to be within ±15% RE of the nominal concentration and ≤15% CV, respectively, for LLQC, LQC, MQC, and HQC samples. The accuracy and precision were required to be within ±20% RE of the nominal concentration and ≤20% CV for LLOQ samples in the intra-batch and inter-batch assays.

Sample stability. The storage stability of dried blood spots and processed sample stabilities in the autosampler were determined at the LQC and HQC concentration levels (n=3). Storage stability of bile acid B in dried blood spots was tested at −20° C. and room temperature for 66 days, and at 37° C. for 90 hours. In the autosampler, stability was tested over seven days by injecting the first batch of the validation samples. The LQC and HQC in whole blood were placed on benchtop at room temperature for 27 hours and then spotted onto newborn screening cards to examine stability of bile acid B in whole blood. Stock solution stability was established by quantification of samples from dilution of two stock solutions that have been stored at −20° C. for 91 days and at room temperature on the bench for 22 hours, respectively, to the final solution (500 ng/mL in water). The storage stability of internal standard working solution was tested at room temperature for 12 days. A fresh standard curve was established each time. Bile acid B was stable in dried blood spots in newborn screening cards for up to 66 days at room temperature storage.

The validation assessment considered the following: sensitivity, selectivity, accuracy, precision, linearity, carry-over, recovery, matrix effect, effect of spotting volumes, effect of hematocrit, effect of punch location, and stabilities in whole blood, dried blood spots, processed samples, and stock solutions.

Sensitivity. The lower limit of quantification (LLOQ) is defined as the lowest concentration that can be determined with suitable accuracy and precision, typically less than 20% relative error (RE) and 20% CV for LC-MS/MS assays, in the biological matrix. During the method validation experiments, the lowest calibration standard for the bile acid B was set at 5 ng/mL. This concentration could be measured with a signal/noise ratio greater than 5:1, and the acceptable precision (≤10% CV) and accuracy (within ±9% RE) for bile acid B were obtained under both short and long LC conditions (Table 10)

Selectivity. Although bile acid B is an endogenous analyte, its level in most normal newborn dried blood spot samples is undetectable. This conclusion was drawn by the analysis of 36 control newborn dried blood spot samples. All the samples demonstrated no significant interference (as defined by having no peak with an area greater than 20% of the LLOQ calibration standard for bile acid B or no greater than 5% for the internal standard). The selectivity of the assay was further confirmed by evaluating plausibly interfering bile acids (glycocholic acid and glycomuricholic acid), and the resulting chromatograms demonstrated no interference at the retention time of bile acid B.

Accuracy and precision. The accuracy and precision of the DBS method were evaluated by analyzing six replicates of QC samples at lower limit (10 ng/mL (LLQC), low (30 ng/ml, LQC), medium (150 ng/ml, MQC) and high level (300 ng/ml, HQC) QC samples in three separate batches (n=6 per batch) against a calibration curve. A summary of the intra-and inter-batch precision and accuracy data of individual QC concentrations for bile acid B is shown in Table 10. For short LC condition, the precision was less than 15% CV and the accuracy was in the range of ±15% RE over the three concentration levels evaluated in all three batches (Table 10). Similar precision and accuracy were also obtained from these batches under long LC condition (Table 10). These results indicated that satisfactory precision and accuracy could be achieved.

Linearity. The calibration range was 5-500 ng/mL for all three batches. The response was linear, and the $r^2$ values for the three batches were more than 0.99.

Carryover. In order to evaluate carryover, a blank dried blood disk extract was analyzed immediately after the upper limit of quantification (ULOQ, 500 ng/mL) sample. Under both short and long LC conditions, no peaks around the same retention time of bile acid B was observed in the chromatogram of the blank matrix sample analyzed immediately after ULOQ. As a result, carryover from previous concentrated samples up to 500 ng/mL of bile acid B is judged to be negligible.

Recovery and matrix effect. The recovery and matrix effect were evaluated by preparing (A) extracts of whole area of LQC and HQC dried blood spot (5 µl of blood); (B) extracts of whole area of blank dried blood spot (5 µl of blood) post-fortified with both the bile acid B and the internal standard with the concentrations the same as in A; and (C) neat solutions with the concentrations of the bile acid B and the internal standard the same as in A and B. The recovery and matrix factor were assessed by comparing the peak area of A and B, B and C, respectively. The recoveries of bile acid B and internal standard are 96% and 91%, respectively. The matrix factors of 1.06 and 1.09 were obtained for bile acid B and internal standard, respectively. A matrix factor value of close to one indicates minimum ionization suppression or enhancement. Furthermore, the internal standard normalized matrix factor is also close to one, suggesting that the matrix effect on analysis of bile acid B in dried blood spot was minimal.

Effect of spotting volumes. Owing to the potential difficulties arising when trying to accurately spot blood in a clinical sampling environment, the effect of spot volume was assessed at LQC and HQC levels in triplicate by spotting different volumes (50, 75, 100 µL) of blood on newborn screening cards. The spot areas of 50, 75, 100 µL of blood are slightly smaller, slightly bigger and significantly bigger than the cycle on newborn screening card, respectively. The bile acid B concentrations of these dried blood spots were quantified against a standard curve with 50 µL spotting volume. Acceptance criteria were mean difference to nominal value within ±15%. The relative errors of all the QC samples with different spotting volumes were within ±5%. The precision (% CV) for all spot volume measurements were <8%. Therefore, dried blood spots with spotting volume in the range of 50 to 100 µl can be accurately quantified with standard curve prepared with spotting volume of 50 µL.

Effect of hematocrit. Hematocrit level is directly proportional to blood viscosity. It affects flux and diffusion properties of the blood spotted on the newborn screening card. A higher viscosity leads to smaller size of blood spot formed and affects spot homogeneity. Variations in hematocrit can also lead to differences in analyte recovery and varying matrix effects. The normal newborn hematocrit ranges from 42 to 65% (Jopling, J., et al., Pediatrics, 123, e333-337, 2009). The inventors tested LQC and HQC dried blood spots with five hematocrit levels (40%, 50%, 55%, 60%, and 70%) in triplicate to evaluate whether the accuracy would be affected. The bile acid B concentrations of these dried blood spots were quantified against a standard curve with hematocrit of 55%. Acceptance criteria were mean difference to nominal value within ±15%. The relative error of all the QC samples with different hematocrit levels were within ±10.2%. The precision (% CV) for all QC measurements were <6.5%. Therefore, dried blood spots with hemotocrit in the range of 40 to 70% can be accurately quantified with standard curve prepared with hematocrit of 55%.

Effect of punch location. Due to chromatographic effects on the paper cards, concentration gradients may occur within the spot. As this behavior is compound dependent, it is recommended to test the influence of punch position for every new method. Sampling was performed from the peripheral areas versus center of the spot to test the effect of punch location. The difference between mean value from the center punch (n=4) and the mean value from the peripheral punch (n=16) was less than 4.4%. These results suggested that effect of punch location on the values was insignificant.

Stability in whole blood, dried blood spots, processed samples, stock and working solutions. The allowable time bile acid B spiked whole blood sample can remain at room temperature prior to spoiling on a newborn screening card was determined with LQC and HQC blood samples, which were remained at room temperature for 27 hours prior to spotting. Three replicates were assessed and the accuracy (within ±4.5% RE) and precision (<7.5% CV) were within the quality control acceptance criteria stated above. Bile acid B is therefore considered stable in whole blood for 27 hours prior to spotting.

The stability of bile acid B in dried blood spots on the newborn screening cards stored at room temperature and −20° C. for 66 days and at 37° C. for 90 hours was assessed by comparisons of three replicates of stored LQC and HQC against freshly prepared calibration standards and QC samples. The results showed the accuracy (−8.3 to 7.5% RE) and precision (≤6% CV) for these two levels of QC samples, indicating that dried blood spot samples were stable for at least 66 days if stored at room temperature or −20° C. and for 90 hours under shipping conditions (37° C.). Processed sample stability was assessed by re-injection of LQC and HQC together with calibration curve from one accuracy/precision run after storage in the autosampler at 4° C. for 7 days. Stability was demonstrated by accuracy (<±5.1% RE) and precision (≤6% CV).

Stock solution stability of bile acid B and internal standard in acetonitrile-water (1:1) was established for 22 hours at room temperature. The internal standard in aqueous working solution (1% sodium dodecyl sulfate (SDS) and 50 mM trisodium citrate at pH 12) was stable for 12 days at room temperature.

Bile acid B was stable in dried blood spots in newborn screening cards for up to 66 days at room temperature storage. Thus, using the first-tier method, more than 500 samples/day can be analyzed. Samples with bile acid B values above the cut-off value due to inability to separate from the second interference peak could then be submitted to the highly selective second-tier assay, permitting adjudication of the false positives from the first-tier assay. Together, this tiered strategy serves as the basis of a novel screen for NPC.

Example 28

This example illustrates the establishment and validation of cut-off value for NPC newborn screening.

Figure 47:
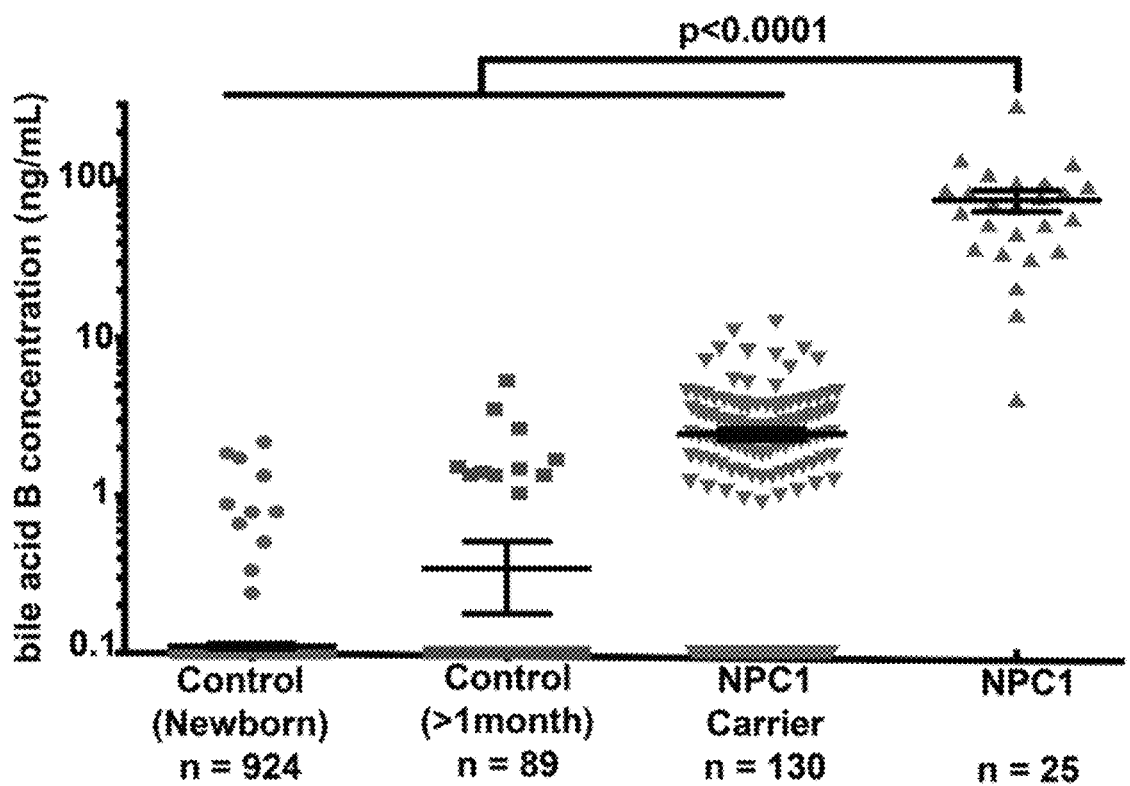
FIG. 47 depicts bile acid B concentrations in dried blood spots from newborn control, control at other age (>1 month old), NPC1 carrier, and NPC1 patients.
Figure 48:
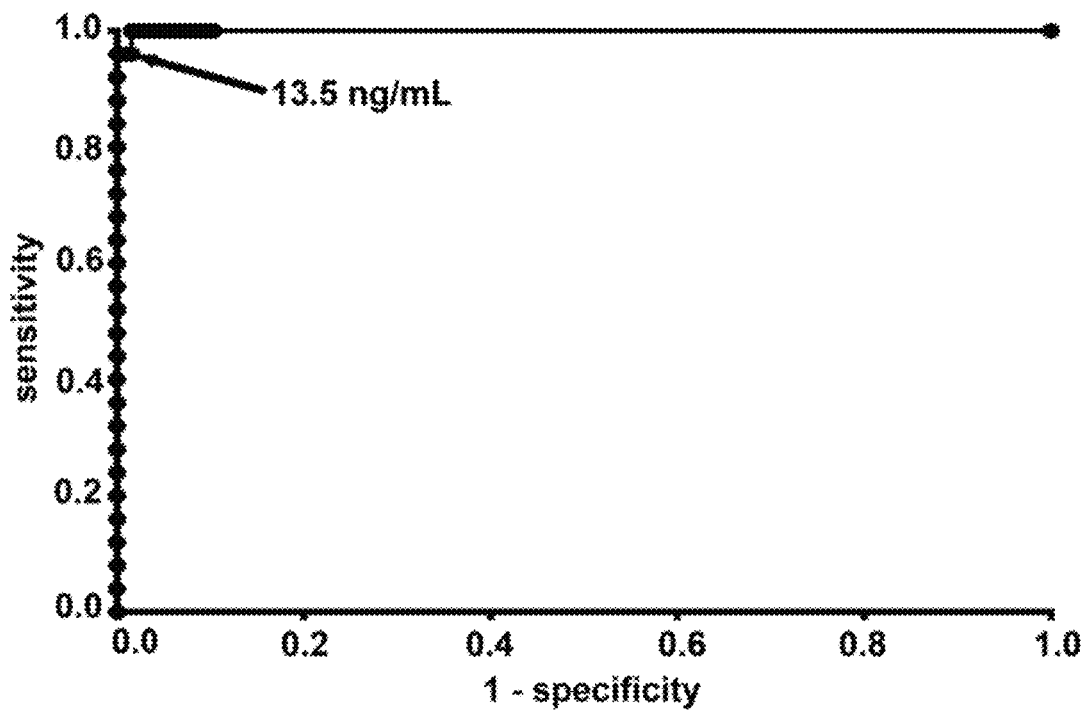
FIG. 48 illustrates the application of cut-off value of 13.5 ng/ml, yields sensitivity and specificity of 96% and 100%, respectively, and ROC area under the curve of 0.9994.
Figure 49:
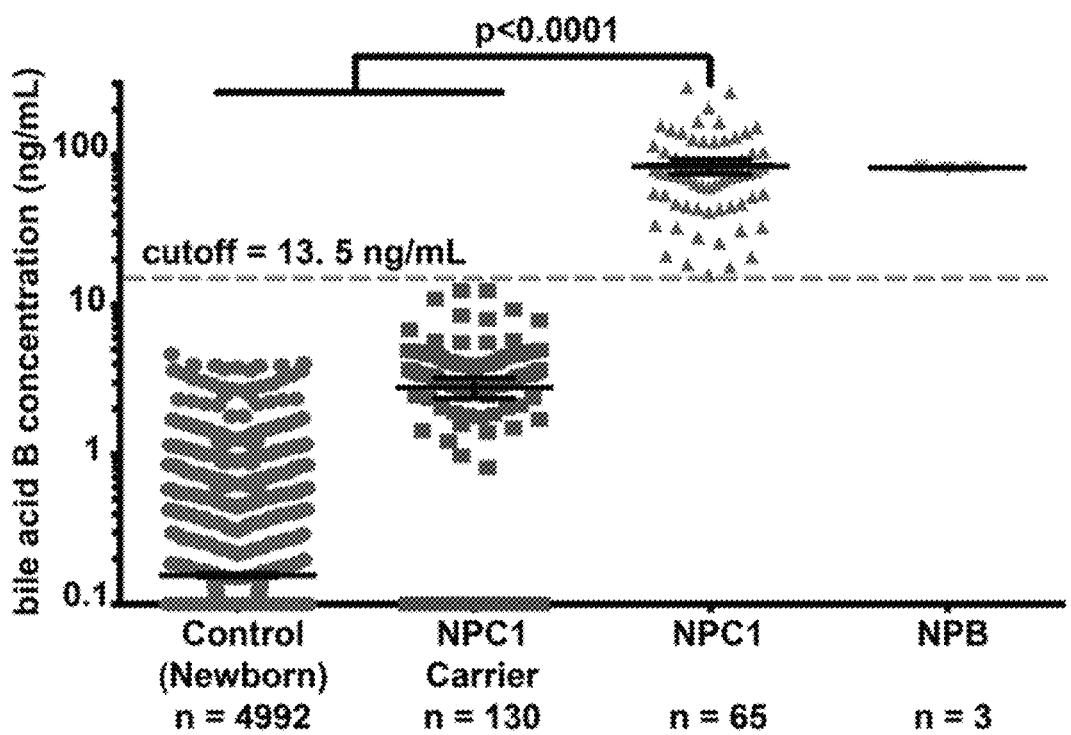
FIG. 49 illustrates bile acid B concentrations in newborn control, NPC1 carrier, NPC1, and NPB dried blood spots from cut-off validation sample set.

The validated bile acid B dried blood spot assay was used to establish the cut-off value for NPC1 newborn screening. Dried blood spot samples from 1013 normal subjects (including 924 newborns and 89 subjects at other ages), 130 NPC1 carriers, and 25 NPC1 subjects were analyzed. FIG. 47 depicts bile acid B concentrations in dried blood spots from newborn control, control at other age (>1 month old), NPC1 carrier, and NPC1 patients. Bile acid B concentrations below the LLOQ (5 ng/mL) were quantifiable though the % CV and % RE for these samples were above acceptance criteria for validated assay. Data are presented on semi-log plots are shown as mean±95% CI. Samples with no detectable bile acid B peak were assigned as 0.1 ng/ml for purposes of plotting. P<0.0001 for NPC1 versus controls and NPC1 carriers. The reference ranges for control, NPC1 carrier, and NPC1 subjects were <5-5.34, <5-12.5, and <5-294 ng/mL, respectively (FIG. 47). Only one NPC1 subject exhibited a biomarker level <5 ng/mL. This subject was completely asymptomatic and was identified because of a sibling diagnosed with NPC1, who carried a high frequency variant (N222S). A cut-off at 13.5 ng/mL provided 100% specificity and 96% sensitivity in identifying NPC1 patients from control and NPC1 carrier subjects, yielding a receiver operator characteristic (ROC) area under the curve of 0.9994 (FIG. 48). Validation of cut-off was achieved by analysis of a second set of dried blood spot samples including 4992 normal newborns, 130 NPC1 carriers, 3 Niemann-Pick B (NPB), and 65 NPC1 patients. The range of bile acid B in normal newborns, NPC1 carriers, NPC1 patients, NPB patients was <5, <5-12.4, 13.8-288, 81.1-82.8 ng/mL, respectively (FIG. 49). Data in FIG. 49 are presented on semi-log plots and are shown as mean±95% CI. *P<0.0001 for NPC1 versus controls and NPC1 carriers. All the normal newborns and NPC1 carriers were below the cut-off, while all the NPC1 samples were above the cut-off. The finding that NPB samples were also above the cut-off indicated the bile acid B assay may also detect NPB disease, though only a small number of samples were analyzed.

Example 29

A physician orders a Niemann-Pick screen for a newborn infant. A laboratory receives a sample from the newborn in the form of a newborn screening card comprising a blood spot. A laboratory technician performs a solid phase extraction on a punch from the blood spot. The technician injects the extracted sample into a mass spectrometer and determines the concentration of THCG. The measured concentration is 27 ng/ml, which is statistically significantly above a reference value of 13.5 ng/ml. The technician sends the lab results back to the physician, who diagnoses Niemann-Pick C disease.

Example 30

A physician orders a Niemann-Pick screen for a newborn infant. A laboratory receives a sample from the newborn in the form of a newborn screening card comprising a blood spot A laboratory technician performs a solid phase extraction on a punch from the blood spot. The technician injects the extracted sample into a mass spectrometer and determines the concentration of THCG. The measured concentration is 28.8 ng/ml, which is statistically significantly above a reference value of 13.5 ng/ml. The technician sends the lab results back to the physician, who orders a liquid chromatography/mass spectroscopy analysis of the blood spot. The lab technician performs a liquid chromatography/mass spectroscopy analysis of the blood spot. The measured concentration is 28.1 ng/ml, which is statistically significantly above a reference value of 13.5 ng/ml. The technician sends the lab results back to the physician, who diagnoses Niemann-Pick C disease.

Example 31

A physician orders a Niemann-Pick screen for a newborn infant. A laboratory receives a sample from the newborn in the form of a newborn screening card comprising a blood spot. A laboratory technician performs a solid phase extraction on a punch from the blood spot. The technician injects the extracted sample into a mass spectrometer and determines the concentration of THCG. The measured concentration is 12.1 ng/ml, which is not statistically significantly above a reference value of 13.5 ng/ml. The technician sends the lab results back to the physician, who determines the patient does not have Niemann-Pick C disease.

All references cited herein are incorporated by reference, each in its entirety. Applicant reserves the right to challenge any conclusions presented by the authors of any reference.

REFERENCES

1. Alvelius, G., et al. *J. Lipid Res*, 2001 October, 42(10), 1571-1577.
2. Beltroy, E. P., et al. *Hepatology* 2005 October, 42(4), 886-893.
3. Birman, V. B., Jiang, X., *Org Lett* 2004, 6, 2369-2371
4. Brown, D. E., el al. *Am. J. Pathol* 1994 June, 144(6), 1412-1415.
5. Carstea, E. D., et al. *Science*, 1997, 277, 228-231
6. Cheng, H., et al., *J Neurochem*, 2007, 101, 57-76.
7. Cheng, H., et al., *Biochemistry*, 2008, 47, 5869-5880.
8. Cluzeau, C. V., et al. *Hum. Mol Genet.* 2012 Aug. 15, 21(16), 3632-3646.
9. Davidson, C. D., et al., *PLoS One* 2009 4, e6951.
10. Fan, M., et al., *J. Lipid Res.*, 2013 October, 54(10), 2800-2814.
11. Hawkins-Salsbury, J. A., et al., *J. Lipid Res.*, 2013, 54, 3303-3311.
12. Heubi, J. E., et al., *Seminars Liver Dis.*, 2007 August, 27(3), 282-294.
13. Jiang, H., et al., *Anal Bioanal Chem.*, 2013, 405, 7357-7365.
14. Jiang, X., et al., *J. Lipid Res.*, 2011 July, 52(7), 1435-1445.
15. Jiang, X., et al., *Anal Biochem*, 2007, 371, 135-145.
16. Jiang, X., et al., *J. Lipid Res.*, 2011, 52, 1435-1445.
17. Jiang, X., et al., *J Lipid Res*, 2009, 50, 162-172.
18. Jiang, X., et al., *Rapid Comman Mass Spectrom* 2007, 21, 141-152.

19. Jiang, X., Han, X., *J Lipid Res*, 2006, 47, 1865-1873.
20. Kakiyama, G., et al. *Steroids* 2009 September, 74(9), 766-772.
21. Kikuchi, S., et al., *J Pharmacol Exp Ther*, 1968, 159, 399-408.
22. Liu, B., et al., *J Lipid Res* 49, 663-669 (2008).
23. Liu, B., et al. *J Lipid Res* 51, 933-944 (2010).
24. Maekawa, M., et al. *Steroids*. 2013 October, 78(10), 967-972.
25. Marsden, D. & Levy, H., 2010, *Clin Chem* 56, 1071-1079.
26. Matern, D., et al., *Developmental Disabilities Research Reviews* 17, 247-253 (2013).
27. Ory, D. S., et al. U.S. Pat. No. 8,497,122.
28. Patterson, M. C., et al., *Lancet Neurol*, 6, 765-772 (2007).
29. Porter, F. F., et al. *Sci. Transl Med.* 2010 Nov. 3; 2(56):56ra81.
30. Porter, F. D., et al. WO2013090857
31. Qin, E. Y., et al., *Mol Genet. Metab.*, 2012, 107, 186-96.
32. Ramirez, C. M., et al., *Pediatr. Res.*, 68, 309-315 (2010).
33. Rinaldo, P., et al., *Ment Retard Dev Disabil Res Rev*, 2006, 12, 255-261.
34. Rolfs, A., et al. WO2013072060 A2
35. Russell, D. W., *Annu. Rev. Biochem.*, 2003, 72, 137-174.
36. Sevin, M., et al., *Brain*, 2007, 130, 120-133.
37. Stampfer, M., et al., *Orphanet J Rare Dis*, 2013, 8, 35.
38. U.S. Department of Health and Human Services, F.D.A., Center for Drug Evaluation and Research and Center for Veterinary Medicine. Guidance for Industry: Bioanalytical Method Validations. (2001).
39. Vanier, M. T., *Orphanet J. Rare Dis.*, 2010, 5, 16.
40. Vanier, M. T. & Millat, G., *Clin Genet.*, 2003, 64, 269-281.
41. Vruchte, D. T., et al. *J Clin Invest* 2014, 124:1320-1328.
42. Zeng, Y., et al., *Biochemical J*, 2008, 410, 81-92.
43. Zervas, M. et al., *Curr. Biol*, 2001, 11, 1283-1287.

TABLE 1

MRM transitions and MS parameters for bile acids in the first-tier biomarker screening

| Q1 | Q3 | ID | DP | CE |
|---|---|---|---|---|
| 407.3 | 407.3 | CA | 100 | 35 |
| 391.3 | 391.3 | CDCA/DCA/UDCA/HDCA | 100 | 35 |
| 375.3 | 375.3 | LCA | 100 | 35 |
| 464.3 | 74 | GCA | 90 | 72 |
| 448.3 | 74 | GCDCA/GDCA/GUDCA/GHDCA | 85 | 70 |
| 432.3 | 74 | GLCA | 85 | 70 |
| 514.3 | 80 | TCA | 140 | 116 |
| 498.3 | 80 | TCDCA/TDCA/TUDCA/THDCA | 140 | 116 |
| 482.3 | 80 | TLCA | 140 | 116 |
| 444.3 | 74 | B^-ol-one-G | 90 | 70 |
| 460.3 | 74 | B^-diol-one-G | 90 | 70 |
| 462.3 | 74 | B-diol-one-G | 90 | 70 |

TABLE 1-continued

MRM transitions and MS parameters for bile acids in the first-tier biomarker screening

| Q1 | Q3 | ID | DP | CE |
|---|---|---|---|---|
| 467.3 | 97 | B^-ol-one-S-1 | 90 | 70 |
| 233.1 | 97 | B^-ol-one-S-2 | 80 | 70 |
| 469.3 | 97 | B^-diol-one-S-1 | 90 | 70 |
| 234.1 | 97 | B^-diol-one-S-2 | 80 | 70 |
| 480.3 | 74 | B-tetrol-G | 90 | 70 |
| 494.3 | 80 | B^-ol-one-T | 140 | 116 |
| 510.3 | 80 | B^-diol-one-T | 140 | 116 |
| 510.3 | 97 | B^-ol-G-S-1 | 90 | 70 |
| 510.3 | 74 | B^-ol-G-S-2 | 90 | 70 |
| 254.7 | 97 | B^-ol-G-S-3 | 80 | 70 |
| 254.7 | 74 | B^-ol-G-S-4 | 80 | 70 |
| 512.3 | 80 | B-diol-one-T | 140 | 116 |
| 524.4 | 97 | B^-ol-one-G-S-1 | 90 | 70 |
| 524.4 | 74 | B^-ol-one-G-S-2 | 90 | 70 |
| 261.7 | 97 | B^-ol-one-G-S-3 | 80 | 70 |
| 261.7 | 74 | B^-ol-one-G-S-4 | 80 | 70 |
| 526.4 | 97 | B^-diol-G-S-1 | 90 | 70 |
| 526.4 | 74 | B^-diol-G-S-2 | 90 | 70 |
| 262.7 | 97 | B^-diol-G-S-3 | 80 | 70 |
| 262.7 | 74 | B^-diol-G-S-4 | 80 | 70 |
| 528.4 | 97 | B-diol-G-S-1 | 90 | 70 |
| 528.4 | 74 | B-diol-G-S-2 | 90 | 70 |
| 263.7 | 97 | B-diol-G-S-3 | 80 | 70 |
| 263.7 | 74 | B-diol-G-S-4 | 80 | 70 |
| 530.4 | 80 | B-tetrol-T | 140 | 116 |
| 544.4 | 97 | B-triol-G-T-1 | 90 | 70 |
| 544.4 | 74 | B-triol-G-T-2 | 90 | 70 |
| 271.6 | 97 | B-triol-G-T-3 | 80 | 70 |
| 271.6 | 74 | B-triol-G-T-4 | 80 | 70 |
| 279.6 | 80 | B^-ol-T-S-1 | 140 | 116 |
| 279.6 | 97 | B^-ol-T-S-2 | 80 | 70 |
| 286.7 | 80 | B^-ol-one-T-S-1 | 140 | 116 |
| 286.7 | 97 | B^-ol-one-T-S-2 | 80 | 70 |
| 287.7 | 80 | B^-diol-T-S-1 | 140 | 116 |
| 287.7 | 97 | B^-diol-T-S-2 | 80 | 70 |
| 288.7 | 80 | B-diol-T-S-1 | 140 | 116 |
| 288.7 | 97 | B-diol-T-S-2 | 80 | 70 |

TABLE 2

MRM transitions and MS parameters for bile acids in the first-tier biomarker screening

| Q1 | Q3 | ID | DP | CE |
|---|---|---|---|---|
| 407.3 | 407.3 | CA | −120 | −35 |
| 391.3 | 391.3 | CDCA/DCA/UDCA/HDCA | −120 | −35 |
| 375.3 | 375.3 | LCA | −150 | −35 |
| 464.3 | 74 | GCA | −120 | −72 |
| 448.3 | 74 | GCDCA/GDCA/GUDCA/GHDCA | −120 | −70 |
| 432.3 | 74 | GLCA | −120 | −70 |
| 514.3 | 80 | TCA | −150 | −120 |
| 498.3 | 80 | TCDCA/TDCA/TUDCA/THDCA | −150 | −120 |
| 482.3 | 80 | TLCA | −150 | −120 |
| 444.3 | 74 | B^-ol-one-G | −90 | −70 |

TABLE 3

Accurate masses and calculated elemental composition of fragment ions of 21,26,27-trinorcholestan-25-oic acid-3β,5α,6β-triol and bile acid A AMPF derivatives

| | 21,26,27-trinorcholestan-25-oic acid-3β,5α,6β-triol | | | Bile acid A | | |
|---|---|---|---|---|---|---|
| Bile acid Fragment | Measured mass (u) (Relative intensity) | Deviation (mmu) | Elemental composition | Measured mass (u) (Relative intensity) | Deviation (mmu) | Elemental composition |
| T | 169.0889 (100) | 0.33 | C12 H11 N | 169.0889 (71.79) | 0.29 | C12 H11 N |
| S | 183.092 (78.64) | 0.36 | C12 H11 N2 | 183.092 (100) | 0.36 | C12 H11 N2 |
| R | 196.0762 (1.86) | 0.51 | C13 H10 O N | 196.0762 (3.32) | 0.5 | C13 H10 O N |

TABLE 3-continued

Accurate masses and calculated elemental composition of fragment ions of 21,26,27-trinorcholestan-25-oic acid-3β,5α,6β-triol and bile acid A AMPF derivatives

| Bile acid Fragment | 21,26,27-trinorcholestan-25-oic acid-3β,5α,6β-triol | | | Bile acid A | | |
|---|---|---|---|---|---|---|
| | Measured mass (u) (Relative intensity) | Deviation (mmu) | Elemental composition | Measured mass (u) (Relative intensity) | Deviation (mmu) | Elemental composition |
| P | 211.0872 (5.58) | 0.57 | C13 H11 O N2 | 211.0871 (3.58) | 0.53 | C13 H11 O N2 |
| Q | 226.1107 (3.87) | 0.61 | C14 H14 O N2 | 226.1106 (2.57) | 0.57 | C14 H14 O N2 |
| O | 239.1185 (33.76) | 0.59 | C15 H15 O N2 | 239.1184 (5.4) | 0.54 | C15 H15 O N2 |
| N | 281.1654 (4.12) | 0.53 | C18 H21 O N2 | 267.1497 (1.69) | 0.53 | C17 H19 O N2 |
| M or M' | 309.1968 (1.7) | 0.62 | C20 H25 O N2 | 293.1654 (1.41) | 0.6 | C19 H21 O N2 |
| L or L' | 323.2123 (0.76) | 0.54 | C21 H27 O N2 | 309.1968 (0.23) | 0.68 | C20 H25 O N2 |
| K | 363.2437 (3.74) | 0.64 | C24 H31 O N2 | 349.2279 (0.66) | 0.47 | C23 H29 O N2 |
| H | 389.2594 (1.24) | 0.64 | C26 H33 O N2 | 375.2438 (0.22) | 0.66 | C25 H31 O N2 |
| J | 417.2907 (1.11) | 0.63 | C28 H37 O N2 | 403.2746 (0.37) | 0.19 | C27 H35 O N2 |
| I | — | — | — | — | — | — |
| G | 521.3533 (0.62) | 0.66 | C36 H45 O N2 | 507.3374 (0.31) | 0.46 | C35 H43 O N2 |
| F | 537.3485 (1.87) | 0.92 | C36 H45 O2 N2 | 523.3687 (0.09) | 0.37 | C36 H47 O N2 |
| C | 539.3641 (8.27) | 0.89 | C36 H47 O2 N2 | 525.3482 (6.17) | 0.61 | C35 H45 O2 N2 |
| E | 553.3798 (1.73) | 0.98 | C37 H49 O2 N2 | 539.3639 (1.43) | 0.66 | C36 H47 O2 N2 |
| D | 555.3589 (4.86) | 0.75 | C36 H47 O3 N2 | 541.3431 (3.51) | 0.67 | C35 H45 O3 N2 |
| B | 557.3745 (2.44) | 0.73 | C36 H49 O3 N2 | 543.3589 (2.35) | 0.76 | C35 H47 O3 N2 |
| A | 571.3903 (7.9) | 0.86 | C37 H51 O3 N2 | 557.3744 (8.9) | 0.6 | C36 H49 O3 N2 |
| M+ | 589.4008 (8.22) | 0.82 | C37 H53 O4 N2 | 575.385 (10.87) | 0.62 | C36 H51 O4 N2 |

TABLE 4

Accurate masses and calculated elemental composition of fragment ions of bile acid B AMPP derivative

| Bile acid Fragment | Bile acid B | | |
|---|---|---|---|
| | Measured mass (u) (Relative intensity) | Deviation (mmu) | Elemental composition |
| GW | 169.0889 (100) | 0.25 | C12H11N |
| GV | 183.0921 (33.23) | 0.38 | C12H11N2 |
| GU | 185.1076 (40.66) | 0.31 | C12H13N2 |
| GT | 195.0921 (13.68) | 0.43 | C13H11N2 |
| GS | 197.1078 (4.7) | 0.44 | C13H13N2 |
| GQ | 211.087 (21.15) | 0.46 | C13H11ON2 |
| GR | 240.1137 (9.86) | 0.54 | C14H14ON3 |
| GP | 268.1085 (0.75) | 0.49 | C15H14O2N3 |
| GO | 296.1398 (1.14) | 0.42 | C17H18O2N3 |
| GN | 324.1711 (0.51) | 0.45 | C19H22O2N3 |
| GM | 336.1713 (0.13) | 0.6 | C20H22O2N3 |
| GL | 350.1867 (0.3) | 0.38 | C21H24O2N3 |
| GJ | 352.2026 (0.14) | 0.65 | C21H26O2N3 |
| GK | 366.2181 (0.04) | 0.49 | C22H28O2N3 |
| GI | 406.2495 (0.1) | 0.56 | C25H32O2N3 |
| GH | 432.2649 (0.05) | 0.34 | C27H34O2N3 |
| GG | 460.2966 (0.07) | −0.62 | C31H40O3 |
| GAB | 507.3587 (0.09) | 0.56 | C32H47O3N2 |
| GZ | 539.3639 (0.11) | 0.72 | C36H47O2N2 |
| GY | 557.3741 (0.14) | 0.32 | C36H49O3N2 |
| GF | — | — | — |
| GX | 575.3845 (0.04) | 0.13 | C36H51O4N2 |
| GE | 582.3697 (0.3) | 0.71 | C37H48O3N3 |
| GAB | 586.4015 (0.02) | 1.17 | C37H52O3N3 |
| GB | 596.3856 (0.06) | 0.9 | C38H50O3N3 |
| GD | 598.3647 (0.15) | 0.74 | C37H48O4N3 |
| GC | 600.3804 (0.09) | 0.83 | C37H50O4N3 |
| GA | 614.3958 (0.29) | 0.57 | C38H52O4N3 |
| M+ | 632.4063 (0.5) | 0.46 | C38H54O5N3 |

TABLE 5

Structures of bile acids and analog that were used to study fragmentation patterns of the AMPP derivatives

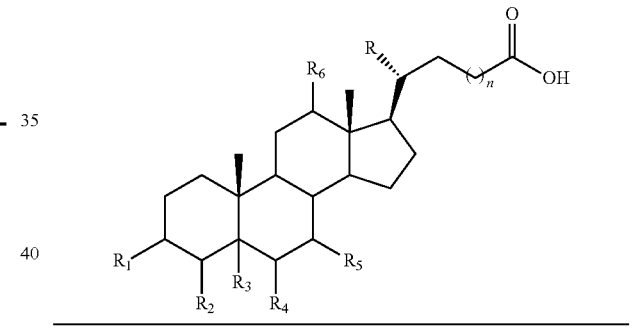

| Analog | Chemical | R | R1 | R2 | R3 | R4 | R5 | R6 |
|---|---|---|---|---|---|---|---|---|
| 1 | deoxycholic acid (DCA) | CH3 (n = 1) | α-OH | H | β-H | H | H | α-OH |
| 2 | chenodeoxycholic acid (CDCA) | CH3 (n = 1) | α-OH | H | β-H | H | α-OH | H |
| 3 | cholic acid (CA) | CH3 (n = 1) | α-OH | H | β-H | H | α-OH | α-OH |
| 4 | α-muricholic acid | CH3 (n = 1) | α-OH | H | β-H | α-OH | α-OH | H |
| 5 | β-muricholic acid | CH3 (n = 1) | α-OH | H | β-H | β-OH | α-OH | H |
| 6 | 5-cholanic acid-3α,4β,7α-triol | CH3 (n = 1) | α-OH | β-OH | β-H | H | α-OH | H |
| 7 | 21,26,27-trinorcholestan-25-oic acid-3β,5α,6α-triol | H (n = 3) | β-OH | H | α-OH | β-OH | H | H |

TABLE 6

Structures of bile acids and analog that were used to study fragmentation patterns of the AMPP derivatives

| Analogue | Chemical Name | R$_1$ | R$_2$ |
|---|---|---|---|
| 8 | glycodeoxycholic acid (GDCA) | H | OH |
| 9 | glycochenodeoxycholic acid (GCDCA) | OH | H |
| 10 | glycocholic acid (GCA) | OH | OH |

TABLE 7

Accurate masses and calculated elemental composition of fragment ions of deoxycholic acid, chenodeoxycholic acid, and 5β-cholanic acid-3α,4β,7α-triol AMPP derivatives

| | Deoxycholic acid | | | Chemodeoxycholic acid | | |
|---|---|---|---|---|---|---|
| Bile acid Fragment | Measured mass (u) (Relative intensity) | Deviation (mmu) | Elemental composition | Measured mass (u) (Relative intensity) | Deviation (mmu) | Elemental composition |
| T | 169.0888 (73.1) | 0.18 | C12H11N | 169.0886 (73.56) | −0.01 | C12H11N |
| S | 183.0919 (100) | 0.18 | C12H11N2 | 183.0917 (100) | −0.02 | C12H11N2 |
| R | 196.076 (3.31) | 0.35 | C13H10ON | 196.0758 (3.26) | 0.12 | C13H10ON |
| P | 211.087 (4.69) | 0.4 | C13H11ON2 | 211.0867 (4.83) | 0.15 | C13H11ON2 |
| Q | 226.1105 (8.34) | 0.42 | C14H14ON2 | 226.1102 (7.26) | 0.14 | C14H14ON2 |
| O | 239.1183 (6.03) | 0.44 | C15H15ON2 | 239.118 (6.37) | 0.14 | C15H15ON2 |
| N | 267.1496 (2.33) | 0.38 | C17H19ON2 | 267.1493 (2.34) | 0.07 | C17H19ON2 |
| M | 293.1653 (1.6) | 0.43 | C19H21ON2 | 293.1649 (1.41) | 0.09 | C19H21ON2 |
| L | 309.1965 (0.6) | 0.4 | C20H25ON2 | 309.1962 (0.46) | 0.01 | C20H25ON2 |
| K | 349.2278 (0.44) | 0.32 | C23H29ON2 | 349.2274 (0.64) | −0.09 | C23H29ON2 |
| H | 375.2433 (0.27) | 0.21 | C25H31ON2 | 391.2378 (0.31) | −0.18 | C25H31O2N2 |
| J | 419.2697 (0.16) | 0.37 | C27H35O2N2 | 403.2742 (0.64) | −0.16 | C27H35ON2 |
| I | 487.3323 (1) | 0.42 | C32H43O2N2 | 487.3316 (0.92) | −0.31 | C32H43O2N2 |
| G | — | — | — | — | — | — |
| F | — | — | — | — | — | — |
| C | — | — | — | — | — | — |
| E | — | — | — | 523.368 (0.17) | −0.24 | C36H47ON2 |
| D | 523.3686 (0.05) | 0.28 | C36H47ON2 | — | — | — |
| B | 527.3636 (1.08) | 0.37 | C35H47O2N2 | 527.3631 (0.25) | −0.14 | C35H47O2N2 |
| A | 541.3793 (2.58) | 0.44 | C36H49O2N2 | 541.3787 (4.48) | −0.17 | C36H49O2N2 |
| M+ | 559.3897 (12.86) | 0.27 | C36H51O3N2 | 559.3891 (9.99) | −0.34 | C36H51O3N2 |

| | 5β-Cholanic acid-3α,4β,7α-triol | | |
|---|---|---|---|
| Bile acid Fragment | Measured mass (u) (Relative intensity) | Deviation (mmu) | Elemental composition |
| T | 169.0885 (75.98) | −0.08 | C12H11N |
| S | 183.0916 (100) | −0.1 | C12H11N2 |
| R | 196.0757 (3.27) | 0.04 | C13H10ON |
| P | 211.0867 (4.72) | 0.06 | C13H11ON2 |
| Q | 226.1101 (6.8) | 0.06 | C14H14ON2 |
| O | 239.1179 (6.71) | 0.05 | C15H15ON2 |
| N | 267.1491 (2.6) | −0.04 | C17H19ON2 |
| M | 293.1648 (1.53) | −0.02 | C19H21ON2 |
| L | 309.1961 (0.45) | −0.05 | C20H25ON2 |
| K | 349.2272 (0.73) | −0.24 | C23H29ON2 |
| H | 391.2377 (0.34) | −0.26 | C25H31O2N2 |
| J | 403.274 (3.87) | −0.41 | C27H35ON2 |
| I | 487.3315 (0.6) | −0.37 | C32H43O2N2 |
| G | — | — | — |
| F | — | — | — |
| C | 525.3473 (0.22) | −0.3 | C35H45O2N2 |

TABLE 7-continued

Accurate masses and calculated elemental composition of fragment ions of deoxycholic acid, chenodeoxycholic acid, and 5β-cholanic acid-3α,4β,7α-triol AMPP derivatives

| | | | |
|---|---|---|---|
| E | 539.3628 (0.3) | −0.41 | C36H47O2N2 |
| D | — | — | — |
| B | 543.3579 (0.45) | −0.25 | C35H47O3N2 |
| A | 557.3732 (3.38) | −0.56 | C36H49O3N2 |
| M+ | 575.3838 (8.29) | −0.58 | C36H51O4N2 |

TABLE 8

Accurate masses and calculated elemental composition of fragment ions of cholic acid, α-muricholic acid, and β-muricholic acid AMPP derivatives

| | Cholic_acid | | | α-Muricholic_acid | | |
|---|---|---|---|---|---|---|
| Bile acid Fragment | Measured mass (u) (Relative intensity) | Deviation (mmu) | Elemental composition | Measured mass (u) (Relative intensity) | Deviation (mmu) | Elemental composition |
| T | 169.0885 (73.77) | −0.11 | C12H11N | 169.0885 (72.21) (72.21) | −0.17 | C12H11N |
| S | 183.0915 (100) | −0.13 | C12H11N2 | 183.0915 (100) (100) | −0.19 | C12H11N2 |
| R | 196.0757 (3.25) | 0 | C13H10ON | 196.0757 (3.5) (3.5) | −0.06 | C13H10ON |
| P | 211.0866 (4.67) | 0.03 | C13H11ON2 | 211.0866 (4.62) (4.62) | −0.05 | C13H11ON2 |
| Q | 226.1101 (8.35) | 0.02 | C14H14ON2 | 226.1101 (7.37) (7.37) | −0.06 | C14H14ON2 |
| O | 239.1179 (5.76) | 0.01 | C15H15ON2 | 239.1179 (6.33) (6.33) | −0.07 | C15H15ON2 |
| N | 267.1491 (2.33) | −0.09 | C17H19ON2 | 267.1491 (2.77) (2.77) | −0.18 | C17H19ON2 |
| M | 293.1648 (1.53) | −0.07 | C19H21ON2 | 293.1647 (1.36) (1.36) | −0.18 | C19H21ON2 |
| L | 309.196 (0.65) | −0.15 | C20H25ON2 | 309.1959 (0.38) (0.38) | −0.27 | C20H25ON2 |
| K | 349.2272 (0.62) | −0.25 | C23H29ON2 | 349.2271 (0.93) (0.93) | −0.4 | C23H29ON2 |
| H | 391.2377 (0.3) | −0.31 | C25H31O2N2 | 391.2376 (0.29) (0.29) | −0.46 | C25H31O2N2 |
| J | 419.2689 (0.5) | −0.42 | C27H35O2N2 | 403.2739 (2) (2) | −0.62 | C27H35ON2 |
| I | 503.3264 (0.94) | −0.41 | C32H43O3N2 | 503.3264 (0.43) (0.43) | −0.6 | C32H43O3N2 |
| G | — | — | — | 507.3364 (0.14) (0.14) | −0.85 | C35H43ON2 |
| F | — | — | — | 523.3315 (0.1) (0.1) | −0.81 | C35H43O2N2 |
| C | 525.3471 (0.11) | −0.48 | C35H45O2N2 | 525.347 (0.47) (0.47) | −0.66 | C35H45O2N2 |
| E | 539.3628 (0.36) | −0.36 | C36H47O2N2 | 539.3627 (0.44) (0.44) | −0.63 | C36H47O2N2 |
| D | 541.3419 (0.06) | −0.58 | C35H45O3N2 | 541.3418 (0.07) (0.07) | −0.91 | C35H45O3N2 |
| B | 543.3577 (0.98) | −0.4 | C35H47O3N2 | 543.3575 (0.31) (0.31) | −0.7 | C35H47O3N2 |
| A | 557.3731 (5.43) | −0.62 | C36H49O3N2 | 557.373 (2.68) (2.68) | −0.85 | C36H49O3N2 |
| M+ | 575.3837 (10.87) | −0.61 | C36H51O4N2 | 575.3836 (5.92) (5.92) | −0.8 | C36H51O4N2 |

| | β-Muricholic_acid | | |
|---|---|---|---|
| Bile acid Fragment | Measured mass (u) (Relative intensity) | Deviation (mmu) | Elemental composition |
| T | 169.0885 (72.21) | −0.12 | C12H11N |
| S | 183.0915 (100) | −0.15 | C12H11N2 |
| R | 196.0757 (3.5) | −0.01 | C13H10ON |
| P | 211.0866 (4.62) | 0.01 | C13H11ON2 |
| Q | 226.1101 (7.37) | −0.01 | C14H14ON2 |
| O | 239.1179 (6.33) | −0.01 | C15H15ON2 |
| N | 267.1491 (2.77) | −0.12 | C17H19ON2 |
| M | 293.1647 (1.36) | −0.1 | C19H21ON2 |
| L | 309.1959 (0.38) | −0.19 | C20H25ON2 |
| K | 349.2271 (0.93) | −0.32 | C23H29ON2 |
| H | 391.2376 (0.29) | −0.43 | C25H31O2N2 |
| J | 403.2739 (2) | −0.5 | C27H35ON2 |
| I | 503.3264 (0.43) | −0.45 | C32H43O3N2 |
| G | 507.3364 (0.14) | −0.6 | C35H43ON2 |
| F | 523.3315 (0.1) | −0.43 | C35H43O2N2 |
| C | 525.347 (0.47) | −0.53 | C35H45O2N2 |
| E | 539.3627 (0.44) | −0.48 | C36H47O2N2 |
| D | 541.3418 (0.07) | −0.64 | C35H45O3N2 |
| B | 543.3575 (0.31) | −0.58 | C35H47O3N2 |
| A | 557.373 (2.68) | −0.72 | C36H49O3N2 |
| M+ | 575.3836 (5.92) | −0.7 | C36H51O4N2 |

TABLE 9

Accurate masses and calculated elemental composition of fragment ions of glycocholic acid, glycochenodeoxycholic acid, and glycodeoxycholic acid AMPP derivatives

| | Glycocholic_acid | | | Glycochenodeoxycholic_acid | | |
|---|---|---|---|---|---|---|
| Bile acid Fragment | Measured mass (u) (Relative intensity) | Deviation (mmu) | Elemental composition | Measured mass (u) (Relative intensity) | Deviation (mmu) | Elemental composition |
| GW | 169.0885 (100) | −0.15 | C12H11N | 169.0889 (100) | 0.28 | C12H11N |
| GV | 183.0917 (34.37) | −0.02 | C12H11N2 | 183.0921 (33.33) | 0.45 | C12H11N2 |
| GU | 185.1072 (44.28) | −0.12 | C12H13N2 | 185.1077 (43.1) | 0.35 | C12H13N2 |
| GT | 195.0917 (15.1) | −0.01 | C13H11N2 | 195.0922 (14.51) | 0.48 | C13H11N2 |
| GS | 197.1073 (5.09) | −0.01 | C13H13N2 | 197.1078 (5.19) | 0.49 | C13H13N2 |
| GQ | 211.0866 (20.95) | −0.02 | C13H11ON2 | 211.0871 (21.18) | 0.52 | C13H11ON2 |
| GR | 240.1131 (11.11) | 0.01 | C14H14ON3 | 240.1138 (10.68) | 0.62 | C14H14ON3 |
| GP | 268.108 (0.79) | −0.09 | C15H14O2N3 | 268.1086 (0.79) | 0.59 | C15H14O2N3 |
| GO | 296.1391 (1.19) | −0.25 | C17H18O2N3 | 296.1398 (1.27) | 0.49 | C17H18O2N3 |
| GN | 324.1704 (0.61) | −0.27 | C19H22O2N3 | 324.1712 (0.59) | 0.57 | C19H22O2N3 |
| GM | 336.1703 (0.09) | −0.31 | C20H22O2N3 | 336.1714 (0.14) | −0.61 | C22H24O3 |
| GL | 350.186 (0.33) | −0.26 | C21H24O2N3 | 350.1869 (0.32) | 0.64 | C21H24O2N3 |
| GJ | 352.2018 (0.2) | −0.18 | C21H26O2N3 | 352.2026 (0.16) | −0.65 | C23H28O3 |
| GK | 366.2173 (0.08) | −0.35 | C22H28O2N3 | 366.2183 (0.07) | 0.65 | C22H28O2N3 |
| GI | 406.2485 (0.11) | −0.44 | C25H32O2N3 | 406.2496 (0.12) | 0.66 | C25H32O2N3 |
| GH | 448.2593 (0.05) | −0.19 | C27H34O3N3 | 448.2601 (0.05) | 0.56 | C27H34O3N3 |
| GG | 476.2903 (0.07) | −0.47 | C29H38O3N3 | 460.2966 (0.1) | −0.59 | C31H40O3 |
| GAB | 507.3575 (0.03) | −0.64 | C32H47O3N2 | 491.3641 (0.15) | 0.88 | C32H47O2N2 |
| GZ | 539.3625 (0.05) | −0.73 | C36H47O2N2 | 523.3691 (0.06) | 0.83 | C36H47ON2 |
| GY | 557.3731 (0.2) | −0.66 | C36H49O3N2 | 541.3799 (0.27) | 1.01 | C36H49O2N2 |
| GF | 560.3477 (0.07) | −0.63 | C34H46O4N3 | 544.3546 (0.09) | −0.09 | C36H48O4 |
| GX | 575.3839 (0.05) | −0.48 | C36H51O4N2 | 559.3903 (0.06) | −0.9 | C36H51O3N2 |
| GE | 582.3677 (0.01) | −1.31 | C37H48O3N3 | — | — | — |
| GAA | 586.3994 (0.03) | −0.93 | C37H52O3N3 | 570.4065 (0.03) | 1.06 | C37H52O2N3 |
| GB | 596.3841 (0.03) | −0.61 | C38H50O3N3 | — | — | — |
| GD | — | — | — | 584.3851 (0.03) | 0.46 | C37H50O3N3 |
| GC | 600.379 (0.09) | −0.62 | C37H50O4N3 | 580.391 (0.01) | 1.25 | C38H50O2N3 |
| GA | 614.3944 (0.34) | −0.83 | C38H52O4N3 | 598.4014 (0.39) | 1.07 | C38H52O3N3 |
| M+ | 632.4049 (0.73) | −0.95 | C38H54O5N3 | 616.4116 (0.89) | 0.72 | C38H54O4N3 |

| | Glycodeoxycholic_acid | | |
|---|---|---|---|
| Bile acid Fragment | Measured mass (u) (Relative intensity) | Deviation (mmu) | Elemental composition |
| GW | 169.0884 (100) | −0.2 | C12H11N |
| GV | 183.0916 (33.79) | −0.06 | C12H11N2 |
| GU | 185.1072 (42.8) | −0.17 | C12H13N2 |
| GT | 195.0916 (14.19) | −0.06 | C13H11N2 |
| OS | 197.1073 (5.03) | −0.05 | C13H13N2 |
| GQ | 211.0865 (20.39) | −0.06 | C13H11ON2 |
| GR | 240.1131 (11.2) | −0.04 | C14H14ON3 |
| GP | 268.1079 (0.76) | −0.12 | C15H14O2N3 |
| GO | 296.1391 (1.16) | −0.25 | C17H18O2N3 |
| GN | 324.1703 (0.57) | −0.32 | C19H22O2N3 |
| GM | 336.1704 (0.08) | −0.21 | C20H22O2N3 |
| GL | 350.186 (0.36) | −0.33 | C21H24O2N3 |
| GJ | 352.2016 (0.18) | −0.36 | C21H26O2N3 |
| OK | 366.2172 (0.07) | −0.36 | C22H28O2N3 |
| GI | 406.2484 (0.09) | −0.5 | C25H32O2N3 |
| GH | 432.2638 (0.04) | −0.75 | C27H34O3N3 |
| GG | 476.2902 (0.03) | −0.62 | C29H38O3N3 |
| GAB | 491.363 (0.03) | −0.23 | C32H47O2N2 |
| GZ | 523.3676 (0.05) | −0.68 | C36H47ON2 |
| GY | 541.3783 (0.27) | −0.57 | C36H49O2N2 |
| GF | 544.353 (0.1) | −0.39 | C34H46O3N3 |
| GX | 559.3889 (0.07) | −0.55 | C36H51O3N2 |
| GE | 570.4049 (0.03) | −0.52 | C37H52O2N3 |
| GAA | 584.3842 (0.12) | −0.5 | C37H50O3N3 |
| GB | — | — | — |
| GD | — | — | — |
| GC | — | — | — |
| GA | 598.3996 (0.27) | −0.71 | C38H53O3N3 |
| M+ | 616.4099 (1.08) | −0.97 | C38H54O4N3 |

TABLE 10

Accuracy and precision of QC samples

| Analytical Batch Number | | First-tier assay | | | | | Second-tier assay | | | | |
|---|---|---|---|---|---|---|---|---|---|---|---|
| | | LLOQ | LLQC | LQC | MQC | HQC | LLOQ | LLQC | LQC | MQC | HQC |
| | | 5 ng/mL | 10 ng/mL | 30 ng/mL | 150 ng/mL | 300 ng/mL | 5 ng/mL | 10 ng/mL | 30 ng/mL | 150 ng/mL | 300 ng/mL |
| 1 | Intra-run Mean | 4.61 | 9.36 | 28.3 | 155 | 308 | 4.92 | 9.59 | 29.0 | 151 | 314 |
| | Intra-run % CV | 6.03 | 4.34 | 7.89 | 7.25 | 5.27 | 7.68 | 6.09 | 9.99 | 5.78 | 7.25 |
| | Intra-run % RE | −7.87 | −6.45 | −5.83 | 3.22 | 2.63 | −1.60 | −4.07 | −3.43 | 0.70 | 4.43 |
| | n | 6 | 6 | 6 | 6 | 6 | 6 | 6 | 6 | 6 | 6 |
| 2 | Intra-run Mean | 5.33 | 9.44 | 28.9 | 153 | 300 | 5.75 | 10.32 | 26.1 | 147 | 294 |
| | Intra-run % CV | 9.22 | 5.90 | 6.48 | 3.67 | 5.10 | 9.17 | 8.68 | 8.54 | 7.02 | 7.01 |
| | Intra-run % RE | 6.73 | −5.65 | −3.70 | 2.27 | 0.03 | 14.90 | 3.22 | −13.22 | −2.30 | −1.98 |
| | n | 6 | 6 | 0 | 6 | 6 | 6 | 6 | 6 | 6 | 6 |
| 3 | Intra-run Mean | 5.33 | 9.13 | 26.2 | 146 | 290 | 5.62 | 9.38 | 28.0 | 149 | 289 |
| | Intra-run % CV | 7.27 | 4.04 | 6.61 | 5.29 | 7.96 | 3.71 | 6.18 | 5.43 | 2.70 | 11.76 |
| | Intra-run % RE | 6.53 | −8.68 | −12.55 | −2.85 | −3.35 | 12.33 | −6.41 | −6.60 | −1.82 | −1.45 |
| | n | 6 | 6 | 6 | 6 | 6 | 6 | 6 | 6 | 6 | 6 |
| Inter-batch | Inter-run Mean | 5.09 | 9.31 | 27.8 | 151 | 299 | 5.43 | 9.76 | 27.7 | 149 | 299 |
| | Inter-run % CV | 9.99 | 4.77 | 7.89 | 6.08 | 6.33 | 9.69 | 7.99 | 8.97 | 5.27 | 9.07 |
| | Inter-run % RE | 1.79 | −6.93 | −7.31 | 0.81 | −0.22 | 8.54 | −2.36 | −7.76 | −0.89 | −0.37 |
| | n | 18 | 18 | 18 | 18 | 18 | 18 | 18 | 18 | 18 | 18 |

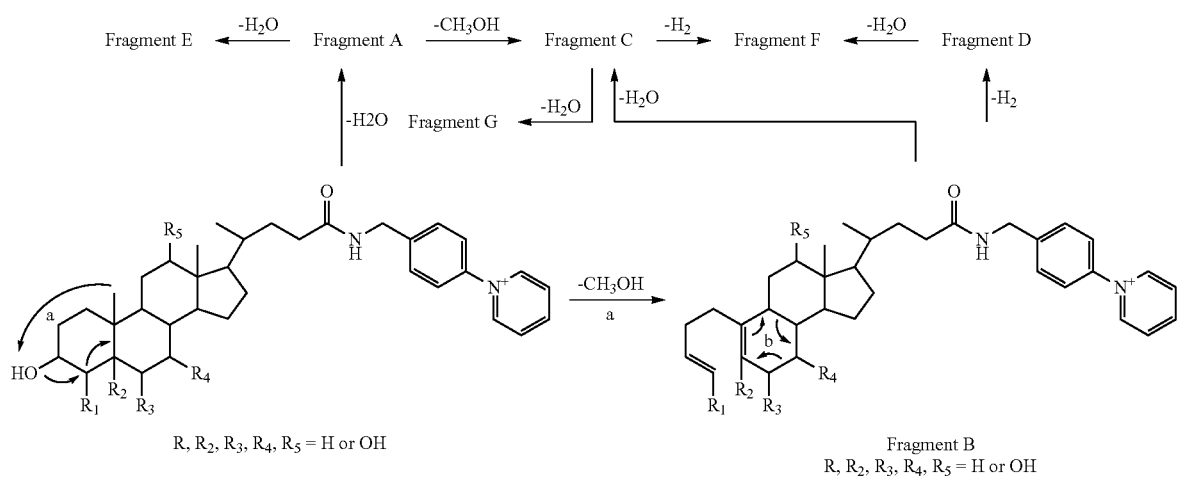

Scheme 1. Proposed fragmentation pathway to fragments A-H in AMPP derivatives of unconjugated bile acids 1-7

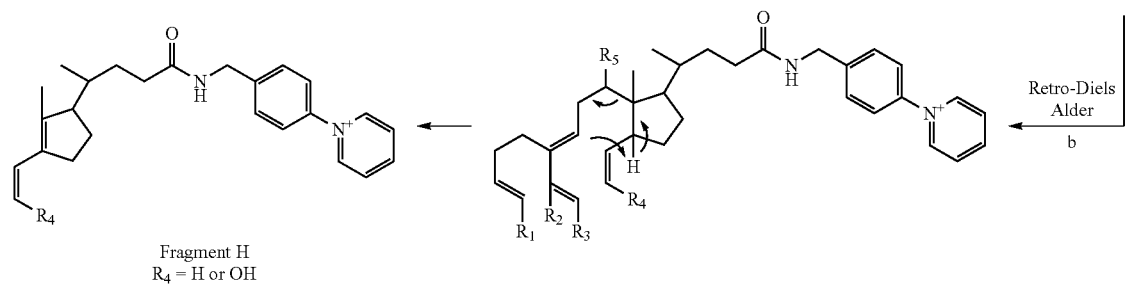
Fragment H
R$_4$ = H or OH
Scheme 2. Proposed fragmentation pathway to fragments I-K in AMPP derivatives of unconjugated bile acids 1-7
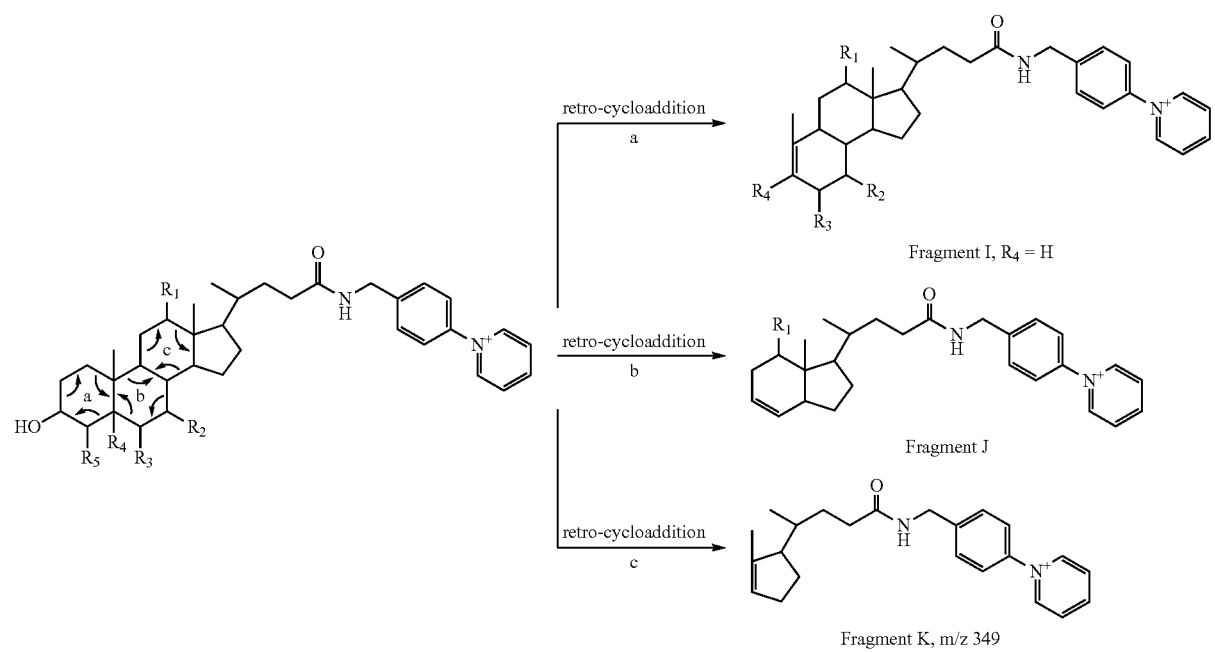
Fragment I, R$_4$ = H
Fragment J
Fragment K, m/z 349
Scheme 3. Proposed fragmentation pathway to fragments L(L′)-M(M′) in AMPP derivatives of unconjugated bile acids 1-7
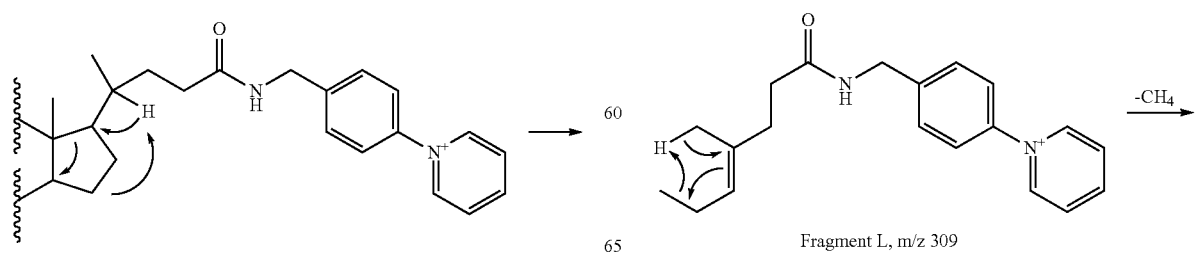
Fragment L, m/z 309
-continued

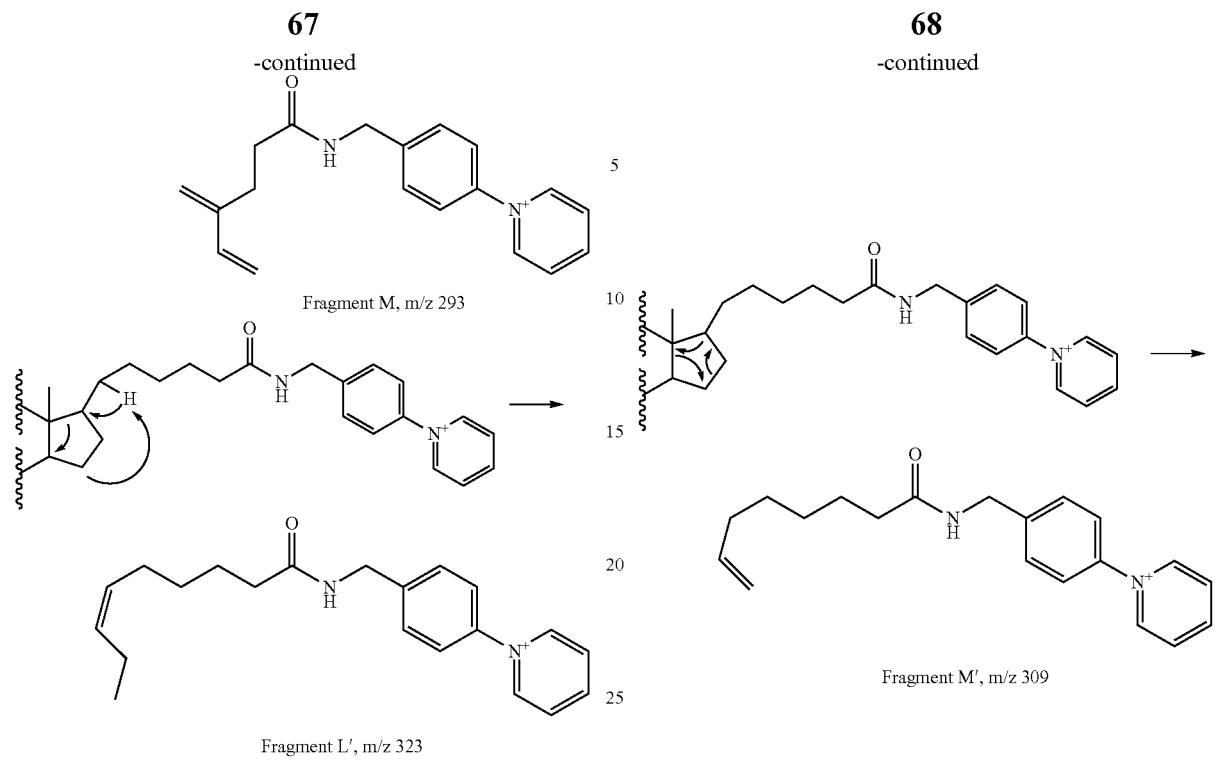
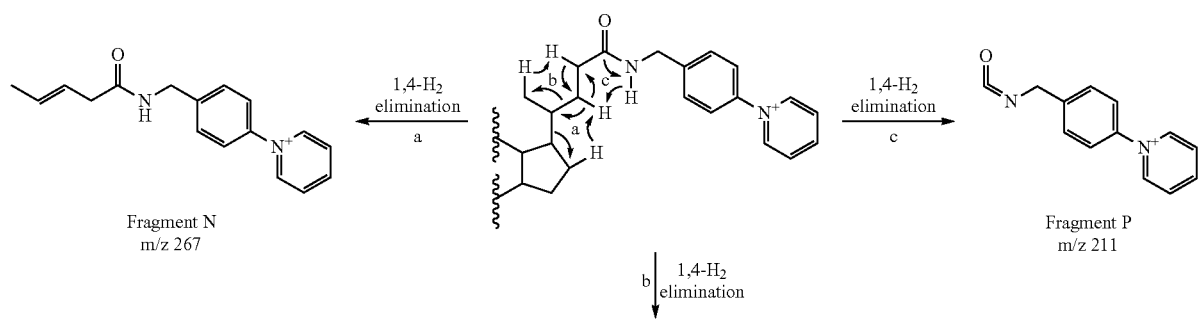
Scheme 4. Proposed fragmentation pathway to fragments N-P in AMPP derivatives of unconjugated bile acids 1-6

Scheme 5. Proposed fragmentation pathway to fragments Q-T in AMPP derivatives of unconjugated bile acids 1-7
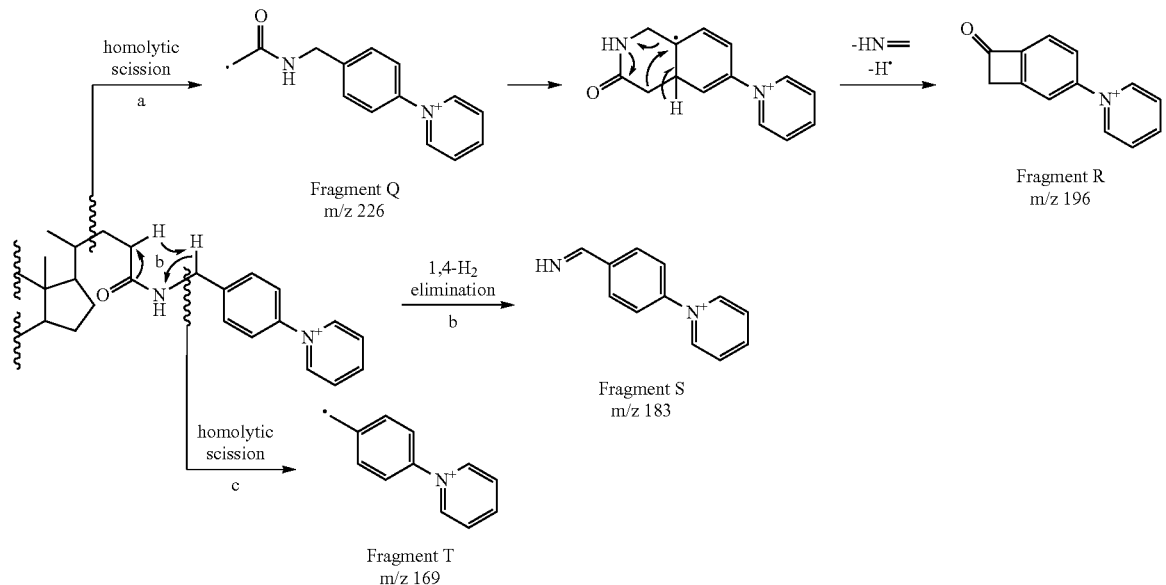
Scheme 6. Proposed fragmentation pathway to fragments GA-GE, GH in AMPP derivatives of glycine conjugated bile acids 8-10
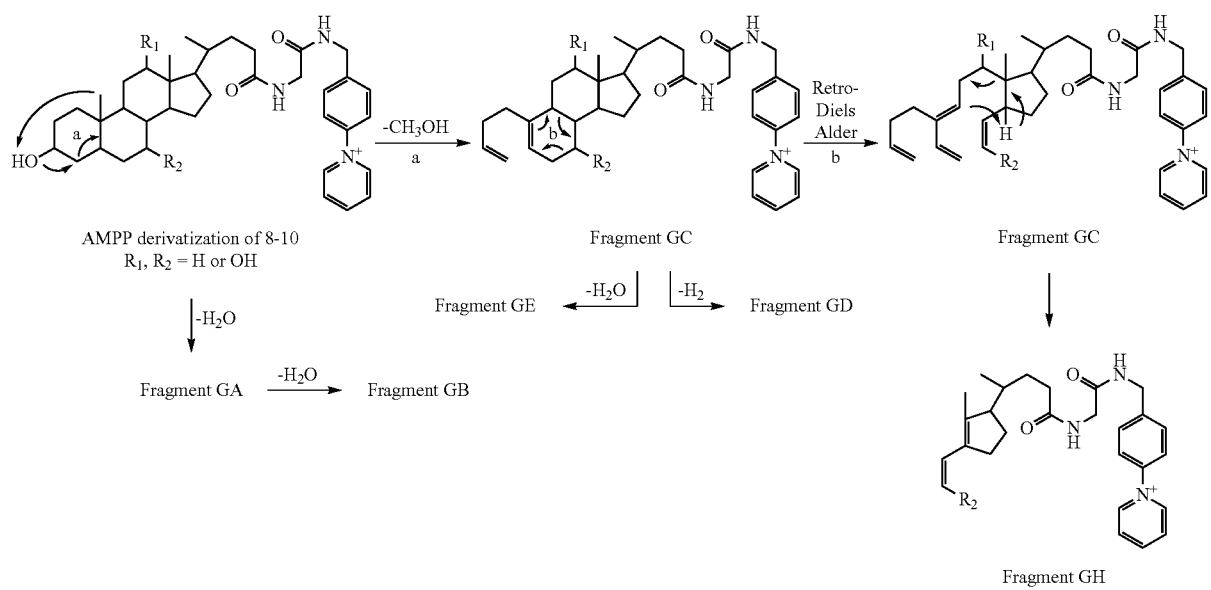

Scheme 7. Proposed fragmentation pathway to fragments GF, GG, GI in AMPP derivatives of glycine conjugated bile acids 8-10
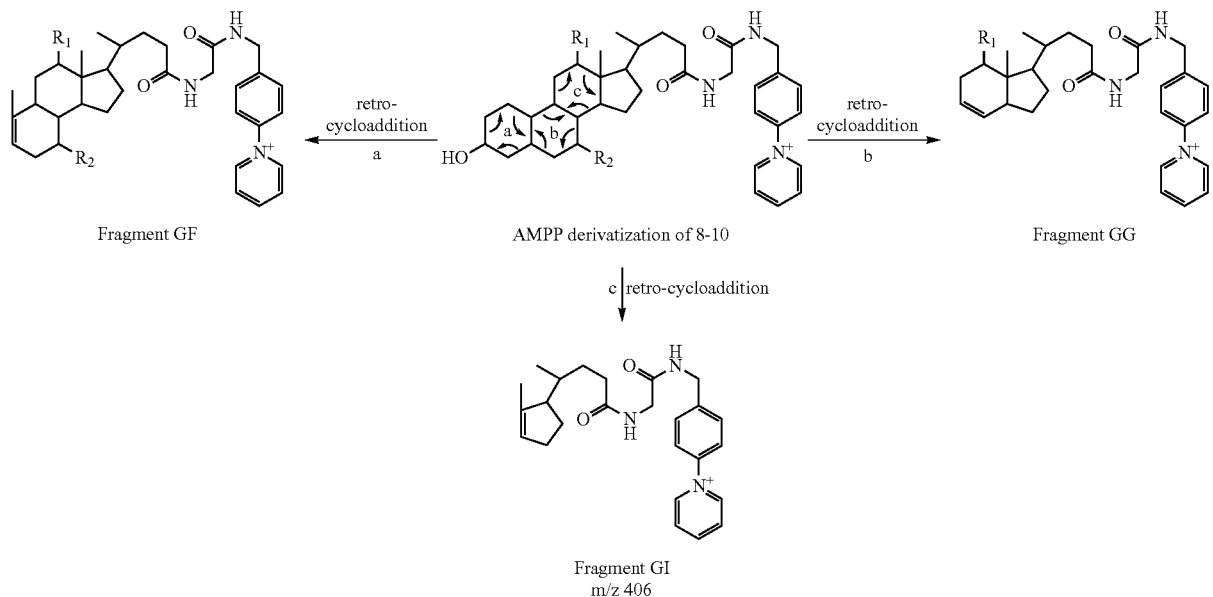
Scheme 8. Proposed fragmentation pathway to fragments GJ-GM in AMPP derivatives of glycine conjugated bile acids 8-10
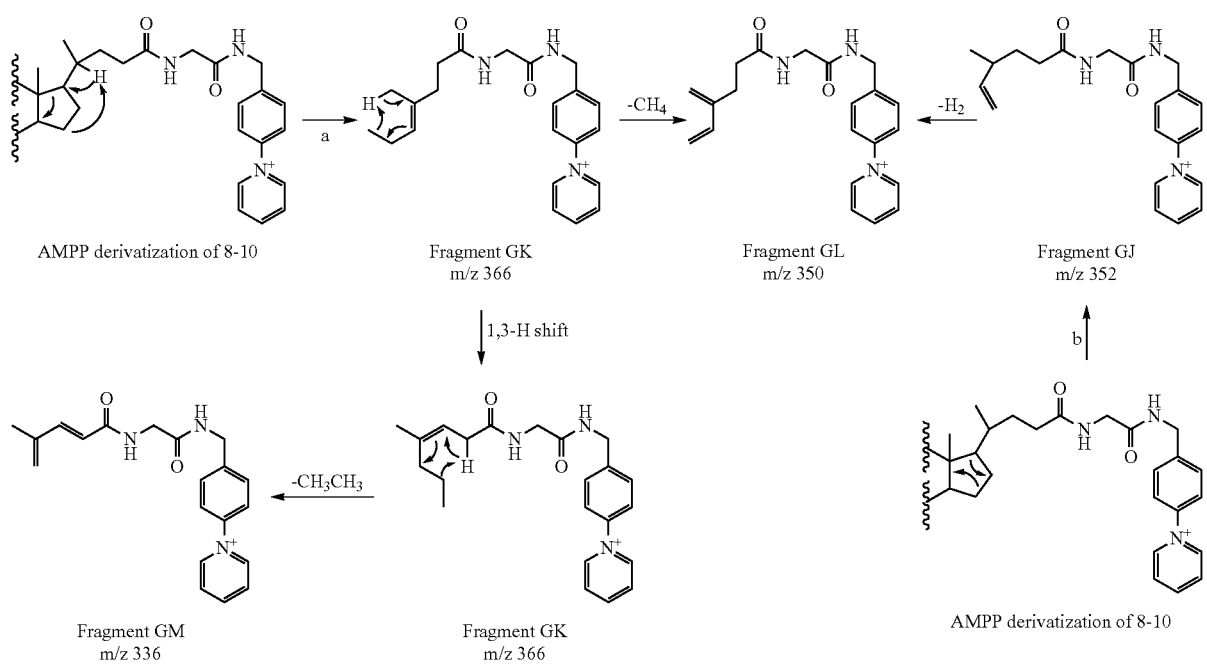

Scheme 9. Proposed fragmentation pathway to fragments GN-GW in AMPP derivatives of glycine conjugated bile acids 8-10
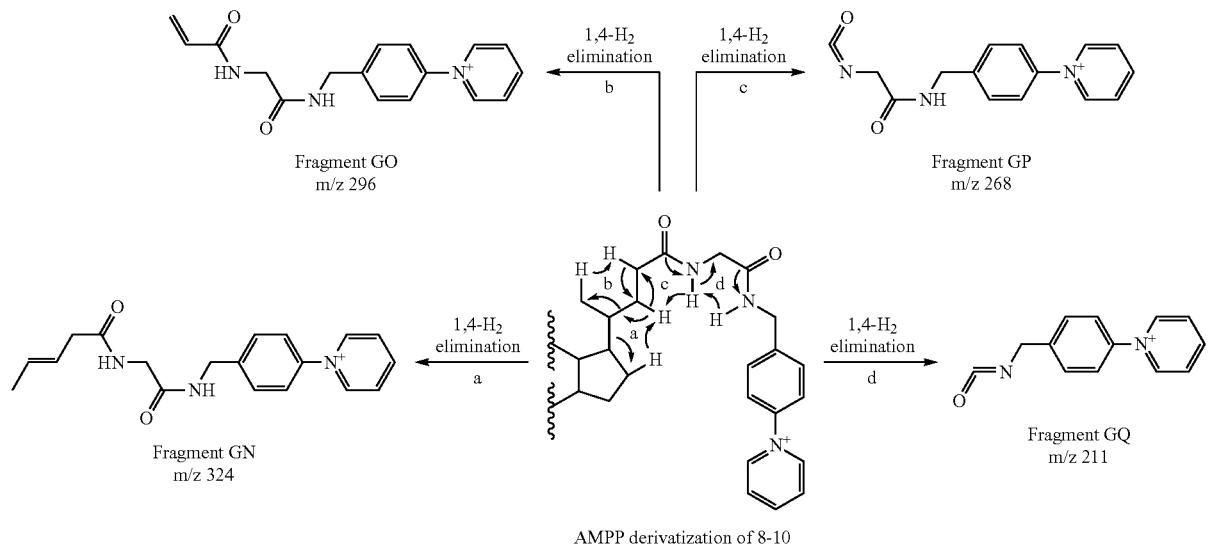
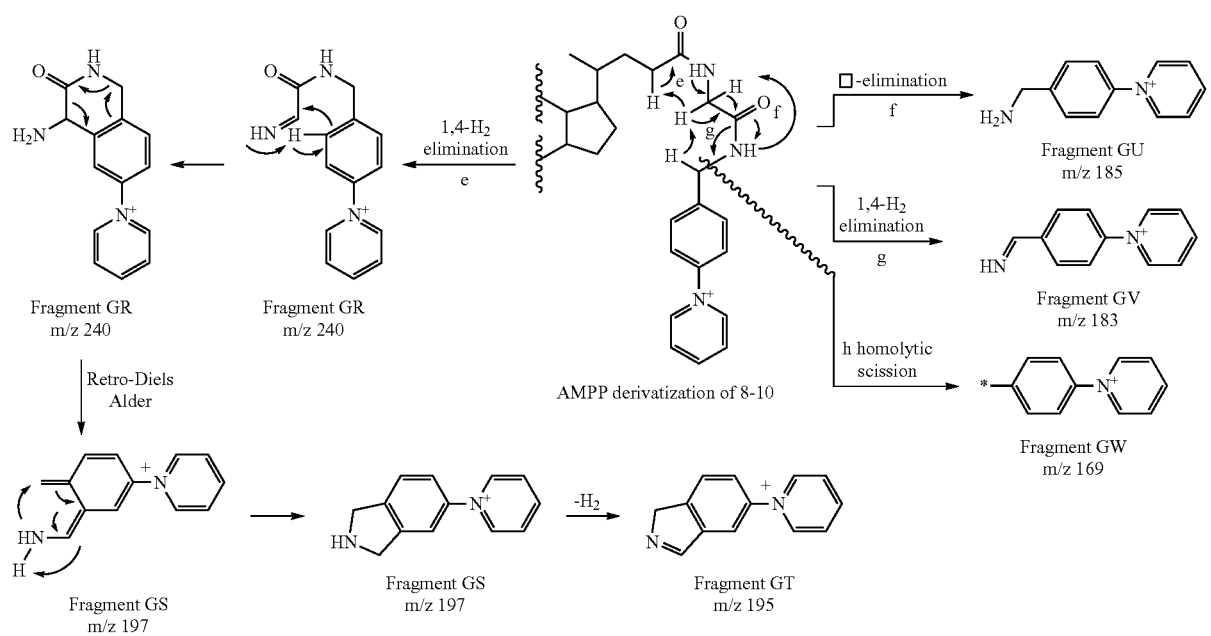

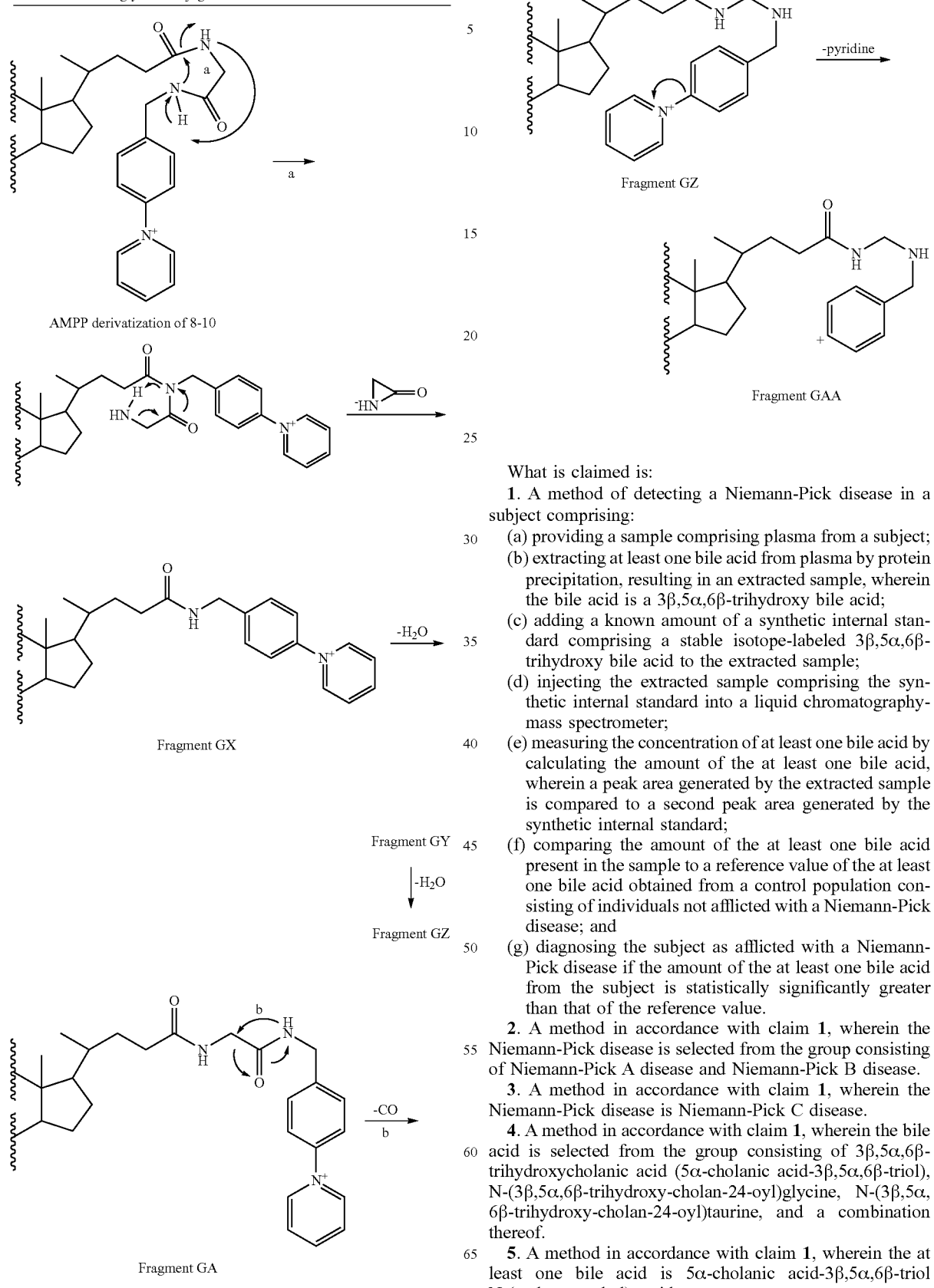

Scheme 10. Proposed fragmentation pathway to fragments GX-GZ, GAA-GAB in glycine conjugated bile acid AMPP derivatives

What is claimed is:

1. A method of detecting a Niemann-Pick disease in a subject comprising:
   (a) providing a sample comprising plasma from a subject;
   (b) extracting at least one bile acid from plasma by protein precipitation, resulting in an extracted sample, wherein the bile acid is a 3β,5α,6β-trihydroxy bile acid;
   (c) adding a known amount of a synthetic internal standard comprising a stable isotope-labeled 3β,5α,6β-trihydroxy bile acid to the extracted sample;
   (d) injecting the extracted sample comprising the synthetic internal standard into a liquid chromatography-mass spectrometer;
   (e) measuring the concentration of at least one bile acid by calculating the amount of the at least one bile acid, wherein a peak area generated by the extracted sample is compared to a second peak area generated by the synthetic internal standard;
   (f) comparing the amount of the at least one bile acid present in the sample to a reference value of the at least one bile acid obtained from a control population consisting of individuals not afflicted with a Niemann-Pick disease; and
   (g) diagnosing the subject as afflicted with a Niemann-Pick disease if the amount of the at least one bile acid from the subject is statistically significantly greater than that of the reference value.

2. A method in accordance with claim 1, wherein the Niemann-Pick disease is selected from the group consisting of Niemann-Pick A disease and Niemann-Pick B disease.

3. A method in accordance with claim 1, wherein the Niemann-Pick disease is Niemann-Pick C disease.

4. A method in accordance with claim 1, wherein the bile acid is selected from the group consisting of 3β,5α,6β-trihydroxycholanic acid (5α-cholanic acid-3β,5α,6β-triol), N-(3β,5α,6β-trihydroxy-cholan-24-oyl)glycine, N-(3β,5α,6β-trihydroxy-cholan-24-oyl)taurine, and a combination thereof.

5. A method in accordance with claim 1, wherein the at least one bile acid is 5α-cholanic acid-3β,5α,6β-triol N-(carboxymethyl)-amide.

6. A method in accordance with claim 1, wherein the sample is a body fluid sample.

7. A method in accordance with claim 6, wherein the body fluid sample is selected from the group consisting of a plasma sample, a serum sample, a blood sample, a sputum sample, a urine sample, an amniotic fluid sample, cord blood, and a combination thereof.

8. A method in accordance with claim 6, further comprising adding a known amount of the synthetic internal standard to the body fluid sample.

9. A method in accordance with claim 1, wherein a Niemann-Pick disease is diagnosed if the at least one bile acid concentration is at least 2 fold greater than the reference value.

10. A method for determining the status of a Niemann-Pick disease in a subject with a Niemann-Pick disease comprising:
(a) obtaining at least one body fluid sample comprising plasma from the subject;
(b) extracting at least one bile acid from plasma by protein precipitation resulting in an extracted sample, wherein the bile acid is a 3β,5α,6β-trihydroxy bile acid;
(c) adding a known amount of a synthetic internal standard comprising a stable isotope-labeled 3β,5α,6β-trihydroxy bile acid to the extracted sample;
(d) determining a quantity of 3β,5α,6β-trihydroxycholanic acid, N-(3β,5α,6β-trihydroxy-cholan-24-oyl)glycine, or N-(3β,5α,6β-trihydroxy-cholan-24-oyl)taurine by a liquid chromatography-mass spectroscopy analysis, wherein a peak area generated by the extracted sample comprising the synthetic internal standard is compared to a second peak area generated by the internal standard; and
(e) determining the magnitude of the difference between the quantity of 3β,5α,6β-trihydroxycholanic acid, N-(3β,5α,6β-trihydroxy-cholan-24-oyl)glycine, or N-(3β,5α,6β-trihydroxy-cholan-24-oyl)taurine and a reference value of the at least one bile acid obtained from the subject at an earlier time, wherein if the quantity of 3β,5α,6β-trihydroxycholanic acid, N-(3β,5α,6β-trihydroxy-cholan-24-oyl)glycine, or N-(3β,5α,6β-trihydroxy-cholan-24-oyl)taurine is statistically significantly greater than or equal to the reference value, then the subject is not deemed to exhibit remission of the Niemann-Pick disease.

11. A method of detecting a Niemann-Pick disease in a subject comprising:
(a) providing a sample comprising plasma from a subject;
(b) extracting at least one bile acid from plasma by protein precipitation, resulting in an extracted sample, wherein the bile acid is a 3β,5α,6β-trihydroxy bile acid;
(c) adding a known amount of a synthetic internal standard comprising a stable isotope-labeled 3β,5α,6β-trihydroxy bile acid to the extracted sample;
(d) injecting the extracted sample comprising the synthetic internal standard into a liquid chromatography-mass spectrometer;
(e) measuring the concentration of the at least one bile acid by calculating the amount of the at least one bile acid, wherein a peak area generated by the extracted sample is compared to a second peak area generated by the synthetic internal standard;
(f) comparing the amount of the at least one bile acid present in the sample to a reference value of the at least one bile acid obtained from a control population consisting of individuals not afflicted with a Niemann-Pick disease; and
(g) diagnosing the subject as afflicted with a Niemann-Pick disease if the amount of the at least one bile acid from the subject is statistically significantly greater than that of the reference value.

12. A method in accordance with claim 11, wherein the Niemann-Pick disease is selected from the group consisting of Niemann-Pick A disease and Niemann-Pick B disease.

13. A method in accordance with claim 11, wherein the Niemann-Pick disease is Niemann-Pick C disease.

14. A method in accordance with claim 11, wherein the at least one bile acid is selected from the group consisting of 3β,5α,6β-trihydroxycholanic acid, N-(3β,5α,6β-trihydroxy-cholan-24-oyl)glycine, N-(3β,5α,6β-trihydroxy-cholan-24-oyl)taurine, and a combination thereof.

15. A method in accordance with claim 11, wherein the at least one bile acid is 5α-cholanic acid-3β,5α,6β-triol N-(carboxymethyl)-amide.

16. A method in accordance with claim 11, wherein the sample is a body fluid sample.

17. A method in accordance with claim 16, wherein the body fluid sample is selected from the group consisting of a plasma sample, a serum sample, a blood sample, a sputum sample, a urine sample, an amniotic fluid sample, cord blood, and a combination thereof.

18. A method in accordance with claim 16, further comprising adding a known amount of the synthetic internal standard to the body fluid sample.

19. A method in accordance with claim 16, wherein a Niemann-Pick disease is diagnosed if the at least one bile acid concentration is at least 2 fold greater than the reference value.

20. A method in accordance with claim 16, wherein the reference value is an average concentration of the at least one bile acid of a non-Niemann-Pick afflicted control group.

21. A method for determining the status of a Niemann-Pick disease in a subject with a Niemann-Pick disease comprising:
(a) obtaining a first body fluid sample comprising plasma from the subject;
(b) extracting at least one bile acid from plasma by protein precipitation, resulting in an extracted sample, wherein the bile acid is a 3β,5α,6β-trihydroxy bile acid;
(c) adding a known amount of a synthetic internal standard comprising a stable isotope-labeled 3β,5α,6β-trihydroxy bile acid to the extracted sample;
(d) comparing a peak area generated by the extracted sample to a second peak area generated by the synthetic internal standard, and calculating the amount of the at least one bile acid and determining a quantity of at least one bile acid selected from the group consisting of 3β,5α,6β-trihydroxycholanic acid, N-(3β,5α,6β-trihydroxy-cholan-24-oyl)glycine, and N-(3β,5α,6β-trihydroxy-cholan-24-oyl)taurine by injecting the extracted sample comprising the synthetic internal standard into a liquid chromatography-mass spectrometer;
(e) administering a treatment for Niemann-Pick disease;
(f) obtaining a second body fluid sample from the subject;
(g) determining a quantity of the at least one bile acid in the second body fluid sample; and
(h) determining the magnitude of the difference between the quantity of at least one bile acid and between the first and second body fluid samples of the at least one bile acid.

22. A method in accordance with claim 1, further comprising treating the subject with a compound selected from the group consisting of an iminosugar inhibitor of glucosylceramide synthase and 2-Hydroxypropyl-β-cyclodextrin.

23. A method in accordance with claim 1, wherein the extracted sample is not chemically derivatized prior to injecting the extracted sample into the liquid chromatography-mass spectrometer.

24. A method in accordance with claim 10, wherein the extracted sample is not chemically derivatized prior to the liquid chromatography-mass spectroscopy analysis.

25. A method in accordance with claim 11, wherein the extracted sample is not chemically derivatized prior to injecting the extracted sample into the liquid chromatography-mass spectrometer.

26. A method in accordance with claim 21, wherein the extracted sample is not chemically derivatized prior to injecting the extracted sample into the liquid chromatography-mass spectrometer.

27. The method of claim 1, wherein the stable isotope is a non-naturally abundant C or N.

28. The method of claim 10, wherein the stable isotope is a non-naturally abundant C or N.

29. The method of claim 11, wherein the stable isotope is a non-naturally abundant C or N.

30. The method of claim 21, wherein the stable isotope is a non-naturally abundant C or N.

31. The method of claim 1, wherein the stable isotope is $^{15}N$ or $^{13}C$.

32. The method of claim 10, wherein the stable isotope is $^{15}N$ or $^{13}C$.

33. The method of claim 11, wherein the stable isotope is $^{15}N$ or $^{13}C$.

34. The method of claim 21, wherein the stable isotope is $^{15}N$ or $^{13}C$.

35. The method of claim 1, wherein the stable isotope is $^{13}C_2$, $^{15}N$-glycine.

36. The method of claim 10, wherein the stable isotope is $^{13}C_2$, $^{15}N$-glycine.

37. The method of claim 11, wherein the stable isotope is $^{13}C_2$, $^{15}N$-glycine.

38. The method of claim 21, wherein the stable isotope is $^{13}C_2$, $^{15}N$-glycine.

* * * * *

UNITED STATES PATENT AND TRADEMARK OFFICE
CERTIFICATE OF CORRECTION

Page 1 of 1

PATENT NO. : 10,983,112 B2
APPLICATION NO. : 15/581389
DATED : April 20, 2021
INVENTOR(S) : Daniel Ory and Xuntian Jiang It is certified that error appears in the above-identified patent and that said Letters Patent is hereby corrected as shown below:

In the Specification

Correct Government Support Paragraph at Column 1, Lines 17-19 as follows:
This invention was made with government support under NS081985 and HD090845 awarded by the National Institutes of Health. The government has certain rights in the invention.

Signed and Sealed this
Sixteenth Day of December, 2025

John A. Squires
*Director of the United States Patent and Trademark Office*